(12) United States Patent
Koul et al.

(10) Patent No.: US 9,643,967 B2
(45) Date of Patent: May 9, 2017

(54) PYRROLO[3,2-C]PYRIDINE DERIVATIVES AS TLR INHIBITORS

(71) Applicant: TAKEDA PHARMACEUTICAL COMPANY LIMITED, Osaka (JP)

(72) Inventors: Summon Koul, Bangalore (IN); Suresh Kurhade, Pune (IN); Sandeep Bhosale, Burnaby, CA (US); Keshav Naik, Pune (IN); Videsh Salunkhe, Dist-Solapur (IN); Yogesh Munot, Pune (IN); Debnath Bhuniya, Pune (IN)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/103,900

(22) PCT Filed: Dec. 12, 2014

(86) PCT No.: PCT/JP2014/083630
§ 371 (c)(1),
(2) Date: Jun. 13, 2016

(87) PCT Pub. No.: WO2015/088045
PCT Pub. Date: Jun. 18, 2015

(65) Prior Publication Data
US 2017/0008885 A1    Jan. 12, 2017

(30) Foreign Application Priority Data
Dec. 13, 2013 (IN) .................. 3656/DEL/2013

(51) Int. Cl.
*C07D 401/14* (2006.01)
*A61K 31/437* (2006.01)
*C07D 471/04* (2006.01)
*C07D 519/00* (2006.01)

(52) U.S. Cl.
CPC ........ *C07D 471/04* (2013.01); *C07D 519/00* (2013.01)

(58) Field of Classification Search
CPC ........................... C07D 401/14; A61K 31/437
USPC ........................................... 546/119; 514/303
See application file for complete search history.

(56) References Cited

U.S. PATENT DOCUMENTS 6,486,171 B2 * 11/2002 Peglion .............. C07D 471/04
514/300

FOREIGN PATENT DOCUMENTS

| WO | 2005/007672 | 1/2005 |
|----|-------------|--------|
| WO | 2010/068806 | 6/2010 |
| WO | 2012/167046 | 12/2012 |
| WO | 2013/181579 | 12/2013 |

OTHER PUBLICATIONS

International Search Report issued Feb. 19, 2015 in corresponding International (PCT) Application No. PCT/JP2014/083630.

* cited by examiner

*Primary Examiner* — Niloofar Rahmani
(74) *Attorney, Agent, or Firm* — Wenderoth, Lind & Ponack, L.L.P.

(57) ABSTRACT

The present invention provides a heterocyclic compound having a TLR7, TLR9, TLR7/8, TLR7/9 or TLR7/8/9 inhibitory action, which is useful as an agent for the prophylaxis or treatment of autoimmune diseases, inflammatory diseases and the like, in particular, systemic lupus erythematosus, Sjogren's syndrome, rheumatoid arthritis, psoriasis, inflammatory bowel disease and the like. The present invention is a compound represented by the formula (1): wherein each symbol is as described in the specification, or a salt thereof.

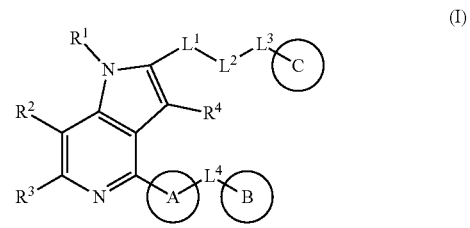

11 Claims, 3 Drawing Sheets

Fig. 1A: Reduction in anti-dsDNA IgG with Example B6 after 6 weeks of treatment
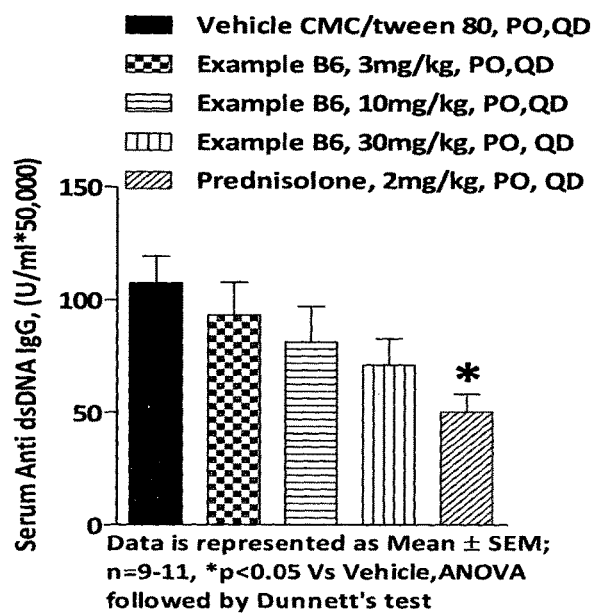
| Treatment | Veh. | Ex.B6 | Ex.B6 | Ex.B6 | Pred |
|---|---|---|---|---|---|
| Dose[QD; (mg/kg)] | - | 3 | 10 | 30 | 2 |
| Duration (weeks) | 6 | 6 | 6 | 6 | 6 |
| Age(Weeks) | 16 | 16 | 16 | 16 | 16 |
| % Reduction | - | 13 | 24 | 34 | 53 |

Fig. 1B: Reduction in anti-dsDNA IgG with Example B6 after 9 weeks of treatment

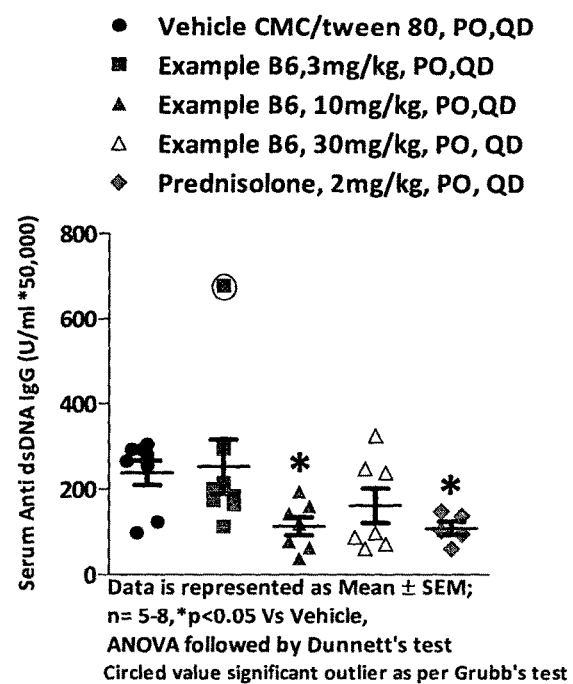

- Vehicle CMC/tween 80, PO,QD
- Example B6, 3mg/kg, PO,QD
- Example B6, 10mg/kg, PO,QD
- Example B6, 30mg/kg, PO, QD
- Prednisolone, 2mg/kg, PO, QD Data is represented as Mean ± SEM;
n= 5-8, *$p<0.05$ Vs Vehicle,
ANOVA followed by Dunnett's test
Circled value significant outlier as per Grubb's test

| Treatment | Veh. | Ex.B6 | Ex.B6 | Ex.B6 | Pred |
|---|---|---|---|---|---|
| Dose [QD; (mg/kg) | - | 3 | 10 | 30 | 2 |
| Duration (weeks) | 9 | 9 | 9 | 9 | 9 |
| Age (Weeks) | 19 | 19 | 19 | 19 | 19 |
| % Reduction | - | 20 | 52 | 32 | 55 |

Fig. 2A: Reduction in anti-dsDNA IgG with Example B11 after 6 weeks of treatment
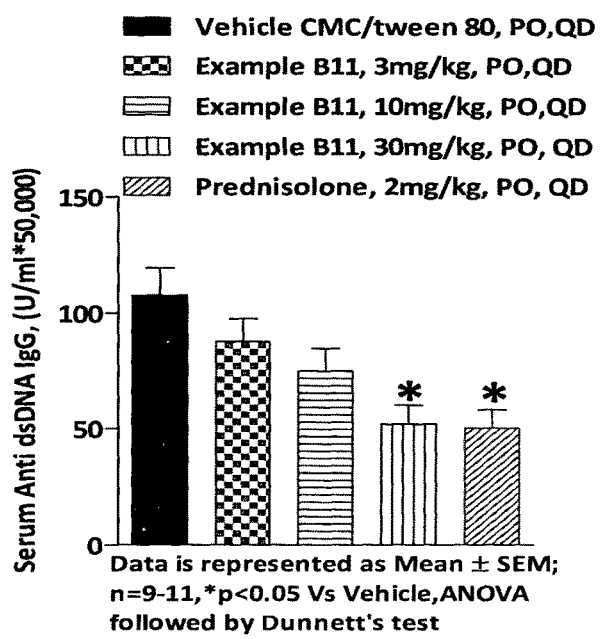
| Treatment | Veh. | Ex.B11 | Ex.B11 | Ex.B11 | Pred |
|---|---|---|---|---|---|
| Dose [QD; (mg/kg) | - | 3 | 10 | 30 | 2 |
| Duration (weeks) | 6 | 6 | 6 | 6 | 6 |
| Age (Weeks) | 16 | 16 | 16 | 16 | 16 |
| % Reduction | - | 19 | 30 | 52 | 53 |

PYRROLO[3,2-C]PYRIDINE DERIVATIVES AS TLR INHIBITORS

TECHNICAL FIELD

The present invention relates to a heterocyclic compound having a Toll-like receptors (TLR)7, TLR9, TLR7/8, TLR7/9 or TLR7/8/9 inhibitory action, which is useful as an agent for the prophylaxis or treatment of TLR7, TLR9, TLR7/8, TLR7/9 or TLR7/8/9 related diseases such as autoimmune diseases, inflammatory diseases and the like, in particular, systemic lupus erythematosus, Sjogren's syndrome, rheumatoid arthritis, psoriasis, inflammatory bowel disease and the like.

BACKGROUND OF THE INVENTION

Toll-Like Receptors (TLRs) are conserved membrane pattern recognition receptors (PRRs) of innate immunity responsible for clearing microbial pathogens. TLRs are expressed in many immune and non-immune cells and detect pattern recognition motifs that recognize microbial products, namely, the pathogen associated molecular patterns (PAMPs, ex: nucleic acids, lipoprotein and polysaccharides) (Kawai et. al., 2011, *Immunity*, 34(5):637-50). In addition to PAMPs, several TLRs also recognize endogenous ligands resulting from cellular insult due to inflammatory response and cell-death, called damage associated molecular patterns (DAMPs) (Abdelsadik et. al, 2011, *Human Immunology*, 72, 1188-1193). Till date, ten functional TLRs (TLR1-10) have been identified in human, of which TLR1, TLR2, TLR4, TLR5 and TLR6, that recognize lipoproteins and lipopolysaccharides are expressed on the plasma membrane and TLR3, TLR7, TLR8 and TLR9 that recognize nucleic acids are expressed in endosomal compartments. While TLR7 and TLR8 both recognize ssRNA, TLR9 recognizes CpG-rich hypomethylated DNA (Table 1).

TABLE 1

Summary of Function and Expression of TLR7 and 9

| TLR | Cellular Expression | PAMPs (Microbial) | DAMPs (Host) |
| --- | --- | --- | --- |
| TLR7 | B-cells, pDCs | ssRNA | ssRNA, Antiphospholipid antibodies, cardiac myosin |
| TLR9 | B-cells, pDCs, GI epithelial, Keratinocytes | CpG DNA | DNA, DNA containing immune complexes, IgG-chromatin complexes |

Engagement of a cognate ligand to TLRs induces conformational changes allowing formation of homo- or heteromeric interactions within TLRs and recruitment of adaptor proteins such as MyD88, TIRAP, TRIF, and TRAM. TLR7 and TLR9 are localized mainly to ER in the steady state but traffic to the endo/lysosomal compartment with the help of UNC93b1 during activation (Kawai T and Akira S, 2007, *Sem Immunol*, 19, 24). TLR7 and TLR9 activate NF-κB and IRF7 via MyD88 to induce pro-inflammatory cytokines (TNFα, IL-1β, IL-6) and type I interferons (IFNα and IFNβ) respectively. The activation of NF-κB during TLR7 and TLR9 signaling is initiated from the endosomes whereas IRF7 activation is initiated from the lysosome-related organelle (LRO) after TLR7 and TLR9 are transported from the endosome to this vesicle. MyD88-dependent IRF7 activation in pDCs is mediated by activation of IRAK1, TRAF6, TRAF3 and IKKα. In conventional DCs and macrophages, TLR7 and TLR9 induce inflammatory responses by activating NF-κB via MyD88 but fail to activate IRF7 [Kawai et. al., 2011, *Immunity*, 34(5):637-50].

TLR7/9 activation plays a major role in the inter-phase of innate and adaptive immunity. They not only activate inflammatory cytokines, up-regulate MHC molecules and co-stimulatory signals in antigen-presentation (innate immune response) but also prime and amplify T-, and B-cell effectors function (adaptive immune response) [Hannessy et. al., 2010, *Nat Rev Drug Discov.*, 9(4):293-307; Koegh et. al., 2011, *Trends Pharmacol Sci*, 32(7):435-42].

There is increasing evidence of role of TLR-7 and 9 in the pathogenesis of various autoimmune diseases including rheumatoid arthritis (RA). Human synovial tissue from RA patients showed the expression of TLR7 and 9 (along with TLR-2/3/4). The expression of TLR7 was significantly up-regulated in RA synovial fibroblasts (RASFs) compared with healthy controls or patients with non-inflammatory arthritis. Stimulation of cultured RASFs with TLR7 ligands resulted in significant up-regulation of chemokines, cytokines, metalloproteinases and type I IFNs. [Roelofs et. al., 2005, *Arthritis Rheum.* 52(8):2313-22].

Recent studies have shown that the development and progression of Systemic Lupus Erythematosus (SLE) are driven by the over-expression of TLR-7, 8 and 9 within B-cells and pDCs [Komatsuda et. al., 2008, *Clin Exp Immunol.*; 152 (3):482-7; Migita et. al., 2007, *J Rheumatol.*, 34 (3): 493-500]. A knockout of TLR7 in a spontaneous murine model of SLE (MRL−/Mplpr/lpr), showed decreased anti-RNA antibodies, diminished spelinic immune activation and suppressed the development of nephritis [Nickerson et. al., 2010, *J Immunol.*, 15, 184 (4):1840-8; Christensen et. al., 2006, *Immunity*, 25 (3): 417-28], validating the target in the pathogenesis of this disease.

Antagonists of these nucleic acid-recognizing TLRs have primarily been oligonucleotide-based molecules. IMO-3100, an oligonucleotide based antagonist of TLR7 and TLR9 has demonstrated clinical activity in psoriasis patients. This antagonist has also shown encouraging results in mouse models of lupus, collagen induced arthritis and psoriasis. IMO-8400, a TLR-7/8/9 antagonist has been shown to suppress the production of autoimmune antibodies, improve kidney histopathology and decrease blood urea nitrogen and proteinuria in lupus prone mice.

The small molecule anti-malarial drugs like chloroquine, hydroxychloroquine and quinacrine, that are also known to show TLR-7/8/9 antagonism, have been used since the 1950s to treat immune-mediated inflammatory disorders (IMID) such as rheumatoid arthritis (RA) and systemic lupus erythematosus (SLE). However, side effects associated with these drugs and also the suboptimal efficacy has limited the use of these anti-malarials in IMID.

There is literature prior art disclosing small molecule TLR-7/8/9, TLR-7/9 and TLR9 antagonists. Coley Pharmaceuticals has disclosed series of 4-aminoquinoline derivatives as inhibitors of immune stimulation involving at least one of TLR9, TLR8, TLR7 and TLR3 (U.S. Pat. No. 7,410,975). Eisai R & D has disclosed benzoxazole compounds as antimalarials, claiming the compounds being antagonists of TLR9 (WO 2010/036908). In a patent application (WO 2011/115183), Dainippon Pharma has disclosed monocyclic pyrimidine derivatives that are effective in the prophylaxis and/or treatment of disorders associated with signal transmission mediated by Toll-like receptors (TLR).

The biological data disclosed in the application substantiate the claimed compounds as TLR9 antagonists. In a very recent patent application by Janus Biotherapeutics (WO 2013/052550), imidazoloquinoline-based compounds have been described as immune system modulators. Two more patent applications from Janus Biotherapeutics (WO 2012/167046 and WO 2012/167053) have described pyrazinopyrimidines and imidazolopyrimidines as immune system modulators. In all the three patent applications, biological data reveal that the claimed compounds demonstrate TLR9 antagonism.

Despite several discoveries in this area, there are no safe and efficacious orally administered small molecule TLR-7/8/9 antagonists available in the market. CPG-52364 from Coley Pharma and Pfizer has been discontinued from clinical trials in 2008 for unknown reason. Therefore, there is a strong need for a novel small molecule TLR-7/8/9 antagonist that will be orally available and will have potential clinical utility. These compounds will have medical application in the disease area of inflammation, autoimmune disorder and cell proliferation, rheumatoid arthritis, psoriasis, psoriatic arthritis, systemic lupus erythematosus, Sjögren's Syndrome, multiple sclerosis, inflammatory bowel disease, allergic diseases, infectious diseases affecting immune system, asthma, type 1 diabetes, myasthenia gravis, hematopoetic disfunction, B-cell malignancies, transplant rejection and graft-versus-host disease.

Patent Document 1 discloses a compound represented by the formula:

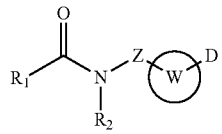

wherein each symbol is as defined in the specification, as a Bruton's tyrosine kinase inhibitor.

DOCUMENT LIST

Patent Document

Patent Document 1: WO 2010/068806

SUMMARY OF THE INVENTION

Problems to be Solved by the Invention

The present invention aims to provide a compound having a TLR7, TLR9, TLR7/8, TLR7/9 or TLR7/8/9 inhibitory action, which is useful as an agent for the prophylaxis or treatment of autoimmune diseases, inflammatory diseases and the like, in particular, systemic lupus erythematosus, Sjogren's syndrome, rheumatoid arthritis, psoriasis, inflammatory bowel disease and the like.

Means of Solving the Problems

The present inventors have conducted intensive studies, and have found that a compound represented by the formula (I) shown below unexpectedly has a TLR7, TLR9, TLR7/8, TLR7/9 or TLR7/8/9 inhibitory action, and therefore, is useful as an agent for the prophylaxis or treatment of autoimmune diseases, inflammatory diseases and the like, in particular, systemic lupus erythematosus, Sjogren's syndrome, rheumatoid arthritis, psoriasis, inflammatory bowel disease and the like, and completed the present invention based on these findings.

Accordingly, the present invention provides the following:

[1] A compound represented by the formula (I):

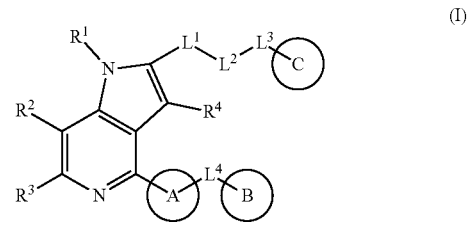

wherein
$R^1$ is a hydrogen atom, an optionally substituted hydrocarbon group, an optionally substituted heterocyclic group, an optionally substituted hydroxy group, an optionally substituted amino group, an optionally substituted sulfanyl group, or an acyl group,
$R^2$, $R^3$ and $R^4$ are independently a hydrogen atom or a substituent,
Ring A is an optionally substituted ring,
Ring B is an optionally substituted heterocycle,
Ring C is an optionally substituted 3- to 10-membered nitrogen-containing heterocycle,
$L^1$ is a bond or a divalent hydrocarbon group,
$L^2$ is a bond, —O—, —C(O)—, —NH—C(O)—, —C(O)—NH—, —S—, —SO—, —SO_2—, —SO_2—O—, —O—SO_2— or —CH(CN)—,
$L^3$ is a bond or a divalent hydrocarbon group, with the proviso that at least one of $L^1$, $L^2$ and $L^3$ is not a bond, and
$L^4$ is a bond or a spacer having 1 to 6 atoms, or a salt thereof (hereinafter to be referred as compound (I)).

[2] The compound or salt of the above-mentioned [1], wherein
$R^1$ is a hydrogen atom, a $C_{1-10}$ alkyl group or a $C_{3-10}$ cycloalkyl group,
$R^2$ is a hydrogen atom or a $C_{1-10}$ alkyl group,
$R^3$ is a hydrogen atom, an optionally substituted hydrocarbon group or an optionally substituted hydroxy group,
$R^4$ is a hydrogen atom, a halogen atom or an optionally substituted hydrocarbon group,
Ring A is an optionally substituted $C_{3-10}$ cycloalkane, an optionally substituted $C_{3-10}$ cycloalkene, an optionally substituted $C_{6-14}$ aromatic hydrocarbon or an optionally substituted aromatic heterocycle optionally fused with benzene,
Ring B is an optionally substituted 3- to 10-membered non-aromatic heterocycle,
Ring C is an optionally substituted 5- or 6-membered nitrogen-containing aromatic heterocycle or an optionally substituted 3- to 10-membered nitrogen-containing non-aromatic heterocycle,
$L^1$ and $L^3$ are independently
(1) a bond,
(2) a $C_{1-10}$ alkylene group, or
(3) a $C_{3-8}$ cycloalkylene group,
$L^2$ is a bond or —C(O)—, and
$L^4$ is a bond, a straight chain $C_{1-6}$ alkylene group, —$X^1$—O—$X^2$—, —$X^1$—C(O)—$X^2$— or —$X^1$—NH—C(O)—

X²—, wherein X¹ and X² are independently a bond or a straight chain $C_{1-5}$ alkylene group, and the total atom number is 6 or less.

[3] 4-[2-[4-[4-(4-Isopropylpiperazin-1-yl)phenyl]-6,7-dimethyl-1H-pyrrolo[3,2-c]pyridin-2-yl]ethyl]morpholine or a salt thereof.

[4] 4-[2-[4-[4-(4-Isopropylpiperazin-1-yl)phenyl]-1,6-dimethyl-pyrrolo[3,2-c]pyridin-2-yl]ethyl]morpholine or a salt thereof.

[5] 4-[[4-[4-(4-Isopropylpiperazin-1-yl)phenyl]-1H-pyrrolo[3,2-c]pyridin-2-yl]methyl]morpholine or a salt thereof.

[6] 4-[4-(4-Isopropylpiperazin-1-yl)phenyl]-2-(1-piperidylmethyl)-1H-pyrrolo[3,2-c]pyridine or a salt thereof.

[7] A medicament comprising the compound or salt of the above-mentioned [1].

[8] The medicament of the above-mentioned [7], which is a TLR7, TLR9, TLR7/8, TLR7/9 or TLR7/8/9 inhibitor.

[9] The medicament of the above-mentioned [7], which is an agent for the prophylaxis or treatment of autoimmune diseases and/or inflammatory diseases.

[10] The medicament of the above-mentioned [9], wherein the autoimmune diseases and/or inflammatory diseases is selected from systemic lupus erythematosus, Sjogren's syndrome, rheumatoid arthritis, psoriasis and inflammatory bowel disease.

[11] The compound or salt of the above-mentioned [1] for use in the prophylaxis or treatment of autoimmune diseases and/or inflammatory diseases.

[12] The compound or salt of the above-mentioned [11], wherein the autoimmune diseases and/or inflammatory diseases is selected from systemic lupus erythematosus, Sjogren's syndrome, rheumatoid arthritis, psoriasis and inflammatory bowel disease.

[13] A method of inhibiting TLR7, TLR9, TLR7/8, TLR7/9 or TLR7/8/9 in a mammal, which comprises administering an effective amount of the compound or salt of the above-mentioned [1] to the mammal.

[14] A method for the prophylaxis or treatment of autoimmune diseases and/or inflammatory diseases in a mammal, which comprises administering an effective amount of the compound or salt of the above-mentioned [1] to the mammal.

[15] The method of the above-mentioned [14], wherein the autoimmune diseases and/or inflammatory diseases is selected from systemic lupus erythematosus, Sjogren's syndrome, rheumatoid arthritis, psoriasis and inflammatory bowel disease.

[16] Use of the compound or salt of the above-mentioned [1] for the production of an agent for the prophylaxis or treatment of autoimmune diseases and/or inflammatory diseases.

[17] Use of the above-mentioned [16], wherein the autoimmune diseases and/or inflammatory diseases is selected from systemic lupus erythematosus, Sjogren's syndrome, rheumatoid arthritis, psoriasis and inflammatory bowel disease.

Effect of the Invention

According to the present invention, the compound having a TLR7, TLR9, TLR7/8, TLR7/9 or TLR7/8/9 inhibitory action, which is useful as an agent for the prophylaxis or treatment of autoimmune diseases, inflammatory diseases and the like, in particular, systemic lupus erythematosus, Sjogren's syndrome, rheumatoid arthritis, psoriasis, inflammatory bowel disease and the like, can be provided.

BRIEF DESCRIPTION OF THE DRAWINGS

FIG. 1A shows reduction in anti-dsDNA IgG with Example B6 after 6 weeks of treatment.

FIG. 1B shows reduction in anti-dsDNA IgG with Example B6 after 9 weeks of treatment.

FIG. 2A shows reduction in anti-dsDNA IgG with Example B11 after 6 weeks of treatment.

DETAILED DESCRIPTION OF THE INVENTION

The definition of each symbol in the formula (I) is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

$R^1$ is a hydrogen atom, an optionally substituted hydrocarbon group, an optionally substituted heterocyclic group, an optionally substituted hydroxy group, an optionally substituted amino group, an optionally substituted sulfanyl group, or an acyl group.

$R^2$, $R^3$ and $R^4$ are independently a hydrogen atom or a substituent.

Examples of the "substituent" for $R^2$, $R^3$ or $R^4$ include a "halogen atom", a "cyano group", a "nitro group", an "optionally substituted hydrocarbon group", an "optionally substituted heterocyclic group", an "optionally substituted hydroxy group", an "optionally substituted amino group", an "optionally substituted sulfanyl group", an "acyl group" and the like.

Examples of the "hydrocarbon group" of the above-mentioned "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Of these, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Of these, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Of these, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group. Examples of the fused ring group include indanyl, dihydronaphthyl, tetrahydronaphthyl, fluorenyl and the like.

In addition, the above-mentioned $C_{3-10}$ cycloalkyl group, $C_{3-10}$ cycloalkenyl group and $C_{4-10}$ cycloalkadienyl group may be each a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each optionally forms a spiro ring group together with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthyl, biphenylyl and the like. Of these, a $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a non-aromatic heterocyclic group (e.g., tetrahydrofuryl, morpholinyl, thiomorpholinyl, piperidinyl, pyrrolidinyl, piperazinyl, oxetanyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms, and
    (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a heterocyclic group (e.g., tetrahydrofuryl), and
    (g) a $C_{3-10}$ cycloalkyl group;

(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 $C_{1-6}$ alkyl groups optionally substituted by 1 to 3 halogen atoms;
(21) a sulfanyl group;
(22) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
  (a) a halogen atom (e.g., a fluorine atom), and
  (b) a $C_{1-6}$ alkoxy group (e.g., methoxy)
and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the above-mentioned "hydrocarbon group", optionally have 1 to 3 substituents at substitutable positions.

Examples of the substituent include
(1) the groups exemplified as the substituents for the above-mentioned $C_{1-10}$ alkyl group and the like;
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(3) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(4) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
and the like. When the number of the substituents is not less than 2, the respective substituents may be the same or different.

Examples of the "heterocyclic group" of the above-mentioned "optionally substituted heterocyclic group" include an "aromatic heterocyclic group" and a "non-aromatic heterocyclic group".

Examples of the aromatic heterocyclic group include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;
fused aromatic heterocyclic groups such as
quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo

[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like;
and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include
monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), 1-oxidothiomorpholine, 1,1-dioxidothiomorpholine, piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like; fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;
and the like.

The above-mentioned non-aromatic heterocyclic group may be bridged. Examples of the bridged non-aromatic heterocyclic group include 3-azabicyclo[2.2.1]heptane, 3-azabicyclo[3.3.1]nonane, 6-azabicyclo[3.1.1]heptane and the like.

Moreover, the above-mentioned non-aromatic heterocyclic group optionally forms a spiro ring group together with a $C_{3-10}$ cycloalkane, a $C_{3-10}$ cycloalkene, a $C_{4-10}$ cycloalkadiene or a non-aromatic heterocycle. Examples of the $C_{3-10}$ cycloalkane, $C_{3-10}$ cycloalkene, $C_{4-10}$ cycloalkadiene and non-aromatic heterocycle include rings corresponding to the above-mentioned $C_{3-10}$ cycloalkyl group, $C_{3-10}$ cycloalkenyl group, $C_{4-10}$ cycloalkadienyl group and non-aromatic heterocyclic group. Examples of the spiro ring group include 6-azaspiro[3.3]heptane, 7-azaspiro[3.5]nonane and the like.

The "heterocyclic group" of the "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the above-mentioned "optionally substituted hydrocarbon group" optionally has. When the heterocyclic group is a "non-aromatic heterocyclic group", the substituent further includes an oxo group. When the number of the substituents is not less than 2, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the above-mentioned "optionally substituted sulfanyl group" include a sulfanyl group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group". Of these, a 5- to 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the "substituent" for $R^2$.

Examples of the "acyl group" exemplified as the "substituent" for $R^2$ include a group represented by the formula: $-COR^A$, $-CO-OR^A$, $-SO_3R^A$, $-S(O)_2R^A$, $-SOR^A$, $-CO-NR^{A\prime}R^{B\prime}$, $-CS-NR^{A\prime}R^{B\prime}$ or $-S(O)_2NR^{A\prime}R^{B\prime}$ wherein $R^A$ is a hydrogen atom, an optionally substituted hydrocarbon group or an optionally substituted heterocyclic group, and $R^{A\prime}$ and $R^{B\prime}$ are the same or different and each is a hydrogen atom, an optionally substituted hydrocarbon group or an optionally substituted heterocyclic group, or $R^{A\prime}$ and $R^{B\prime}$ form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A\prime}$ or $R^{B\prime}$ include those similar to the "optionally substituted hydrocarbon group" and "optionally substituted heterocyclic group", which are exemplified as the "substituent" for $R^2$.

Examples of the "nitrogen-containing heterocycle" of the "optionally substituted nitrogen-containing heterocycle" formed by $R^{A\prime}$ and $R^{B\prime}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable positions. Examples of the substituent include those similar to the substituent that the "heterocyclic group" of the "optionally substituted heterocyclic group", which is exemplified as the "substituent" for $R^2$, optionally has. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinylcarbonyl) optionally substituted by 1 to 3 substituents selected from a $C_{1-6}$ alkyl group optionally substituted by 1 to 3 halogen atoms; and the like.

$R^1$ is preferably a hydrogen atom, an optionally substituted $C_{1-10}$ alkyl group (preferably an optionally substituted $C_{1-6}$ alkyl group (e.g. methyl)) or an optionally substituted $C_{3-10}$ cycloalkyl group (preferably an optionally substituted $C_{3-6}$ cycloalkyl group (e.g., cyclopropyl)).

$R^1$ is more preferably a hydrogen atom, a $C_{1-10}$ alkyl group (preferably a $C_{1-6}$ alkyl group (e.g. methyl)) or a $C_{3-10}$ cycloalkyl group (preferably a $C_{3-6}$ cycloalkyl group (e.g., cyclopropyl)).

$R^1$ is still more preferably a hydrogen atom or a $C_{1-10}$ alkyl group (preferably a $C_{1-6}$ alkyl group (e.g. methyl)).

In another embodiment, R is still more preferably a hydrogen atom.

$R^2$ is preferably a hydrogen atom, a halogen atom or an optionally substituted $C_{1-10}$ alkyl group (preferably an optionally substituted $C_{1-6}$ alkyl group (e.g. methyl)).

$R^2$ is more preferably a hydrogen atom or an optionally substituted $C_{1-10}$ alkyl group (preferably an optionally substituted $C_{1-6}$ alkyl group (e.g. methyl)).

$R^2$ is further more preferably a hydrogen atom or a $C_{1-10}$ alkyl group (preferably a $C_{1-6}$ alkyl group (e.g. methyl)).

$R^2$ is still more preferably a hydrogen atom.

$R^3$ is preferably a hydrogen atom, a halogen atom, an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl)) or an optionally substituted $C_{1-10}$ alkoxy group (preferably an optionally substituted $C_{1-6}$ alkoxy group (e.g. ethoxy)).

In another embodiment, $R^3$ is preferably a hydrogen atom, an optionally substituted hydrocarbon group [preferably an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl))], or an optionally substituted hydroxy group [preferably an optionally substituted $C_{1-10}$ alkoxy group (preferably an optionally substituted $C_{1-6}$ alkoxy group (e.g. ethoxy))].

$R^3$ is more preferably a hydrogen atom, an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl)) or an optionally substituted $C_{1-10}$ alkoxy group (preferably an optionally substituted $C_{1-6}$ alkoxy group (e.g. ethoxy)).

$R^3$ is further more preferably
(1) a hydrogen atom,
(2) a $C_{1-10}$ alkyl group (preferably a $C_{1-6}$ alkyl group (e.g. methyl)) optionally substituted by 1 to 3 halogen atoms (e.g., a fluorine atom),
(3) a $C_{3-10}$ cycloalkyl group (preferably a $C_{3-6}$ cycloalkyl group (e.g., cyclopropyl, cyclobutyl)), or
(4) a $C_{1-10}$ alkoxy group (preferably a $C_{1-6}$ alkoxy group (e.g. ethoxy)) optionally substituted by 1 to 3 halogen atoms (e.g., a fluorine atom).

$R^3$ is still more preferably
(1) a hydrogen atom,
(2) a $C_{1-10}$ alkyl group (preferably a $C_{1-6}$ alkyl group (e.g. methyl)) optionally substituted by 1 to 3 halogen atoms (e.g., a fluorine atom), or
(3) a $C_{3-10}$ cycloalkyl group (preferably a $C_{3-6}$ cycloalkyl group (e.g., cyclopropyl)).

In another embodiment, $R^3$ is still more preferably a hydrogen atom or a $C_{1-10}$ alkyl group (preferably a $C_{1-6}$ alkyl group (e.g. methyl)).

$R^4$ is preferably a hydrogen atom, a halogen atom (e.g., a chlorine atom), or an optionally substituted hydrocarbon group [preferably an optionally substituted $C_{1-10}$ alkyl group (preferably an optionally substituted $C_{1-6}$ alkyl group (e.g. methyl)), or an optionally substituted $C_{3-10}$ cycloalkyl group (preferably an optionally substituted $C_{3-6}$ cycloalkyl group (e.g., cyclopropyl))].

$R^4$ is more preferably a hydrogen atom, a halogen atom (e.g., a chlorine atom), an optionally substituted $C_{1-10}$ alkyl group (preferably an optionally substituted $C_{1-6}$ alkyl group (e.g. methyl)), or an optionally substituted $C_{3-10}$ cycloalkyl group (preferably an optionally substituted $C_{3-6}$ cycloalkyl group (e.g., cyclopropyl)).

$R^4$ is further more preferably a hydrogen atom, a halogen atom (e.g., a chlorine atom), a $C_{1-6}$ alkyl group (e.g. methyl) optionally substituted by 1 to 3 halogen atoms (e.g., a fluorine atom), or a $C_{3-6}$ cycloalkyl group (e.g., cyclopropyl).

$R^4$ is still more preferably a hydrogen atom or a halogen atom (e.g., a chlorine atom).

In another embodiment, $R^4$ is still more preferably a hydrogen atom.

Ring A is an optionally substituted ring.

Examples of the "ring" of the "optionally substituted ring" for Ring A include a $C_{6-14}$ aromatic hydrocarbon, a $C_{3-10}$ cycloalkane, a $C_{3-10}$ cycloalkene, a $C_{4-10}$ cycloalkadiene, an aromatic heterocycle and a non-aromatic heterocycle.

Examples of the $C_{6-14}$ aromatic hydrocarbon, $C_{3-10}$ cycloalkane, $C_{3-10}$ cycloalkene and $C_{4-10}$ cycloalkadiene include rings corresponding to the above-mentioned $C_{6-14}$ aryl group, $C_{3-10}$ cycloalkyl group, $C_{3-10}$ cycloalkenyl group and $C_{4-10}$ cycloalkadienyl group exemplified as the "hydrocarbon group" of the "optionally substituted hydrocarbon group", which is exemplified as the "substituent" for $R^2$, $R^3$ or $R^4$.

Examples of the aromatic heterocycle and non-aromatic heterocycle include rings corresponding to the above-mentioned aromatic heterocyclic group and non-aromatic heterocyclic group exemplified as the "heterocyclic group" of the "optionally substituted heterocyclic group", which is exemplified as the "substituent" for $R^2$, $R^3$ or $R^4$.

The "ring" of the "optionally substituted ring" for Ring A optionally has 1 to 3 substituents at substitutable positions. Examples of the substituent include those similar to the substituents that the "heterocyclic group" of the "optionally substituted heterocyclic group", which is exemplified as the "substituent" for $R^2$, $R^3$ or $R^4$, optionally has. When the number of the substituents is not less than 2, respective substituents may be the same or different.

Ring A is preferably an optionally substituted $C_{6-14}$ aromatic hydrocarbon (preferably an optionally substituted $C_{6-12}$ aromatic hydrocarbon (e.g., benzene)) or an optionally substituted aromatic heterocycle optionally fused with benzene (preferably an optionally substituted 5- or 6-membered aromatic heterocycle optionally fused with benzene (e.g., pyridine, pyrazole, indole, thiazole)).

Ring A is more preferably
(1) a $C_{6-14}$ aromatic hydrocarbon (preferably a $C_{6-12}$ aromatic hydrocarbon (e.g., benzene)) optionally substituted by 1 to 3 substituents selected from a halogen atom (e.g., a fluorine atom) and a cyano group, or
(2) an aromatic heterocycle (preferably a 5- or 6-membered aromatic heterocycle optionally fused with benzene (e.g., pyridine, pyrazole, indole, thiazole)).

Ring A is still more preferably a $C_{6-14}$ aromatic hydrocarbon (preferably a $C_{6-12}$ aromatic hydrocarbon (e.g., benzene)).

In another embodiment, Ring A is preferably an optionally substituted $C_{3-10}$ cycloalkane (preferably an optionally substituted $C_{3-6}$ cycloalkane (e.g., cyclohexane)), an optionally substituted $C_{3-10}$ cycloalkene (preferably an optionally substituted $C_{3-6}$ cycloalkene (e.g., cyclohexene)), an optionally substituted $C_{6-14}$ aromatic hydrocarbon (preferably an optionally substituted $C_{6-12}$ aromatic hydrocarbon (e.g., benzene)) or an optionally substituted aromatic heterocycle optionally fused with benzene (preferably an optionally substituted 5- or 6-membered aromatic heterocycle optionally fused with benzene (e.g., pyridine, pyrazole, indole, thiazole)).

In this embodiment, Ring A is more preferably
(1) a $C_{3-10}$ cycloalkane (preferably a $C_{3-6}$ cycloalkane (e.g., cyclohexane)),
(2) a $C_{3-10}$ cycloalkene (preferably a $C_{3-6}$ cycloalkene (e.g., cyclohexene)),
(3) a $C_{6-14}$ aromatic hydrocarbon (preferably a $C_{6-12}$ aromatic hydrocarbon (e.g., benzene)) optionally substituted by 1 to 3 substituents selected from
  (i) a halogen atom (e.g., a fluorine atom),
  (ii) a $C_{1-6}$ alkyl group (e.g. methyl) optionally substituted by 1 to 3 halogen atoms (e.g., a fluorine atom),
  (iii) a $C_{1-6}$ alkoxy group (e.g. methoxy), and
  (iv) a cyano group, or
(4) an aromatic heterocycle optionally fused with benzene (preferably a 5- or 6-membered aromatic heterocycle optionally fused with benzene (e.g., pyridine, pyrazole, indole, thiazole)).

In this embodiment, Ring A is still more preferably
(1) a $C_{3-10}$ cycloalkane (preferably a $C_{3-6}$ cycloalkane (e.g., cyclohexane)),
(2) a $C_{3-10}$ cycloalkene (preferably a $C_{3-6}$ cycloalkene (e.g., cyclohexene)),
(3) a $C_{6-14}$ aromatic hydrocarbon (preferably a $C_{6-12}$ aromatic hydrocarbon (e.g., benzene)) optionally substituted by 1 to 3 substituents selected from
  (i) a halogen atom (e.g., a fluorine atom),
  (ii) a $C_{1-6}$ alkyl group (e.g. methyl) optionally substituted by 1 to 3 halogen atoms (e.g., a fluorine atom), and
  (iii) a $C_{1-6}$ alkoxy group (e.g. methoxy), or
(4) an aromatic heterocycle optionally fused with benzene (preferably a 5- or 6-membered aromatic heterocycle optionally fused with benzene (e.g., pyridine, pyrazole, thiazole)).

Ring B is an optionally substituted heterocycle.

Examples of the "heterocycle" of the "optionally substituted heterocycle" for Ring B include an aromatic heterocycle and a non-aromatic heterocycle.

Examples of the aromatic heterocycle and non-aromatic heterocycle include rings corresponding to the above-mentioned aromatic heterocyclic group and non-aromatic heterocyclic group exemplified as the "heterocyclic group" of the "optionally substituted heterocyclic group", which is exemplified as the "substituent" for $R^2$, $R^3$ or $R^4$.

The "heterocycle" of the "optionally substituted heterocycle" for Ring B optionally has 1 to 3 substituents at substitutable positions. Examples of the substituent include those similar to the substituents that the "heterocyclic group" of the "optionally substituted heterocyclic group", which is exemplified as the "substituent" for $R^2$, $R^3$ or $R^4$, optionally has. When the number of the substituents is not less than 2, respective substituents may be the same or different.

Ring B is preferably an optionally substituted 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane).

Ring B is more preferably a 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane) optionally substituted by 1 to 3 substituents selected from
(1) a halogen atom (e.g., a fluorine atom),
(2) a hydroxy group,
(3) a carboxy group,
(4) a $C_{1-6}$ alkyl group (e.g. methyl, ethyl, isopropyl) optionally substituted by 1 to 3 hydroxy groups,
(5) a $C_{3-10}$ cycloalkyl group (e.g., cyclopropyl),
(6) a $C_{1-6}$ alkoxy-carbonyl group (e.g. methoxycarbonyl, tert-butoxycarbonyl), and
(7) a non-aromatic heterocyclic group (preferably a 3- to 10-membered non-aromatic heterocyclic group (e.g., oxetanyl)).

Ring B is still more preferably a 5- or 6-membered non-aromatic heterocycle (e.g. piperidine, piperazine) optionally substituted by 1 to 3 substituents selected from
(1) a hydroxy group,
(2) a carboxy group,
(3) a $C_{1-6}$ alkyl group (e.g. methyl, ethyl, isopropyl), and
(4) a $C_{1-6}$ alkoxy-carbonyl group (e.g. methoxycarbonyl, tert-butoxycarbonyl).

In another embodiment, Ring B is more preferably a 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane) optionally substituted by 1 to 3 substituents selected from
(1) a halogen atom (e.g., a fluorine atom),
(2) a hydroxy group,
(3) a carboxy group,
(4) a $C_{1-6}$ alkyl group (e.g. methyl, ethyl, isopropyl) optionally substituted by 1 to 3 substituents selected from
  (i) a hydroxy group,
  (ii) a halogen atom (e.g., a fluorine atom), and
  (iii) an aromatic heterocyclic group (preferably a 5- or 6-membered aromatic heterocyclic group (e.g., oxazolyl)),
(5) a $C_{3-10}$ cycloalkyl group (e.g., cyclopropyl),
(6) a $C_{1-6}$ alkoxy-carbonyl group (e.g. methoxycarbonyl, ethoxycarbonyl, tert-butoxycarbonyl), and
(7) a non-aromatic heterocyclic group (preferably a 3- to 10-membered non-aromatic heterocyclic group (e.g., oxetanyl)).

In this embodiment, Ring B is still more preferably a 3- to 10-membered non-aromatic heterocycle (e.g. piperidine, piperazine, tetrahydropyridine, morpholine) optionally substituted by 1 to 3 substituents selected from
(1) a hydroxy group,
(2) a carboxy group,
(3) a $C_{1-6}$ alkyl group (e.g. methyl, ethyl, isopropyl) optionally substituted by 1 to 3 substituents selected from
  (i) a halogen atom (e.g., a fluorine atom), and
  (ii) an aromatic heterocyclic group (preferably a 5- or 6-membered aromatic heterocyclic group (e.g., oxazolyl)),
(4) a $C_{1-6}$ alkoxy-carbonyl group (e.g. methoxycarbonyl, ethoxycarbonyl, tert-butoxycarbonyl), and
(5) a non-aromatic heterocyclic group (preferably a 3- to 10-membered non-aromatic heterocyclic group (e.g., oxetanyl)).

Ring C is an optionally substituted 3- to 10-membered nitrogen-containing heterocycle.

Examples of the "3- to 10-membered nitrogen-containing heterocycle" of the "optionally substituted 3- to 10-membered nitrogen-containing heterocycle" for Ring C include a 3- to 10-membered nitrogen-containing heterocycle, from among rings corresponding to the above-mentioned aromatic heterocyclic group and non-aromatic heterocyclic group exemplified as the "heterocyclic group" of the "optionally substituted heterocyclic group", which is exemplified as the "substituent" for $R^2$, $R^3$ or $R^4$.

Specific examples thereof include azetidine, pyrrolidine, imidazolidine, pyrazolidine, piperidine, piperazine, morpholine, thiomorpholine, 1-oxidothiomorpholine, 1,1-dioxidothiomorpholine, 3-azabicyclo[2.2.1]heptane, 3-azabicyclo[3.3.1]nonane, 6-azabicyclo[3.1.1]heptane, 6-azaspiro[3.3]heptane, 7-azaspiro[3.5]nonane and the like.

The "3- to 10-membered nitrogen-containing heterocycle" of the "optionally substituted 3- to 10-membered nitrogen-containing heterocycle" for Ring C optionally has 1 to 3 substituents at substitutable positions. Examples of the substituent include those similar to the substituents that the "heterocyclic group" of the "optionally substituted heterocyclic group", which is exemplified as the "substituent" for $R^2$, $R^3$ or $R^4$, optionally has. When the number of the substituents is not less than 2, respective substituents may be the same or different.

Ring C is preferably an optionally substituted 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane).

Ring C is more preferably a 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane) optionally substituted by 1 to 3 substituents selected from
(1) a halogen atom (e.g., a fluorine atom),
(2) a hydroxyl group,
(3) a $C_{1-6}$ alkyl group (e.g. methyl),
(4) a carboxy group, and
(5) a $C_{1-6}$ alkoxy-carbonyl group (e.g. methoxycarbonyl).

Ring C is still more preferably a 5- or 6-membered nitrogen-containing non-aromatic heterocycle (e.g., morpholine).

In another embodiment, Ring C is preferably an optionally substituted 5- or 6-membered nitrogen-containing aromatic heterocycle (e.g., pyrazole) or an optionally substituted 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane).

In this embodiment, Ring C is more preferably
(1) a 5- or 6-membered nitrogen-containing aromatic heterocycle (e.g., pyrazole), or
(2) a 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane) optionally substituted by 1 to 3 substituents selected from
(1) a halogen atom (e.g., a fluorine atom),
(2) a hydroxyl group,
(3) a $C_{1-6}$ alkyl group (e.g. methyl),
(4) a carboxy group, and
(5) a $C_{1-6}$ alkoxy-carbonyl group (e.g. methoxycarbonyl).

In this embodiment, Ring C is still more preferably
(1) a 5- or 6-membered nitrogen-containing aromatic heterocycle (e.g., pyrazole), or
(2) a 3- to 10-membered nitrogen-containing non-aromatic heterocycle (e.g., morpholine, azetidine, pyrrolidine, piperidine, 7-azaspiro[3.5]nonane) optionally substituted by 1 to 3 substituents selected from
(1) a halogen atom (e.g., a fluorine atom),
(2) a hydroxyl group,
(3) a $C_{1-6}$ alkyl group (e.g. methyl),
(4) a carboxy group, and
(5) a $C_{1-6}$ alkoxy-carbonyl group (e.g. methoxycarbonyl).

$L^1$ is a bond or a divalent hydrocarbon group.
$L^3$ is a bond or a divalent hydrocarbon group.

Examples of the "divalent hydrocarbon group" for $L^1$ or $L^3$ include a divalent chain hydrocarbon group, a divalent cyclic hydrocarbon group, a divalent chain-cyclic hydrocarbon group and the like, specifically,
(1) a $C_{1-10}$ alkylene group (preferably a $C_{1-6}$ alkylene group (e.g., —$CH_2$—, —$(CH_2)_2$—, —$(CH_2)_3$—, —$(CH_2)_4$—, —$(CH_2)_5$—, —$(CH_2)_6$—, —$CHCH_3$—, —$C(CH_3)_2$—, —$(CH(CH_3))_2$—, —$(CH_2)_2C(CH_3)_2$—, —$(CH_2)_3C(CH_3)_2$—));
(2) a $C_{2-10}$ alkenylene group (preferably a $C_{2-6}$ alkenylene group (e.g., —CH=CH—, —$CH_2$—CH=CH—, —CH=CH—$CH_2$—, —CH=CH—$CH_2$—$CH_2$—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$—));
(3) a $C_{2-10}$ alkynylene group (preferably a $C_{2-6}$ alkynylene group (e.g., —C≡C—, —$CH_2$—C≡C—, —$CH_2$—C≡C—$CH_2$—$CH_2$—));
(4) a $C_{3-8}$ cycloalkylene group (preferably a $C_{3-6}$ cycloalkylene group (e.g., 1,1-cyclopropylene, 1,2-cyclopropylene, 1,3-cyclobutylene, 1,3-cyclopentylene, 1,3-cyclohexylene, 1,4-cyclohexylene, 1,4-cycloheptylene, 1,5-cyclooctylene));
(5) a $C_{6-14}$ arylene group (preferably a $C_{6-12}$ arylene group (e.g., phenylene (e.g., 1,2-phenylene, 1,3-phenylene, 1,4-phenylene), naphthylene (e.g., 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,6-naphthylene, 2,7-naphthylene), biphenylene (e.g., 2,2'-biphenylene, 3,3'-biphenylene, 4,4'-biphenylene) and the like. The $C_{6-14}$ arylene may be saturated partially, and examples of the partially saturated $C_{6-14}$ arylene include tetrahydronaphthylene and the like));
(6) a combination of any two selected from the above-mentioned (1) to (5) (e.g., methylene-phenylene, phenylene-methylene, ethylene-phenylene, phenylene-ethylene, methylene-cyclohexylene, cyclohexylene-methylene, methylene-naphthylene, naphthylene-methylene);
and the like.

$L^1$ and $L^3$ are preferably independently
(1) a bond,
(2) a $C_{1-10}$ alkylene group (preferably a $C_{1-6}$ alkylene group, more preferably a $C_{1-3}$ alkylene group (e.g., —$CH_2$—, —$(CH_2)_2$—, —$(CH_2)_3$—, —$C(CH_3)_2$—)), or
(3) a $C_{3-8}$ cycloalkylene group (preferably a $C_{3-6}$ cycloalkylene group (e.g., 1,1-cyclopropylene)).

$L^1$ and $L^3$ are more preferably independently
(1) a bond, or
(2) a $C_{1-6}$ alkylene group, (preferably a $C_{1-3}$ alkylene group (e.g., —$CH_2$—, —$(CH_2)_2$—, —$(CH_2)_3$—)).

In another embodiment, $L^1$ and $L^3$ are more preferably independently
(1) a bond, or
(2) a $C_{1-6}$ alkylene group, (preferably a $C_{1-3}$ alkylene group (e.g., —$CH_2$—, —$(CH_2)_2$—))

$L^2$ is a bond, —O—, —C(O)—, —NH—C(O)—, —C(O)—NH—, —S—, —SO—, —SO$_2$—, —SO$_2$—O—, —O—SO$_2$— or —CH(CN)—.

$L^2$ is preferably a bond or —C(O)—.

$L^2$ is more preferably a bond.

$L^1$-$L^2$-$L^3$ is preferably (1) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—, —C(CH$_3$)$_2$—)), (2) a $C_{3-8}$ cycloalkylene group (preferably a $C_{3-6}$ cycloalkylene group (e.g., 1,1-cyclopropylene)), or (3) —C(O)—.

$L^1$-$L^2$-$L^3$ is more preferably (1) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—), or (2) —C(O)—.

In another embodiment, $L^1$-$L^2$-$L^3$ is more preferably a $C_{1-6}$ alkylene group (preferably a $C_{1-3}$ alkylene group (e.g., —CH$_2$—, —(CH$_2$)$_2$—)).

$L^4$ is a bond or a spacer having 1 to 6 atoms.

The "spacer having 1 to 6 atoms" for $L^4$ is a straight chain connecting Ring A and Ring B, and the atom number is counted such that the number of atoms will be minimum. The straight chain consists of 1 to 6 atoms selected from a carbon atom and a hetero atom (e.g., O, S, N etc.), and may be saturated or unsaturated. In addition, S may be oxidized.

Examples of the "spacer having 1 to 6 atoms" include a straight chain $C_{1-6}$ alkylene group, —X$^1$—NH—X$^2$—, —X$^1$—O—X$^2$—, —X$^1$—S—X$^2$— —X$^1$—C(O)—X$^2$—, —X$^1$—NH—C(O)—X$^2$—, —X$^1$—C(O)—NH—X$^2$—, —X$^1$—NH—C(O)—O—X$^2$—, —X$^1$—O—C(O)—NH—X$^2$—, —X$^1$—SO—X$^2$—, —X$^1$—SO$_2$—X$^2$—, —X$^1$—SO$_2$—O—X$^2$— and —X$^1$—O—SO$_2$—X$^2$— [wherein X$^1$ and X$^2$ are independently a bond or a straight chain $C_{1-5}$ alkylene group, and the total atom number is 6 or less] and the like.

Examples of the "straight chain $C_{1-6}$ alkylene group" include —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$—. Of these, a straight chain $C_{1-3}$ alkylene group is preferable.

Examples of the "straight chain $C_{1-5}$ alkylene group" for X$^1$ or X$^2$ include —CH$_2$—, —CH$_2$CH$_2$—, —CH$_2$CH$_2$CH$_2$—, —CH$_2$CH$_2$CH$_2$CH$_2$— and —CH$_2$CH$_2$CH$_2$CH$_2$CH$_2$—. Of these, a straight chain $C_{1-3}$ alkylene group is preferable.

The "spacer having 1 to 6 atoms" optionally has substituent(s) (preferably 1 to 3 substituents) at substitutable position(s) (optionally at the carbon atom and nitrogen atom constituting the main chain). Examples of the substituent include those similar to the substituents that the "heterocyclic group" of the "optionally substituted heterocyclic group", which is exemplified as the "substituent" for R$^2$, R$^3$ or R$^4$, optionally has. When the number of the substituents is not less than 2, respective substituents may be the same or different.

$L^4$ is preferably a bond, a straight chain $C_{1-6}$ alkylene group (preferably a straight chain $C_{1-3}$ alkylene group (e.g., —CH$_2$—, —CH$_2$CH$_2$—)), —X$^1$—O—X$^2$—, —X$^1$—C(O)—X$^2$— or —X$^1$—NH—C(O)—X$^2$— [wherein X$^1$ and X$^2$ are independently a bond or a straight chain $C_{1-5}$ alkylene group, and the total atom number is 6 or less].

$L^4$ is more preferably a bond, a straight chain $C_{1-6}$ alkylene group (preferably a straight chain $C_{1-3}$ alkylene group (e.g., —CH$_2$—, —CH$_2$CH$_2$—)), —O—, —C(O)— or —NH—C(O)—.

$L^4$ is still more preferably a bond, a straight chain $C_{1-6}$ alkylene group (preferably a straight chain $C_{1-3}$ alkylene group (e.g., —CH$_2$—)), —O— or —C(O)—.

In another embodiment, $L^4$ is still more preferably a bond.

Preferable examples of compound (I) include the following compounds.

[Compound A-1]

Compound (I) wherein

R$^1$ is a hydrogen atom, an optionally substituted $C_{1-10}$ alkyl group (preferably an optionally substituted $C_{1-6}$ alkyl group (e.g. methyl)) or an optionally substituted $C_{3-10}$ cycloalkyl group (preferably an optionally substituted $C_{3-6}$ cycloalkyl group (e.g., cyclopropyl));

R$^2$ is a hydrogen atom or an optionally substituted $C_{1-10}$ alkyl group (preferably an optionally substituted $C_{1-6}$ alkyl group (e.g. methyl));

R$^3$ is a hydrogen atom, an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl)) or an optionally substituted $C_{1-10}$ alkoxy group (preferably an optionally substituted $C_{1-6}$ alkoxy group (e.g. ethoxy));

R$^4$ is a hydrogen atom, a halogen atom (e.g., a chlorine atom), an optionally substituted $C_{1-10}$ alkyl group (preferably an optionally substituted $C_{1-6}$ alkyl group (e.g. methyl)), or an optionally substituted $C_{3-10}$ cycloalkyl group (preferably an optionally substituted $C_{3-6}$ cycloalkyl group (e.g., cyclopropyl));

Ring A is an optionally substituted $C_{6-14}$ aromatic hydrocarbon (preferably an optionally substituted $C_{6-12}$ aromatic hydrocarbon (e.g., benzene)) or an optionally substituted aromatic heterocycle optionally fused with benzene (preferably an optionally substituted 5- or 6-membered aromatic heterocycle optionally fused with benzene (e.g., pyridine, pyrazole, indole, thiazole));

Ring B is an optionally substituted 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane);

Ring C is an optionally substituted 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane);

$L^1$ and $L^3$ are independently (1) a bond, (2) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—, —C(CH$_3$)$_2$—)), or (3) a $C_{3-8}$ cycloalkylene group (preferably a $C_{3-6}$ cycloalkylene group (e.g., 1,1-cyclopropylene));

$L^2$ is a bond or —C(O)—;

[preferably, $L^1$-$L^2$-$L^3$ is (1) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—, —C(CH$_3$)$_2$—)), (2) a $C_{3-8}$ cycloalkylene group (preferably a $C_{3-6}$ cycloalkylene group (e.g., 1,1-cyclopropylene)), or (3) —C(O)—]; and $L^4$ is a bond, a straight chain $C_{1-6}$ alkylene group (preferably a straight chain $C_{1-3}$ alkylene group (e.g., —CH$_2$—, —CH$_2$CH$_2$—)), —X$^1$—O—X$^2$—, —X$^1$—C(O)—X$^2$— or —X$^1$—NH—C(O)—X$^2$— [wherein X$^1$ and X$^2$ are independently a bond or a straight chain $C_{1-5}$ alkylene group, and the total atom number is 6 or less].

[Compound B-1]
Compound (I) wherein
$R^1$ is a hydrogen atom, a $C_{1-10}$ alkyl group (preferably a $C_{1-6}$ alkyl group (e.g. methyl)) or a $C_{3-10}$ cycloalkyl group (preferably a $C_{3-6}$ cycloalkyl group (e.g., cyclopropyl));
$R^2$ is a hydrogen atom or a $C_{1-10}$ alkyl group (preferably a $C_{1-6}$ alkyl group (e.g. methyl));
$R^3$ is
(1) a hydrogen atom,
(2) a $C_{1-10}$ alkyl group (preferably a $C_{1-6}$ alkyl group (e.g. methyl)) optionally substituted by 1 to 3 halogen atoms (e.g., a fluorine atom),
(3) a $C_{3-10}$ cycloalkyl group (preferably a $C_{3-6}$ cycloalkyl group (e.g., cyclopropyl, cyclobutyl)), or
(4) a $C_{1-10}$ alkoxy group (preferably a $C_{1-6}$ alkoxy group (e.g. ethoxy)) optionally substituted by 1 to 3 halogen atoms (e.g., a fluorine atom);
$R^4$ is a hydrogen atom, a halogen atom (e.g., a chlorine atom), a $C_{1-6}$ alkyl group (e.g. methyl) optionally substituted by 1 to 3 halogen atoms (e.g., a fluorine atom), or a $C_{3-6}$ cycloalkyl group (e.g., cyclopropyl);
Ring A is
(1) a $C_{6-14}$ aromatic hydrocarbon (preferably a $C_{6-12}$ aromatic hydrocarbon (e.g., benzene)) optionally substituted by 1 to 3 substituents selected from a halogen atom (e.g., a fluorine atom) and a cyano group, or
(2) an aromatic heterocycle (preferably a 5- or 6-membered aromatic heterocycle optionally fused with benzene (e.g., pyridine, pyrazole, indole, thiazole));
Ring B is a 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane) optionally substituted by 1 to 3 substituents selected from
(1) a halogen atom (e.g., a fluorine atom),
(2) a hydroxy group,
(3) a carboxy group,
(4) a $C_{1-6}$ alkyl group (e.g. methyl, ethyl, isopropyl) optionally substituted by 1 to 3 hydroxy groups,
(5) a $C_{3-10}$ cycloalkyl group (e.g., cyclopropyl),
(6) a $C_{1-6}$ alkoxy-carbonyl group (e.g. methoxycarbonyl, tert-butoxycarbonyl), and
(7) a non-aromatic heterocyclic group (preferably a 3- to 10-membered non-aromatic heterocyclic group (e.g., oxetanyl));
Ring C is a 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane) optionally substituted by 1 to 3 substituents selected from
(1) a halogen atom (e.g., a fluorine atom),
(2) a hydroxyl group,
(3) a $C_{1-6}$ alkyl group (e.g. methyl),
(4) a carboxy group, and
(5) a $C_{1-6}$ alkoxy-carbonyl group (e.g. methoxycarbonyl);
$L^1$ and $L^3$ are independently
(1) a bond,
(2) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—, —C(CH$_3$)$_2$—)), or
(3) a $C_{3-8}$ cycloalkylene group (preferably a $C_{3-6}$ cycloalkylene group (e.g., 1,1-cyclopropylene));
$L^2$ is a bond or —C(O)—;
[preferably, $L^1$-$L^2$-$L^3$ is
(1) a $C_{1-10}$ alkylene group (preferably a $C_{1-6}$ alkylene group, more preferably a $C_{1-3}$ alkylene group (e.g., —CH$_2$—, —(CH$_2$)$_2$—, —(CH$_2$)$_3$—, —C(CH$_3$)$_2$—)),
(2) a $C_{3-8}$ cycloalkylene group (preferably a $C_{3-6}$ cycloalkylene group (e.g., 1,1-cyclopropylene)), or
(3) —C(O)—]; and
$L^4$ is a bond, a straight chain $C_{1-6}$ alkylene group (preferably a straight chain $C_{1-3}$ alkylene group (e.g., —CH$_2$—, —CH$_2$CH$_2$—)), —O—, —C(O)— or —NH—C(O)—.

[Compound C-1]
Compound (I) wherein
$R^1$ is a hydrogen atom;
$R^2$ is a hydrogen atom;
$R^3$ is a hydrogen atom or a $C_{1-10}$ alkyl group (preferably a $C_{1-6}$ alkyl group (e.g. methyl));
$R^4$ is a hydrogen atom;
Ring A is a $C_{6-14}$ aromatic hydrocarbon (preferably a $C_{6-12}$ aromatic hydrocarbon (e.g., benzene));
Ring B is a 5- or 6-membered non-aromatic heterocycle (e.g. piperidine, piperazine) optionally substituted by 1 to 3 substituents selected from
(1) a hydroxy group,
(2) a carboxy group,
(3) a $C_{1-6}$ alkyl group (e.g. methyl, ethyl, isopropyl), and
(4) a $C_{1-6}$ alkoxy-carbonyl group (e.g. methoxycarbonyl, tert-butoxycarbonyl);
Ring C is a 5- or 6-membered nitrogen-containing non-aromatic heterocycle (e.g., morpholine);
$L^1$ and $L^3$ are independently
(1) a bond, or
(2) a $C_{1-6}$ alkylene group, (preferably a $C_{1-3}$ alkylene group (e.g., —CH$_2$—, —(CH$_2$)$_2$—));
$L^2$ is a bond;
[preferably, $L^1$-$L^2$-$L^3$ is a $C_{1-6}$ alkylene group (preferably a $C_{1-3}$ alkylene group (e.g., —CH$_2$—, —(CH$_2$)$_2$—))]; and
$L^4$ is a bond.

[Compound A-2]
Compound (I) wherein
$R^1$ is a hydrogen atom, an optionally substituted $C_{1-10}$ alkyl group (preferably an optionally substituted $C_{1-6}$ alkyl group (e.g. methyl)) or an optionally substituted $C_{3-10}$ cycloalkyl group (preferably an optionally substituted $C_{3-6}$ cycloalkyl group (e.g., cyclopropyl));
$R^2$ is a hydrogen atom or an optionally substituted $C_{1-10}$ alkyl group (preferably an optionally substituted $C_{1-6}$ alkyl group (e.g. methyl));
$R^3$ is a hydrogen atom, an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl)) or an optionally substituted $C_{1-10}$ alkoxy group (preferably an optionally substituted $C_{1-6}$ alkoxy group (e.g. ethoxy));
$R^4$ is a hydrogen atom, a halogen atom (e.g., a chlorine atom), an optionally substituted $C_{1-10}$ alkyl group (preferably an optionally substituted $C_{1-6}$ alkyl group (e.g. methyl)), or an optionally substituted $C_{3-10}$ cycloalkyl group (preferably an optionally substituted $C_{3-6}$ cycloalkyl group (e.g., cyclopropyl));
Ring A is an optionally substituted $C_{3-10}$ cycloalkane (preferably an optionally substituted $C_{3-6}$ cycloalkane (e.g., cyclohexane)), an optionally substituted $C_{3-10}$ cycloalkene (preferably an optionally substituted $C_{3-6}$ cycloalkene (e.g., cyclohexene)), an optionally substituted $C_{6-14}$ aromatic hydrocarbon (preferably an optionally substituted $C_{6-12}$ aromatic hydrocarbon (e.g., benzene)) or an optionally substituted aromatic heterocycle optionally fused with benzene (preferably an optionally substituted 5- or 6-membered aromatic heterocycle optionally fused with benzene (e.g., pyridine, pyrazole, indole, thiazole));

Ring B is an optionally substituted 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane);

Ring C is an optionally substituted 5- or 6-membered nitrogen-containing aromatic heterocycle (e.g., pyrazole) or an optionally substituted 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane);

$L^1$ and $L^3$ are independently
(1) a bond,
(2) a $C_{1-10}$ alkylene group (preferably a $C_{1-6}$ alkylene group, more preferably a $C_{1-3}$ alkylene group (e.g., —$CH_2$—, —$(CH_2)_2$—, —$(CH_2)_3$—, —$C(CH_3)_2$—)), or
(3) a $C_{3-8}$ cycloalkylene group (preferably a $C_{3-6}$ cycloalkylene group (e.g., 1,1-cyclopropylene));

$L^2$ is a bond or —C(O)—;
[preferably, $L^1$-$L^2$-$L^3$ is
(1) a $C_{1-10}$ alkylene group (preferably a $C_{1-6}$ alkylene group, more preferably a $C_{1-3}$ alkylene group (e.g., —$CH_2$—, —$(CH_2)_2$—, —$(CH_2)_3$—, —$C(CH_3)_2$—)),
(2) a $C_{3-8}$ cycloalkylene group (preferably a $C_{3-6}$ cycloalkylene group (e.g., 1,1-cyclopropylene)), or
(3) —C(O)—]; and $L^4$ is a bond, a straight chain $C_{1-6}$ alkylene group (preferably a straight chain $C_{1-3}$ alkylene group (e.g., —$CH_2$—, —$CH_2CH_2$—)), —$X^1$—O—$X^2$—, —$X^1$—C(O)—$X^2$— or —$X^1$—NH—C(O)—$X^2$— [wherein $X^1$ and $X^2$ are independently a bond or a straight chain $C_{1-5}$ alkylene group, and the total atom number is 6 or less].

[Compound B-2]

Compound (I) wherein
$R^1$ is a hydrogen atom, a $C_{1-10}$ alkyl group (preferably a $C_{1-6}$ alkyl group (e.g. methyl)) or a $C_{3-10}$ cycloalkyl group (preferably a $C_{3-6}$ cycloalkyl group (e.g., cyclopropyl));

$R^2$ is a hydrogen atom or a $C_{1-10}$ alkyl group (preferably a $C_{1-6}$ alkyl group (e.g. methyl));

$R^3$ is
(1) a hydrogen atom,
(2) a $C_{1-10}$ alkyl group (preferably a $C_{1-6}$ alkyl group (e.g. methyl)) optionally substituted by 1 to 3 halogen atoms (e.g., a fluorine atom),
(3) a $C_{3-10}$ cycloalkyl group (preferably a $C_{3-6}$ cycloalkyl group (e.g., cyclopropyl, cyclobutyl)), or
(4) a $C_{1-10}$ alkoxy group (preferably a $C_{1-6}$ alkoxy group (e.g. ethoxy)) optionally substituted by 1 to 3 halogen atoms (e.g., a fluorine atom);

$R^4$ is a hydrogen atom, a halogen atom (e.g., a chlorine atom), a $C_{1-6}$ alkyl group (e.g. methyl) optionally substituted by 1 to 3 halogen atoms (e.g., a fluorine atom), or a $C_{3-6}$ cycloalkyl group (e.g., cyclopropyl);

Ring A is
(1) a $C_{3-10}$ cycloalkane (preferably a $C_{3-6}$ cycloalkane (e.g., cyclohexane)),
(2) a $C_{3-10}$ cycloalkene (preferably a $C_{3-6}$ cycloalkene (e.g., cyclohexene)),
(3) a $C_{6-14}$ aromatic hydrocarbon (preferably a $C_{6-12}$ aromatic hydrocarbon (e.g., benzene)) optionally substituted by 1 to 3 substituents selected from
(i) a halogen atom (e.g., a fluorine atom),
(ii) a $C_{1-6}$ alkyl group (e.g. methyl) optionally substituted by 1 to 3 halogen atoms (e.g., a fluorine atom),
(iii) a $C_{1-6}$ alkoxy group (e.g. methoxy), and
(iv) a cyano group, or
(4) an aromatic heterocycle optionally fused with benzene (preferably a 5- or 6-membered aromatic heterocycle optionally fused with benzene (e.g., pyridine, pyrazole, indole, thiazole));

Ring B is a 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane) optionally substituted by 1 to 3 substituents selected from
(1) a halogen atom (e.g., a fluorine atom),
(2) a hydroxy group,
(3) a carboxy group,
(4) a $C_{1-6}$ alkyl group (e.g. methyl, ethyl, isopropyl) optionally substituted by 1 to 3 substituents selected from
(i) a hydroxy group,
(ii) a halogen atom (e.g., a fluorine atom), and
(iii) an aromatic heterocyclic group (preferably a 5- or 6-membered aromatic heterocyclic group (e.g., oxazolyl)),
(5) a $C_{3-10}$ cycloalkyl group (e.g., cyclopropyl),
(6) a $C_{1-6}$ alkoxy-carbonyl group (e.g. methoxycarbonyl, ethoxycarbonyl, tert-butoxycarbonyl), and
(7) a non-aromatic heterocyclic group (preferably a 3- to 10-membered non-aromatic heterocyclic group (e.g., oxetanyl));

Ring C is
(1) a 5- or 6-membered nitrogen-containing aromatic heterocycle (e.g., pyrazole), or
(2) a 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane) optionally substituted by 1 to 3 substituents selected from
(1) a halogen atom (e.g., a fluorine atom),
(2) a hydroxyl group,
(3) a $C_{1-6}$ alkyl group (e.g. methyl),
(4) a carboxy group, and
(5) a $C_{1-6}$ alkoxy-carbonyl group (e.g. methoxycarbonyl));

$L^1$ and $L^3$ are independently
(1) a bond,
(2) a $C_{1-10}$ alkylene group (preferably a $C_{1-6}$ alkylene group, more preferably a $C_{1-3}$ alkylene group (e.g., —$CH_2$—, —$(CH_2)_2$—, —$(CH_2)_3$—, —$C(CH_3)_2$—)), or
(3) a $C_{3-8}$ cycloalkylene group (preferably a $C_{3-6}$ cycloalkylene group (e.g., 1,1-cyclopropylene));

$L^2$ is a bond or —C(O)—;
[preferably, $L^1$-$L^2$-$L^3$ is
(1) a $C_{1-10}$ alkylene group (preferably a $C_{1-6}$ alkylene group, more preferably a $C_{1-3}$ alkylene group (e.g., —$CH_2$—, —$(CH_2)_2$—, —$(CH_2)_3$—, —$C(CH_3)_2$—)),
(2) a $C_{3-8}$ cycloalkylene group (preferably a $C_{3-6}$ cycloalkylene group (e.g., 1,1-cyclopropylene)), or
(3) —C(O)—]; and $L^4$ is a bond, a straight chain $C_{1-6}$ alkylene group (preferably a straight chain $C_{1-3}$ alkylene group (e.g., —$CH_2$—, —$CH_2CH_2$—)), —O—, —C(O)— or —NH—C(O)—.

[Compound C-2]

Compound (I) wherein
$R^1$ is a hydrogen atom or a $C_{1-10}$ alkyl group (preferably a $C_{1-6}$ alkyl group (e.g. methyl));

R² is a hydrogen atom or a $C_{1-10}$ alkyl group (preferably a $C_{1-6}$ alkyl group (e.g. methyl));

R³ is (1) a hydrogen atom, (2) a $C_{1-10}$ alkyl group (preferably a $C_{1-6}$ alkyl group (e.g. methyl)) optionally substituted by 1 to 3 halogen atoms (e.g., a fluorine atom), or (3) a $C_{3-10}$ cycloalkyl group (preferably a $C_{3-6}$ cycloalkyl group (e.g., cyclopropyl));

R⁴ is a hydrogen atom or a halogen atom (e.g., a chlorine atom);

Ring A is (1) a $C_{3-10}$ cycloalkane (preferably a $C_{3-6}$ cycloalkane (e.g., cyclohexane)), (2) a $C_{3-10}$ cycloalkene (preferably a $C_{3-6}$ cycloalkene (e.g., cyclohexene)), (3) a $C_{6-14}$ aromatic hydrocarbon (preferably a $C_{6-12}$ aromatic hydrocarbon (e.g., benzene)) optionally substituted by 1 to 3 substituents selected from (i) a halogen atom (e.g., a fluorine atom),
   (ii) a $C_{1-6}$ alkyl group (e.g. methyl) optionally substituted by 1 to 3 halogen atoms (e.g., a fluorine atom), and
   (iii) a $C_{1-6}$ alkoxy group (e.g. methoxy), or (4) an aromatic heterocycle optionally fused with benzene (preferably a 5- or 6-membered aromatic heterocycle optionally fused with benzene (e.g., pyridine, pyrazole, thiazole));

Ring B is a 3- to 10-membered non-aromatic heterocycle (e.g. piperidine, piperazine, tetrahydropyridine, morpholine) optionally substituted by 1 to 3 substituents selected from (1) a hydroxy group, (2) a carboxy group, (3) a $C_{1-6}$ alkyl group (e.g. methyl, ethyl, isopropyl) optionally substituted by 1 to 3 substituents selected from (i) a halogen atom (e.g., a fluorine atom), and
   (ii) an aromatic heterocyclic group (preferably a 5- or 6-membered aromatic heterocyclic group (e.g., oxazolyl)), (4) a $C_{1-6}$ alkoxy-carbonyl group (e.g. methoxycarbonyl, ethoxycarbonyl, tert-butoxycarbonyl), and (5) a non-aromatic heterocyclic group (preferably a 3- to 10-membered non-aromatic heterocyclic group (e.g., oxetanyl));

Ring C is (1) a 5- or 6-membered nitrogen-containing aromatic heterocycle (e.g., pyrazole), or (2) a 3- to 10-membered nitrogen-containing non-aromatic heterocycle (e.g., morpholine, azetidine, pyrrolidine, piperidine, 7-azaspiro[3.5]nonane) optionally substituted by 1 to 3 substituents selected from (1) a halogen atom (e.g., a fluorine atom),
   (2) a hydroxyl group,
   (3) a $C_{1-6}$ alkyl group (e.g. methyl),
   (4) a carboxy group, and
   (5) a $C_{1-6}$ alkoxy-carbonyl group (e.g. methoxycarbonyl);

$L^1$ and $L^3$ are independently (1) a bond, or (2) a $C_{1-6}$ alkylene group, (preferably a $C_{1-3}$ alkylene group (e.g., —CH₂—, —(CH₂)₂—, —(CH₂)₃—));

$L^2$ is a bond or —C(O)—;

[preferably, $L^1$-$L^2$-$L^3$ is (1) a $C_{1-10}$ alkylene group (preferably a $C_{1-6}$ alkylene group, more preferably a $C_{1-3}$ alkylene group (e.g., —CH₂—, —(CH₂)₂—, —(CH₂)₃—), or (2) —C(O)—]; and $L^4$ is a bond, a straight chain $C_{1-6}$ alkylene group (preferably a straight chain $C_{1-3}$ alkylene group (e.g., —CH₂—)), —O— or —C(O)—.

[Compound D-2]

Compound (I) wherein

R¹ is a hydrogen atom, a $C_{1-10}$ alkyl group (preferably a $C_{1-6}$ alkyl group (e.g. methyl)) or a $C_{3-10}$ cycloalkyl group (preferably a $C_{3-6}$ cycloalkyl group (e.g., cyclopropyl));

R² is a hydrogen atom or a $C_{1-10}$ alkyl group (preferably a $C_{1-6}$ alkyl group (e.g. methyl));

R³ is a hydrogen atom, an optionally substituted hydrocarbon group [preferably an optionally substituted $C_{1-10}$ alkyl group (preferably an optionally substituted $C_{1-6}$ alkyl group (e.g. methyl)), an optionally substituted $C_{3-10}$ cycloalkyl group (preferably an optionally substituted $C_{3-6}$ cycloalkyl group (e.g., cyclopropyl, cyclobutyl))], or an optionally substituted hydroxy group [preferably an optionally substituted $C_{1-10}$ alkoxy group (preferably an optionally substituted $C_{1-6}$ alkoxy group (e.g. ethoxy))];

R⁴ is a hydrogen atom, a halogen atom (e.g., a chlorine atom), or an optionally substituted hydrocarbon group [preferably an optionally substituted $C_{1-10}$ alkyl group (preferably an optionally substituted $C_{1-6}$ alkyl group (e.g. methyl)), or an optionally substituted $C_{3-10}$ cycloalkyl group (preferably an optionally substituted $C_{3-6}$ cycloalkyl group (e.g., cyclopropyl))];

Ring A is an optionally substituted $C_{3-10}$ cycloalkane (preferably an optionally substituted $C_{3-6}$ cycloalkane (e.g., cyclohexane)), an optionally substituted $C_{3-10}$ cycloalkene (preferably an optionally substituted $C_{3-6}$ cycloalkene (e.g., cyclohexene)), an optionally substituted $C_{6-14}$ aromatic hydrocarbon (preferably an optionally substituted $C_{6-12}$ aromatic hydrocarbon (e.g., benzene)) or an optionally substituted aromatic heterocycle optionally fused with benzene (preferably an optionally substituted 5- or 6-membered aromatic heterocycle optionally fused with benzene (e.g., pyridine, pyrazole, indole, thiazole));

Ring B is an optionally substituted 3- to 10-membered non-aromatic heterocycle (e.g. azetidine, pyrrolidine, piperidine, piperazine, tetrahydropyridine, morpholine, 1,1-dioxidothiomorpholine, oxetane, 3-azabicyclo[2.2.1]heptane, 3-azabicyclo[3.3.1]nonane, 7-azaspiro[3.5]nonane);

Ring C is an optionally substituted 5- or 6-membered nitrogen-containing aromatic heterocycle (e.g., pyrazole) or an optionally substituted 3- to 10-membered nitrogen-containing non-aromatic heterocycle (e.g., morpholine, azetidine, pyrrolidine, piperidine, 6-azaspiro[3.3]heptane, 7-azaspiro[3.5]nonane, 6-azabicyclo[3.1.1]heptane, 3-azabicyclo[2.2.1]heptane);

$L^1$ and $L^3$ are independently (1) a bond, (2) a $C_{1-10}$ alkylene group (preferably a $C_{1-6}$ alkylene group, more preferably a $C_{1-3}$ alkylene group (e.g., —CH₂—, —(CH₂)₂—, —(CH₂)₃—, —C(CH₃)₂—)), or (3) a $C_{3-8}$ cycloalkylene group (preferably a $C_{3-6}$ cycloalkylene group (e.g., 1,1-cyclopropylene));

$L^2$ is a bond or —C(O)—;

[preferably, $L^1$-$L^2$-$L^3$ is (1) a $C_{1-10}$ alkylene group (preferably a $C_{1-6}$ alkylene group, more preferably a $C_{1-3}$ alkylene group (e.g., —CH₂—, —(CH₂)₂—, —(CH₂)₃—, —C(CH₃)₂—)), (2) a $C_{3-8}$ cycloalkylene group (preferably a $C_{3-6}$ cycloalkylene group (e.g., 1,1-cyclopropylene)), or (3) —C(O)—]; and $L^4$ is a bond, a straight chain $C_{1-6}$ alkylene group (preferably a straight chain $C_{1-3}$ alkylene group (e.g., —CH$_2$—, —CH$_2$CH$_2$—)), —X$^1$—O—X$^2$—, —X$^1$—C(O)—X$^2$— or —X$^1$—NH—C(O)—X$^2$— [wherein X$^1$ and X$^2$ are independently a bond or a straight chain $C_{1-5}$ alkylene group, and the total atom number is 6 or less].

Examples of the salt of the compound represented by the formula (I) include metal salts, ammonium salts, salts with an organic base, salt with an inorganic acid, salts with an organic acid, salts with a basic or acidic amino acid, and the like.

Preferable examples of the metal salt include alkaline metal salts such as sodium salt, potassium salt and the like; alkaline earth metal salts such as calcium salt, magnesium salt, barium salt and the like; aluminum salt, and the like.

Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with an inorganic acid include salts with hydrochloric acid, hydrobromic acid, nitric acid, sulfuric acid, phosphoric acid and the like.

Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with a basic amino acid include salts with arginine, lysine, ornithine and the like. Preferable examples of the salt with an acidic amino acid include salt with aspartic acid, glutamic acid and the like.

Among the above-mentioned salts, pharmaceutically acceptable salts are preferable.

Compound (I) may be in the form of a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to a $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Among them, a compound esterified by $C_{1-6}$ alkyl (e.g., methyl, ethyl, tert-butyl and the like) are preferably used. These compounds can be produced from compound (I) according to a method known per se.

The prodrug of compound (I) may also be one which is converted into compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

Each symbol of the compound in the following Schemes is as defined above, unless otherwise specified. Each compound described in the following Schemes may be in the form of a salt as long as it does not inhibit the reaction. Examples of the salt include those similar to the salt of compound (I).

The compound obtained in each step can be used directly for the next reaction as the reaction mixture or as a crude product, or can also be isolated according to a conventional method from the reaction mixture, and can also be easily purified according to a separation means (e.g., recrystallization, distillation, chromatography etc.).

The production methods of the compound of the present invention are described in the following.

Compound (I) can be produced according to a method known per se, for example, the production method shown in Scheme 1, 4 or 7, or a method analogous thereto.

In each of the following production methods, each starting compound used for the production of compound (I) may be in the form of a salt. Examples of the salt include those similar to the salt of compound (I).

Each starting compound to be used for the production of compound (I) can be used directly for the next reaction as the reaction mixture or as a crude product, or can also be isolated according to a conventional method from the reaction mixture, and can also be purified according to a separation means (e.g., extraction, concentration, neutralization, filtration, distillation, recrystallization, chromatography etc.). Examples of the solvent used for the above-mentioned recrystallization include water, alcohols, ethers, hydrocarbons, amides, halogenated hydrocarbons, nitriles, ketones, esters, sulfoxides, organic acids and the like. These solvents may be used alone, or two or more kinds of solvents may be mixed at a suitable ratio, for example, 1:1-1:10. In addition, the compounds in the Schemes may be commercially available, or can be produced according to a method known per se or a method analogous thereto.

When compound (I) and intermediate for the production of compound (I) have a convertible functional group (e.g., a carboxyl group, an amino group, a hydroxy group, a carbonyl group, a sulfanyl group, a $C_{1-6}$ alkoxy-carbonyl group, a $C_{6-14}$ aryloxy-carbonyl group, a $C_{7-16}$ aralkyloxy-carbonyl group, a sulfo group, a halogen atom, an optionally halogenated $C_{1-6}$ alkylsulfonyloxy group, a cyano group, an aminocarbonyl group, a boryl group etc.), various compounds can be produced by converting such functional group according to a method known per se or a method analogous thereto.

Carboxyl group can be converted, for example, by reactions such as esterification, reduction, amidation, conversion reaction to optionally protected amino group and the like.

Amino group can be converted, for example, by reactions such as amidation, sulfonylation, nitrosation, alkylation, arylation, imidation and the like.

Hydroxy group can be converted, for example, by reactions such as esterification, carbamoylation, sulfonylation, alkylation, fluorination, arylation, oxidation, halogenation and the like.

Carbonyl group can be converted, for example, by reactions such as reduction, oxidation, fluorination, imination (including oximation, hydrazonation), (thio)ketalization, alkylidenation, thiocarbonylation and the like.

Sulfanyl group can be converted, for example, by reactions such as alkylation, oxidation and the like.

$C_{1-6}$ alkoxy-carbonyl group, $C_{6-14}$ aryloxy-carbonyl group and $C_{7-16}$ aralkyloxy-carbonyl group can be converted, for example, by reactions such as reduction, hydrolysis and the like.

Sulfo group can be converted, for example, by reactions such as sulfonamidation, reduction and the like.

Halogen atom can be converted, for example, by various nucleophilic substitution reactions, various coupling reactions and the like.

Optionally halogenated $C_{1-6}$ alkylsulfonyloxy group can be converted, for example, by various nucleophilic substitution reactions, various coupling reactions and the like.

Cyano group can be converted, for example, by reactions such as reduction, hydrolysis and the like.

Aminocarbonyl group can be converted, for example, by reactions such as dehydration, reduction and the like.

Boryl group can be converted, for example, by oxidation, various coupling reactions and the like.

In each of the above-mentioned reactions, when the compound is obtained in a free form, it may be converted to a salt according to a conventional method. When it is obtained as a salt, it may be converted to a free form or other salt according to a conventional method.

The conversion of these functional group can be carried out according to a method known per se, for example, the method described in Comprehensive Organic Transformations, Second Edition, Wiley-VCH, Richard C. Larock, or the like.

In each reaction in the production method of compound (I) and each reaction of the synthesis of the starting materials, when the starting compound has an amino group, a carboxyl group, a hydroxy group, a carbonyl group or a sulfanyl group as a substituent, a protecting group generally used in peptide chemistry and the like may be introduced into these substituents. By removing the protecting group as necessary after the reaction, the object compound can be obtained.

Examples of the amino-protecting group include a formyl group; and a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl (Alloc) group, a phenyloxycarbonyl group, a fluorenylmethoxycarbonyl (Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl (Z) etc.), a $C_{7-10}$ aralkyl group (e.g., benzyl etc.), a 2-(trimethylsilyl)ethoxymethyl (SEM) group, a trityl group, a phthaloyl group, an N,N-dimethylaminomethylene group, an allyl group and the like, each of which optionally has substituent(s), and the like. As these substituents, a phenyl group, a halogen atom (e.g., a fluorine atom, a chlorine atom, a bromine atom, an iodine atom etc.), a $C_{1-6}$ alkyl-carbonyl group (e.g., methylcarbonyl, ethylcarbonyl, butylcarbonyl etc.), a nitro group and the like are used, and the number of the substituents is about 1 to 3.

Examples of the carboxyl-protecting group include a $C_{1-6}$ alkyl group (e.g., methyl, ethyl, n-propyl, isopropyl, n-butyl, tert-butyl etc.), an allyl group, a benzyl group, a phenyl group, a trityl group, a trialkylsilyl group and the like, each of which optionally has substituent(s). As these substituents, a halogen atom (e.g., a fluorine atom, a chlorine atom, a bromine atom, an iodine atom etc.), a formyl group, a $C_{1-6}$ alkyl-carbonyl group (e.g., acetyl, ethylcarbonyl, butylcarbonyl etc.), a nitro group and the like are used, and the number of the substituents is about 1 to 3.

Examples of the hydroxyl-protecting group include a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group, a silyl group and the like, each of which optionally has substituent(s). As these substituents, a halogen atom (e.g., a fluorine atom, a chlorine atom, a bromine atom, an iodine atom etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like are used, and the number of the substituents is about 1 to 4.

Examples of the protected carbonyl group include cyclic acetal (e.g., 1,3-dioxane), noncyclic acetal (e.g., di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7_{14}}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These protecting groups are optionally substituted by 1 to 3 substituents selected from a halogen atom, a $C_{1-6}$ alkyl group, a $C_{1-6}$ alkoxy group and a nitro group.

These protecting groups can be introduced and removed by a method known per se, for example, the method described in Greene's Protective Groups in Organic Synthesis, $4^{th}$ Edition, Wiley-Interscience, Theodora W. Greene, Peter G. M. Wuts or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

When compound (I) is present as a configurational isomer, a diastereomer, a conformer and the like, each can be isolated by a known means. When compound (I) has an optical isomer, racemates can be resolved by a general optical resolution means, whereby an optically active forms ((+) form, (−) form) can be obtained.

When compound (I) has an optical isomer, a stereoisomer, a positional isomer, a rotamer or a tautomer, these are also encompassed in compound (I), and can be obtained as a single product according to synthesis and separation methods known per se.

For example, the method of optical resolution may be a method known per se, such as a fractional recrystallization method, a chiral column method, a diastereomer method etc.
1) Fractional Recrystallization Method A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

The solvent, acid and base recited in the production methods of the compound of the present invention are explained in the following.

Examples of the "solvent" include "alcohols", "ethers", "hydrocarbons", "amides", "halogenated hydrocarbons", "nitriles", "ketones", "esters", "sulfoxides", "water" and the like.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane, tert-butyl methyl ether and the like.

Examples of the "hydrocarbons" include benzene, toluene, cyclohexane, hexane, petroleum ether and the like.

Examples of the "amides" include N,N-dimethylformamide, N,N-dimethylacetamide, N-methylpyrrolidone, hexamethylphosphoric triamide and the like.

Examples of the "halogenated hydrocarbons" include dichloromethane, chloroform, carbon tetrachloride, 1,2-dichloroethane, chlorobenzene, benzotrifluoride and the like.

Examples of the "nitriles" include acetonitrile, propionitrile and the like.

Examples of the "ketones" include acetone, ethyl methyl ketone and the like.

Examples of the "esters" include ethyl acetate, tert-butyl acetate and the like.

Examples of the "sulfoxides" include dimethyl sulfoxide and the like.

Examples of the "acid" include "organic acids", "mineral acids", "Lewis acids" and the like.

Examples of the "organic acids" include formic acid, acetic acid, propionic acid, trifluoroacetic acid, citric acid, methanesulfonic acid, p-toluenesulfonic acid and the like.

Examples of the "mineral acids" include hydrochloric acid, sulfuric acid and the like.

Examples of the "Lewis acids" include boron trichloride, boron tribromide and the like.

Examples of the "base" include "inorganic bases", "basic salts", "aromatic amines", "tertiary amines", "alkali metal hydrides", "alkali metals", "metal amides", "alkyl metals", "aryl metals", "metal alkoxides" and the like.

Examples of the "inorganic bases" include sodium hydroxide, potassium hydroxide, lithium hydroxide, barium hydroxide and the like.

Examples of the "basic salts" include sodium carbonate, potassium carbonate, cesium carbonate, sodium hydrogen carbonate, sodium acetate, ammonium acetate and the like.

Examples of the "aromatic amines" include pyridine, 2,6-lutidine and the like.

Examples of the "tertiary amines" include triethylamine, tripropylamine, tributylamine, N,N-diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like.

Examples of the "alkali metal hydrides" include sodium hydride, potassium hydride and the like.

Examples of the "alkali metals" include sodium, lithium, potassium and the like.

Examples of the "metal amides" include sodium amide, lithium diisopropylamide, lithium hexamethyldisilazide and the like.

Examples of the "alkyl metals" include butyllithium, sec-butyllithium, tert-butyllithium and the like.

Examples of the "aryl metals" include phenyllithium and the like.

Examples of the "metal alkoxides" include sodium methoxide, sodium ethoxide, sodium tert-butoxide, potassium tert-butoxide and the like.

Compound (I) can be produced, for example, according to the method shown in the following Scheme 1, 4 or 7 or a method analogous thereto.

Compound (I) can be prepared by subjecting intermediates (II) and (III) to Suzuki coupling as shown in Scheme 1.

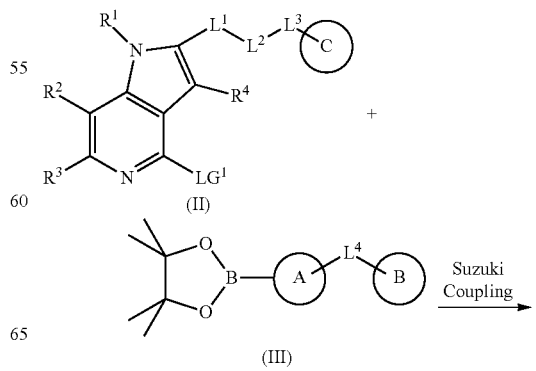

-continued

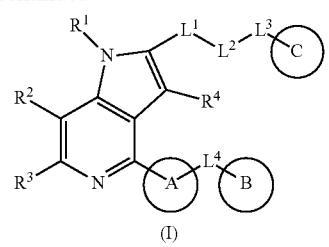

(I)

wherein LG$^1$ is a leaving group selected from a halogen atom, trifluoromethanesulfonyloxy and the like, and the other symbols are as defined above.

The Suzuki coupling can be carried out according to the method described in *Chemical Reviews* 95 (7): 2457-2483, for example, by reacting intermediate (II) with intermediate (III) in the presence of a catalysis and a base, in a solvent.

Examples of the catalysis include palladium(0) complexes such as tetrakis(triphenylphosphine)palladium, 1,1-bis(diphenylphosphino)ferrocene-palladium(II) dichloride dichloromethane complex and the like.

Intermediate (II) wherein L$^1$-L$^2$-L$^3$ is —CH$_2$— or —CH$_2$CH$_2$— can be prepared by subjecting intermediates (IV) and (V) to reductive amination as shown in Scheme 2.

Scheme 2: Preparation of intermediate (II)

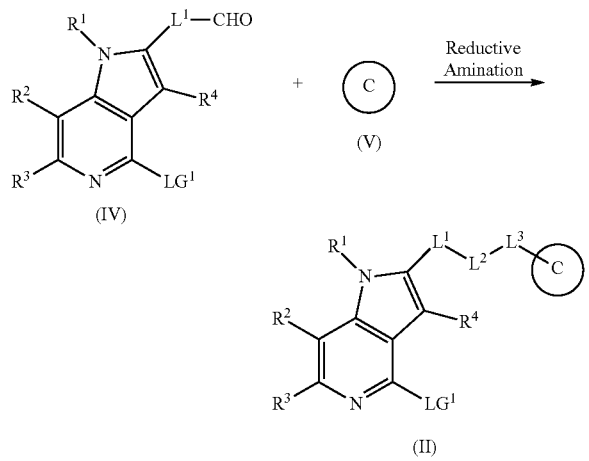

wherein L$^1$ in intermediate. (IV) is either absent or is —CH$_2$, and the other symbols are as defined above.

The reductive amination can be carried out according to the method described in *Organic Reactions*, 1, 59, 2002, for example, by reacting intermediate (IV) with intermediate (V) in the presence of a reducing agent, in a solvent.

Examples of the reducing agent include sodium cyanoborohydride (NaBH$_3$CN), sodium triacetoxyborohydride (NaBH(OCOCH$_3$)$_3$ and the like.

Intermediate (IV) and intermediate (V) may be commercially available, or can also be produced according to a method known per se or a method analogous thereto.

Alternatively, intermediate (II) can also be prepared by subjecting intermediates (VI) and (V) to substitution reaction as shown in Scheme 3.

Scheme 3: Preparation of intermediate (II)

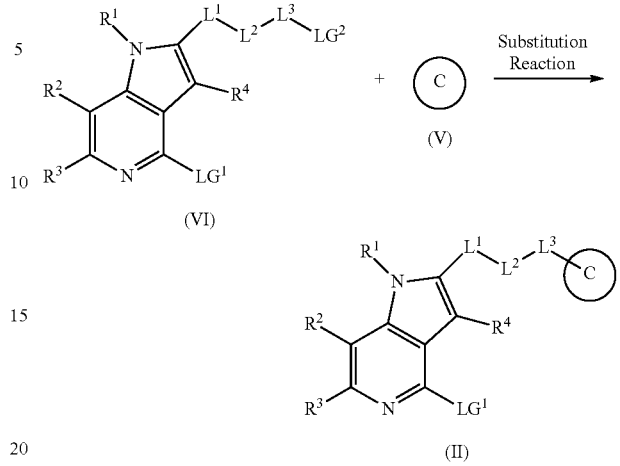

wherein LG$^2$ is a leaving group selected from a chlorine atom, a bromine atom, methanesulfonyloxy, trifluoromethanesulfonyloxy and the like, and the other symbols are as defined above.

The substitution reaction can be carried out according to the method described in J. March, *Advanced Organic Chemistry*, 4th ed., Wiley, New York, 1992, for example, by reacting intermediate (VI) with intermediate (V) in the presence of a base, in a solvent.

Intermediate (VI) may be commercially available, or can also be produced according to a method known per se or a method analogous thereto.

Intermediate (III) may be commercially available, or can also be produced according to a method known per se or a method analogous thereto.

Compound (I) wherein L$^4$ is a bond can also be prepared by subjecting intermediates (VII) and (VIII) to Buchwald coupling as shown in Scheme 4.

Scheme 4: Preparation of compound (I)

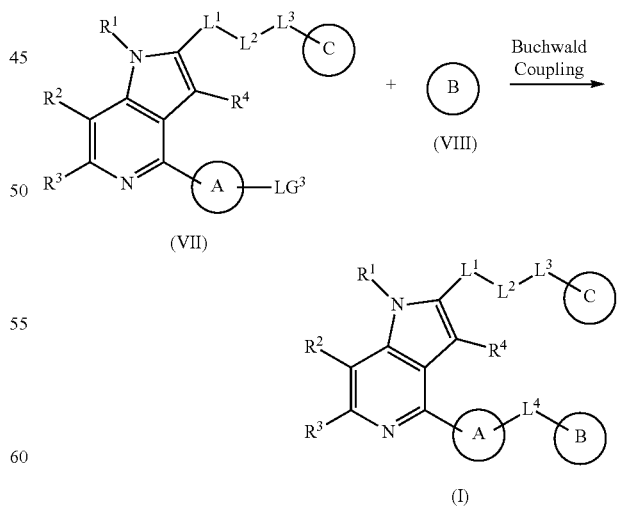

wherein LG$^3$ is a halogen atom, and the other symbols are as defined above.

The Buchwald coupling can be carried out according to the method described in *Chem. Sci.* 2: 27-50, 2011, for example, by reacting intermediate (VII) with intermediate (VIII) in the presence of a palladium compound, a ligand and a base, in a solvent.

Examples of the palladium compound include tris(dibenzylideneacetone)dipalladium(0) and the like.

Examples of the ligand include (2,2'-bis(diphenylphosphino)-1,1'-binaphthyl) and the like.

Intermediate (VIII) may be commercially available, or can also be produced according to a method known per se or a method analogous thereto.

Intermediate (VII) wherein $L^1$-$L^2$-$L^3$ is —CH$_2$— can be prepared by subjecting intermediates (IX) and (V) to reductive amination as shown in Scheme 5.

Scheme 5: Preparation of intermediate (VII)

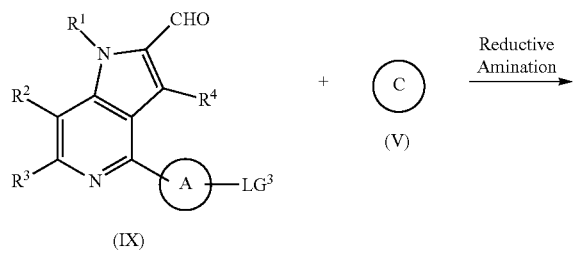

wherein each symbol is as defined above.

The reductive amination can be carried out in the same manner as in Scheme 2.

Intermediate (IX) may be commercially available, or can also be produced according to a method known per se or a method analogous thereto.

Alternatively, intermediate (VII) can also be prepared by subjecting intermediates (X) and (V) to substitution reaction as shown in Scheme 6.

Scheme 6: Preparation of intermediate (VII)

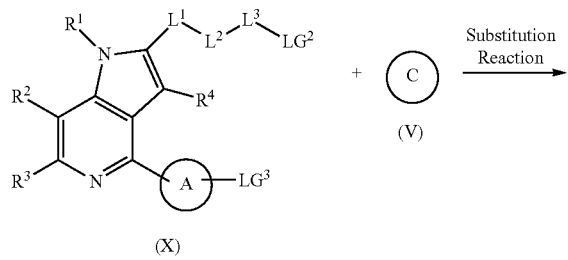

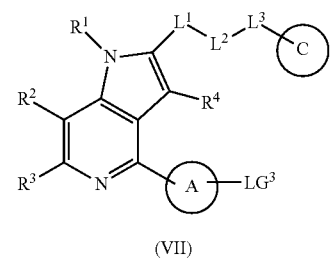

wherein each symbol is as defined above.

The substitution reaction can be carried out in the same manner as in Scheme 3.

Intermediate (X) may be commercially available, or can also be produced according to a method known per se or a method analogous thereto.

Compound (I) wherein $L^1$-$L^2$-$L^3$ is —CH$_2$— can also be prepared by subjecting intermediates (XI) and (V) to reductive amination as shown in Scheme 7.

Scheme 7: Preparation of compound (I)

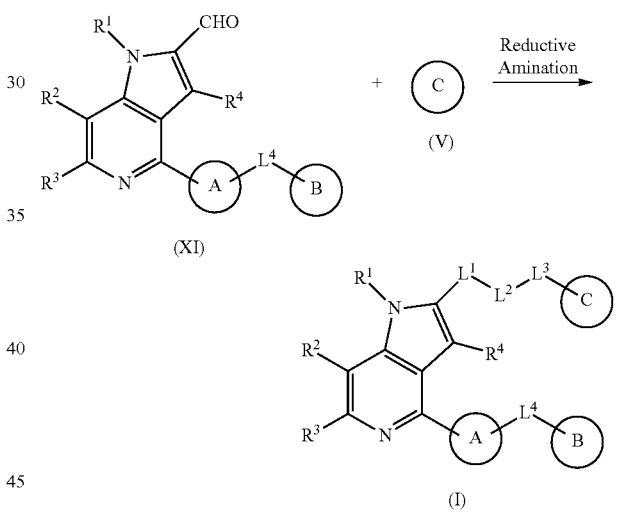

wherein each symbol is as defined above.

The reductive amination can be carried out in the same manner as in Scheme 2.

Intermediate (XI) can be prepared by subjecting intermediates (IV) and (III) to Suzuki coupling as shown in Scheme 8.

Scheme 8: Preparation of intermediate (XI)

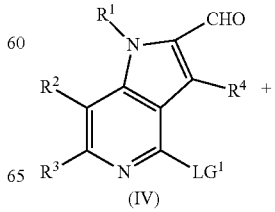

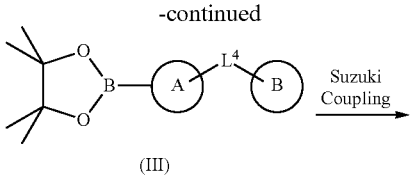

(III)

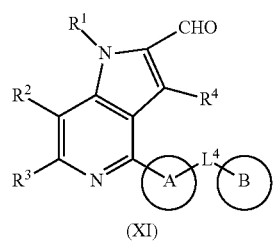

(XI)

wherein each symbol is as defined above.

The Suzuki coupling can be carried out in the same manner as in Scheme 1.

Intermediate (IV) may be commercially available, or can also be produced according to a method known per se or a method analogous thereto.

Compound (I) wherein $L^1$-$L^2$-$L^3$ is —CO— can be prepared by subjecting intermediates (XII) and (V) to amide coupling reaction as shown in Scheme 9.

Scheme 9: Preparation of compound (I)

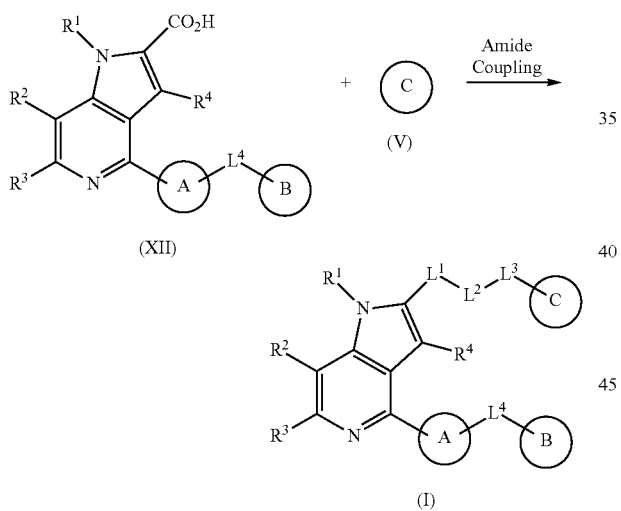

(I)

wherein each symbol is as defined above.

The amide coupling may be carried out using any suitable amide coupling regents such as oxalyl chloride, thionyl chloride, BOP-Cl, DCC, HOBt, HOAt, HATU, EDCI, alkyl chloroformate and the like, in the presence of an organic non-nucleophilic base such as triethyl amine, di-isopropyl-ethyl amine, pyridine, N-methyl pyrrolidine, N,N-dimethylaminopyridine, DBU, DABCO, other hindered amines and pyridines. The amide coupling reaction may be carried out in the presence of a solvent such as dichloromethane, dichloroethane, DMF, dimethylacetamide, THF, acetonitrile, and mixtures thereof, at a temperature ranging from −5 to 150° C. The reaction may be carried out optionally in presence of a catalytic amount of DMF. The amide coupling may also be carried out by heating the corresponding ester and amine either in the absence of a solvent or in presence of a high boiling solvent such as toluene, xylene and DMSO. The amide coupling may be carried out in presence of a trialkyl aluminium (Chem. Commun., 2008, 1100-1102).

Intermediate (XII) can be prepared by subjecting intermediates (XIII) and (III) to Suzuki coupling to give intermediate (XIV) which on hydrolysis can give intermediate (XII) as shown in Scheme 10.

Scheme 10: Preparation of intermediate (XII)

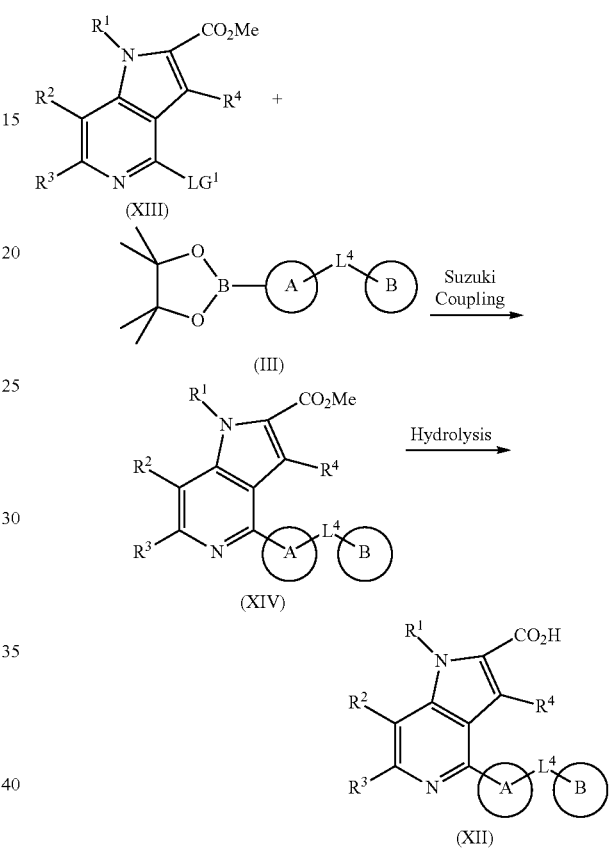

wherein each symbol is as defined above.

The Suzuki coupling can be carried out in the same manner as in Scheme 1.

Intermediate (XIII) may be commercially available, or can also be produced according to a method known per se or a method analogous thereto.

Compound (I) wherein $R^1$ is a hydrogen atom can alternatively be prepared by subjecting intermediate (XV) to Suzuki coupling with intermediate (III) to give intermediate (XVI) as shown in Scheme 11. Acid or base catalyzed deprotection of intermediate (XVI) can give compound (I).

Scheme 11: Preparation of compound (I)

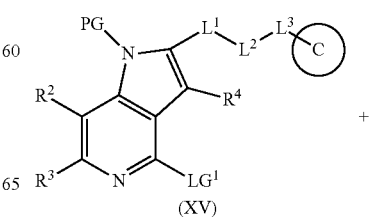

(XV)

-continued

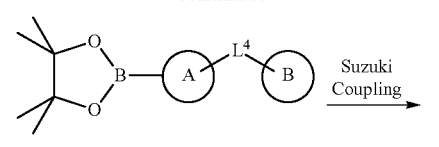

(III)

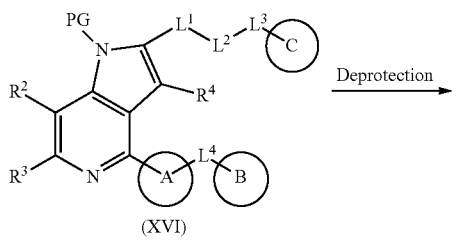

(XVI)

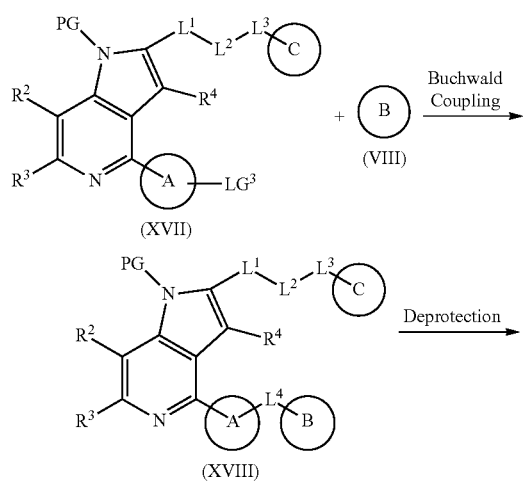

(I)

wherein PG is a suitable protecting group such as benzenesulfonyl, tert-butoxycarbonyl or the like, and the other symbols are as defined above.

Intermediate (XV) can be produced according to a methods analogous to the synthesis of intermediate (II).

Compound (I) wherein $R^1$ is a hydrogen atom can alternatively be prepared by subjecting intermediate (XVII) to Buchwald coupling with intermediate (VIII) to give intermediate (XVIII) as shown in Scheme 12. Acid or base catalyzed deprotection of intermediate (XVIII) can give compound (I).

Scheme 12: Preparation of compound (I)

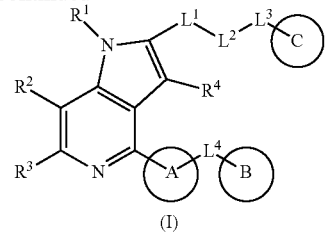

-continued (I)

wherein each symbol is as defined above.

Intermediate (XVII) can be produced according to a method analogous to the synthesis of intermediate (VII).

Compound (I) can alternatively be prepared by subjecting intermediate (II) to Stille coupling with intermediate (XIX) as shown in Scheme 13.

Scheme 13: Preparation of compound (I)

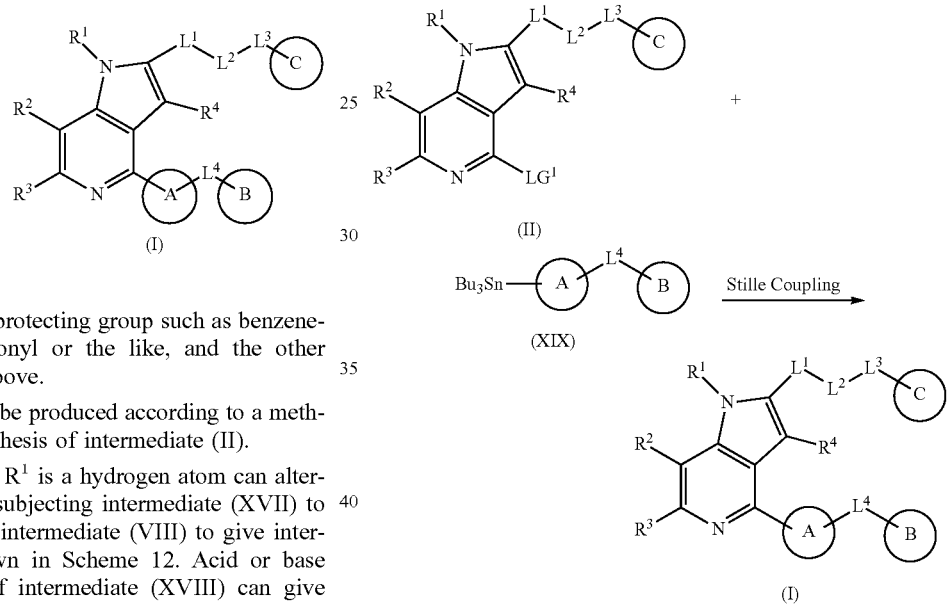

wherein each symbol is as defined above.

Intermediate (XIX) can be produced according to the method known in literature or a method known per se or a method analogous thereto.

The Stille coupling is a palladium catalyzed C—C bond forming reaction which involves coupling of an organotin compound (also known as organostannanes) with a halide or a pseudohalide [Angew. Chem. Int. Ed. Engl. 1986, 25, 508-524; J. Org. React. 1998, 50, 1-652]. Examples of the palladium catalysts to be used include tetrakistriphenylphosphinepalladium, 1,1-bis(diphenylphosphino)ferrocene-palladium(II) dichloride dichloromethane complex and the like.

Compound (I) obtained in each scheme can be isolated and purified by known separation and purification means such as concentration, concentration under reduced pressure, solvent extraction, crystallization, recrystallization, phase transfer, chromatography and the like. In addition, each material compound used in each scheme can be isolated and purified by those similar to the above-mentioned known separation and purification means. The material compound may be used directly in the next step as the reaction mixture without isolation.

When compound (I) has isomers such as an optical isomer; a stereoisomer, a regioisomer and a rotamer and the like, such isomers and a mixture thereof are also encompassed in compound (I). For example, when compound (I) has an optical isomer, the optical isomer resolved from racemate is also encompassed in compound (I). These isomers can be obtained as single products according to synthetic methods known per se, separation methods known per se (e.g., concentration, solvent extraction, column chromatography, recrystallization etc.), optical resolutions (e.g., fractional recrystallization method, chiral column method, diastereomer method and the like).

Compound (I) may be a crystal, and the crystal form may be single or a mixture of crystal forms, both of which are encompassed in compound (I). The crystal can be produced according to a crystallization method known per se.

The compound (I) may be a solvate (e.g., hydrate) or a non-solvate (e.g., non-hydrate etc.) and both are encompassed in compound (I).

The compounds labeled with isotopes (e.g., $^3$H, $^{14}$C, $^{35}$S, $^{125}$I etc.) and the like are also encompassed in compound (I).

A deuterium conversion form wherein 1H is converted to $^2$H(D) is also encompassed in compound (I).

Compound (I) labeled or substituted with an isotope can be used as, for example, a tracer (PET tracer) used for Positron Emission Tomography (PET), and therefore, it is useful in the fields of medical diagnosis and the like.

Since the compound of the present invention has a superior TLR7, TLR9, TLR7/8, TLR7/9 or TLR7/8/9 inhibitory action, shows low toxicity (e.g., phototoxicity, acute toxicity, chronic toxicity, genetic toxicity, reproductive toxicity, cardiac toxicity, drug interactions, carcinogenicity and the like, particularly phototoxicity), and is superior in stability (particularly metabolic stability), pharmacokinetics (absorption, distribution, metabolism, excretion etc.) and high solubility, it is useful as a medicament. The compound of the present invention has a TLR7, TLR9, TLR7/8, TLR7/9 or TLR7/8/9 inhibitory action to mammals (e.g., mouse, rat, hamster, rabbit, cat, dog, bovine, horse, sheep, monkey, human etc.), and can be used for the prophylaxis or treatment of the following diseases and symptoms:

(1) inflammatory disease (e.g., acute pancreatitis, chronic pancreatitis, asthma, adult respiratory distress syndrome, chronic obstructive pulmonary diseases (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, stomach mucosa injury, meningitis, spondylitis, arthritis, dermatitis, chronic pneumonia, bronchitis, lung infarction, silicosis, pulmonary sarcoidosis, etc.), (2) autoimmune disease (e.g., psoriasis, rheumatoid arthritis, inflammatory bowel disease (e.g., Crohn's disease, ulcerative colitis), Sjogren's syndrome, Behcet's disease, multiple sclerosis, systemic lupus erythematosus, ankylopoietic spondylarthritis, polymyositis, dermatomyositis (DM), polyarteritis nodosa (PN), mixed connective tissue disease (MCTD), scleroderma, lupus erythematosus profundus, chronic thyroiditis, Graves' disease, autoimmune gastritis, Type I and Type II diabetes, autoimmune hemolytic anemia, autoimmune neutrophenia, thrombocytopenia, atopic dermatitis, chronic active hepatitis, myasthenia gravis, graft-versus-host disease, Addison's disease, abnormal immune response, arthritis, dermatitis, radiodermatitis, etc.), (3) osteoarticular degenerative disease (e.g., rheumatoid arthritis, osteoporosis, osteoarthritis, etc.), (4) neoplastic disease (e.g., malignant tumor, neovascular glaucoma, infantile hemangioma, multiple myeloma, acute myeloblastic leukemia, chronic sarcoma, multiple myeloma, chronic myeloid leukemia, metastasis melanoma, Kaposi's sarcoma, vascular proliferation, cachexia, metastasis of breast cancer and the like, cancer (e.g., colorectal cancer (e.g., familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic ductal carcinoma, etc.), stomach cancer (e.g., papillary adenocarcinoma, mucinous adenocarcinoma, adenosquamous carcinoma, etc.), breast cancer (e.g., infiltrating ductal carcinoma, noninfiltrating ductal carcinoma, inflammatory breast cancer, etc.), ovarian cancer (e.g., epithelial ovarian cancer, extragonadal germ cell tumor, ovarian germ cell tumor, ovarian low malignant potential tumor, etc.), prostate cancer (e.g., hormone-dependent prostate cancer, hormone-independent prostate cancer, etc.), liver cancer (e.g., primary liver cancer, extrahepatic bile duct cancer, etc.), thyroid cancer (e.g., medullary thyroid carcinoma, etc.), kidney cancer (e.g., renal cell carcinoma, transitional cell carcinoma of renal pelvis and urinary duct, etc.) uterine cancer, brain tumor (e.g., pineal astrocytoma, pilocytic astrocytoma, diffuse astrocytoma, anaplastic astrocytoma, etc.), melanoma, sarcoma, urinary bladder cancer, hematologic cancer including multiple myeloma and the like, pituitary adenoma, glioma, acoustic schwannoma, retina sarcoma, pharyngeal cancer, laryngeal cancer, tongue cancer, thymoma, esophageal cancer, duodenal cancer, colon cancer, rectal cancer, hepatoma, pancreatic endocrine tumor, cholangiocarcinoma, gallbladder cancer, penile cancer, ureteral cancer, testicular tumor, vulvar cancer, cervical cancer, cancer of uterine body, uterus sarcoma, trophoblastic disease, vaginal cancer, skin cancer, mycosis fungoides, basal cell tumor, soft tissue sarcoma, malignant lymphoma, Hodgkin's disease, myelodysplastic syndrome, acute lymphocytic leukemia, chronic lymphocytic leukemia, adult T-cell leukemia, chronic myeloproliferative disorder, pancreatic endocrine tumor, fibrous histiocytoma, leiomyosarcoma, rhabdomyosarcoma, unknown primary cancer)).

The pharmaceutical agent of the present invention can be used as an agent for the prophylaxis or treatment of, preferably, autoimmune disease, inflammatory disease, osteoarticular degenerative disease or neoplastic disease, particularly preferably, psoriasis, rheumatoid arthritis, inflammatory bowel disease (e.g., Crohn's disease, ulcerative colitis), Sjogren's syndrome, Behcet's disease, multiple sclerosis, systemic lupus erythematosus.

As used herein, the "prophylaxis" of the above-mentioned diseases means, for example, administration of a pharmaceutical containing the compound of the present invention to patients before onset of a disease but having a high risk of the onset due to some factor associated with the disease or patients who developed the disease but without subjective symptoms, or administration of a pharmaceutical containing the compound of the present invention to patients having a risk of recurrence of disease after treatment of the disease.

In particular, the compound of the present invention is useful for the prophylaxis or treatment of TLR7, TLR9, TLR7/8, TLR7/9 or TLR7/8/9-related diseases such as autoimmune diseases, inflammatory diseases and the like, in particular, systemic lupus erythematosus, Sjogren's syndrome, rheumatoid arthritis, psoriasis, inflammatory bowel disease and the like.

Since the compound of the present invention is superior in metabolic stability, it can be expected to have an excellent therapeutic effect on the above-mentioned diseases even in a low dose.

Since the compound of the present invention has low toxicity, a pharmaceutical composition containing the compound of the present invention (hereinafter to be referred to as the "medicament of the present invention") is obtained as, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable films, oral cavity mucosa patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparations, pulmonary preparation (inhalant), eye drop and the like by using the compound of the present invention alone or along with a pharmacologically acceptable carrier according to a method known per se as a production method of pharmaceutical preparations (e.g., the method described in the Japanese Pharmacopoeia etc.). It can be safely administered orally or parenterally (e.g., intravenous, intramuscular, subcutaneous, intraorgan, intranasal, intradermal, instillation, intracerebral, rectal, vaginal, intraperitoneal, intratumor, tumor proximal administration, administration to a lesion and the like).

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener, absorbent, humectant and the like can also be appropriately used in suitable amounts.

Examples of the excipient include lactose, sucrose, D-mannitol, D-sorbitol, starch, pregelatinized starch, corn-starch, dextrin, microcrystalline cellulose, low-substituted hydroxypropyl cellulose, sodium carboxymethylcellulose, gum arabic, pullulan, light anhydrous silicic acid, synthetic aluminum silicate, magnesium aluminate metasilicate and the like.

Examples of the lubricant include magnesium stearate, calcium stearate, talc, colloidal silica and the like.

Examples of the binder include pregelatinized starch, microcrystalline cellulose, sucrose, gum arabic, D-mannitol, trehalose, dextrin, pullulan, hydroxypropyl cellulose, hydroxypropyl methylcellulose, polyvinylpyrrolidone, starch, saccharose, gelatin, methylcellulose, carboxymethylcellulose, sodium carboxymethylcellulose and the like.

Examples of the disintegrant include lactose, sucrose, starch, carboxymethylcellulose, calcium carboxymethylcellulose, croscarmellose sodium, sodium carboxymethyl starch, light anhydrous silicic acid, low-substituted hydroxypropyl cellulose and the like.

Examples of the solvent include water for injection, physiological saline, Ringer's solution, alcohol, propylene glycol, polyethylene glycol, macrogol, sesame oil, corn oil, olive oil, cottonseed oil and the like.

Examples of the solubilizing agent include polyethylene glycol, propylene glycol, D-mannitol, trehalose, benzyl benzoate, ethanol, tris(hydroxymethyl)aminomethane, cholesterol, triethanolamine, sodium carbonate, sodium citrate, sodium salicylate, sodium acetate and the like.

Examples of the suspending agent include surfactants such as stearyltriethanolamine, sodium lauryl sulfate, laurylaminopropionic acid, lecithin, benzalkonium chloride, benzethonium chloride, glyceryl monostearate and the like; and hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose, polysorbate, polyoxyethylene hydrogenated castor oil and the like.

Examples of the isotonicity agent include glucose, D-sorbitol, sodium chloride, glycerol, D-mannitol and the like.

Examples of the buffer include buffers such as phosphates, acetates, carbonates, citrates and the like, and the like.

Examples of the soothing agent include benzyl alcohol and the like.

Examples of the preservative include p-hydroxybenzoate, chlorobutanol, benzyl alcohol, phenethyl alcohol, dehydroacetic acid, sorbic acid and the like.

Examples of the antioxidant include sulfites, ascorbic acid, α-tocopherols and the like.

Examples of the colorant include water-soluble edible tar pigments (e.g., Food Color Red Nos. 2 and 3, Food Color Yellow Nos. 4 and 5, Food Color Blue Nos. 1 and 2), water insoluble lake pigments (e.g., aluminum salts of the above-mentioned water-soluble edible tar pigment), natural pigments (e.g., beta-carotene, chlorophyll, red iron oxide) and the like.

Examples of the sweetening agent include saccharin sodium, dipotassium glycyrrhizinate, aspartame, stevia and the like.

While the content of the compound of the present invention in the medicament of the present invention varies depending on the dosage form, dose of the compound of the present invention, and the like, it is, for example, about 0.1 to 100 wt %, preferably about 0.1-95 wt %.

While the dose of the compound of the present invention varies depending on the subject of administration, administration route, target disease, symptom and the like, for example, for oral administration to a systemic lupus erythematosus patient (adult, about 60 kg weight), it is generally about 0.1-about 20 mg/kg body weight, preferably about 0.2-about 10 mg/kg body weight, more preferably about 0.5-about 10 mg/kg body weight, which is desirably administered once to several times (e.g., once to 3 times) a day depending on the symptom.

The compound of the present invention can be administered as a single active substance, or can be administered in combination with other medicaments such as other drugs used in the treatment of TLR7, TLR9, TLR7/8, TLR7/9 or TLR7/8/9-related diseases such as autoimmune diseases, inflammatory diseases and the like, in particular, systemic lupus erythematosus, Sjogren's syndrome, rheumatoid arthritis, psoriasis, inflammatory bowel disease and the like (hereinafter to be abbreviated as concomitant drug).

Examples of the concomitant drug include
(1) non-steroidal antiinflammatory drugs (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor, COX-2 selective inhibitor and the like)
salicylic acid derivatives (e.g., celecoxib, aspirin), etoricoxib, valdecoxib, diclofenac, indomethacin, loxoprofen and the like.

(iii) nitric oxide-releasing NSAIDs (2) disease-modifying anti-rheumatic drugs (DMARDs)

(i) Gold preparation
auranofin and the like.

(ii) penicillamine
D-penicillamine and the like.

(iii) aminosalicylic acid preparation
sulfasalazine, mesalazine, olsalazine, balsalazide and the like.

(iv) antimalarial drug
chloroquine and the like.

(v) pyrimidine synthesis inhibitor
leflunomide and the like.

(vi) prograf (3) anti-cytokine drug (I) protein drug (i) TNF inhibitor
etanercept, infliximab, adalimumab, certolizumab pegol, golimumab, PASSTNF-α, soluble TNF-α receptor, TNF-α binding protein, anti-TNF-α antibody and the like.

(ii) interleukin-1 inhibitor
anakinra (interleukin-1 receptor antagonist), soluble interleukin-1 receptor and the like.

(iii) interleukin-6 inhibitor
tocilizumab (anti-interleukin-6 receptor antibody), anti-interleukin-6 antibody and the like.

(iv) interleukin-10 drug
interleukin-10 and the like.

(v) interleukin-12/23 inhibitor
ustekinumab, briakinumab (anti-interleukin-12/23 antibody) and the like.

(vi) B cell activation inhibitor
rituxan, benlysta and the like.

(vii) co-stimulatory molecules-related protein preparation
abatacept and the like.

(II) non-protein drug (i) MAPK inhibitor
BMS-582949 and the like.

(ii) gene modulator
inhibitor of molecule involved in signal transduction, such as NF-κ, NF-κB, IKK-1, IKK-2, AP-1 and the like, and the like.

(iii) cytokine production inhibitor
iguratimod, tetomilast and the like.

(iv) TNF-α converting enzyme inhibitor (v) interleukin-1β converting enzyme inhibitor
VX-765 and the like.

(vi) interleukin-6 antagonist
HMPL-004 and the like.

(vii) interleukin-8 inhibitor
IL-8 antagonist, CXCR1 & CXCR2 antagonist, reparixin and the like.

(viii) chemokine antagonist
CCR9 antagonist (CCX-282, CCX-025), MCP-1 antagonist and the like.

(ix) interleukin-2 receptor antagonist
denileukin, diftitox and the like.

(x) therapeutic vaccines
TNF-α vaccine and the like.

(xi) gene therapy drug
gene therapy drugs aiming at promoting the expression of gene having an anti-inflammatory action such as interleukin-4, interleukin-10, soluble interleukin-1 receptor, soluble TNF-α receptor and the like.

(xii) antisense compound
ISIS-104838 and the like.

(4) integrin inhibitor
natalizumab, vedolizumab, AJM300, TRK-170, E-6007 and the like.

(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon, intravenous immunoglobulin, anti-thymocyte globulin, RSLV-132 and the like.

(6) proteasome inhibitor
bortezomib, MLN9708, MLN2238, delanzomib and the like.

(7) steroid
dexamethasone, hexestrol, methimazole, betamethasone, triamcinolone, triamcinolone acetonide; fluocinonide, fluocinolone acetonide, predonisolone, methylpredonisolone, cortisone acetate, hydrocortisone, fluorometholone, beclomethasone dipropionate, estriol and the like.

(8) angiotensin converting enzyme inhibitor
enalapril, captopril, ramipril, lisinopril, cilazapril, perindopril and the like.

(9) angiotensin II receptor antagonist
candesartan, candesartan cilexetil, azilsartan, azilsartan medoxomil, valsartan, irbesartan, olmesartan, eprosartan and the like.

(10) diuretic drug
hydrochlorothiazide, spironolactone, furosemide, indapamide, bendrofluazide, cyclopenthiazide and the like.

(11) cardiotonic drug
digoxin, dobutamine and the like.

(12) β receptor antagonist
carvedilol, metoprolol, atenolol and the like.

(13) Ca sensitizer
MCC-135 and the like.

(14) Ca channel antagonist
nifedipine, diltiazem, verapamil and the like.

(15) anti-platelet drug, anticoagulator
heparin, aspirin, warfarin and the like.

(16) HMG-CoA reductase inhibitor
atorvastatin, simvastatin and the like.

(17) contraceptive (i) sex hormone or derivatives thereof
gestagen or a derivative thereof (e.g., progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.

(ii) antiestrogen
   ormeloxifene, mifepristone, Org-33628 and the like.
(iii) spermatocide
   ucarcide and the like.

(18) others
(i) T cell inhibitors
(ii) inosine monophosphate dehydrogenase (IMPDH) inhibitor
   mycophenolate mofetil and the like.
(iii) adhesion molecule inhibitor
   ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
   V-85546 and the like.
(vii) glucose-6-phosphate dehydrogenase inhibitor
(viii) dihydroorotate dehydrogenase (DHODH) inhibitor
(ix) phosphodiesterase IV (PDE IV) inhibitor
   roflumilast, CG-1088 and the like.
(x) phospholipase $A_2$ inhibitor
(xi) iNOS inhibitor
   VAS-203 and the like.
(xii) microtubule stimulating drug
   paclitaxel and the like.
(xiii) microtubule inhibitor
   reumacon and the like.
(xiv) MHC class II antagonist
(xv) prostacyclin agonist
   iloprost and the like.
(xvi) CD4 antagonist
   zanolimumab and the like.
(xvii) CD23 antagonist
(xviii) LTB4 receptor antagonist
   DW-1305 and the like.
(xix) 5-lipoxygenase inhibitor
   zileuton and the like.
(xx) cholinesterase inhibitor
   galanthamine and the like.
(xxi) tyrosine kinase inhibitor
   Tyk2 inhibitor (the compounds described in WO 2010/142752) and the like.
(xxii) cathepsin B inhibitor
(xxiii) adenosine deaminase inhibitor
   pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
   synvisc (hylan G-F 20), orthovisc and the like.
(xxix) glucosamine sulfate
(xxx) amiprilose
(xxxi) CD-20 inhibitor
   rituximab, ibritumomab, tositumomab, ofatumumab and the like.
(xxxii) BAFF inhibitor
   belimumab, tabalumab, atacicept, A-623 and the like.

(xxxiii) CD52 inhibitor
   alemtuzumab and the like.
(xxxiv) IL-17 inhibitor
   secukinumab (AIN-457), LY-2439821, AMG827 and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, anticonvulsant, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, antiasthmatic, therapeutic agent for pollakisuria/anischuria, antipruritic agent, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial agent
(i) sulfa drug
   sulfamethizole, sulfisoxazole, sulfamonomethoxine, sulfamethizole, salazosulfapyridine, silver sulfadiazine and the like.
(ii) quinolone antibacterial agent
   nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like.
(iii) antiphthisic
   isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
   diaphenylsulfone, rifampicin and the like.
(v) antiviral drug
   idoxuridine, acyclovir, vidarabine, gancyclovir and the like.
(vi) anti-HIV agent zidovudine, didanosine, zalcitabine,
   indinavir sulfate ethanolate, ritonavir and the like.
(vii) antispirochetele
(viii) antibiotic
   tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor, cefalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [Journal of Antibiotics (J. Antibiotics), 38, 877-885 (1985)], azole compounds [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) antifungal agent
(i) polyethylene antibiotic (e.g., amphotericin B, nystatin, trichomycin, etc.)
(ii) griseofulvin, pyrrolnitrin and the like.
(iii) cytosine metabolism antagonist (e.g., flucytosine)
(iv) imidazole derivative (e.g., econazole, clotrimazole, miconazole nitrate, bifonazole and croconazole)
(v) triazole derivative (e.g. fluconazole and itraconazole)
(vi) thiocarbamic acid derivative (e.g. trinaphthol), and the like.
(3) antiprotozoal agent
metronidazole, tinidazole, diethylcarbamazine citrate, quinine hydrochloride, quinine sulfate and the like.
(4) antitussive and expectorant drug
ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terbutaline, oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.
(5) sedative
chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.
(6) anesthetic
(6-1) local anesthetic
cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) general anesthetic
(i) inhalation anesthetic (e.g., ether, halothane, nitrous oxide, isoflurane, enflurane, etc.)
(ii) intravenous anesthetic (e.g., ketamine hydrochloride, droperidol, thiopental sodium, thiamylal sodium, pentobarbital, etc.) and the like.
(7) antiulcer drug
histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.
(8) antiarrhythmic agent
(i) Na channel blocker (e.g., quinidine, procainamide, disopyramide, ajmaline, lidocaine, mexiletine, phenytoin)
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride)
(iii) K channel blocker (e.g., amiodarone)
(iv) Ca channel blocker (e.g., verapamil, diltiazem) and the like.
(9) hypotensive diuretic drug
hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant
heparin sodium, sodium citrate, activated protein C, tissue factor pathway inhibitor, antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase and the like.
(11) tranquilizer
diazepam, lorazepam, oxazepam, chlordiazepoxide, medazepam, oxazolam, cloxazolam, clotiazepam, bromazepam, etizolam, fludiazepam, hydroxyzine and the like.
(12) antipsychotic
chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.
(13) antitumor drug
6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.
(14) antihypolipidemic drug
clofibrate, ethyl 2-chloro-3-[4-(2-methyl-2-phenyl-propoxy)phenyl]propionate [Chem. Pharm. Bull, 38, 2792-2796 (1990)], pravastatin, simvastatin, probucol, bezafibrate, clinofibrate, nicomol, cholestyramine, dextran sulfate sodium and the like.
(15) muscle relaxant
pridinol, tubocurarine, pancuronium, tolperisone hydrochloride, chlorphenesin carbamate, baclofen, chlormezanone, mephenesin, chlorzoxazone, eperisone, tizanidine and the like.
(16) anticonvulsant
phenytoin, ethosuximide, acetazolamide, chlordiazepoxide, trimethadione, carbamazepine, phenobarbital, primidone, sulthiame, sodium valproate, clonazepam, diazepam, nitrazepam and the like.
(17) antidepressant
imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.
(18) antiallergic drug
diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.
(19) cardiac
trans-π-oxocamphor, terephyllol, aminophylline, etilefrine, dopamine, dobutamine, denopamine, bencirin, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic

Hexamethonium bromide, pentolinium, mecamylamine, ecarazine, clonidine, diltiazem, nifedipine and the like.

(23) antidiabetic drug tolbutamide, chlorpropamide, acetohexamide, glibenclamide, tolazamide, acarbose, epalrestat, troglitazone, glucagon, glymidine, glipizide, phenformin, buformin, metformin and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like. (28) therapeutic agent for pollakisuria/anischuria flavoxate hydrochloride and the like.

(29) therapeutic agent for atopic dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(31) hypertensive drug dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

The dosage form of concomitant drugs is not particularly limited, and is acceptable as long as the compound of the present invention is combined with concomitant drugs at the time of administration. Examples of such dosage forms are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order).

These forms of administration are summarized below and abbreviated as a combination drug of the present invention.

When administering the combination drug of the present invention, the concomitant drug and the compound of the present invention can be administered simultaneously. Alternatively, the compound of the present invention can be administered after a concomitant drug is administered, or a concomitant drug can be administered after the compound of the present invention is administered. When administering at different times, the time difference depends upon the active ingredients to be administered, drug forms and methods of administration.

For example, when the concomitant drug or a pharmaceutical composition thereof is administered first, the compound of the present invention or a pharmaceutical composition thereof can be administered within 1 min. to 3 days, preferably within 10 min to 1 day and more preferably within 15 min to 1 hour after the concomitant drug or a pharmaceutical composition thereof is administered. When the compound of the present invention or a pharmaceutical composition thereof is administered first, the concomitant drug or a pharmaceutical composition thereof can be administered within 1 min to 1 day, preferably within 10 min to 6 hours and more preferably within 15 min to 1 hour after the compound of the present invention or a pharmaceutical composition thereof is administered.

If there are no problems with side effects of the concomitant drugs, any dosages can be set. A dosage as a concomitant drug varies depending on dosages, administration subjects, administration routes, target diseases, symptoms, etc. For example, in the case of oral administration in patients with systemic lupus erythematosus (adults, body weight of approximately 60 kg), a dosage range is generally about 0.1 to 20 mg/kg body weight, preferably from about 0.2 to 10 mg/kg body weight and more preferably from about 0.5 to 10 mg/kg body weight. It is preferable that this dosage is administered once daily to several times daily (e.g., once to 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or(and) the concomitant drug can be combined with a pharmaceutically acceptable carrier according to the known method to prepare a pharmaceutical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal, venous routes etc.).

The pharmaceutically acceptable carriers that can be used for manufacturing the combination drug of the present invention can be the same as those used in the medicament of the present invention as mentioned above.

A mixing ratio between the compound of the present invention and the concomitant drug in the combination drug of the present invention can be selected appropriately based on the administration subjects, administration routes, diseases and the like.

The concomitant drug in the combination drug of the present invention can be combined at an appropriate proportion if two or more drugs are combined.

A dosage of the concomitant drug can be selected appropriately based on the dosages used clinically. In addition, a mixing ratio between the compound of the present invention and the concomitant drug can be selected appropriately based on the administration subjects, administration routes, target diseases, symptoms, combinations, etc. For example, if the administration subject is humans, a concomitant drug may be used in an amount ranging from about 0.01 to 100 parts by weight relative to 1 part by weight of the compound of the present invention.

For example, the content of the compound of the present invention in the combination drug of the present invention varies with the form of formulations. Generally, it is present in a range from about 0.01 to 99.9 wt %, preferably from about 0.1 to about 50 wt % and more preferably from about 0.5 to about 20 wt % relative to the entire formula.

The content of the concomitant drug in the combination drug of the present invention varies with the form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the form of formulations. Generally it is present in a range from about 1 to 99.99 wt % and preferably from about 10 to about 90-wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLE

The present invention is explained in detail in the following by referring to Examples, Formulation Examples and Experimental Examples and which are merely exemplified and not to be construed as limitative, and the invention may be changed within the scope of the present invention. In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bound silica gel. The ratios of elution solvents are volume mixing ratios, unless otherwise specified.

$^1$H NMR (proton nuclear magnetic resonance spectrum) was measured by Fourier-transform type NMR. Peaks with very mild protons such as a hydroxyl group, an amino group and the like are not described.

In the following Reference Examples and Examples, mass spectrum (MS), nuclear magnetic resonance spectrum (NMR) and melting point were measured by the following apparatus.

MS (mass spectrum) was measured by LC/MS (liquid chromatograph mass spectrometer). As the ionization method, API (Atmospheric Pressure Ionization, atmospheric pressure chemical ionization) method or ESI (Electron Spray Ionization) method was used. The data indicate measured value (found) found. Generally, a molecular ion peak is observed. In the case of a compound having an amino group ($—NH_2$), a peak after elimination of $NH_3$ may be observed as a fragment ion. In the case of a salt, a molecular ion peak or fragment ion peak of free form is generally observed.

Synthesis of Intermediates

Intermediate 1-I: 1-methyl-4-[4-(4,4,5,5-tetramethyl-1,3,2-dioxaborolan-2-yl)phenyl]piperazine

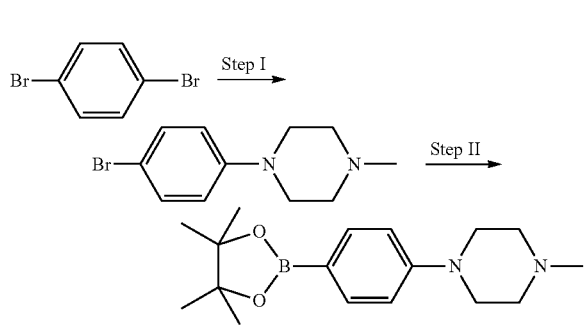

Intermediate 1-I

Intermediate 1-I was prepared from 1,4-dibromobenzene in two steps according to the procedure described in WO 2008/088881.

Intermediates 1-II to 1-VII as shown in Table 2 were prepared in the same manner as Intermediate 1-I.

TABLE 2

| Int. No. | IUPAC name | Structure | LCMS |
|---|---|---|---|
| 1-II | 1-isopropyl-4-[4-(4,4,5,5-tetramethyl-1,3,2-dioxaborolan-2-yl)phenyl]piperazine | 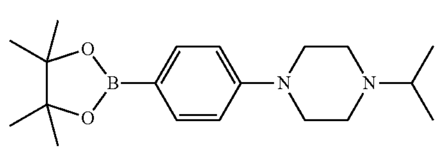 [SMILES: CC(C)N1CCN(c2ccc(B3OC(C)(C)C(C)(C)O3)cc2)CC1] | LCMS: m/z 331.3 [M$^+$ + 1] |

TABLE 2-continued

| Int. No. | IUPAC name | Structure | LCMS |
|---|---|---|---|
| 1-III | tert-butyl 4-[4-(4,4,5,5-tetramethyl-1,3,2-dioxaborolan-2-yl)phenyl]piperazine-1-carboxylate | 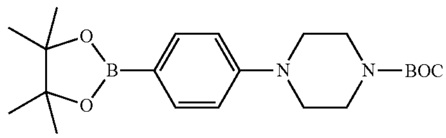 [SMILES: CC(C)(C)OC(=O)N1CCN(c2ccc(B3OC(C)(C)C(C)(C)O3)cc2)CC1] | LCMS: m/z 389.2 [M$^+$ + 1] |
| 1-IV | 1-ethyl-4-[4-(4,4,5,5-tetramethyl-1,3,2-dioxaborolan-2-yl)phenyl]piperazine | 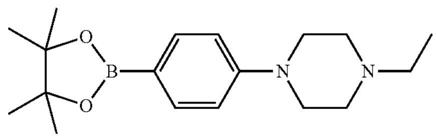 | LCMS: m/z 317.2 [M$^+$ + 1] |
| 1-V | 1-[4-(4,4,5,5-tetramethyl-1,3,2-dioxaborolan-2-yl)phenyl]piperidin-4-ol | 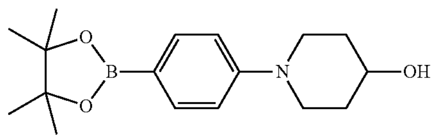 [SMILES: CC1(C)OB(c2ccc(N3CCC(O)CC3)cc2)OC1(C)C] | LCMS: m/z 304.2 [M$^+$ + 1] |
| 1-VI | ethyl 1-[4-(4,4,5,5-tetramethyl-1,3,2-dioxaborolan-2-yl)phenyl]piperidine-4-carboxylate | 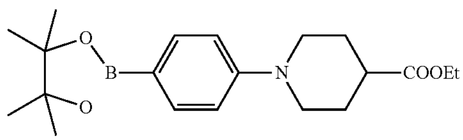 | LCMS: m/z 360.2 [M$^+$ + 1] |
| 1-VII | tert-butyl 4-[3-(4,4,5,5-tetramethyl-1,3,2-dioxaborolan-2-yl)phenyl]piperazine-1-carboxylate | 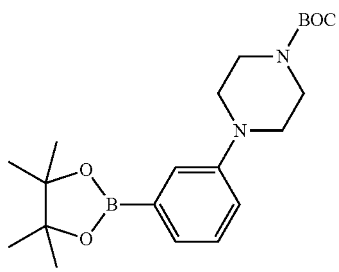 [SMILES: CC(C)(C)OC(=O)N1CCN(c2cccc(B3OC(C)(C)C(C)(C)O3)c2)CC1] | LCMS: m/z 389.2 [M$^+$ + 1] |

Intermediate 1-VIII: tert-butyl 4-[4-(4,4,5,5-tetramethyl-1,3,2-dioxaborolan-2-yl)phenyl]-3,6-dihydro-2H-pyridine-1-carboxylate

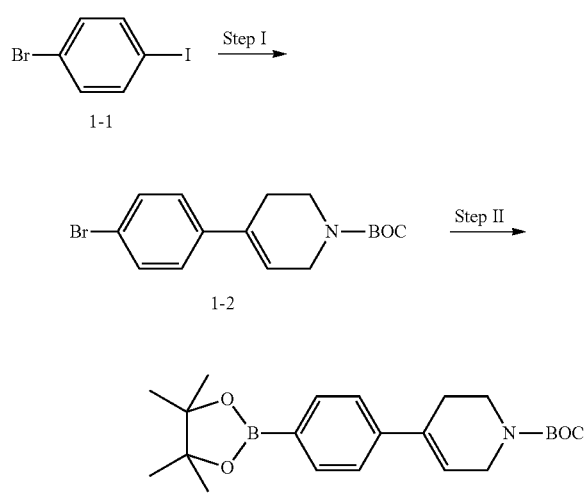

Step I: tert-butyl 4-(4-bromophenyl)-3,6-dihydro-2H-pyridine-1-carboxylate (1-2)

A mixture of 1-bromo-4-iodobenzene 1-1 (6 g, 212 mmol), tert-butyl 4-(4,4,5,5-tetramethyl-1,3,2-dioxaborolan-2-yl)-3,6-dihydro-2H-pyridine-1-carboxylate (4.62 g, 149.4 mmol) and K$_2$CO$_3$ (8.76 g, 635.4 mmol) in a 4:1 mixture of dioxane/water (40 mL) was degassed in a stream of argon for 15 minutes. To the mixture was added 1,1-bis(diphenylphosphino)ferrocene-palladium(II) dichloride dichloromethane complex (0.345 g, 0.42 mmol), and the reaction mixture was again degassed for additional 15 minutes. After stirring at 100° C. for 24 hours, the volatiles were removed by evaporation, and the obtained crude reaction mixture was diluted with water (100 mL), followed by extraction with ethyl acetate (75 mL×3). The combined organic layers were washed with brine (50 mL), dried over anhydrous Na$_2$SO$_4$, and concentrated under reduced pressure, followed by purification on silica gel column chromatography (100-200 mesh) using 10% EtOAc in hexanes to give the desired product 1-2 as a yellow syrup (3.8 g, 53%); LCMS: m/z 284.0 [M$^+$-t-Bu+2].

1-Bromo-4-iodobenzene 1-1 may be commercially available, or can also be produced according to a method known per se or a method analogous thereto.

Step II: tert-butyl 4-[4-(4,4,5,5-tetramethyl-1,3,2-dioxaborolan-2-yl)phenyl]-3,6-dihydro-2H-pyridine-1-carboxylate (Intermediate 1-VIII)

A mixture of 1-2 (3.8 g, 112 mmol), bis(pinacolato) diboron (3.41 g, 134 mmol) and KOAc (3.30 g, 336 mmol) in DMSO (50 mL) was degassed in a stream of argon for 15 minutes. To the mixture was added 1,1-bis(diphenylphosphino) ferrocene-palladium(II) dichloride dichloromethane complex (0.182 g, 0.22 mmol), and the reaction mixture was again degassed for additional 15 minutes. After stirring at 100° C. for 24 hours, the volatiles were removed by evaporation, and the obtained crude reaction mixture was diluted with water (50 mL), followed by extraction with ethyl acetate (50 mL×3). The combined organic layers were washed with brine (50 mL), dried over anhydrous Na$_2$SO$_4$, and concentrated under reduced pressure, followed by purification on silica gel column chromatography (100-200 mesh) using 10% EtOAc in hexanes to give the desired product Intermediate 1-VIII as a yellow solid (3.5 g, 81%); LCMS: m/z 330.1 [M$^+$-t-Bu+2].

Intermediate 1-IX: tert-butyl 4-[4-(4,4,5,5-tetramethyl-1,3,2-dioxaborolan-2-yl)phenyl]piperidine-1-carboxylate

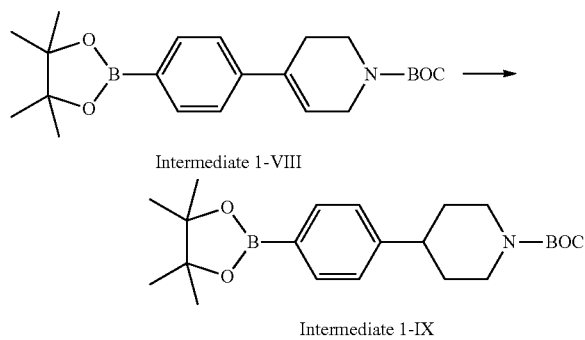

A solution of Intermediate 1-VIII (4.1 g, 10.64 mmol) in EtOAc (60 mL) was treated with Pd/C (10% dry, 0.5 g), and the resulting reaction mixture was stirred under hydrogen atmosphere at room temperature for 18 hours. The catalyst was removed by filtration and washed with EtOAc (100 mL). The obtained filtrate was concentrated in vacuo to give the desired product Intermediate 1-IX as a white solid (3.4 g, 85%).

Intermediate 1-X: 4-methyl-1-[4-(4,4,5,5-tetramethyl-1,3,2-dioxaborolan-2-yl)phenyl]piperidin-4-ol

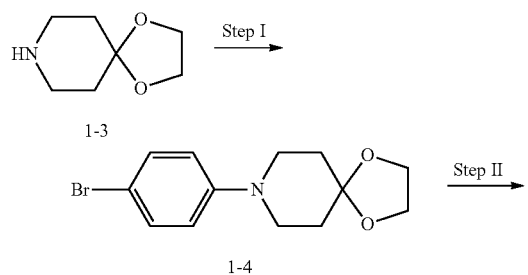

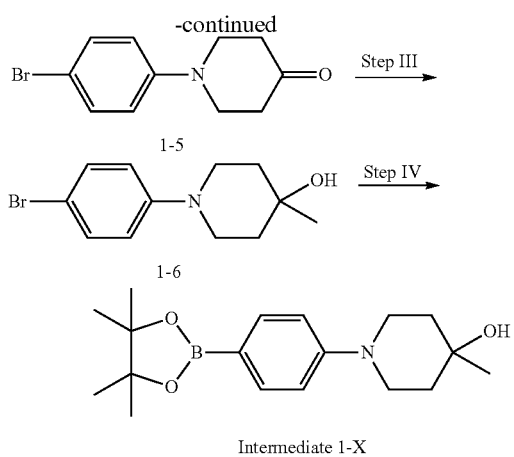

Intermediate 1-X

Step I: 8-(4-bromophenyl)-1,4-dioxa-8-azaspiro[4.5]decane (1-4)

A mixture of 1-3 (5.5 g, 38.4 mmol), 1,4-dibromobenzene (23 g, 96.1 mmol), BINAP (1.43 g, 7.6 mmol) and Cs$_2$CO$_3$ (18.70 g, 57.6 mmol) in 1,4-dioxane (150 mL) was degassed in a stream of argon for 30 minutes. To the mixture was added tris(dibenzylideneacetone)dipalladium(0) (0.703 g, 7.60 mmol), and the reaction mixture was again degassed for additional 15 minutes. After stirring at 100° C. for 18 hours, the volatiles were removed by evaporation, and the obtained residue was diluted with water (100 mL), followed by extraction with ethyl acetate (150 mL×3). The combined organic layers were washed with brine (150 mL), dried over anhydrous Na$_2$SO$_4$ and concentrated under reduced pressure. The obtained residue was purified by silica gel column chromatography (100-200 mesh) using 8% EtOAc in hexanes to give the desired product 1-4 as a yellow solid (3.1 g, 26%); LCMS: m/z 300.0[M$^+$+1].

Step II: 1-(4-bromophenyl)piperidin-4-one (1-5)

To a solution of 1-4 (3.0 g, 10.0 mmol) in methanol (15 mL) was added 1N aq. HCl (15 mL), and the mixture was stirred for 16 hours at 90° C. The volatiles were removed by evaporation, and the obtained residue was diluted with water (20 mL), and the mixture was basified using saturated aq. NaHCO$_3$ solution (50 mL) to pH 9, followed by extraction with ethyl acetate (50 mL×3). The combined organic layers were washed with brine (50 mL), dried over anhydrous Na$_2$SO$_4$ and concentrated under reduced pressure. The obtained residue was purified by silica gel column chromatography (100-200 mesh) using 10% EtOAc in hexanes to give the desired product 1-5 (1.5 g, 59%) as a yellow solid; LCMS: m/z 254.0 [M$^+$+1].

Step III: 1-(4-bromophenyl)-4-methyl-piperidin-4-ol (1-6)

To a solution of 1-5 (1.4 g, 5.5 mmol) in anhydrous tetrahydrofuran (20 mL) was added methylmagnesium bromide (1.4 M in THF) at −78° C. After addition, the reaction mixture was allowed to warm to 0° C. and held at this temperature for another 1 hour. The reaction mixture was diluted with saturated aqueous NH$_4$Cl solution (10 mL) and ethyl acetate (25 mL). The organic layer was separated, and the aqueous layer was extracted with ethyl acetate (25 mL×2). The combined organic layers were washed with brine (25 mL), dried over anhydrous $Na_2SO_4$ and concentrated under reduced pressure. The obtained residue was purified by silica gel column chromatography (100-200 mesh) using 8% EtOAc in hexanes to give the desired product 1-6 as a yellow solid (1.1 g, 74%); LCMS: m/z 270.0 [$M^++1$].

Step IV: 4-methyl-1-[4-(4,4,5,5-tetramethyl-1,3,2-dioxaborolan-2-yl)phenyl]piperidin-4-ol (Intermediate 1-X)

A mixture of 1-6 (0.9 g, 3.34 mmol), bis(pinacolato)diboron (1.0 g, 4.01 mmol) and KOAc (0.984 g, 10.03 mmol) in 1,4-dioxane (20 mL) was degassed in a stream of argon for 15 minutes. To the mixture was added 1,1-bis(diphenylphosphino)ferrocene-palladium(II) dichloride dichloromethane complex (0.055 g, 0.0669 mmol), and the reaction mixture was again degassed for additional 15 minutes. After stirring at 80° C. for 20 hours, the volatiles were removed by evaporation, and the obtained residue was diluted with water (50 mL), followed by extraction with ethyl acetate (50 mL×3). The combined organic layers were washed with brine (50 mL), dried over anhydrous $Na_2SO_4$ and concentrated under reduced pressure. The obtained residue was purified by silica gel column chromatography (100-200 mesh) using 10% EtOAc in hexanes to give the desired product Intermediate 1-X (1.0 g, 94%) as a yellow solid; LCMS: m/z 318.2 [$M^++1$].

Intermediate 1-XI: 1-(oxetan-3-yl)-4-[4-(4,4,5,5-tetramethyl-1,3,2-dioxaborolan-2-yl)phenyl]-3,6-dihydro-2H-pyridine

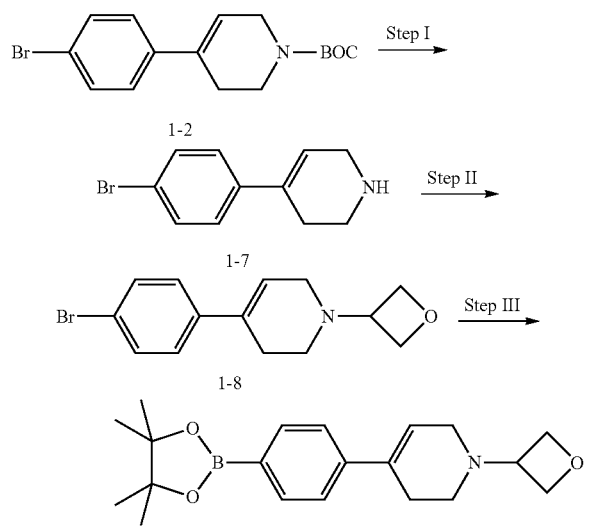

Intermediate 1-XI

Step I:
4-(4-bromophenyl)-1,2,3,6-tetrahydropyridine (1-7)

A solution of 1-2 (6.4 g, 18.93 mmol) in methanol (50 mL) was treated with 2 M HCl ether solution (20 mL) at 0° C. After stirring for 3 hours at room temperature, the volatiles were removed by evaporation, and the obtained residue was basifed with saturated aqueous $NaHCO_3$ solution (50 mL) to pH~8, and the mixture was diluted with ethyl acetate (150 mL). The organic layer was separated, and the aqueous layer was again extracted with ethyl acetate (50 mL×2). The combined organic layers were washed with brine (50 mL), dried over anhydrous $Na_2SO_4$ and concentrated under reduced pressure to give the desired product 1-7 as a white solid (3.8 g, 84%); LCMS: m/z 238.0 [$M^++1$], 240.0 [$M^++2$].

Step II: 4-(4-bromophenyl)-1-(oxetan-3-yl)-3,6-dihydro-2H-pyridine (1-8)

To a solution of 1-7 (1.10 g, 4.61 mmol) in methanol (15 mL) were added oxetan-3-one (1.66 g, 23.01 mmol), 4 Å molecular sieves (0.5 g) and zinc chloride (3.14 g, 23.01 mmol) successively. After stirring for 2 hours, the reaction mixture was treated with sodium cyanoborohydride at 0° C., and stirring was continued for another 4 hours. The reaction mixture was diluted with water (20 mL), ethyl acetate (25 mL) and saturated aqueous $NaHCO_3$ solution (10 mL). The organic layer was separated, and the aqueous layer was again extracted with ethyl acetate (25 mL×3). The combined organic layers were washed with brine (50 mL), dried over anhydrous $Na_2SO_4$ and concentrated under reduced pressure. The obtained residue was purified by silica gel column chromatography (100-200 mesh) using 50% EtOAc in hexanes to give the desired product 1-8 (1.1 g, 81%) as a colourless syrup; LCMS: m/z 294.0 [$M^++1$], 296.0 [$M^++2$].

Step III: 1-(oxetan-3-yl)-4-[4-(4,4,5,5-tetramethyl-1,3,2-dioxaborolan-2-yl)phenyl]-3,6-dihydro-2H-pyridine (Intermediate 1-XI)

A mixture of 1-8 (1.1 g, 3.74 mmol), bis(pinacolato)diboron (1.10 g, 4.48 mmol) and KOAc (1.09 g, 11.22 mmol) in 1,4-dioxane (10 mL) was degassed in a stream of argon for 15 minutes. To the mixture was added 1,1-bis(diphenylphosphino)ferrocene-palladium(II) dichloride dichloromethane complex (0.091 g, 0.112 mmol), and the reaction mixture was again degassed for additional 15 minutes. After stirring at 100° C. for 20 hours, the volatiles were removed by evaporation, and the obtained residue was diluted with water (50 mL), followed by extraction with ethyl acetate (50 mL×3). The combined organic layers were washed with brine (50 mL), dried over anhydrous $Na_2SO_4$ and concentrated under reduced pressure. The obtained residue was purified by silica gel column chromatography (100-200 mesh) using 1% MeOH in dichloromethane to give the desired product Intermediate 1-XI (1.12 g, crude yield 88%) as a pale brown solid; LCMS: m/z 342.2 [$M^++1$].

Intermediate 1-XII: tert-butyl 4-[5-(4,4,5,5-tetramethyl-1,3,2-dioxaborolan-2-yl)-2-pyridyl]-3,6-dihydro-2H-pyridine-1-carboxylate

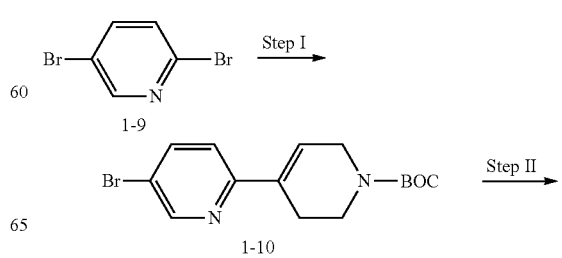

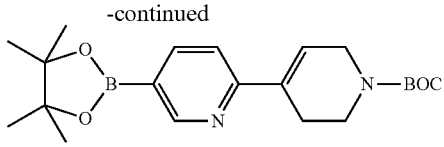

Intermediate 1-XII

Step I: tert-butyl 4-(5-bromo-2-pyridyl)-3,6-dihydro-2H-pyridine-1-carboxylate (1-10)

1-10 was prepared from 1-9 according to the procedure described in WO 2011/008663.

Step II: tert-butyl 4-[5-(4,4,5,5-tetramethyl-1,3,2-dioxaborolan-2-yl)-2-pyridyl]-3,6-dihydro-2H-pyridine-1-carboxylate (Intermediate 1-XII)

A mixture of 1-10 (3.30 g, 9.73 mmol), bis(pinacolato)diboron (2.96 g, 11.68 mmol) and KOAc (2.27 g, 29.19 mmol) in 1,4-dioxane (30 mL) was degassed in a stream of argon for 15 minutes. To the mixture was added 1,1-bis(diphenylphosphino)ferrocene-palladium(II) dichloride dichloromethane complex (0.237 g, 0.29 mmol), and the reaction mixture was again degassed for additional 15 minutes. After stirring at 100° C. for 20 hours, the volatiles were removed by evaporation, and the obtained residue was diluted with water (50 mL), followed by extraction with ethyl acetate (50 mL×3). The combined organic layers were washed with brine (50 mL), dried over anhydrous $Na_2SO_4$ and concentrated under reduced pressure. The obtained residue was purified by silica gel column chromatography (100-200 mesh) using 1% to 5% MeOH in dichloromethane to give the desired product Intermediate 1-XII as a mixture of minor boronate ester together with major boronic acid as a white solid (2.6 g, crude yield 70%); LCMS (for boronic acid): m/z 305.3 [M$^+$+1].

Intermediate 1-XIII: tert-butyl 4-[5-(4,4,5,5-tetramethyl-1,3,2-dioxaborolan-2-yl)-2-pyridyl]piperazine-1-carboxylate

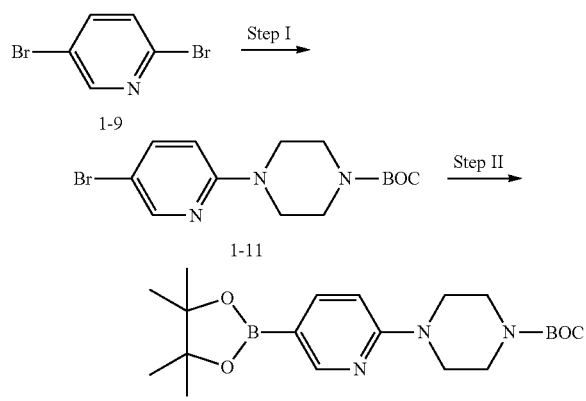

Intermediate 1-XIII

Step I: tert-butyl 4-(5-bromo-2-pyridyl)piperazine-1-carboxylate (1-11)

1-11 was prepared from 1-9 according to the procedure described in WO 2008/146914.

Step II: tert-butyl 4-[5-(4,4,5,5-tetramethyl-1,3,2-dioxaborolan-2-yl)-2-pyridyl]piperazine-1-carboxylate (Intermediate 1-XIII)

A mixture of 1-11 (4.30 g, 12.57 mmol), bis(pinacolato)diboron (3.82 g, 15.07 mmol) and KOAc (2.94 g, 37.69 mmol) in 1,4-dioxane (30 mL) was degassed in a stream of argon for 15 minutes. To the mixture was added 1,1-bis(diphenylphosphino) ferrocene-palladium(II) dichloride dichloromethane complex (0.307 g, 0.376 mmol), and the reaction mixture was again degassed for additional 15 minutes. After stirring at 100° C. for 20 hours, the volatiles were removed by evaporation, and the obtained residue was diluted with water (50 mL), followed by extraction with ethyl acetate (50 mL×3). The combined organic layers were washed with brine (50 mL), dried over anhydrous $Na_2SO_4$ and concentrated under reduced pressure. The obtained residue was purified by silica gel column chromatography (100-200 mesh) using 50% EtOAc in hexanes to give the desired product Intermediate 1-XIII as a mixture of minor boronate ester together with major boronic acid (4.8 g, crude yield 98%) as a yellow solid; LCMS (for boronate ester): m/z 390.2 [M+1]; LCMS (for boronic acid): m/z 308.1 [M$^+$+1].

Intermediate 1-XIV: (4-isopropylpiperazin-1-yl)-[4-(4,4,5,5-tetramethyl-1,3,2-dioxaborolan-2-yl)phenyl]methanone

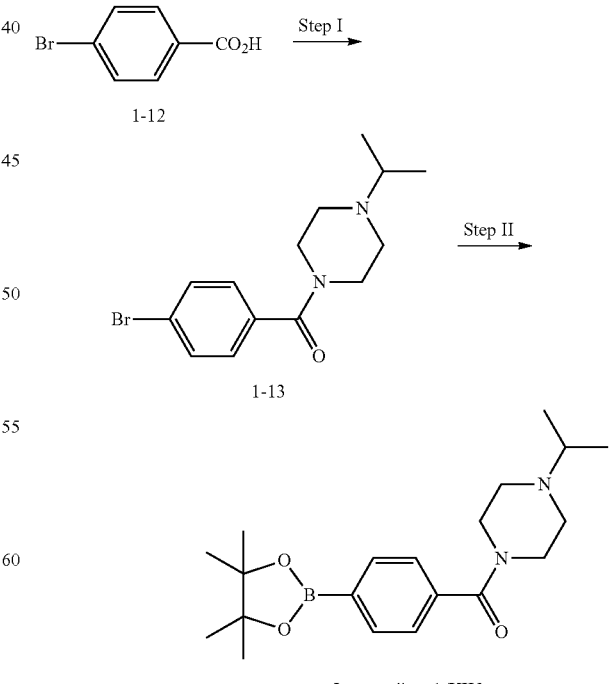

Intermediate 1-XIV

Step I: (4-bromophenyl)-(4-isopropylpiperazin-1-yl)methanone (1-13)

To a stirred solution of 4-bromobenzoic acid 1-12 at 0° C. (2 g, 9.94 mmol) in a mixture of MeCN:DMF (4:1, 20 mL) were added HATU (4.53 g, 11.93 mmol) and 1-isopropylpiperazine (1.91 g, 14.92 mmol). The reaction mixture was allowed to stir for 30 minutes, and then diisopropylethylamine (3.85 g, 5.2 mL, 29.84 mmol) was added thereto. The resulting reaction mixture was stirred for 16 hours at room temperature. After completion of reaction, the reaction mixture was diluted with water and extracted with ethyl acetate (25 mL×3). The combined organic layer was washed with water and brine, dried over anhydrous sodium sulfate and concentrated under reduced pressure. The obtained residue was purified by silica gel (60-120 mesh size) column chromatography using 0-5% methanol in dichloromethane as eluent to give the desired product 1-13 (3.0 g, 97%) as brown solid; LCMS: m/z 312.00 (M$^+$+1).

Step II: (4-isopropylpiperazin-1-yl)-[4-(4,4,5,5-tetramethyl-1,3,2-dioxaborolan-2-yl)phenyl]methanone (Intermediate 1-XIV)

A mixture of 1-13 (3.0 g, 9.64 mmol), bis(pinacolato)diboron (3.65 g, 14.46 mmol) and potassium acetate (2.83 g, 28.92 mmol) in dioxane (35 mL) was degassed in a stream of argon for 30 minutes. To this reaction mixture was added dppf PdCl$_2$:CH$_2$Cl$_2$ complex (0.17 g, 0.21 mmol), and the reaction mixture was again degassed for additional 15 minutes. The reaction mixture was stirred at 90° C. for 18 h. After completion of reaction, the reaction mixture was cooled to 25° C., the solid was removed by filtration through a celite pad, and the filtrate was concentrated under reduced pressure. The obtained residue was purified by silica gel (60-12.0 mesh size) column chromatography using 0-5% methanol in dichloromethane as eluent to give the desired product Intermediate 1-XIV (2.2 g, 63%) as a brown oil; LCMS: m/z 359.10 (M$^+$+1).

Intermediate 1-XV as shown in Table 3 was prepared in the same manner as Intermediate 1-XIV

TABLE 3

| Int. No. | IUPAC name | Structure | LCMS |
|---|---|---|---|
| 1-XV | (4-methylpiperazin-1-yl)-[4-(4,4,5,5-tetramethyl-1,3,2-dioxaborolan-2-yl)phenyl]methanone | 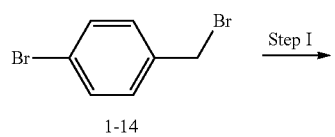 | m/z 331.3 (M$^+$ + 1) |

Intermediate 1-XVI: tert-butyl 4-[[4-(4,4,5,5-tetramethyl-1,3,2-dioxaborolan-2-yl)phenyl]methyl]piperazine-1-carboxylate

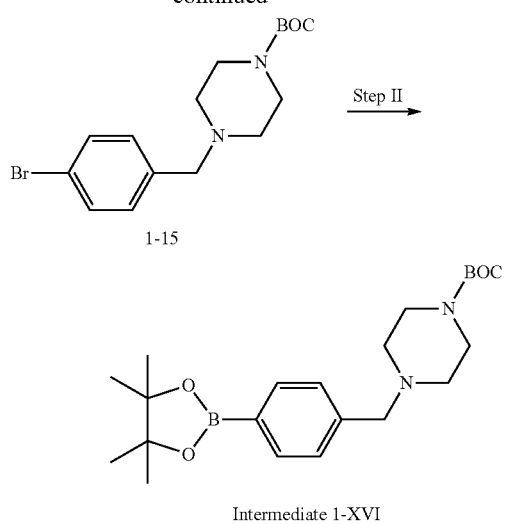

Intermediate 1-XVI was prepared from 1-14 according to procedures described in WO 2013/157022.

Intermediate 1-XVII: tert-butyl 4-[4-(4,4,5,5-tetramethyl-1,3,2-dioxaborolan-2-yl)phenoxy]piperidine-1-carboxylate

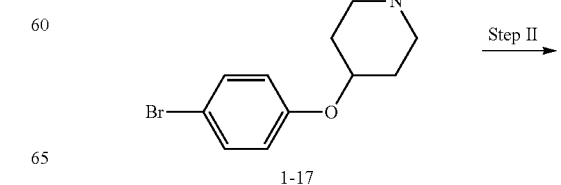

-continued

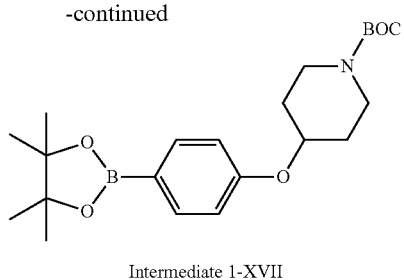

Intermediate 1-XVII

Step I: tert-butyl 4-(4-bromophenoxy)piperidine-1-carboxylate (1-17)

To a stirred suspension of sodium hydride (5.96 g, 149.04 mmol) in 30 mL DMF was added tert-butyl 4-hydroxypiperidine-1-carboxylate (15 g, 74.52 mmol), and the mixture was stirred at 80° C. for 2.5 hours. 1-Bromo-4-fluoro benzene 1-16 was added to the reaction mixture, and the mixture was again stirred at 120° C. for 12 hours. The reaction mixture was cooled to 0° C. and then poured into ice (200 g). The mixture was extracted with ethyl acetate (200 mL×3). The organic layer was washed with brine (200 mL), dried over anhydrous $Na_2SO_4$, and concentrated under reduced pressure. The obtained residue was purified by silica gel column chromatography (100-200 mesh) using 5% EtOAc in hexanes as eluent to give the desired product 0.1-17 (17.02 g, 64%); LCMS: m/z 301.9 [$M^+$-t-Bu+2].

Step II: tert-butyl 4-[4-(4,4,5,5-tetramethyl-1,3,2-dioxaborolan-2-yl)phenoxy]piperidine-1-carboxylate (Intermediate 1-XVII)

A mixture of 1-17 (5.0 g, 14.08 mmol), bis(pinacolato)diboron (5.36 g, 21.12 mmol) and potassium acetate (2.76 g, 28.92 mmol) in dioxane (70 mL) was degassed in a stream of argon for 30 minutes. To this reaction mixture was added dppf $PdCl_2$:$CH_2Cl_2$ complex (1.15 g, 1.41 mmol), and the reaction mixture was again degassed for additional 15 minutes. The reaction mixture was stirred at 90° C. for 18 h. After completion of reaction, the reaction mixture was cooled to 25° C., the solid was removed by filtration through a celite pad, and the filtrate was concentrated under reduced pressure. The obtained residue was purified by silica gel (100-200 mesh size) column chromatography using 5% ethyl acetate in hexanes as eluent to give the desired product Intermediate 1-XVII (4.09 g, 72%); LCMS: m/z 348.1 [$M^+$-t-Bu+2].

Intermediate 1-XVIII: tert-butyl 4-[4-(4,4,5,5-tetramethyl-1,3,2-dioxaborolan-2-yl)pyrazol-1-yl]piperidine-1-carboxylate

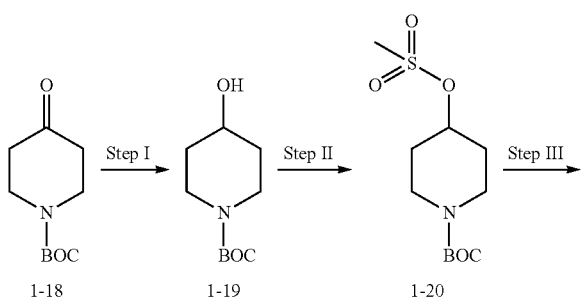

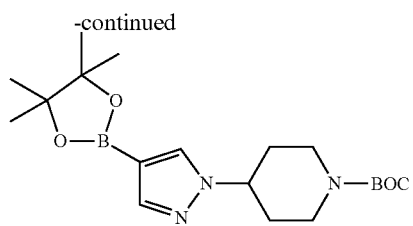

Intermediate 1-XVIII

Step I: tert-butyl 4-hydroxypiperidine-1-carboxylate (1-19)

1-19 was prepared from 1-18 according to the procedure described in WO 2013/160810.

Step II: tert-butyl 4-methylsulfonyloxypiperidine-1-carboxylate (1-20)

1-20 was prepared from 1-19 according to the procedure described in WO 2012/167733.

Step III: tert-butyl 4-[4-(4,4,5,5-tetramethyl-1,3,2-dioxaborolan-2-yl)pyrazol-1-yl]piperidine-1-carboxylate (Intermediate 1-XVIII)

Intermediate 1-XVIII was prepared from 1-20 according to the procedure described in WO 2012/167733; LCMS: m/z 378.1 [$M^+$+1].

Intermediate 1-XIX: [2-(4-tert-butoxycarbonylpiperazin-1-yl)thiazol-5-yl]-tert-butyl-tin

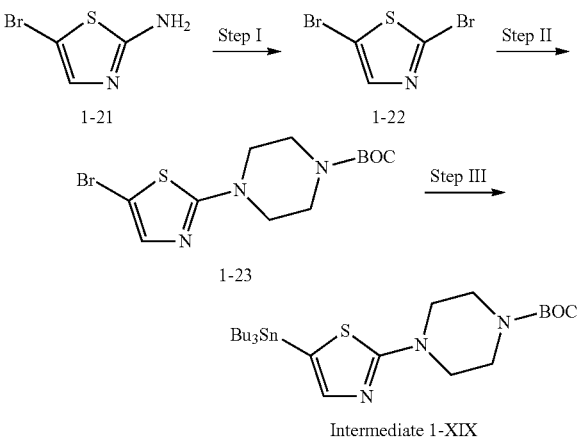

Intermediate 1-XIX

Step I: 2,5-dibromothiazole (1-22)

A solution of 2-amino-5-bromothiazole (1-21) (5.5 g, 30.72 mmol) in acetonitrile (50 mL) was treated with copper(II) bromide (3.43 g, 15.36 mmol) and isoamyl nitrite (4.9 mL, 36.87 mmol), and the resulting reaction mixture was heated at 60° C. for 4 hours. The volatiles were removed by evaporation, and the obtained residue was diluted with water (50 mL), followed by extraction with ethyl acetate (25 mL×2). The combined organic layers were washed with brine (50 mL), dried over anhydrous $Na_2SO_4$ and concentrated under reduced pressure. The obtained residue was purified by silica gel column chromatography (60-120 mesh) using 10% EtOAc in hexanes to give the desired product 1-22 (5.05 g, 68%) as a yellow liquid; LCMS: m/z 243.6 [M$^+$+2].

Step II: tert-butyl 4-(5-bromothiazol-2-yl)piperazine-1-carboxylate (1-23)

A solution of 1-22 (5.0 g, 20.58 mmol) in DMF (50 mL) was treated with 1-Boc-piperizine (5.71 g, 30.87 mol) and K$_2$CO$_3$. After stirring at 70° C. for 18 hours, the volatiles were removed by evaporation, and the obtained residue was diluted with ice water (50 mL), followed by extraction with ethyl acetate (25 mL×2). The combined organic layers were washed with brine (50 mL), dried over anhydrous Na$_2$SO$_4$ and concentrated under reduced pressure. The obtained residue was purified by silica gel column chromatography (60-120 mesh) using 10% EtOAc in hexanes to give the desired product 1-23 (5.95 g, 83%) as a yellow syrup; LCMS: m/z 347.9 [M$^+$+1].

Step III: [2-(4-tert-butoxycarbonylpiperazin-1-yl)thiazol-5-yl]-tert-butyl-tin (Intermediate 1-XIX)

A solution of 1-23 (0.7 g, 0.2 mmol) in anhydrous THF (4 mL) was treated with n-BuLi (1.6 M in hexane, 1.50 mL, 2.41 mmol) at −78° C. The resulting reaction mixture was stirred for 2 hours, and then tri-n-butyltin chloride (0.708 mL, 2.61 mmol) was added dropwise thereto, and the mixture was stirred for another 1.5 hour at −78° C. The reaction mixture was diluted with saturated aqueous NH$_4$Cl solution (3 mL), water (20 mL) and EtOAc (25 mL). The organic layer was separated, and the aqueous layer was back extracted with EtOAc (25 mL×2). The combined organic layers were washed with brine (25 mL), dried over anhydrous Na$_2$SO$_4$ and concentrated under reduced pressure. The obtained residue was purified by silica gel column chromatography (60-120 mesh) using 10% EtOAc in hexanes to give the desired product Intermediate 1-XIX (0.51 g, crude yield 42%) together with the des-bromo compound as a pale yellow syrup. Intermediate 1-XIX was found to be highly unstable on silica gel column, and hence the crude product was used for the next step without purification.

Intermediate 1-XX: tert-butyl 4-[2-fluoro-4-(4,4,5,5-tetramethyl-1,3,2-dioxaborolan-2-yl)phenyl]piperazine-1-carboxylate

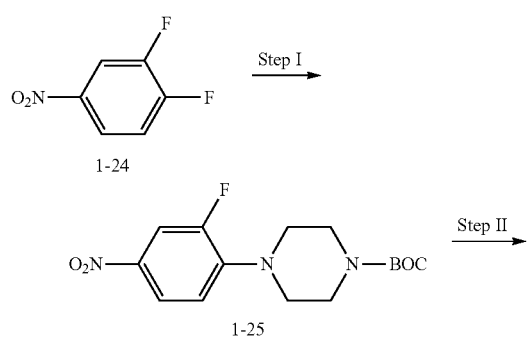

1-24

1-25

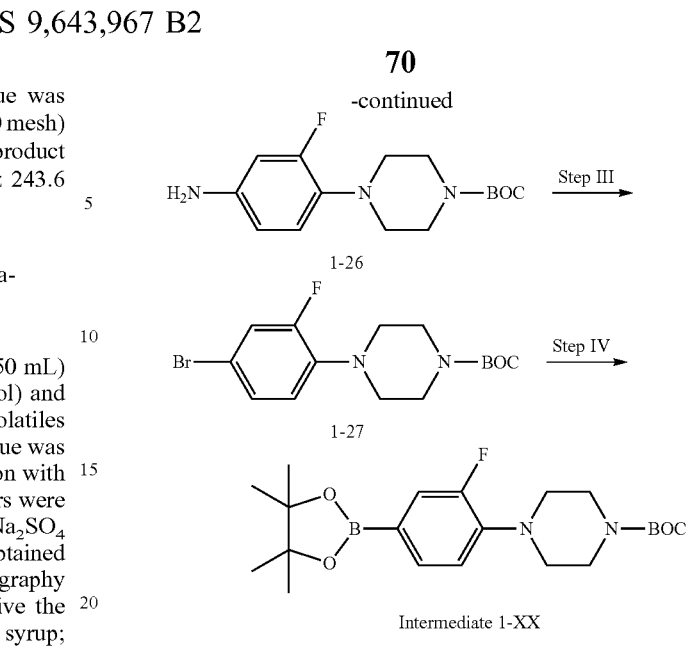

1-26

1-27

Intermediate 1-XX

Step I: tert-butyl 4-(2-fluoro-4-nitro-phenyl)piperazine-1-carboxylate (1-25)

1-25 was prepared from 1-24 according to the procedure described in WO 2009/079597.

Step II: tert-butyl 4-(4-amino-2-fluoro-phenyl)piperazine-1-carboxylate (1-26)

1-26 was prepared from 1-25 according to the procedure described in WO 2009/079597.

Step III: tert-butyl 4-(4-bromo-2-fluoro-phenyl)piperazine-1-carboxylate (1-27)

A solution of 1-26 (3 g, 10.16 mmol) in acetonitrile (30 mL) was treated with copper(II) bromide (1.13 g, 5.00 mmol) and heated at 60° C. To this reaction mixture was added dropwise isoamyl nitrite (2 mL, 15.25 mmol), and the mixture was stirred for another 4 hours. The volatiles were removed by evaporation, and the obtained residue was diluted with water (50 mL), followed by extraction with ethyl acetate (25 mL×2) The combined organic layers were washed with brine (25 mL), dried over anhydrous-Na$_2$SO$_4$, and concentrated under reduced pressure. The obtained residue was purified by combiflash using 30% EtOAc as mobile phase to give the desired product 1-27 (1.4 g, 39%) as a brown solid; LCMS: m/z 302.9 [M$^+$-t-Bu+1], 305.0 [M$^+$-t-Bu+2].

Step IV: tert-butyl 4-[2-fluoro-4-(4,4,5,5-tetramethyl-1,3,2-dioxaborolan-2-yl)phenyl]piperazine-1-carboxylate (Intermediate 1-XX)

A mixture of 1-27 (1 g, 2.78 mmol), bis(pinacolato)diboron (0.849 g, 3.34 mmol) and KOAc (0.818 g, 8.34 mmol) in 1,4-dioxane (10 mL) was degassed in a stream of argon for 15 minutes. To the mixture was added 1,1-bis(diphenylphosphino) ferrocene-palladium(II) dichloride dichloromethane complex (0.068 g, 0.0834 mmol), and the reaction mixture was again degassed for additional 15 minutes. After stirring at 90° C. for 16 hours, the reaction mixture was filtered through a celite pad and washed with EtOAc (50 mL), and the filtrate was concentrated under reduced pressure. The obtained residue was purified by combiflash using 20% EtOAc in hexanes to give the desired product Intermediate 1-XX (1.1 g, yield 98%) as an off white solid; LCMS: m/z 407 [M⁺+1].

¹HNMR (400 MHz, CDCl3): δ 1.32 (s, 12H), 1.48 (s, 9H), 3.07 (t, J=8.0 Hz, 4H), 3.59 (t, J=8.0 Hz, 4H), 6.90 (app. t, J=8.0 Hz, 1H), 7.44 (dd, J=1.2 Hz, J=13.2 Hz, 1H), 7.50 (dd, J=0.8 Hz, J=7.6 Hz, 1H)

Intermediates 1-XXI to 1-XXVI as shown in Table 4 were prepared in the same manner as Intermediate 1-XX.

TABLE 4

| Int. No. | IUPAC name | Structure | Analytical Data |
|---|---|---|---|
| 1-XXI | tert-butyl 4-[2-methyl-4-(4,4,5,5-tetramethyl-1,3,2-dioxaborolan-2-yl)phenyl]piperazine-1-carboxylate | 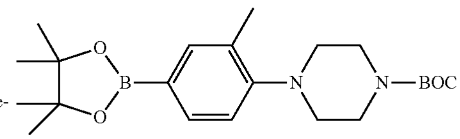 | LCMS: m/z 403 [M⁺ + 1] ¹HNMR (400 MHz, CDCl₃): δ 1.34 (s, 12H), 1.50 (s, 9H), 2.30 (s, 3H), 2.96-2.88 (m, 4H), 3.55-3.57 m, 4H), 6.96 (d, J = 8 Hz, 1H), 7.61-7.64 (m, 2H) |
| 1-XXII | tert-butyl 4-[4-(4,4,5,5-tetramethyl-1,3,2-dioxaborolan-2-yl)-2-(trifluoromethyl)phenyl]piperazine-1-carboxylate | 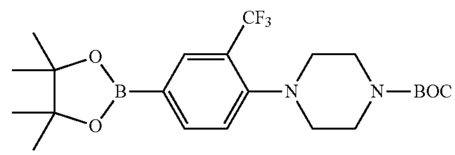 [SMILES: CC(C)(C)OC(=O)N1CCN(c2ccc(B3OC(C)(C)C(C)(C)O3)cc2C(F)(F)F)CC1] | LCMS: m/z 457 [M⁺ + 1] ¹HNMR (400 MHz, CDCl₃): δ 1.32 (s, 12H), 1.49 (s, 9H), 2.88-2.90 (m, 4H), 3.54-3.57 (m, 4H), 7.27 (s, 1H), 7.93 (d, J = 7.2 Hz, 1H), 8.06 (s, 1H) |
| 1-XXIII | tert-butyl 4-[2-methoxy-4-(4,4,5,5-tetramethyl-1,3,2-dioxaborolan-2-yl)phenyl]piperazine-1-carboxylate | 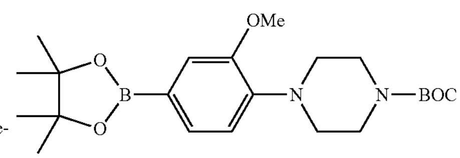 | LCMS: m/z 419.3 [M⁺ + 1] ¹HNMR (400 MHz, CDCl₃): δ 1.33 (s, 12H), 1.48 (s, 9H), 3.03 (t, J = 4.8 Hz, 4H), 3.60 (t, J = 4.8 Hz, 4H), 3.91 (s, 3H), 6.90 (J = 7.6 Hz, 1H), 7.26-7.27 (m, 1H), 7.40 (d, J = 7.6 Hz, 1H) |
| 1-XXIV | tert-butyl 4-[3-methyl-4-(4,4,5,5-tetramethyl-1,3,2-dioxaborolan-2-yl)phenyl]piperazine-1-carboxylate | 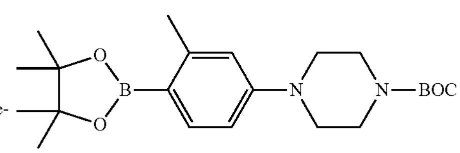 | LCMS: m/z 403 [M⁺ + 1] ¹HNMR (400 MHz, CDCl₃): δ 1.12 (s, 12H), 1.48 (s, 9H), 2.50 (s, 3H), 3.18-3.20 (m, 4H), 3.54-3.57 (m, 4H), 6.69-6.70 (m, 2H), 7.67-7.69 (m, 1H) |
| 1-XXV | tert-butyl 4-[4-(4,4,5,5-tetramethyl-1,3,2-dioxaborolan-2-yl)-3-(trifluoromethyl)phenyl]piperazine-1-carboxylate | 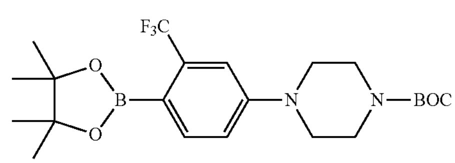 [SMILES: CC(C)(C)OC(=O)N1CCN(c2ccc(B3OC(C)(C)C(C)(C)O3)c(C(F)(F)F)c2)CC1] | LCMS: m/z 457 [M⁺ + 1] ¹HNMR (400 MHz, CDCl₃): δ 1.34 (s, 12H), 1.48 (s, 9H), 3.21-3.24 (m, 4H), 3.56-3.59 (m, 4H), 6.96 (dd, J = 8 Hz, 1H), 7.15 (s, 1H), 7.67 (d, J = 8 Hz, 1H) |

TABLE 4-continued

| Int. No. | IUPAC name | Structure | Analytical Data |
|---|---|---|---|
| 1-XXVI | tert-butyl 4-[3-methoxy-4-(4,4,5,5-tetramethyl-1,3,2-dioxaborolan-2-yl)phenyl]piperazine-1-carboxylate | 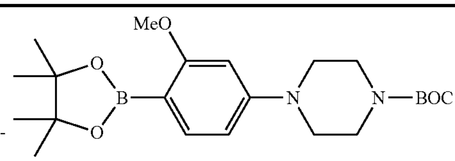 | LCMS: m/z 419.3 [M+ + 1] <br> ¹HNMR (400 MHz, CDCl₃): <br> δ 1.26 (s, 9H), 1.36 (s, 12H), 3.21 (t, J = 10.0 Hz, 4H), 3.57 (t, J = 10.0 Hz 4H), 3.82 (s, 3H), 6.37-6.40 (m, 1H), 6.46 (dd, J = 2.0 Hz, J = 8.0 Hz, 1H), 7.60 (d, J = 8 Hz, 1H) |

Intermediate 1-XXVII: tert-butyl 4-[3-fluoro-4-(4,4,5,5-tetramethyl-1,3,2-dioxaborolan-2-yl)phenyl]piperazine-1-carboxylate

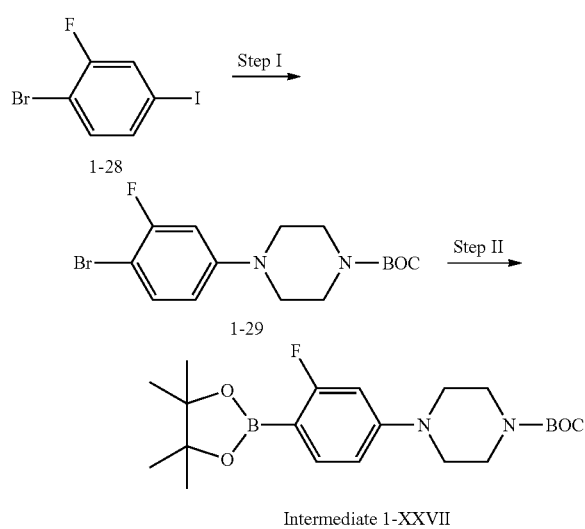

Step I: tert-butyl 4-(4-bromo-3-fluoro-phenyl)piperazine-1-carboxylate (1-29)

A mixture of 1-28 (5.0 g, 16.6 mmol), 1-Boc-piperizine (1.2 g, 6.66 mmol), BINAP (0.610 g, 0.99 mmol) and Cs₂CO₃ (8.0 g, 24.9 mmol) in toluene (50 mL) was degassed in a stream of argon for 30 minutes. To the mixture was added tris(dibenzylideneacetone)dipalladium(0) (0.30 g, 0.33 mmol), and the reaction mixture was again degassed for additional 15 minutes. After stirring at 90° C. for 18 hours, the volatiles were removed by evaporation, and the obtained residue was diluted with water (50 mL), followed by extraction with ethyl acetate (50 mL×3). The combined organic layers were washed with brine (150 mL), dried over anhydrous Na₂SO₄ and concentrated under reduced pressure. The obtained residue was purified by silica gel column chromatography (60-120 mesh) using 10% EtOAc in hexanes to give the desired product 1-29 (1.5 g, 30%) as a yellow solid; LCMS: m/z 303 [M+-ᵗBu+1], 305.0 [M+-ᵗBu+2].

Step II: tert-butyl 4-[3-fluoro-4-(4,4,5,5-tetramethyl-1,3,2-dioxaborolan-2-yl)phenyl]piperazine-1-carboxylate (Intermediate 1-XXVII)

A mixture of 1-29 (0.8 g, 2.21 mmol), bis(pinacolato)diboron (0.723 g, 2.91 mmol) and KOAc. (0.650 g, 6.62 mmol) in 1,4-dioxane (10 mL) was degassed in a stream of argon for 15 minutes. To the mixture was added 1,1-bis(diphenylphosphino) ferrocene-palladium(II) dichloride dichloromethane complex (0.1 g, 0.0132 mmol), and the reaction mixture was again degassed for additional 15 minutes. After stirring at 90° C. for 16 hours, the reaction mixture was filtered through a celite pad and washed with EtOAc (50 mL), and the filtrate was concentrated under reduced pressure. The obtained residue was purified by combiflash using 15% EtOAc in hexanes to give the desired product Intermediate 1-XXVII (0.25 g, 26%) as an off white solid; LCMS: m/z 407 [M++1].

¹HNMR (400 MHz, CDCl₃): δ 1.27 (s, 12H), 1.41 (s, 9H), 3.23 (t, J=10.0 Hz, 4H), 3.56 (t, J=10.0 Hz, 4H), 6.49 (dd, J=2.0 Hz, J=8.0 Hz, 1H), 6.62 (dd, J=2.0 Hz, J=8.0 Hz, 1H), 7.61 (t, J=15.2 Hz, 1H)

Intermediate 1-XXVIII: 1-isopropyl-4-[4-(4,4,5,5-tetramethyl-1,3,2-dioxaborolan-2-yl)cyclohex-3-en-1-yl]piperazine

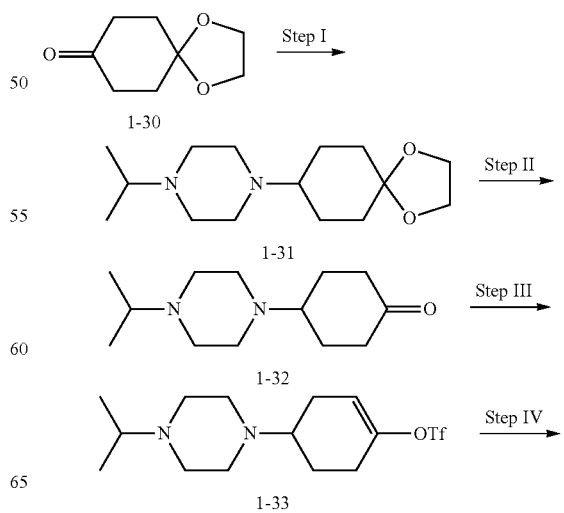

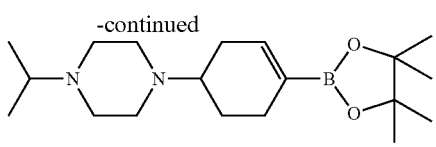

Intermediate 1-XXVIII

Intermediate 1-XXVIII was prepared from 1-30 according to the procedures described in WO 2008/095944.

Intermediate 1-XXIX: tert-butyl (2S)-2-methyl-4-[4-(4,4,5,5-tetramethyl-1,3,2-dioxaborolan-2-yl)phenyl]piperazine-1-carboxylate

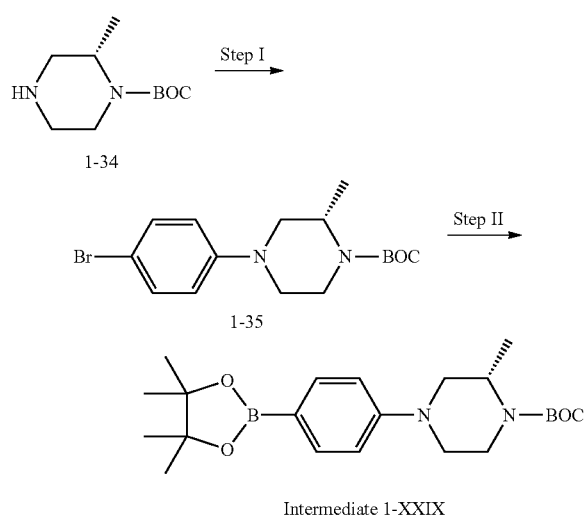

Intermediate 1-XXIX

Step I: tert-butyl (2S)-4-(4-bromophenyl)-2-methyl-piperazine-1-carboxylate (1-35)

A mixture of 1-34 (10 g, 50 mmol), 1,4-dibromobenzene (29.4 g, 125 mmol), cesium carbonate (24.3 g, 75 mmol) and BINAP (1.5 g, 2.5 mmol) in 1,4-dioxane (250 mL) was degassed in a stream of argon for 15 minutes. To the mixture was added tris(dibenzylideneacetone)dipalladium(0) (0.900 g, 2.5 mmol), and the reaction mixture was again degassed for additional 15 minutes. After stirring at 90° C. for 18 hours, the volatiles were removed by evaporation, and the obtained residue was diluted with water (250 mL), followed by extraction with ethyl acetate (250 mL×3). The combined organic layers were washed with brine (50 mL), dried over anhydrous $Na_2SO_4$ and concentrated under reduced pressure. The obtained residue was purified by silica gel column chromatography (60-120 mesh) using 10% EtOAc in hexanes to give the desired product 1-35 as a white solid (5.5 g, 31%); LCMS: m/z 357.1 [M$^+$+1], 359.1 [M$^+$+2].

Step II: tert-butyl (2S)-2-methyl-4-[4-(4,4,5,5-tetramethyl-1,3,2-dioxaborolan-2-yl)phenyl]piperazine-1-carboxylate (Intermediate 1-XXIX)

A mixture of 1-35 (5.0 g, 14 mmol), bis(pinacolato)diboron (5.3 g, 21 mmol) and KOAc (2.7 g, 28 mmol) in 1,4-dioxane (70 mL) was degassed in a stream of argon for 15 minutes. To the mixture was added 1,1-bis(diphenylphosphino) ferrocene-palladium(II) dichloride dichloromethane complex (1.1 g, 1.40 mmol), and the reaction mixture was again degassed for additional 15 minutes. After stirring at 90° C. for 15 hours, the volatiles were removed by evaporation, and the obtained residue was diluted with water (150 mL), followed by extraction with ethyl acetate (150 mL×3). The combined organic layers were washed with brine (150 mL), dried over anhydrous $Na_2SO_4$ and concentrated under reduced pressure. The obtained residue was purified by silica gel column chromatography (60-120 mesh) using 10% EtOAc in hexanes to give the desired product Intermediate 1-XXIX (5.0 g, 89%) as a white solid; LCMS: m/z 403.3 [M$^+$+1].

$^1$HNMR (400 MHz, DMSO): δ 1.15-1.16 (m, methyl doublet proton merged in diborane impurity, 3H), 1.16 (s, 12H), 1.41 (s, 9H), 2.66-2.76 (m, 1H), 2.96 (dd, J=12.4, 3.6 Hz, 1H), 3.13-3.20 (m, 1H), 3.57-3.67 (m, 2H), 3.76 (dt, J=6.8, 3.6 Hz, 1H), 4.16-4.79 (m, 1H), 6.87 (d, J=8.4 Hz, 2H), 7.50 (d, J=9.2 Hz, 2H)

Intermediate 2-I: 4-[(4-chloro-1H-pyrrolo[3,2-c]pyridin-2-yl)methyl]morpholine

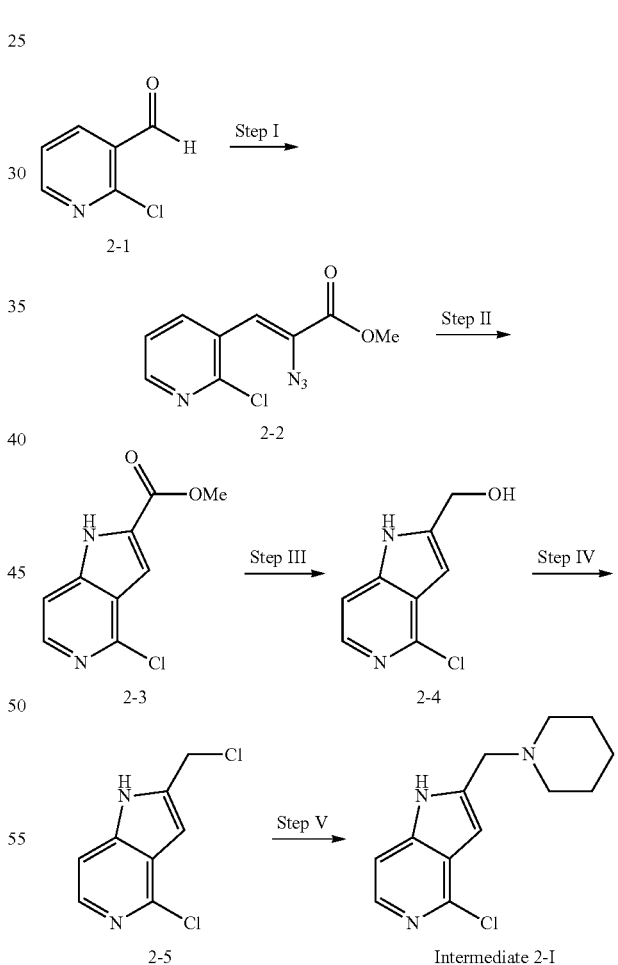

Step I: methyl (Z)-2-azido-3-(2-chloro-3-pyridyl)prop-2-enoate (2-2)

To a stirred solution of 2-chloronicotinaldehyde 2-1 (5 g, 35.3 mmol) and methyl 2-azidoacetate (8.64 mL, 88.2 mmol) in methanol (100 mL) was added a freshly prepared NaOMe methanol solution [prepared by dissolving sodium (2 g, 88.25 mmol) in methanol (100 mL)] at −20° C. over 30 minutes. The resulting reaction mixture was stirred at 0-5° C. for 16 hours. The resulting pale yellow solid was removed by filtration from the reaction mixture. The filtrate was poured into ice-water (500 mL) containing saturated NH$_4$Cl (150 mL). The resulting solid was collected by filtration, and dried under vacuum to give the desired product 2-2 as a pale brown solid (3.9 g, 46%).

2-Chloronicotinaldehyde 2-1 may be commercially available, or can also be produced according to a method known per se or a method analogous thereto.

Step II: methyl 4-chloro-1H-pyrrolo[3,2-c]pyridine-2-carboxylate (2-3)

A solution of 2-2 (3.8 g, 12.1 mmol) in xylene (35 mL) was added dropwise to boiling xylene (250 mL) over a period of 30 minutes, and the mixture was stirred at the same temperature for 6 hours. The reaction mixture was allowed to cool to room temperature, and then stirred at 0° C. for additional 1 hour. The resulting solid was collected by filtration, and dried under vacuum to give the desired product 2-3 as a yellow solid (1.7 g, 56%); LCMS: m/z 211 (M$^+$+1).

Step III: (4-chloro-1H-pyrrolo[3,2-c]pyridin-2-yl)methanol (2-4)

To a stirred solution of 2-3 (1 g, 4.73 mmol) in anhydrous THF (25 mL) was added LiAlH$_4$ (0.36 g, 9.47 mmol) in portions at 0° C. After stirring at the same temperature at for 2 hours, the reaction mixture was allowed to cool to room temperature, and stirred for additional 2 hours. Excess of LiAlH$_4$ was decomposed by adding saturated Na$_2$SO$_4$ solution and ethyl acetate (25 mL). The inorganic solid was removed by filtration through a celite pad. The filtrate was concentrated under reduced pressure, and the resulting solid was triturated with diethyl ether to give the desired product 2-4 as a yellow solid (0.86 g, 95%); LCMS: m/z 183 (M$^+$+1)

Step IV: 4-chloro-2-(chloromethyl)-1H-pyrrolo[3,2-c]pyridine (2-5)

Thionyl chloride (0.77 mL, 10.3 mmol) was added to a stirred solution of 2-4 (0.95 g, 5.19 mmol) in 1:1 mixture of THF/CH$_2$Cl$_2$ (30 mL) at 0° C. After stirring at room temperature for additional 2 hours, the reaction mixture was cooled, and saturated aqueous NaHCO$_3$ solution (15 mL) was added thereto. The organic layer was separated, and the aqueous layer was extracted with CH$_2$Cl$_2$ (15 mL×3). The combined organic layers were dried over anhydrous Na$_2$SO$_4$ and concentrated under reduced pressure to give the desired product 2-5 as a light brown solid (0.9 g, 87%); LCMS: m/z 201 (M$^+$+1).

Step V: 4-[(4-chloro-1H-pyrrolo[3,2-c]pyridin-2-yl)methyl]morpholine (Intermediate 2-I)

To a mixture of 2-5 (0.85 g, 4.25 mmol) and morpholine (0.44 mL, 5.1 mmol) in DMF (10 mL) was added N,N-diisopropylethylamine (1.08 mL, 6.37 mmol) at room temperature. After stirring for 16 hours, the excess solvent was removed under reduced pressure, and the obtained residue was diluted with ice water. The resulting solid was collected by filtration and triturated with diethyl ether to give the desired product Intermediate 2-I as a yellow solid (0.8 g, 75%); LCMS: m/z 252.1 (M$^+$+1).

$^1$HNMR (400 MHz, CDCl$_3$): 2.50 (t, J=4 Hz, 4H), 3.68 (s, 2H), 3.73 (t, J=4.8 Hz, 4H), 6.51 (s, 1H), 7.21 (d, J=5.6 Hz, 1H), 8.04 (d, J=6 Hz, 1H), 9.04 (br s, 1H)

Intermediates 2-II to 2-XVI as shown in Table 5 were prepared from their corresponding starting materials [prepared according to the procedures reported in literature] in the same manner as Intermediate 2-I.

TABLE 5

| Int. No. | IUPAC name | Structure | Analytical Data |
|---|---|---|---|
| 2-II | 1-[(4-chloro-1H-pyrrolo[3,2-c]pyridin-2-yl)methyl]piperidin-4-ol | 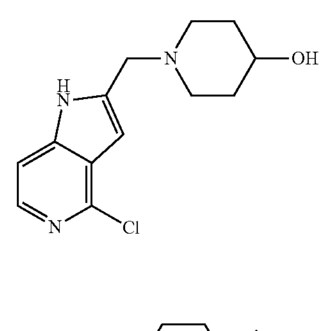 | LCMS: m/z 266.1 [M$^+$ + 1] |
| 2-III | 7-[(4-chloro-1H-pyrrolo[3,2-c]pyridin-2-yl)methyl]-7-azaspiro[3.5]nonan-2-ol | 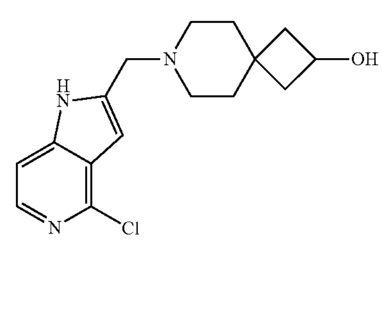 [SMILES: OC1CC2(CCN(Cc3cc4c(Cl)nccc4[nH]3)CC2)C1] | LCMS: m/z 306.1 [M$^+$ + 1] |

TABLE 5-continued

| Int. No. | IUPAC name | Structure | Analytical Data |
| --- | --- | --- | --- |
| 2-IV | 4-chloro-2-[(3-fluoroazetidin-1-yl)methyl]-1H-pyrrolo[3,2-c]pyridine | 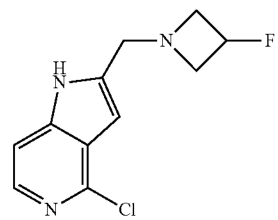 [SMILES: FC1CN(Cc2cc3c(Cl)nccc3[nH]2)C1] | LCMS: m/z 240.1 [M$^+$ + 1] |
| 2-V | 4-chloro-2-(1-piperidylmethyl)-1H-pyrrolo[3,2-c]pyridine | 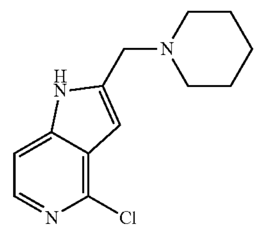 [SMILES: Clc1nccc2[nH]c(CN3CCCCC3)cc12] | LCMS: m/z 250.1 [M$^+$ + 1] |
| 2-VI | 4-chloro-2-[(3,3-difluoropyrrolidin-1-yl)methyl]-1H-pyrrolo[3,2-c]pyridine | 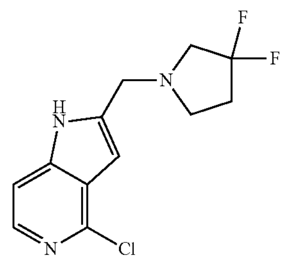 [SMILES: FC1(F)CCN(Cc2cc3c(Cl)nccc3[nH]2)C1] | LCMS: m/z 272.0 [M$^+$ + 1] |
| 2-VII | 4-chloro-2-(pyrrolidin-1-ylmethyl)-1H-pyrrolo[3,2-c]pyridine | 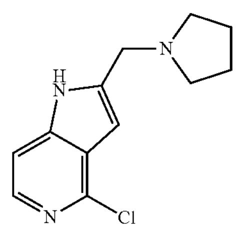 [SMILES: Clc1nccc2[nH]c(CN3CCCC3)cc12] | LCMS: m/z 236.0 [M$^+$ + 1] |
| 2-VIII | 4-chloro-2-[(4-fluoro-1-piperidyl)methyl]-1H-pyrrolo[3,2-c]pyridine | 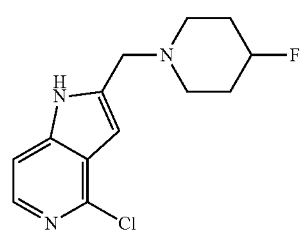 [SMILES: FC1CCN(Cc2cc3c(Cl)nccc3[nH]2)CC1] | — |
| 2-IX | 4-[(4-chloro-6-methyl-1H-pyrrolo[3,2-c]pyridin-2-yl)methyl]morpholine | 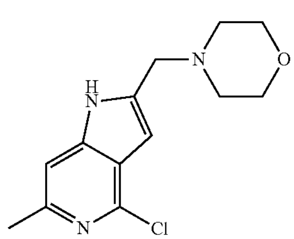 [SMILES: Cc1cc2[nH]c(CN3CCOCC3)cc2c(Cl)n1] | LCMS: m/z 266.10 [M$^+$ + 1] |

TABLE 5-continued

| Int. No. | IUPAC name | Structure | Analytical Data |
| --- | --- | --- | --- |
| 2-X | 4-chloro-2-[(4-fluoro-1-piperidyl)methyl]-6-methyl-1H-pyrrolo[3,2-c]pyridine | 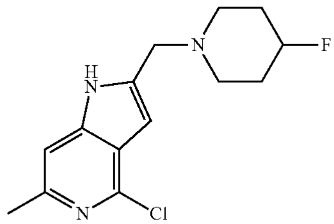 [SMILES: Cc1cc2[nH]c(CN3CCC(F)CC3)cc2c(Cl)n1] | LCMS: m/z 282.1 [M⁺ + 1] |
| 2-XI | 7-[(4-chloro-6-methyl-1H-pyrrolo[3,2-c]pyridin-2-yl)methyl]-7-azaspiro[3.5]nonan-2-ol | 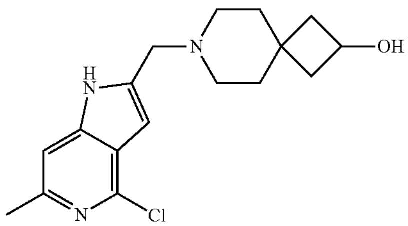 [SMILES: Cc1cc2[nH]c(CN3CCC4(CC3)CC(O)C4)cc2c(Cl)n1] | LCMS: m/z 320.2 [M⁺ + 1] |
| 2-XII | 4-chloro-6-methyl-2-[(2-methyl-7-azaspiro[3.5]nonan-7-yl)methyl]-1H-pyrrolo[3,2-c]pyridine | 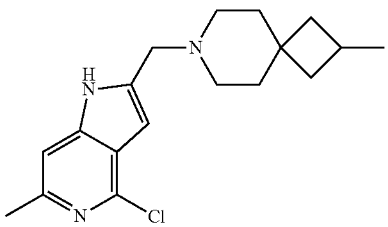 | — |
| 2-XIII | 4-[(4-chloro-6,7-dimethyl-1H-pyrrolo[3,2-c]pyridin-2-yl)methyl]morpholine | 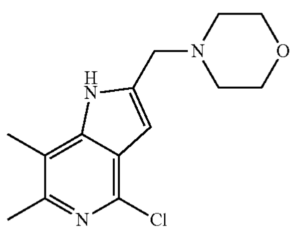 [SMILES: Cc1nc(Cl)c2cc(CN3CCOCC3)[nH]c2c1C] | LCMS: m/z 280.3 (M⁺ + 1) ¹HNMR (400 MHz, DMSO): δ 2.37 (s, 3H), 2.38-2.41 (m, 7H), 3.58 (t, J = 4.8 Hz, 4H), 3.61 (s, 2H), 6.32 (s, 1H), 11.4 (bs, 1H, —NH) |
| 2-XIV | 4-chloro-6,7-dimethyl-2-(1-piperidylmethyl)-1H-pyrrolo[3,2-c]pyridine | 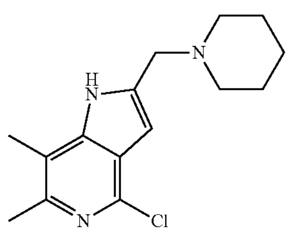 [SMILES: Cc1nc(Cl)c2cc(CN3CCCCC3)[nH]c2c1C] | LCMS: m/z 278.2 (M⁺ + 1) ¹HNMR (400 MHz, DMSO): δ 1.33-1.40 (m, 2H), 1.47-1.52 (m, 4H), 2.36-2.40 (m, 7H), 2.50-2.51 (m, 2H), 3.56 (s, 3H), 6.29 (s, 1H), 11.4 (bs, 1H, —NH) |
| 2-XV | 4-chloro-6,7-dimethyl-2-(pyrrolidin-1-ylmethyl)-1H-pyrrolo[3,2-c]pyridine | 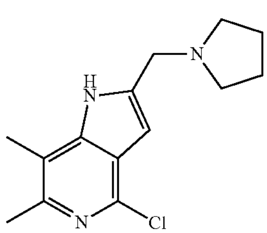 [SMILES: Cc1nc(Cl)c2cc(CN3CCCC3)[nH]c2c1C] | LCMS: m/z 264.2 (M⁺ + 1) ¹HNMR (400 MHz, DMSO): δ 1.70-1.72 (m, 4H), 2.37 (s, 3H), 2.41 (s, 3H), 2.48-2.50 (m, 4H), 3.71 (s, 2H), 6.29 (s, 1H), 11.4 (bs, 1H, —NH) |

TABLE 5-continued

| Int. No. | IUPAC name | Structure | Analytical Data |
| --- | --- | --- | --- |
| 2-XVI | 4-[[4-chloro-6-(trifluoromethyl)-1H-pyrrolo[3,2-c]pyridin-2-yl]methyl]morpholine | 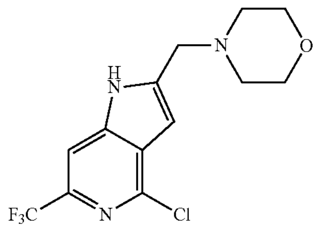 [SMILES: FC(F)(F)c1cc2[nH]c(CN3CCOCC3)cc2c(Cl)n1] | LCMS: m/z 320.0 (M⁺ + 1) ¹HNMR (400 MHz, DMSO): δ 2.41 (t, J = 4.4 Hz, 4H), 3.60 (t, J = 5.2 Hz, 4H), 3.72 (s, 2H), 6.62 (s, 1H), 7.79 (s, 1H), 12.42 (bs, 1H, —NH) |

Intermediate 2-XVII: 4-[[1-(benzenesulfonyl)-4-chloro-pyrrolo[3,2-c]pyridin-2-yl]methyl]morpholine Intermediate 2-XVIII: 4-[(4-chloro-6-cyclopropyl-1H-pyrrolo[3,2-c]pyridin-2-yl)methyl]morpholine To a solution of Intermediate 2-I (1.40 g, 5.9 mmol) in dry THF (25 mL) at 0° C. was added NaH (60% in mineral oil, 0.478 g, 11.9 mmol) portion wise. The resulting reaction mixture was gradually allowed to attain room temperature. After 1 hour, the reaction mixture was again cooled to 0° C., and benzenesulfonyl chloride (0.9 mL, 7.1 mmol) was added thereto over a period of 10 minutes. After stirring at room temperature for 16 hours, the reaction mixture was diluted with saturated aqueous NH₄Cl solution (10 mL) and ice water (100 mL), followed by extraction using ethyl acetate (50 mL×3). The combined organic layers were washed with brine (20 mL), dried over anhydrous Na₂SO₄ and concentrated under reduced pressure. The obtained residue was purified by silica gel column chromatography using 2% MeOH in dichloromethane to give the desired product Intermediate 2-XVII (0.95 g, 44%) as a yellow solid; LCMS: m/z 392.0 [M⁺+1].

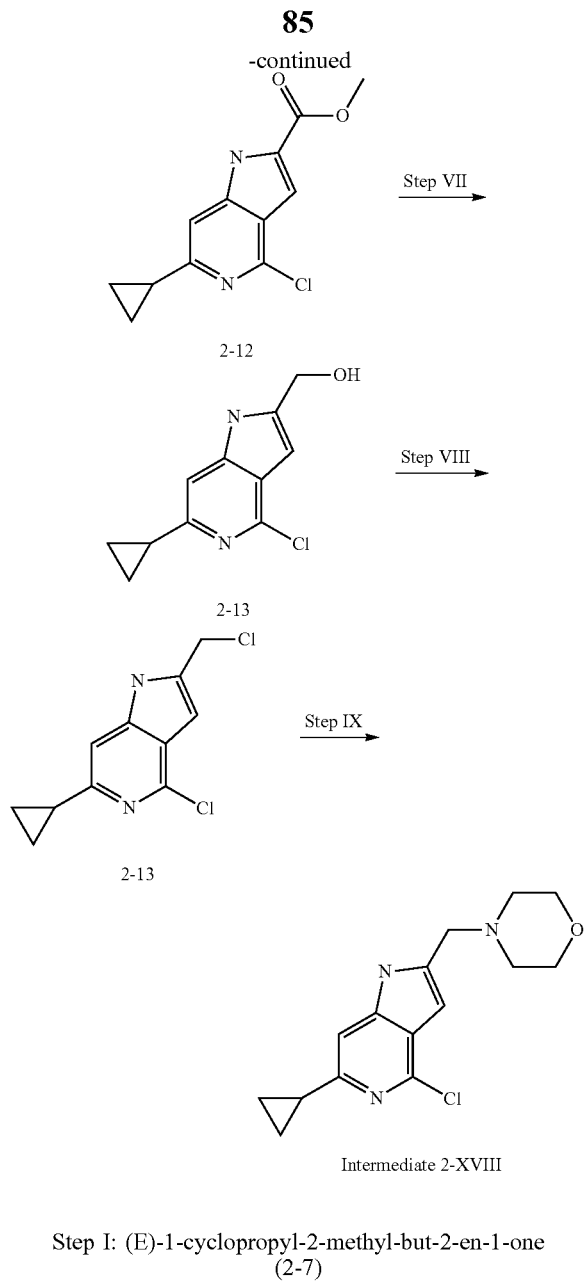

Step I: (E)-1-cyclopropyl-2-methyl-but-2-en-1-one (2-7)

2-7 was prepared from 0.2-6 according to the procedure described in U.S. Pat. No. 5,438,033.

Step II: 6-cyclopropyl-2-hydroxy-pyridine-3-carbonitrile (2-8)

2-8 was prepared from 2-7 according to the procedure described in U.S. Pat. No. 5,438,033.

Step III: 2-chloro-6-cyclopropyl-pyridine-3-carbonitrile (2-9)

2-9 was prepared from 2-8 according to the procedure described in U.S. Pat. No. 5,438,033.

Step IV: 2-chloro-6-cyclopropyl-pyridine-3-carbaldehyde (2-10)

To a stirred solution of 2-9 (7 g, 39.3 mmol) at −40° C. in toluene (70 mL) was added DIBAL-H (1M in toluene, 5.59 g, 39.3 mmol, 39.3 mL) in drop wise manner over a period of 30 mins. The reaction mixture was stirred for additional 1 hour. After completion of reaction (monitored by TLC), the reaction mixture was poured over cold 2 N HCl solution (300 mL). The resulting milky mass was stirred for 1 hour. EtOAc (300 mL) was added thereto, the layers were separated, and the aqueous layer was extracted with EtOAc (100 mL×3). The combined organic layers were dried over anhydrous $Na_2SO_4$ and concentrated under reduced pressure to give the desired product 2-10 (6 g, 84%) as a yellow solid; LCMS: m/z 182.0 ($M^++1$).

Step V: methyl (Z)-2-azido-3-(2-chloro-6-cyclopropyl-3-pyridyl)prop-2-enoate (2-11)

2-11 was prepared from 2-10 in the same manner as in the preparation of 2-2 from 2-1.

Step VI: methyl 4-chloro-6-cyclopropyl-1H-pyrrolo[3,2-c]pyridine-2-carboxylate (2-12)

2-12 was prepared from 2-11 in the same manner as in the preparation of 2-3 from 2-2.

Step VII: (4-chloro-6-cyclopropyl-1H-pyrrolo[3,2-c]pyridin-2-yl)methanol (2-13)

2-13 was prepared from 2-12 in the same manner as in the preparation of 2-4 from 2-3.

Step VIII: 4-chloro-2-(chloromethyl)-6-cyclopropyl-1H-pyrrolo[3,2-c]pyridine (2-14)

2-14 was prepared from 2-13 in the same manner as in the preparation of 2-5 from 2-4.

Step IX: 4-[(4-chloro-6-cyclopropyl-H-pyrrolo[3,2-c]pyridin-2-yl)methyl]morpholine (Intermediate 2-XVIII)

Intermediate 2-XVIII was prepared from 2-14 in the same manner as in the preparation of Intermediate 2-I from 2-5.

Intermediate 2-XIX: 4-[(4-chloro-1-methyl-pyrrolo[3,2-c]pyridin-2-yl)methyl]morpholine

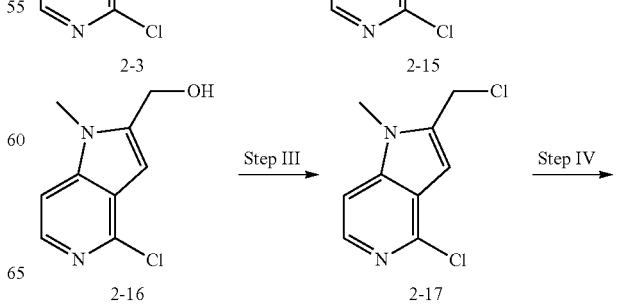

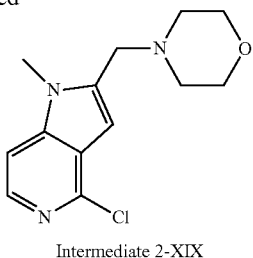

Intermediate 2-XIX

Step I: methyl 4-chloro-1-methyl-pyrrolo[3,2-c]pyridine-2-carboxylate (2-15)

To an ice cold solution of 2-3 (0.5 g, 2.36 mmol) in anhydrous DMF (3 mL) was added NaH (60% in mineral oil) (0.113 g, 2.84 mmol), and the mixture was stirred at room temperature for 1 hour. The reaction mixture was recooled to 0° C. and treated with MeI (0.402 g, 2.83 mmol), and stirring was continued for 1 hour. The reaction mixture was allowed to attain room temperature and stirred for 1 more hour. The reaction mixture was diluted with ice water, and the solid separated was collected by filtration and dried under vacuum to give the desired product 2-15 (0.460 g, 86%) as a yellow solid; LCMS: m/z 225.0 (M$^+$+1).

Step II: (4-chloro-1-methyl-pyrrolo[3,2-c]pyridin-2-yl)methanol (2-16)

To a stirred solution of 2-15 (0.46 g, 2.04 mmol) in anhydrous THF (5 mL) was added LiAlH$_4$ (0.116 g, 3.8 mmol) in portions at 0° C. After stirring at the same temperature for 2 hours, the reaction mixture was allowed to cool to room temperature and stirred for additional 2 hours. Excess of LiAlH$_4$ was decomposed by adding saturated Na$_2$SO$_4$ solution and ethyl acetate (25 mL). The inorganic solid was removed by filtration through a celite pad. The filtrate was concentrated under reduced pressure, and the obtained residue was purified by silica gel column chromatography (60-120 mesh) by eluting with 1% MeOH in DCM to give the desired product 2-16 (0.32 g, 80%) as a pale brown solid; LCMS: m/z 197.1 (M$^+$+1).

Step III: 4-chloro-2-(chloromethyl)-1-methyl-pyrrolo[3,2-c]pyridine (2-17)

Thionyl chloride (0.58 mL, 8.15 mmol) was added to a stirred solution of 2-16 (0.32 g, 1.63 mmol) in CH$_2$Cl$_2$ (15 mL) at 0° C. After stirring at room temperature for additional 2 hours, the reaction mixture was cooled, and saturated aqueous NaHCO$_3$ solution (15 mL) was added thereto. The organic layer was separated, and the aqueous layer was extracted with CH$_2$Cl$_2$ (15 mL×3). The combined organic layers were dried over anhydrous Na$_2$SO$_4$ and concentrated under reduced pressure to give the desired product 2-17 as a light brown solid (0.31 g, crude yield 88%); LCMS: m/z 215.0 (M$^+$+1).

Step IV: 4-[(4-chloro-1-methyl-pyrrolo[3,2-c]pyridin-2-yl)methyl]morpholine (Intermediate 2-XIX)

To a mixture of 2-17 (0.3 g, 1.39 mmol) and morpholine (0.24 mL, 2.78 mmol) in DMF (2 mL) was added N,N-diisopropylethylamine (0.7 mL, 4.17 mmol) at room temperature. After stirring for 16 hours, the excess solvent was removed under reduced pressure, and the obtained residue was diluted with ice water. The resulting solid was collected by filtration and purified using preparative TLC in 50% EtOAc in hexanes to give the desired product Intermediate 2-XIX (0.250 g, 68%) as a pale yellow solid; LCMS: m/z 266.0 (M$^+$+1).

$^1$HNMR (400 MHz, CDCl$_3$): δ 2.43 (t, J=4.4 Hz, 4H), 3.64 (s, 2H), 3.69 (t, J=4.8 Hz, 4H), 3.82 (s, 3H), 6.50 (d, J=0.4 Hz, 1H), 7.15 (dd, J=6, 0.8 Hz, 1H), 8.06 (d, J=6 Hz, 1H)

Intermediate 2-XX as shown in Table 6 was prepared from its corresponding intermediate in the same manner as Intermediate 2-XIX.

TABLE 6

| Int. No. | IUPAC name | Structure | Analytical Data |
|---|---|---|---|
| 2-XX | 4-[(4-chloro-1,6-dimethyl-pyrrolo[3,2-c]pyridin-2-yl)methyl]morpholine | 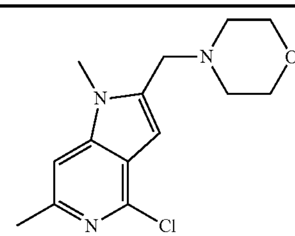 | LCMS: m/z 280.0 [M$^+$ + 1] $^1$HNMR (400 MHz, CDCl$_3$): δ 2.47 (t, J = 4.4 Hz, 4H), 2.61 (s, 3H), 3.61 (s, 2H), 3.67 (t, J = 4.9 Hz, 4H), 3.77 (s, 3H), 6.44 (s, 1H), 6.97 (s, 1H) |

Intermediate 2-XXI: 4-chloro-6-methyl-2-(pyrazol-1-ylmethyl)-1H-pyrrolo[3,2-c]pyridine

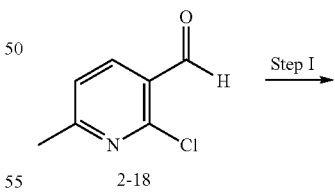

2-18

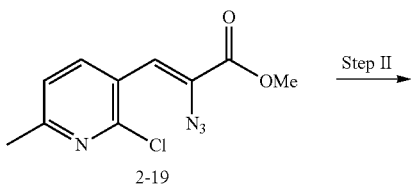

2-19

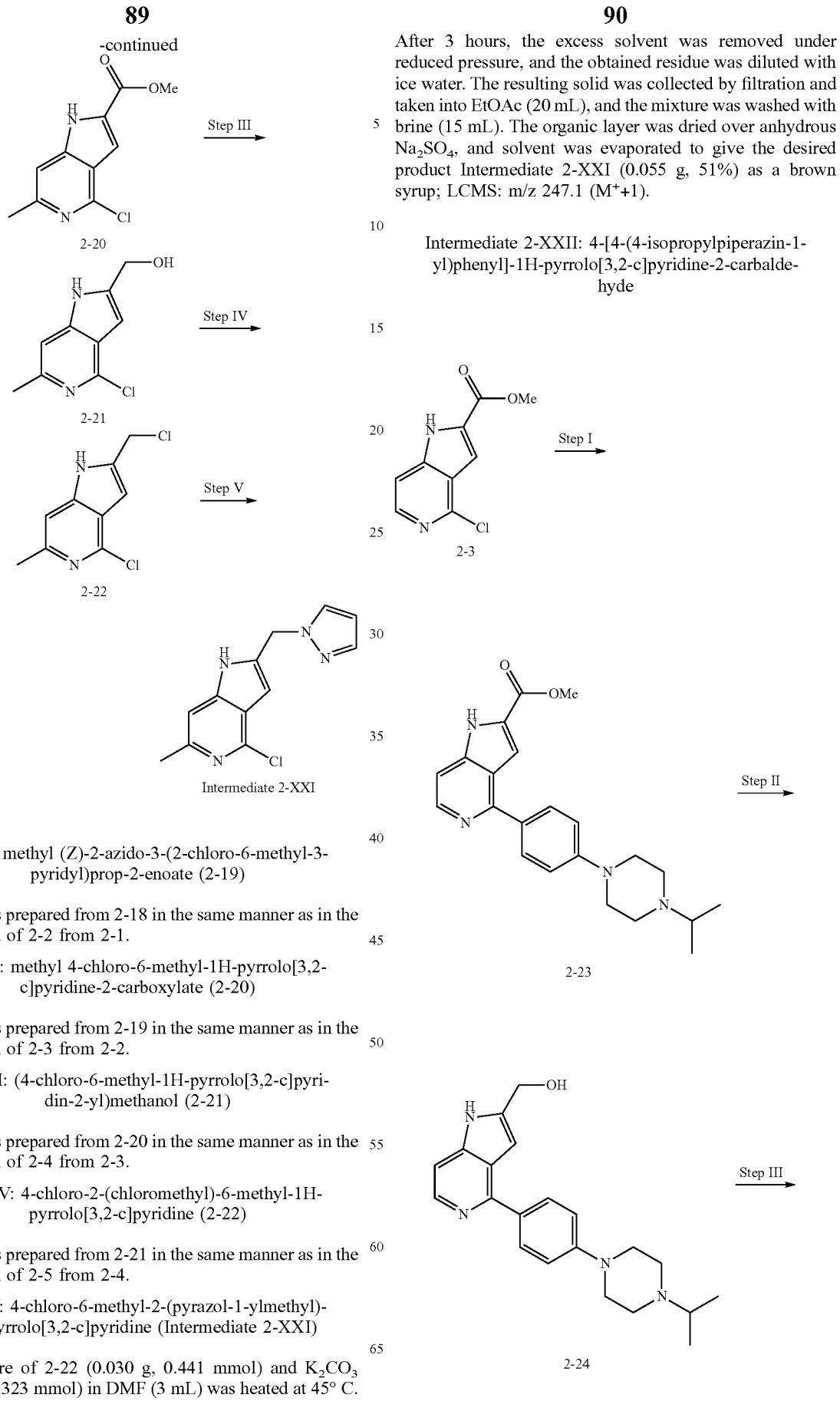

After 3 hours, the excess solvent was removed under reduced pressure, and the obtained residue was diluted with ice water. The resulting solid was collected by filtration and taken into EtOAc (20 mL), and the mixture was washed with brine (15 mL). The organic layer was dried over anhydrous $Na_2SO_4$, and solvent was evaporated to give the desired product Intermediate 2-XXI (0.055 g, 51%) as a brown syrup; LCMS: m/z 247.1 ($M^+$+1).

Intermediate 2-XXII: 4-[4-(4-isopropylpiperazin-1-yl)phenyl]-1H-pyrrolo[3,2-c]pyridine-2-carbaldehyde Step I: methyl (Z)-2-azido-3-(2-chloro-6-methyl-3-pyridyl)prop-2-enoate (2-19)

2-19 was prepared from 2-18 in the same manner as in the preparation of 2-2 from 2-1.

Step II: methyl 4-chloro-6-methyl-1H-pyrrolo[3,2-c]pyridine-2-carboxylate (2-20)

2-20 was prepared from 2-19 in the same manner as in the preparation of 2-3 from 2-2.

Step III: (4-chloro-6-methyl-1H-pyrrolo[3,2-c]pyridin-2-yl)methanol (2-21)

2-21 was prepared from 2-20 in the same manner as in the preparation of 2-4 from 2-3.

Step IV: 4-chloro-2-(chloromethyl)-6-methyl-1H-pyrrolo[3,2-c]pyridine (2-22)

2-22 was prepared from 2-21 in the same manner as in the preparation of 2-5 from 2-4.

Step V: 4-chloro-6-methyl-2-(pyrazol-1-ylmethyl)-1H-pyrrolo[3,2-c]pyridine (Intermediate 2-XXI)

A mixture of 2-22 (0.030 g, 0.441 mmol) and $K_2CO_3$ (0.183 g, 1.323 mmol) in DMF (3 mL) was heated at 45° C.

-continued

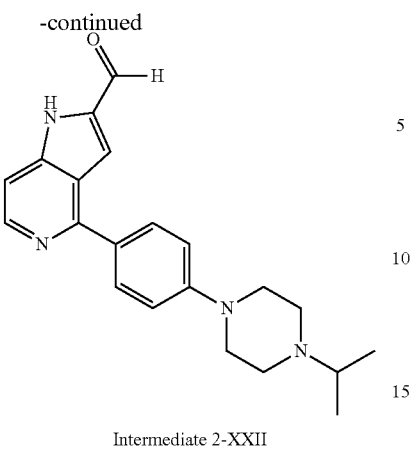

Intermediate 2-XXII

Step I: methyl 4-[4-(4-isopropylpiperazin-1-yl)phenyl]-1H-pyrrolo[3, 2-c]pyridine-2-carboxylate (2-23)

A mixture of 2-3 (1.5 g, 7.10 mmol), Intermediate 1-II (2.64 g, 7.8 mmol) and $K_2CO_3$ (2.9 g, 21.3 mmol) in 4:1 mixture of dioxane/water (120 mL) was degassed in a stream of argon for 30 minutes. To the mixture was added tetrakis (triphenylphosphine)palladium (0.411 g, 0.351 mmol), and the reaction mixture was again degassed for additional 30 minutes. After stirring at 90° C. for 18 hours, the volatiles were removed by evaporation, and the obtained residue was diluted with water (50 mL), followed by extraction with ethyl acetate (50 mL×3). The combined organic layers were washed with brine (500 mL), dried over anhydrous $Na_2SO_4$ and concentrated under reduced pressure. The obtained residue was purified by silica gel column chromatography using 5% MeOH in dichloromethane to give the desired product 2-23 (1.65 g, 62%) as a yellow solid; LCMS: m/z 379.1 [M$^+$+1].

Step II: [4-[4-(4-isopropylpiperazin-1-yl)phenyl]-1H-pyrrolo[3,2-c]pyridin-2-yl]methanol (2-24)

To a stirred solution of 2-23 (1.50 g, 3.96 mmol) in anhydrous THF (25 mL) was added LiAlH$_4$ (0.377 g, 9.92 mmol) in portions at 0° C. After stirring at the same temperature for 2 hours, the reaction mixture was allowed to cool to room temperature and stirred for additional 2 hours. Excess of LiAlH$_4$ was decomposed by adding saturated Na$_2$SO$_4$ solution (10 mL) and ethyl acetate (25 mL). The inorganic solid was removed by filtration through a celite pad. The filtrate was concentrated under reduced pressure, and the obtained residue was purified by silica gel column chromatography (60-120 mesh) by eluting with 10% MeOH in dichloromethane to give the desired product 2-24 (0.85 g, 61%) as a yellow solid; LCMS: m/z 351.1 (M$^+$+1)

Step III: 4-[4-(4-isopropylpiperazin-1-yl)phenyl]-1H-pyrrolo[3,2-c]pyridine-2-carbaldehyde (Intermediate 2-XXII)

Dess Martin periodinate (1.18 g, 2.78 mmol) was added to a stirred solution of 2-24 (0.650 g, 1.857 mmol) in CH$_2$Cl$_2$ (20 mL) at 0° C., and the reaction mixture was stirred for 18 hours at room temperature. The reaction mixture was diluted with dichloromethane (50 mL), and insoluble substance was removed by filtration through a celite pad. The filtrate was washed with 10% aqueous sodium thiosulfate solution (20 mL), followed by saturated aqueous NaHCO$_3$ solution. The organic layer was separated, and the aqueous layer was extracted with CH$_2$Cl$_2$ (50 mL×3). The combined organic layers were dried over anhydrous Na$_2$SO$_4$ and concentrated under reduced pressure to give the desired product Intermediate 2-XXII. (0.450 g, 70%) as a yellow solid; LCMS: m/z 349.2 (M$^+$+1).

Intermediate 2-XXIII: lithium 4-[4-(4-isopropylpiperazin-1-yl)phenyl]-1H-pyrrolo[3,2-c]pyridine-2-carboxylate

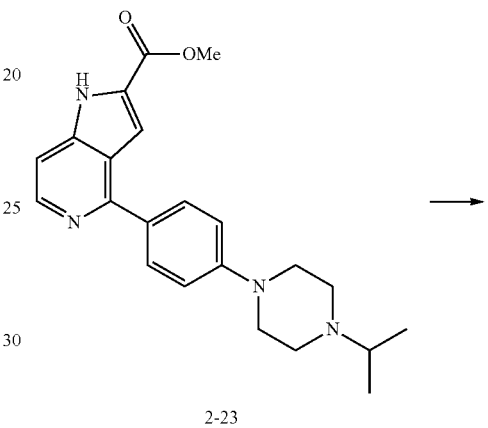

2-23

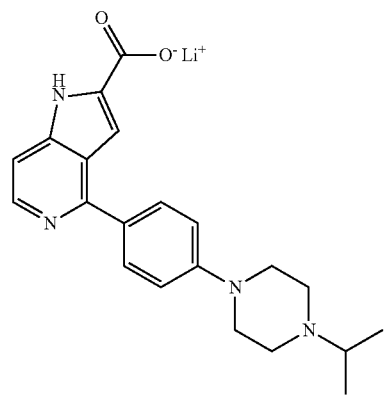

Intermediate 2-XXIII

LiOH H$_2$O (0.017 g, 0.396 mmol) was added to a stirred solution of 2-23 (0.150 g, 0.396 mmol) in a mixture of THF:MeOH:H$_2$O (3:2:1 ratio, 5 mL) at room temperature, and the reaction mixture was stirred for 18 hours at the same temperature. The volatiles were concentrated under reduced pressure to give the desired product Intermediate 2-XXIII (0.144 g, 83%) as a yellow solid; LCMS: m/z 365.1 [M$^+$+1].

Intermediate 2-XXIV: tert-butyl 4-(4-bromophenyl)-2-(morpholinomethyl)pyrrolo[3,2-c]pyridine-1-carboxylate

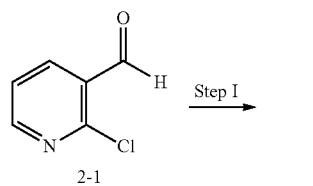
2-1

Step I

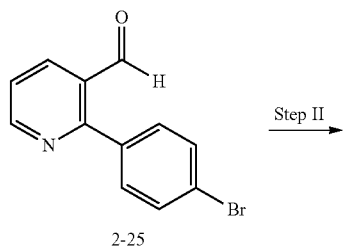
2-25

Step II

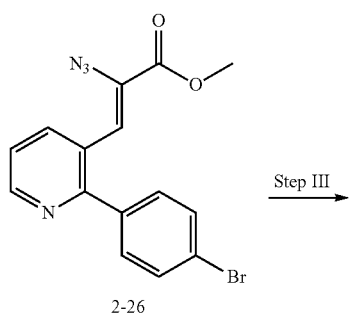
2-26

Step III

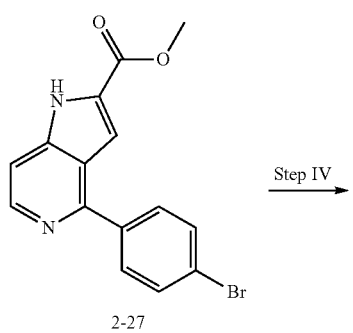
2-27

Step IV

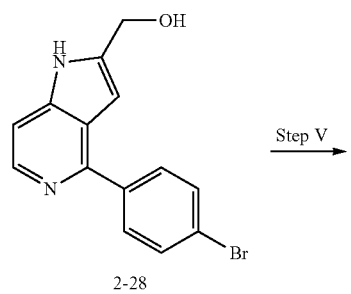
2-28

Step V

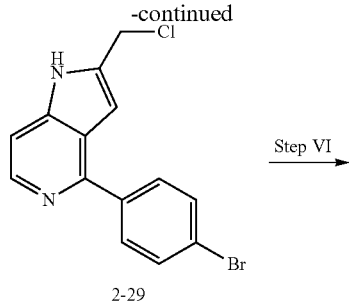
2-29

Step VI

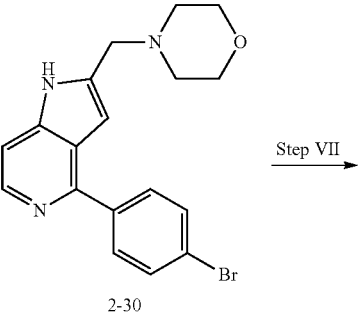
2-30

Step VII

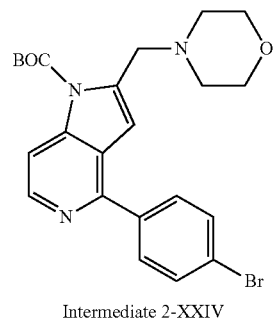
Intermediate 2-XXIV

Step I: 2-(4-bromophenyl)pyridine-3-carbaldehyde (2-25)

A solution of 2-1 (10 g, 70.6 mmol), (4-bromophenyl)boronic acid (14 g, 70.6 mmol) and Na$_2$CO$_3$ (14.98 g, 141.2 mmol) in a mixture of toluene:EtOH:H$_2$O (4:2:2, 440 mL) was degassed for 30 minutes. To the mixture was added tetrakis (triphenyl phosphine)palladium (0.021 g, 0.018 mmol), and the reaction mixture was again degassed for additional 15 minutes. After stirring at 90° C. for 18 hours, the volatiles were removed by evaporation, and the obtained residue was diluted with water (50 mL), followed by extraction with ethyl acetate (50 mL×3). The combined organic layers were washed with brine (50 mL), dried over anhydrous Na$_2$SO$_4$ and concentrated under reduced pressure. The obtained residue was purified by silica gel column chromatography using 8% EtOAc in hexanes as eluent to give the desired product 2-25 (8.5 g, 46%) as a white solid; LCMS: m/z 263.10 [M$^+$+1], 264.0 [M$^+$+2].

Step II: methyl (Z)-2-azido-3-[2-(4-bromophenyl)-3-pyridyl]prop-2-enoate (2-26)

To a stirred solution of 2-25 (8.5 g, 32.43 mmol) and methyl 2-azidoacetate (9.33 g, 7.90 ml, 81.07 mmol) in methanol (210 mL) was added a freshly prepared NaOMe solution [prepared by dissolving sodium (1.86 g, 81.07 mmol) in methanol (60 mL)] at −10° C. over 20 minutes.

The resulting reaction mixture was stirred at 0-5° C. for 12 hours. The reaction mixture was poured into cold saturated NH₄Cl solution (100 mL). The solid separated was collected by filtration and dried under vacuum to give the desired product 2-26 (2.5 g, 21%) as yellowish solid; LCMS: m/z 360.90 [M⁺+1].

Step III: methyl 4-(4-bromophenyl)-1H-pyrrolo[3,2-c]pyridine-2-carboxylate (2-27)

A solution of 2-26 (2.5 g, 6.96 mmol) in xylene (100 mL) was added dropwise to boiling xylene (200 mL) over a period of 20 minutes and held at this temperature for 2 hours. The reaction mixture was allowed to cool to room temperature and then stirred at 0° C. for another 1 hour. The solid separated was collected by filtration and dried under vacuum to give the desired product 2-27 (1.4 g, 61%) as a white solid; LCMS: m/z 333.0 (M⁺+2)

Step IV: [4-(4-bromophenyl)-1H-pyrrolo[3,2-c]pyridin-2-yl]methanol (2-28)

To a stirred solution of 2-27 (1.4 g, 4.22 mmol) in anhydrous THF (20 mL) was added LiAlH₄ (0.40 g, 10.56 mmol) in portions at 0° C. After completion of addition, the reaction mixture was allowed to warm at room temperature and stirred for 3 hours. Excess of LiAlH₄ was decomposed by adding saturated aqueous solution of Na₂SO₄ and ethyl acetate (50 mL) The inorganic substance was removed by filtration through a celite pad and washed with EtOAc (25 mL). The filtrate was concentrated under reduced pressure, and the resulting solid was triturated with diethyl ether to give the desired product 2-28 (1.0 g, 78%) as a white solid; LCMS: m/z 304.00 [M⁺+1], 305.00 [M⁺+2].

Step V: 4-(4-bromophenyl)-2-(chloromethyl)-1H-pyrrolo[3,2-c]pyridine (2-29)

Thionyl chloride (1.97 g, 1.2 mL, 16.4 mmol) and DMF (catalytic, 1 drop) were added to a stirred solution of 2-28 (1 g, 3.29 mmol) in 1:1 mixture of THF/CH₂Cl₂ (10 mL) at 0° C. After stirring at room temperature for additional 2 hours, the reaction mixture was cooled, and saturated aqueous NaHCO₃ solution (15 mL) was added thereto. The organic layer was separated, and the aqueous layer was extracted with CH₂Cl₂ (15 mL×3). The combined organic layers were dried over anhydrous Na₂SO₄ and concentrated under reduced pressure to give the desired product 2-29 (0.95 g, 90%) as a brown solid; LCMS: m/z 322.90 (M+1)

Step VI: 4-[[4-(4-bromophenyl)-1H-pyrrolo[3,2-c]pyridin-2-yl]methyl]morpholine (2-30)

To a mixture of 2-29 (0.95 g, 2.95 mmol) and morpholine (0.28 mL, 3.25 mmol) in DMF (15 mL) was added N,N-diisopropylethylamine (0.77 mL, 4.43 mmol) at room temperature. After stirring for 16 hours, the excess solvent was removed under reduced pressure, and the obtained residue was diluted with water (15 mL), and the mixture was extracted with EtOAc (50 mL×3). The combined organic layers were washed with brine (50 mL), dried over anhydrous Na₂SO₄, and concentrated under reduced pressure. The obtained residue was purified by silica gel column chromatography using 5% MeOH in dichloromethane as eluent to give the desired product 2-30 (0.9 g, 82%) as a yellow solid; LCMS: m/z 374.0 (M⁺+2).

Step VII: tert-butyl 4-(4-bromophenyl)-2-(morpholinomethyl)pyrrolo[3,2-c]pyridine-1-carboxylate (Intermediate 2-XXIV)

To a stirred solution of 2-30 (0.49 g, 0.40 mmol) in THF (5 mL) at room temperature were added Boc anhydride (0.105 g, 0.48 mmol), triethylamine (0.10 g, 0.14 mL, 1.0 mmol) and DMAP (0.005 g, 0.04 mmol). The resulting reaction mixture was stirred for 18 hours. The solvent was removed under reduced pressure. The obtained residue was taken into EtOAc (10 mL) and the mixture was washed with water (10 mL) followed by brine (10 mL). The organic layer was dried over anhydrous Na₂SO₄ and concentrated under reduced pressure to give the desired product Intermediate 2-XXIV (0.34, 55%) as an off white solid; LCMS: m/z 474.0 (M⁺+2)

Intermediate 3-I: 4-[2-[1-(benzenesulfonyl)-4-chloro-pyrrolo[3,2-c]pyridin-2-yl]ethyl]morpholine

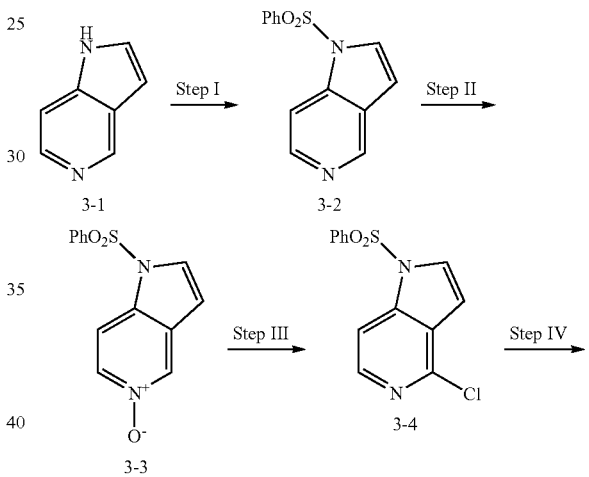

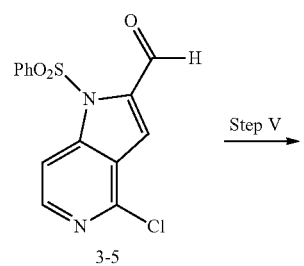

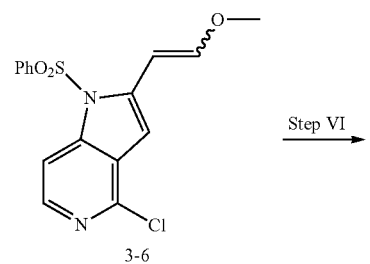

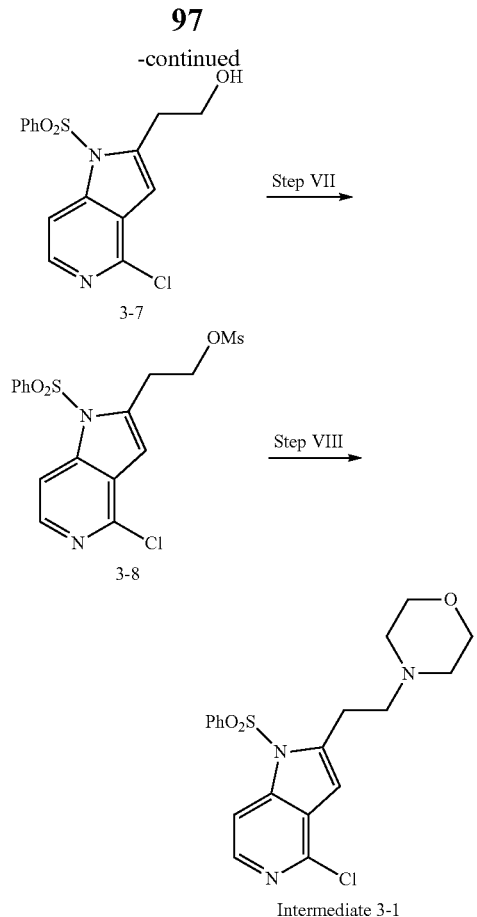

Step I: 1-(benzenesulfonyl)pyrrolo[3,2-c]pyridine (3-2)

A solution of 5-azaindole 3-1 (5 g, 42.3 mmol) in THF (50 mL) was added to a suspension of NaH (60% in mineral oil, 2 g, 50.8 mmol) in THF (50 mL) at 0° C. over 30 minutes. The resulting reaction mixture was allowed to warm to room temperature and stirred for 30 minutes. The reaction mixture was again cooled to 0° C., and benzenesulfonyl chloride (6.5 mL, 50.8 mmol) was added thereto over a period of 10 minutes, and the mixture was stirred at room temperature for 2 hours. The reaction mixture was diluted with saturated NH$_4$Cl solution (25 mL) and ethyl acetate (50 mL). The organic layer was separated, and the aqueous layer was extracted with ethyl acetate (25 mL×3). The combined organic layers were washed with brine (50 mL), dried over anhydrous Na$_2$SO$_4$, and concentrated under reduced pressure to give the crude product 3-2 (10.5 g, 96%) which was used for next step without purification; LCMS: m/z 259.1 [M$^+$+1].

5-Azaindole 3-1 may be commercially available, or can also be produced according to a method known per se or a method analogous thereto.

Step II: 1-(benzenesulfonyl)pyrrolo[3,2-c]pyridine-N-oxide (3-3)

m-Chloroperoxybenzoic acid (~70%, 63 g, 369.7 mmol) was added in portions to a stirred solution of 3-2 (9.5 g, 36.9 mmol) in CHCl$_3$ (250 mL) at room temperature, and the reaction mixture was stirred for 24 hours. The reaction mixture was cooled to 0° C., and 10% aqueous sodium sulfite solution (50 mL) was added thereto followed by saturated aqueous NaHCO$_3$ solution. The organic layer was separated, and the aqueous layer was extracted with CH$_2$Cl$_2$ (50 mL×3). The combined organic layers were dried over anhydrous Na$_2$SO$_4$, and concentrated under reduced pressure. The obtained residue was triturated with diethyl ether to give the desired product 3-3 as a creamy solid (8.5 g, 84%); LCMS: m/z 275.1[M$^+$+1].

Step III: 1-(benzenesulfonyl)-4-chloro-pyrrolo[3,2-c]pyridine (3-4)

To a solution of POCl$_3$ (100 ml) at 0° C. was added 3-3 (8.5 g, 31.11 mmol) in portions. The reaction mixture was heated at 90° C. for 18 hours. The excess POCl$_3$ was removed under reduced pressure, and the residue was dissolved in ethyl acetate (200 mL). The solution was washed with saturated aqueous NaHCO$_3$ solution (100 mL). The organic layer was dried over anhydrous Na$_2$SO$_4$, and concentrated under reduced pressure. The obtained residue was purified by silica gel column chromatography using 10% ethyl acetate in hexanes as eluent to give the desired product 3-4 as a white solid (5.5 g, 70%); LCMS: m/z 293.1[M$^+$+1].

Step IV: 1-(benzenesulfonyl)-4-chloro-pyrrolo[3,2-c]pyridine-2-carbaldehyde (3-5)

To a stirred mixture of 3-4 (5.5 g, 18.83 mmol) and tetramethylethylenediamine (2.95 mL, 18.83 mmol) in anhydrous THF was added dropwise lithium diisopropylamide heptane solution (1M in heptane, 38 mL, 37.67 mmol) at −20° C., and the mixture was stirred at this temperature for additional 45 minutes. DMF (2.75 g, 37.67 mmol) was added dropwise thereto over 15 min, and stirring was continued for additional 1 h. The reaction mixture was diluted with saturated aqueous NH$_4$Cl solution (20 mL) and ethyl acetate (100 mL). The organic layer was separated, and the aqueous layer was extracted with ethyl acetate (50 mL×3). The combined organic layers were washed with brine (100 mL), dried over anhydrous Na$_2$SO$_4$, and concentrated under reduced pressure. The obtained residue was purified by silica gel column chromatography using 15% ethyl acetate in hexanes as eluent to give the desired product 3-5 as yellow solid (3.5 g, 58%); LCMS: m/z 321.1 [M$^+$+1].

Step V: 1-(benzenesulfonyl)-4-chloro-2-[(E,Z)-2-methoxyvinyl]pyrrolo[3,2-c]pyridine (3-6)

To a suspension of methoxymethyltriphenylphosphonium chloride (4.88 g, 14.25 mmol) in anhydrous THF (20 mL) at 0° C. was added t-BuOK (0.95 g, 8.55 mmol), and the resulting brown reaction mixture was stirred for 1.5 hour. The reaction mixture was cooled to −78° C., and a solution of 3-5 (1.0 g, 9.25 mmol) in THF (5 mL) was added thereto, and the mixture was stirred at the same temperature for additional 1 hour. The reaction mixture was diluted with saturated NH$_4$Cl solution (15 mL) and ethyl acetate (25 mL). The organic layer was separated, and the aqueous layer was extracted with ethyl acetate (25 mL×2). The combined organic layers were washed with brine (25 mL), dried over anhydrous Na$_2$SO$_4$, and concentrated under reduced pressure. The obtained residue was purified by silica gel column chromatography using 5% ethyl acetate in hexanes as eluent to give the desired product 3-6 (0.62 g, 62%) as yellow oil together with inseparable impurity; LCMS: m/z 349.1 [M++1].

Step VI: 2-(1-(benzenesulfonyl)-4-chloro-pyrrolo[3,2-c]pyridin-2-yl)ethanol (3-7)

A solution of 3-6 (0.62 g, 1.78 mmol) in THF (30 mL) was treated with 6N aqueous HCl (15 mL) at room temperature and stirred at 60° C. for 4 h. The volatiles were removed under reduced pressure. The obtained residue was dissolved in ethyl acetate (25 mL), and the solution was washed with saturated aqueous NaHCO$_3$ solution (15 mL). The organic layer was washed with brine (20 mL), dried over anhydrous Na$_2$SO$_4$, and concentrated under reduced pressure. The obtained crude product 2-(1-(benzenesulfonyl)-4-chloro-pyrrolo[3,2-c]pyridin-2-yl)acetaldehyde (0.51 g) was used for next step without any purification. To a solution of the crude aldehyde (0.51 g, 1.52 mmol) in THF (20 mL) and 10% aqueous methanol was added NaBH$_4$ (0.134 g, 3.56 mmol) in portions at 0° C., and the resulting reaction mixture was stirred at room temperature for 2 hours. The reaction mixture was diluted with 10% aqueous, NH$_4$Cl and ethyl acetate (25 mL). The layers were separated, and the organic layer was washed with brine (15 mL) and dried over anhydrous Na$_2$SO$_4$, and concentrated under reduced pressure. The obtained residue was purified by combiflash using 40% ethyl acetate in hexanes as eluent to give the desired product 3-7 (0.46 g, 77% over two steps) as thick yellow liquid; LCMS: m/z 337.0 [M$^+$+1]

Step VII: 2-(1-(benzenesulfonyl)-4-chloro-pyrrolo[3,2-c]pyridin-2-yl)ethyl methanesulfonate (3-8)

To a solution of 3-7 (0.46 g, 1.36 mmol) in CH$_2$Cl$_2$ (8 mL) were added methanesulfonyl chloride (0.16 mL, 2.05 mmol) and Et$_3$N at 0° C. After 1 h, the reaction mixture was diluted with water (15 mL) and CH$_2$Cl$_2$ (25 mL). The layers were separated, and the organic layer was washed with brine (15 mL), dried over anhydrous Na$_2$SO$_4$, and concentrated under reduced pressure to give the crude product 3-8 (0.47 g) as a pale yellow liquid which was used for next step as such without any purification.

Step VIII: 4-[2-[1-(benzenesulfonyl)-4-chloro-pyrrolo[3,2-c]pyridin-2-yl]ethyl]morpholine (Intermediate 3-I)

To a mixture of crude 3-8 (0.470 g, 1.15 mmol) in anhydrous DMF (5 mL) were added morpholine (0.3 g, 3.39 mmol) and N,N-diisopropylethylamine (0.44 g, 3.39 mmol) at room temperature. After stirring at 60° C. for 16 hours, the excess solvent was removed in vacuo, and the obtained residue was diluted with ice water, followed by extraction with ethyl acetate (20 mL×3). The combined organic layers were washed with brine (25 mL), dried over anhydrous Na$_2$SO$_4$, and concentrated under reduced pressure. The obtained residue was purified by silica gel column chromatography using 50% ethyl acetate in hexanes as eluent to give the desired-product Intermediate 3-I (0.17 g, 31% over two steps from mesylate, intermediate) as a yellow solid; LCMS: m/z 406.0 [M$^+$+1].

$^1$HNMR (400 MHz, CDCl$_3$): δ 2.52-2.58 (m, 2H), 2.78 (t, J=7.6 Hz, 2H), 3.20 (t, J=7.2 Hz, 2H), 3.40 (t, J=4.8 Hz, 1H), 3.58 (t, J=4.8 Hz, 1H), 3.67-3.75 (m, 4H), 6.57 (s, 1H), 7.49 (app. t, J=7.6 Hz, 2H), 7.62 (app. t, J=5.2 Hz, 1H), 7.78 (d, J=7.6 Hz, 2H), 8.01 (d, J=6 Hz, 1H), 0.8.21 (d, J=6 Hz, 1H)

Intermediate 3-II: 4-[2-[1-(benzenesulfonyl)-4-chloro-6-methyl-pyrrolo[3,2-c]pyridin-2-yl]ethyl]morpholine

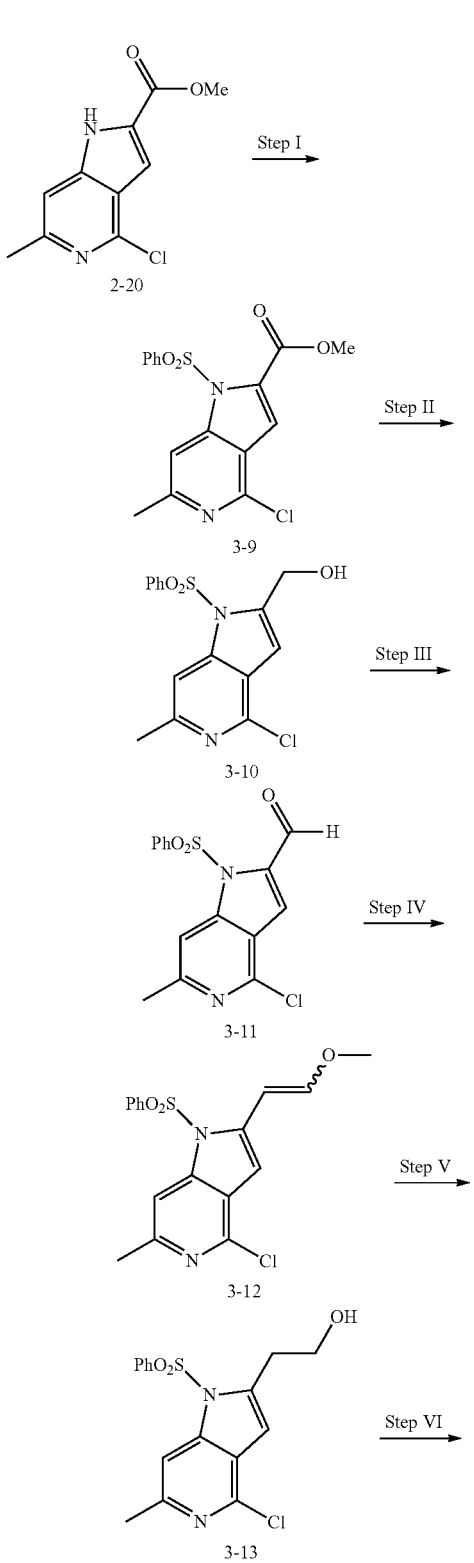

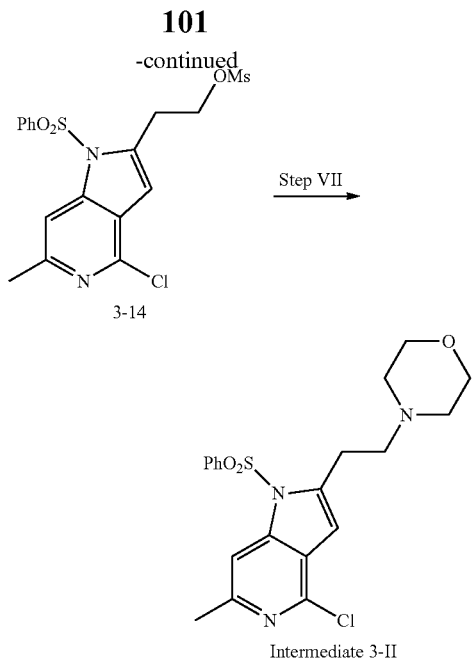

3-14

Intermediate 3-II

Step I: methyl 1-(benzenesulfonyl)-4-chloro-6-methyl-pyrrolo[3,2-c]pyridine-2-carboxylate (3-9)

To a stirred solution of 2-20 (9 g, 40.17 mmol) in DMF (100 mL) at 0° C. was added NaH (2.4 g, 60.26 mmol), and the mixture was stirred for 1.5 hours at room temperature. The reaction mixture was again cooled to 0° C., and benzenesulfonyl chloride (10.6 g, 7.77 mL, 60.26 mmol) was added thereto. The resulting reaction mixture was allowed to warm to room temperature, and stirred for 18 hours. The reaction mixture was poured into ice water, and the resulting precipitate was filtered over a buchner funnel and dried under high vacuum to give the desired product 3-9 (13.8 g, 94%) as an off white solid which was used for next step without purification; LCMS: m/z 365.0 [M$^+$+1].

Step II: [1-(benzenesulfonyl)-4-chloro-6-methyl-pyrrolo[3,2-c]pyridin-2-yl]methanol (3-10)

To a stirred solution of 3-9 (12.6 g, 34.53 mmol) in anhydrous THF (50 mL) was added LiAlH$_4$ (2.62 g, 69.0 mmol) in portions at 0° C. After completion of addition, the reaction mixture was allowed to attain room temperature and stirred for 30 minutes. Excess of LiAlH$_4$ was decomposed by adding saturated solution of Na$_2$SO$_4$. Ethyl acetate (100 mL) was added thereto, and the resulting inorganic solid was removed by filtration through a celite pad. The filtrate was concentrated under reduced pressure, and the resulting solid was triturated with diethyl ether to give the desired product 3-10 (11 g, 95%) as a white solid; LCMS: m/z 337.1 (M$^+$+1).

Step III: 1-(benzenesulfonyl)-4-chloro-6-methyl-pyrrolo[3,2-c]pyridine-2-carbaldehyde (3-11)

To a solution of 3-10 (11 g, 32.73 mmol) in CH$_2$Cl$_2$ (150 mL) at 0° C. was added Dess-martin periodinate (20.8 g, 49.1 mmol) in portions, and the resulting reaction mixture was stirred for 1 hour at 0° C. After completion of reaction (monitored by TLC), the reaction mixture was quenched with saturated sodium thiosulfate solution and washed with saturated sodium bicarbonate solution, water and brine. The organic layer was dried over anhydrous Na$_2$SO$_4$ and concentrated under reduced pressure. The obtained residue was triturated with diethyl ether. The obtained solid was collected by filtration and dried under vacuum to give the desired product 3-11 (9 g, 82%) as a white solid; LCMS: m/z 335.0 (M$^+$+1).

Step IV: 1-(benzenesulfonyl)-4-chloro-2-[(E)-2-methoxyvinyl]-6-methyl-pyrrolo[3,2-c]pyridine (3-12)

t-BuOK (12.09 g, 107.78 mmol) was added to a suspension of methoxymethyltriphenylphosphonium chloride (41.05 g, 119.7 mmol) in anhydrous THF (100 mL) at 0° C. The resulting brown reaction mixture was stirred for 1.5 hours at room temperature. The reaction mixture was cooled to −78° C., 3-11 (8.0 g, 23.95 mmol) was added in one portion, and the resulting reaction mixture was allowed to attain room temperature and stirred for 12 hours. The reaction mixture was diluted with saturated NH$_4$Cl solution (30 mL) and ethyl acetate (50 mL). The layers were separated. The aqueous layer was back extracted with ethyl acetate (30 mL×3), and the combined organic layers were washed with brine (50 mL) and dried over anhydrous Na$_2$SO$_4$. The obtained residue after evaporation in vacuo was purified by silica gel column chromatography using 15% EtOAc in hexanes to give the desired product 3-12 (3.1 g, 36%) as a yellow solid; LCMS: m/z 363.0 (M$^+$+1).

Step V: 2-[1-(benzenesulfonyl)-4-chloro-6-methyl-pyrrolo[3,2-c]pyridin-2-yl]ethanol (3-13)

A stirred solution of 3-12 (3.1 g, 8.54 mmol) in THF (8 mL) was treated with 6N aqueous HCl (8 mL) at room temperature and heated to 60° C. for 40 minutes. The reaction mixture was taken into ethyl acetate (20 mL), and the mixture was neutralized with saturated aqueous NaHCO$_3$ solution (15 mL) The organic layer was separated and washed with brine (15 mL), dried over anhydrous Na$_2$SO$_4$ and concentrated under reduced pressure. The obtained residue was taken into THF:MeOH (3:1, 8 mL), and to this solution was added NaBH$_4$ (0.65 g, 17.08 mmol) portion wise over a period of 15 minutes. The reaction mixture was stirred for 1 hour at room temperature. The reaction mixture was diluted with water (30 mL) and ethyl acetate (50 mL). The layers were separated. The aqueous layer was back extracted with ethyl acetate (30 mL×3), and the combined organic layers were washed with brine (50 mL) and dried over anhydrous Na$_2$SO$_4$. The organic layer was evaporated under reduced pressure, and the obtained residue was purified by silica gel column chromatography using 25% EtOAc in hexanes to give the desired product 3-13 (0.35 g, 12%) as a yellow oil; LCMS: m/z 350.9 (M$^+$+1).

Step VI: 2-[1-(benzenesulfonyl)-4-chloro-6-methyl-pyrrolo[3,2-c]pyridin-2-yl]ethyl methanesulfonate (3-14)

To a solution of 3-13 (0.35 g, 1.0 mmol) in CH$_2$Cl$_2$ (8 mL) were added methanesulfonyl chloride (0.13 mL, 1.20 mmol) and Et$_3$N (0.30 g, 3.0 mmol) at 0° C. After 1 h, the reaction mixture was diluted with water (15 mL) and CH$_2$Cl$_2$ (25 mL). The layers were separated, and the organic layer was washed with brine (15 mL), dried over anhydrous Na$_2$SO$_4$, and concentrated under reduced pressure to give the crude product 3-14 (0.42 g) as a pale yellow liquid which was used for next step as such without any purification.

Step VII: 4-[2-[1-(benzenesulfonyl)-4-chloro-6-methyl-pyrrolo[3,2-c]pyridin-2-yl]ethyl]morpholine (Intermediate 3-II)

To a mixture of crude 3-14 (0.42 g, 0.97 mmol) in anhydrous DMF (5 mL) were added morpholine (0.25 g, 2.93 mmol) and N,N-diisopropylethylamine (0.38 g, 2.93 mmol) at room temperature. After stirring at 60° C. for 16 hours, the excess solvent was removed in vacuo, and the obtained residue was diluted with ice water, followed by extraction with ethyl acetate (20 mL×3). The combined organic layers were washed with brine (25 mL), dried over anhydrous Na₂SO₄, and concentrated under reduced pressure. The obtained residue was purified by silica gel column chromatography using 50% ethyl acetate in hexanes as eluent to give the desired product Intermediate 3-II (0.195 g, 68%, over two steps from mesylate) as a yellow solid; LCMS: m/z 420.0 [M⁺+1].

¹H NMR (400 MHz, CDCl₃), δ 2.52 (t, J=4.4 Hz, 4H), 2.64 (s, 3H), 2.75 (t, J=7.6 Hz, 2H), 3.15 (t, J=7.6 Hz, 2H), 3.73 (t, J=4.8 Hz, 4H), 6.51 (s, 1H), 7.50 (d, J=8.0 Hz, 2H), 7.61 (app. t, J=7.6 Hz, 1H), 7.74 (d, J=7.6 Hz, 2H), 7.85 (s, 1H)

Intermediate 3-III: 4-chloro-6-methyl-1-methylsulfonyl-2-[2-(1-piperidyl)ethyl]pyrrolo[3,2-c]pyridine

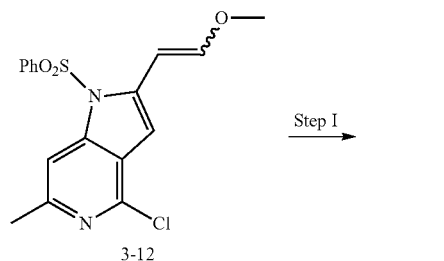

3-12

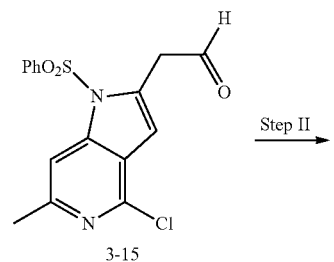

3-15

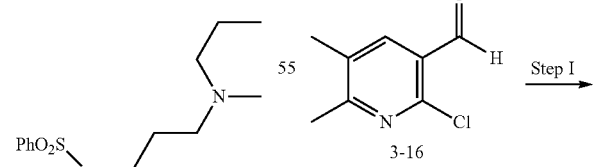

Intermediate 3-III

Step I: 2-[1-(benzenesulfonyl)-4-chloro-6-methyl-pyrrolo[3,2-c]pyridin-2-yl]acetaldehyde (3-15)

A stirred solution of 3-12 (0.5 g, 1.37 mmol) in THF (8 mL) was treated with 6 N aqueous HCl (8 mL) at room temperature and heated to 60° C. for 1.5 hours. The reaction mixture was taken into ethyl acetate (20 mL), and the mixture was neutralized with saturated aqueous NaHCO₃ solution (15 mL) The organic layer was separated, washed with brine (15 mL), dried over anhydrous Na₂SO₄ and concentrated under reduced pressure. The crude 3-15 (0.42 g) obtained as a yellow oil was used for next step without any purification.

Step II: 4-chloro-6-methyl-1-methylsulfonyl-2-[2-(1-piperidyl)ethyl]pyrrolo[3,2-c]pyridine (Intermediate 3-III)

To a stirred solution of crude 3-15 (0.42 g, 1.20 mmol) and piperidine (0.15 g, 1.80 mmol) in a mixture of MeOH:dichloroethane (1:1, 8 mL) were added acetic acid (1 drop, catalytic amount) and powdered molecular sieves (1 g). The reaction mixture was stirred for 3 hours at room temperature. Sodium cyanoborohydride (0.11 g, 1.80 mmol) was added thereto, and the reaction mixture was stirred for 16 hours. After completion of reaction, the reaction mixture was filtered through a celite pad, and the filtrate was concentrated under reduced pressure. The obtained residue was diluted with ethyl acetate (25 mL), and the mixture was washed with saturated aqueous NaHCO₃ solution (15 mL) followed by water and brine. The organic layer was dried over anhydrous sodium sulfate and concentrated under reduced pressure. The obtained residue was purified by preparative TLC using 60% EtOAc in hexanes as solvent system to give the desired product Intermediate 3-III (0.22 g, 44%) as a brownish solid; LCMS: m/z 418.2 (M+1).

¹H NMR (400 MHz, CDCl₃): δ 1.24-1.28 (m, 3H), 1.47-1.50 (m, 3H), 2.52-2.58 (m, 4H), 2.64 (s, 3H), 2.77 (t, J=8.0 Hz, 2H), 3.19 (t, J=8.0 Hz, 2H), 6.50 (s, 1H), 7.50 (d, J=7.6 Hz, 2H), 7.61 (app. t, J=7.6 Hz, 1H), 7.76 (d, J=7.2 Hz, 2H), 7.85 (s, 1H)

Intermediate 3-IV: 4-[2-(4-chloro-6,7-dimethyl-1H-pyrrolo[3,2-c]pyridin-2-yl)ethyl]morpholine

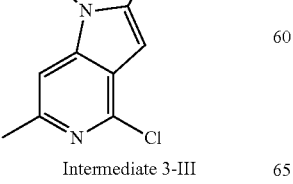

3-16

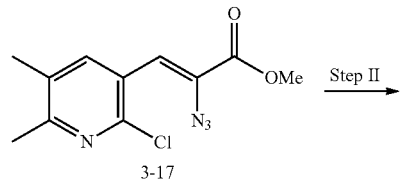

3-17

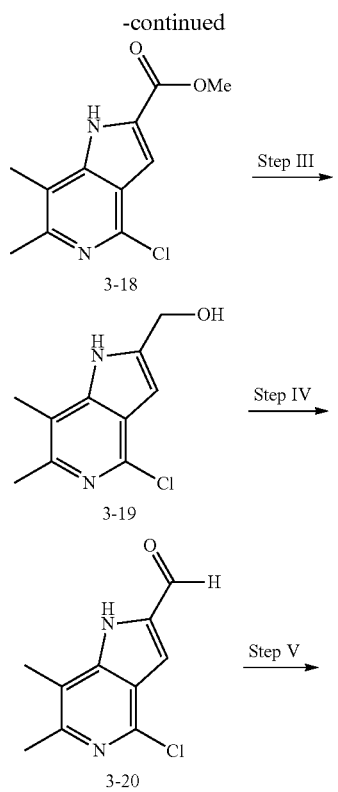

Step I: methyl (Z)-2-azido-3-(2-chloro-5,6-dimethyl-3-pyridyl)prop-2-enoate (3-17)

To a stirred solution of 3-16 (3.5 g, 20.7 mmol) and methyl 2-azidoacetate (9.53 g, 8.07 mL, 82.8 mmol) in methanol (210 mL) was added a freshly prepared NaOMe solution [prepared by dissolving sodium (1.90 g, 82.8 mmol) in methanol (60 mL)] at 0-5° C. over 20 minutes. The resulting reaction mixture was stirred at 0-5° C. for 12 hours. The reaction mixture was poured into cold saturated NH$_4$Cl solution (50 mL). The solid separated was collected by filtration and dried under vacuum to give the desired product 3-17 as yellowish solid (3.5 g, 63%).

Step II: methyl 4-chloro-6,7-dimethyl-1H-pyrrolo[3,2-c]pyridine-2-carboxylate (3-18)

A solution of 3-17 (3.5 g, 14.58 mmol) in xylene (100 mL) was added dropwise to boiling xylene (200 mL) over a period of 20 minutes and held at this temperature for 2 hours. The reaction mixture was allowed to cool to room temperature and then stirred at 0° C. for another 1 hour. The solid separated was collected by filtration and dried under vacuum to give the desired product 3-18 as a white solid (1.1 g, 35%); LCMS: m/z 239.0 (M$^+$+1).

Step III: (4-chloro-6,7-dimethyl-1H-pyrrolo[3,2-c]pyridin-2-yl)methanol (3-19)

To a stirred solution of 3-18 (3.1 g, 13.02 mmol) in anhydrous THF (50 mL) was added LiAlH$_4$ (0.98 g, 26.05 mmol) in portions at 0° C. After completion of addition, the reaction mixture was allowed to attain room temperature and stirred for 3 hours. Excess of LiAlH$_4$ was decomposed by adding saturated solution of Na$_2$SO$_4$ and ethyl acetate (100 mL). The inorganic solid was removed by filtration through a celite pad. The filtrate was concentrated under reduced pressure, and the resulting solid was triturated with diethyl ether to give the desired product 3-19 as a white solid (2.51 g, 91%); LCMS: m/z 211.1 (M$^+$+1).

Step IV: 4-chloro-6,7-dimethyl-1H-pyrrolo[3,2-c]pyridine-2-carbaldehyde (3-20)

To a solution of 3-19 (2.5 g, 11.9 mmol) in CH$_2$Cl$_2$ (30 mL) at 0° C. was added Dess-martin periodinate (7.60 g, 17.8 mmol) in portions, and the resulting reaction mixture was stirred for 1 hour at 0° C. After completion of reaction (monitored by TLC), it was quenched with saturated sodium thiosulfate solution and washed with saturated sodium bicarbonate solution, water and brine, dried over anhydrous Na$_2$SO$_4$ and concentrated under reduced pressure. The obtained residue was triturated with diethyl ether, and the solid was collected by filtration and dried under vacuum to give the desired product 3-20 (1.87 g, 75%); LCMS: m/z 209.0 (M$^+$+1).

Step V: 4-chloro-2-[(E,Z)-2-methoxyvinyl]-6,7-dimethyl-1H-pyrrolo[3,2-c]pyridine (3-21)

t-BuOK (3.39 g, 30.28 mmol) was added to a suspension of methoxymethyltriphenylphosphonium chloride (10.38 g, 30.28 mmol) in anhydrous THF (30 mL) at 0° C., and t-butanol (2.87 mL, 30.28 mmol) was added thereto. The resulting brown reaction mixture was stirred for 3 hours at room temperature. The reaction mixture was cooled to −78° C., 3-20 (0.7 g, 3.36 mmol) was added thereto in one portion, and the resulting reaction mixture was allowed to attain room temperature and stirred for 12 hours. The reaction mixture was diluted with saturated NH$_4$Cl (30 mL) and ethyl acetate (50 mL). The organic layer was separated. The aqueous layer was back extracted with ethyl acetate (30 mL×3), and the combined organic layers were washed with brine (50 mL) and dried over anhydrous Na$_2$SO$_4$. The obtained residue after evaporation in vacuo was purified by silica gel column chromatography using 15% EtOAc in hexanes to give the desired product 3-21 (0.789 g, 99%) as a yellow solid; LCMS: m/z 237.0 (M$^+$+1)

Step VI: 2-(4-chloro-6,7-dimethyl-1H-pyrrolo[3,2-c]pyridin-2-yl)acetaldehyde (3-22)

A stirred solution of 3-21 (0.65 g, 2.74 mmol) in THF (4 mL) was treated with 6N aqueous HCl (4 mL) at room temperature and heated to 60° C. for 40 minutes. The reaction mixture was taken into ethyl acetate (20 mL), and the mixture was neutralized with saturated aqueous NaHCO$_3$ solution (15 mL) The organic layer was separated and washed with brine (15 mL) and dried over anhydrous Na$_2$SO$_4$. The crude compound 3-22 (0.60 g, 98%) obtained after evaporation of organic layer was used for next step without any purification.

Step VII: 4-[2-(4-chloro-6,7-dimethyl-1H-pyrrolo[3,2-c]pyridin-2-yl)ethyl]morpholine (Intermediate 3-IV)

To a stirred solution of 3-22 (0.60 g, 2.70 mmol) and morpholine (0.35 g, 4.05 mmol) in a mixture of MeOH: dichloroethane (1:1, 10 mL) were added acetic acid (0.24 g, 4.05 mmol) and powdered molecular sieves (1 g), and the reaction mixture was stirred for 3 hours at room temperature. Sodium cyanoborohydride (0.25 g, 4.05 mmol) was added thereto, and the reaction mixture was stirred for 16 hours. After completion of reaction, the reaction mixture was filtered through a celite pad, and the filtrate was concentrated. The obtained residue was diluted with ethyl acetate (25 mL), and the mixture was washed with saturated aqueous NaHCO$_3$ solution (15 mL) followed by water and brine, dried over anhydrous sodium sulfate and concentrated under reduced pressure. The obtained residue was purified by silica gel column chromatography using 2% MeOH in dichloromethane to give the desired product Intermediate 3-IV (0.40 g, 50%) as a brownish solid; LCMS: m/z 294.1 (M$^+$+1).

$^1$H NMR (400 MHz, CDCl$_3$): δ 2.35 (s, 3H), 2.54 (s, 3H), 2.60-2.64 (m, 4H), 2.77 (t, J=6.0 Hz, 2H), 2.95 (t, J=6.0 Hz, 2H), 3.84 (t, J=4.4 Hz, 4H), 6.26 (s, 1H), 10.61 (bs, 1H, —NH)

Intermediates 3-V and 3-VI as shown in Table 7 were prepared from 3-9 in the same manner as Intermediate 3-IV

TABLE 7

| Int. No. | IUPAC name | Structure | Analytical Data |
| --- | --- | --- | --- |
| 3-V | 4-chloro-6,7-dimethyl-2-[2-(1-piperidyl)ethyl]-1H-pyrrolo[3,2-c]pyridine | 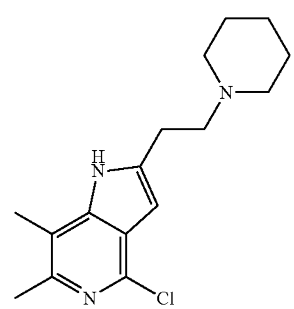 [SMILES: Cc1nc(Cl)c2cc(CCN3CCCCC3)[nH]c2c1C] | LCMS: m/z 292.1 (M$^+$ + 1) $^1$H NMR (400 MHz, DMSO): δ 1.38-1.42 (m, 2H), 1.48-1.53 (m, 4H), 2.34 (s, 3H), 2.37-2.46 (m, 7H), 2.62 (t, J = 7.2 Hz, 2H), 2.89 (t, J = 7.2 Hz, 2H), 6.21 (s, 1H), 11.42 (bs, 1H, —NH) |
| 3-VI | 4-chloro-6,7-dimethyl-2-(2-pyrrolidin-1-ylethyl)-1H-pyrrolo[3,2-c]pyridine | 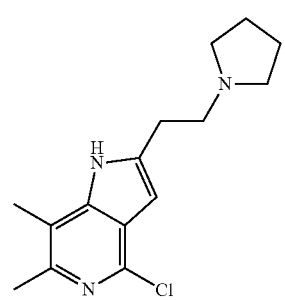 [SMILES: Cc1nc(Cl)c2cc(CCN3CCCC3)[nH]c2c1C] | LCMS: m/z 278.2 (M$^+$ + 1) $^1$H NMR (400 MHz, DMSO): δ 1.65-1.75 (m, 4H), 2.35 (s, 3H), 2.40 (s, 3H), 2.45-2.55 (m, 4H), 2.78-2.81 (m, 2H), 2.89-2.93 (m, 2H), 6.21 (s, 1H), 11.42 (bs, 1H, —NH) |

Intermediate 3-VII: 4-[2-(4-chloro-1,6-dimethyl-pyrrolo[3,2-c]pyridin-2-yl)ethyl]morpholine

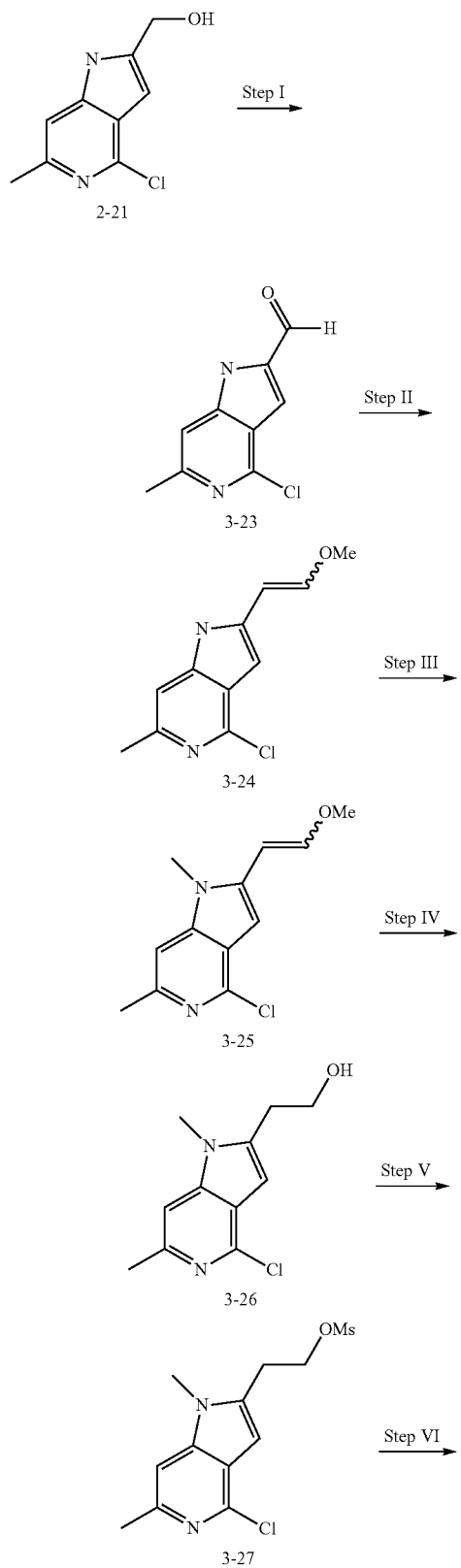

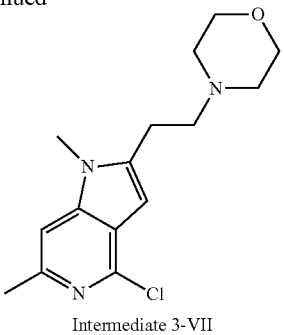

Intermediate 3-VII

Step I: 4-chloro-6-methyl-1H-pyrrolo[3,2-c]pyridine-2-carbaldehyde (3-23)

To a stirred solution of 2-21 (12 g, 61.22 mmol) in dichloromethane (200 mL) at 0° C. was added Dess-martin reagent (31.1 g, 73.46 mmol) in portion wise manner over a period of 30 minutes. The resulting suspension was allowed to stir for additional 2 hours. After completion of reaction (monitored by TLC), the reaction mixture was diluted with aqueous sodium thiosulfate saturated solution (100 mL) and aqueous saturated sodium bicarbonate solution (100 mL). The resulting suspension was then stirred for 1 hour. The organic layer was separated, and the aqueous layer was extracted with dichloromethane (100 mL×2). The combined organic layers were washed with water (100 mL) and brine (100 mL), dried over anhydrous sodium sulfate and concentrated under reduced pressure to give the desired product 3-23 (10.1 g, 85%) as a yellow solid; LCMS: m/z 195.1 [M$^+$+1].

Step II: 4-chloro-2-[(E,Z)-2-methoxyvinyl]-6-methyl-1H-pyrrolo[3,2-c]pyridine (3-24)

To a suspension of methoxymethyltriphenylphosphonium chloride (159 g, 463.86 mmol) and t-BuOH (15.2 g, 206.16 mmol) in anhydrous THF (300 mL) at 0° C. was added t-BuOK (52.05 g, 463.86 mmol), and the resulting orange brown reaction mixture was stirred for 2 hours. The reaction mixture was cooled to −78° C., and a solution of 3-23 (10 g, 51.54 mmol) in THF (50 mL) was added thereto. The reaction mixture was allowed to warm to room temperature during 2 hours and stirred for next 18 hours. The reaction mixture was diluted with saturated NH$_4$Cl solution (150 mL) and ethyl acetate (500 mL). The organic layer was separated, and the aqueous layer was extracted with ethyl acetate (500 mL×3). The combined organic layers were washed with brine (500 mL), dried over anhydrous Na$_2$SO$_4$ and concentrated under reduced pressure. The obtained residue was purified by silica gel column chromatography using 10% acetone in hexanes as eluent to give the desired product 3-24 (6.1 g, 54%) as a pale yellow solid; LCMS: m/z 222.9 [M$^+$+1].

Step III: 4-chloro-2-[(E,Z)-2-methoxyvinyl]-1,6-dimethyl-pyrrolo[3,2-c]pyridine (3-25)

A solution of 3-24 (20 g, 90.04 mmol) in anhydrous DMF (150 mL) was treated with NaH (60% in mineral oil) (5.4 g, 135.17 mmol) at 0° C. and stirred for 1 hour. To the mixture was added MeI (6.7 mL, 101.6 mmol), and stirring was continued for 1 h at 0° C. and then for additional 1 hour at room temperature. The reaction mixture was diluted with ice water, and the solid separated was collected by filtration and dried under vacuum to give the desired product 3-25 (21 g, crude yield 94%) as a yellow solid; LCMS: m/z 236.9 [M⁺+1].

Step IV: 2-(4-chloro-1,6-dimethyl-pyrrolo[3,2-c]pyridin-2-yl)ethanol (3-26)

A solution of 3-25 (21 g, 88.98 mmol) in THF (250 mL) was treated with 6 N aqueous HCl (50 mL) at room temperature and stirred at 60° C. for 4 hours. The volatiles were removed under reduced pressure. The obtained residue was dissolved in ethyl acetate (250 mL), and the solution was washed with saturated aqueous NaHCO₃ solution (150 mL). The organic layer was washed with brine (150 mL), dried over anhydrous Na₂SO₄ and concentrated under reduced pressure. The crude product 2-(4-chloro-1,6-dimethyl-pyrrolo[3,2-c]pyridin-2-yl)acetaldehyde (18 g) obtained was used for next step without any purification.

To a solution of the crude aldehyde (18 g crude, 87.0 mmol) in THF (80 mL) and 10% aqueous methanol (20 mL) was added NaBH₄ (4.90 g, 133.47 mmol) in portions at 000° C., and the resulting reaction mixture was stirred at room temperature for 2 hours. The reaction mixture was diluted with 10% aqueous NH₄Cl and ethyl acetate (500 mL). The layers were separated, the organic layer was washed with brine (150 mL), dried over anhydrous Na₂SO₄ and concentrated under reduced pressure. The obtained residue was purified by silica gel column chromatography using 2% methanol in DCM as eluent to give the desired product 3-26 (12.2 g, 61% over two steps) as thick yellow liquid; LCMS: m/z 224.9[M⁺+1].

Step V: 2-(4-chloro-1,6-dimethyl-pyrrolo[3,2-c]pyridin-2-yl)ethyl methanesulfonate (3-27)

To a solution of 3-26 (12.1 g, 5.38 mmol) in CH₂Cl₂ (200 mL) were added Et₃N (22.5 mL, 161.5 mmol) and methanesulfonyl chloride (6.50 g, 80.70 mmol) successively at 0° C. After 2 hours, the reaction mixture was diluted with water (150 mL) and CH₂Cl₂ (250 mL). The layers were separated, and the organic layer was washed with brine (150 mL), dried over anhydrous Na₂SO₄ and concentrated under reduced pressure to give the crude product 3-27 (13.91 g, crude yield 85%) as a yellow liquid which was used for next step as such without any purification.

Step VI: 4-[2-(4-chloro-1,6-dimethyl-pyrrolo[3,2-c]pyridin-2-yl)ethyl]morpholine (Intermediate 3-VII)

To a mixture of crude 3-27 (2.9 g, 9.57 mmol) in anhydrous DMF (20 mL) were added morpholine (2.50 g, 28.73 mmol) and N,N-diisopropylethylamine (3.70 g, 28.73 mmol) at room temperature. After stirring at 60° C. for 16 hours, the excess solvent was removed in vacuo, and the obtained residue was diluted with ice water, followed by extraction with ethyl acetate (50 mL×3). The combined organic layers were washed with brine (25 mL), dried over anhydrous Na₂SO₄ and concentrated under reduced pressure. The obtained residue was purified by Combiflash using 1% MeOH in dichloromethane as eluent to give the desired product Intermediate 3-VII (1.88 g, 48% over two steps from mesylate intermediate) as a light yellow solid; LCMS: m/z 294.2 [M⁺+1].

¹HNMR (400 MHz, CDCl₃): δ 2.55-2.57 (t, J=4.8 Hz, 4H), 2.60 (s, 3H), 2.73-2.77 (t, J=8.8 Hz, 2H), 2.88-2.95 (t, J=8.4 Hz, 2H), 3.66 (s, 3H), 3.74-3.77 (t, J=4.8 Hz, 4H), 6.34 (s, 1H), 6.94 (s, 1H)

Intermediate 4-I: 4-[3-[1-(benzenesulfonyl)-4-chloro-pyrrolo[3,2-c]pyridin-2-yl]propyl]morpholine

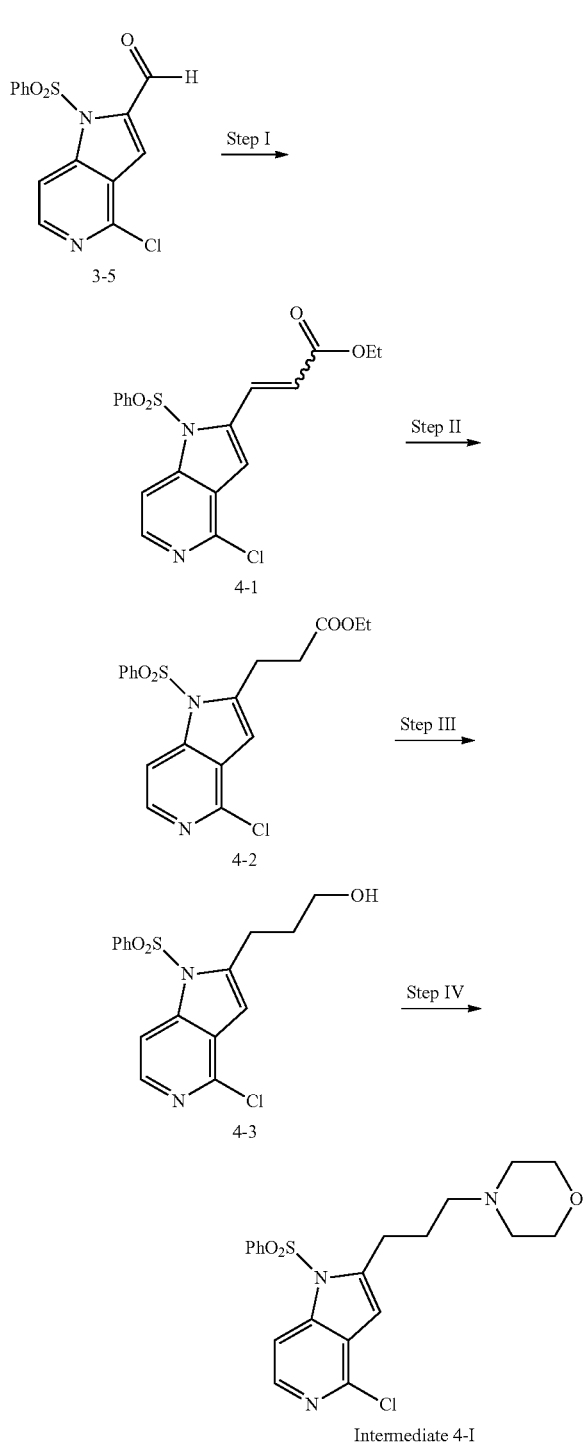

Step I: ethyl (E,Z)-3-[1-(benzenesulfonyl)-4-chloro-pyrrolo[3,2-c]pyridin-2-yl]prop-2-enoate (4-1)

A mixture of 3-5 (1.0 g, 3.11 mmol) and (carbethoxymethylene)triphenylphosphorane (2.11 g, 6.22 mmol) in toluene (30 mL) was refluxed for 16 hours. Excess of solvent was removed by evaporation under-reduced pressure, and the obtained residue was purified by silica gel column chromatography to give the desired product 4-1 (1.05 g, 84%) as a white solid; LCMS: m/z 390.9 [M$^+$+1].

Step II: ethyl 3-[1-(benzenesulfonyl)-4-chloro-pyrrolo[3,2-c]pyridin-2-yl]propanoate (4-2)

To a mixture of crude 4-1 (0.7 g, 1.79 mmol) in EtOAc (25 mL) was added PtO$_2$ (0.150 g) at room temperature. After stirring under hydrogen atmosphere (balloon pressure) at room temperature for 16 hours, the catalyst was removed by filtration through a celite pad and washed with EtOAc, and the filtrate was concentrated under reduced pressure. The obtained residue was purified by silica gel column chromatography using 20% AcOEt in hexanes as eluent to give the desired product 4-2 (0.610 g, 86%) as a light yellow solid; 392.9 [M$^+$+1].

Step III: 3-[1-(benzenesulfonyl)-4-chloro-pyrrolo[3,2-c]pyridin-2-yl]propan-1-ol (4-3)

A solution of 4-2 (0.75 g, 1.90 mmol) in dichloromethane (20 mL) was treated with DIBAL-H (1M in toluene; 5.40 mL, 3.81 mmol) at −0.78° C., and the reaction mixture was stirred at this temperature for another 30 minutes and allowed to warm to room temperature over 2 hours. Excess reagent was quenched with saturated aqueous NH$_4$Cl solution (30 mL), followed by extraction with ethyl acetate (25 mL×3). The combined organic layers were washed with brine (25 mL), dried over anhydrous Na$_2$SO$_4$ and concentrated under reduced pressure. The obtained residue was purified by silica gel column chromatography using 20% AcOEt in hexanes as eluent to give the desired product 4-3 (0.6 g, 89%) as a light yellow liquid; LCMS: m/z 351.0 [M$^+$+1].

Step IV: 4-[3-[1-(benzenesulfonyl)-4-chloro-pyrrolo[3,2-c]pyridin-2-yl]propyl]morpholine (Intermediate 4-I)

Intermediate 4-I was prepared from 4-3 in the same manner as in the preparation of Intermediate 3-VII from 3-26; LCMS: m/z 420.0 [M$^+$+1]

Intermediates 4-II and 4-III as shown in Table 8 were prepared from the corresponding starting material in the same manner as Intermediate 4-I

TABLE 8

| Int. No. | IUPAC name | Structure | Analytical Data |
| --- | --- | --- | --- |
| 4-II | 4-[3-1-(benzenesulfonyl)-(4-chloro-6-methyl-pyrrolo[3,2-c]pyridin-2-yl)propyl]morpholine | 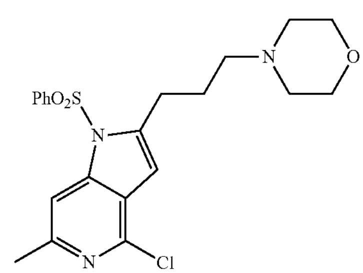 | LCMS: m/z 434.3 [M$^+$ + 1] $^1$HNMR (400 MHz, CDCl$_3$): δ 1.95 (quin., 2H), 2.42-2.50 (m, 6H), 2.64 (s, 3H), 2.98 (t, J = 7.6 Hz, 2H), 3.70-3.72 (t, J = 4.4 Hz, 4H), 6.46 (s, 1H), 7.47-7.52 (m, 2H), 7.59-7.63 (m, 1H), 7.75 (dd, J = 8.4, 0.8 Hz, 2H), 7.86 (s, 1H) |
| 4-III | 1-(benzenesulfonyl)-4-chloro-6-methyl-2-[3-(1-piperidyl)propyl]pyrrolo[3,2-c]pyridine | 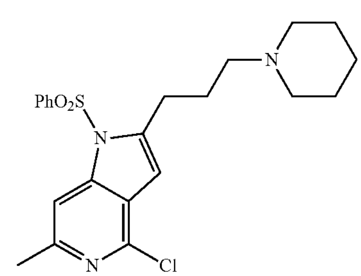 | LCMS: m/z 432.2 [M$^+$ + 1] |

Example A1

4-[[4-[4-(4-isopropylpiperazin-1-yl)phenyl]-1H-pyrrolo[3,2-c]pyridin-2-yl]methyl]morpholine

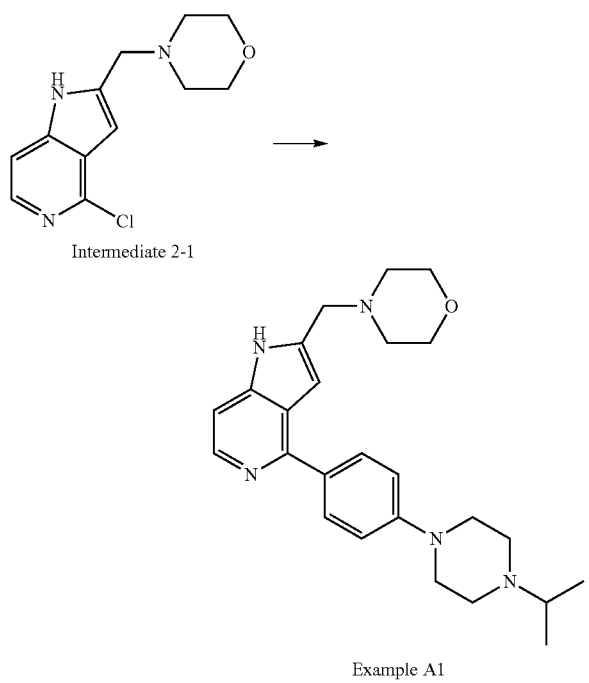

Intermediate 2-I

Example A1

A mixture of Intermediate 2-I (0.3 g, 1.19 mmol), 1-isopropyl-4-[4-(4,4,5,5-tetramethyl-1,3,2-dioxaborolan-2-yl)phenyl]piperazine (Intermediate 1-II). (0.2 g, 1.43 mmol) and $K_2CO_3$ (0.49 g, 3.58 mmol) in 4:1 mixture of dioxane/water (6 mL) was degassed in a stream of argon for 15 minutes. To the mixture was added tetrakis(triphenylphosphine)palladium (0.021 g, 0.018 mmol), and the reaction mixture was again degassed for additional 15 minutes. After stirring at 90° C. for 24 hours, the volatiles were removed by evaporation, and the obtained residue was diluted with water (20 mL) followed by extraction with ethyl acetate (25 mL×3). The combined organic layers were washed with brine (25 mL), dried over anhydrous $Na_2SO_4$, and concentrated under reduced pressure, followed by preparative TLC purification to give the desired product Example A1 as a dark yellow solid (0.095 g, 19%); LCMS: m/z 420.2 [$M^+$+1].

$^1$H NMR (400 MHz, $CDCl_3$): δ 1.44 (d, J=6.4 Hz, 6H), 2.35 (s, 1H), 2.45-2.56 (m, 4H), 2.70-2.85 (m, 4H), 3.36 (t, J=4.6 Hz, 4H), 3.68 (s, 0.2H), 3.71 (t, J=4.4 Hz, 4H), 6.71 (s, 1H), 7.02 (d, J=8.8 Hz, 2H), 7.13-7.25 (m, 1H), 7.92 (d, J=8.4 Hz, 2H), 8.33 (d, J=6 Hz, 1H), 9.11 (br s, 1H)

The following compounds Examples A2-A40 as shown in Table 9 were prepared from the corresponding intermediates in the same manner as Example A1.

TABLE 9

| Ex. No. | IUPAC name | Structure | Int. from which prepared | Analytical Data |
|---|---|---|---|---|
| A2 | 4-[[4-[4-(4-methylpiperazin-1-yl)phenyl]-1H-pyrrolo[3,2-c]pyridin-2-yl]methyl]morpholine | 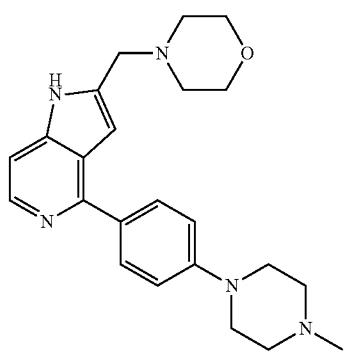 [SMILES: CN1CCN(c2ccc(-c3nccc4[nH]c(CN5CCOCC5)cc34)cc2)CC1] | 2-I and 1-I | LCMS: m/z 392.1 [$M^+$ + 1] $^1$H NMR (400 MHz, $CDCl_3$): δ 2.38 (s, 3H), 2.42-2.57 (m, 4H), 2.61 (t, J = 4.8 Hz, 4H), 3.32 (t, J = 4.8 Hz, 4H), 3.68 (s, 2H), 3.72 (t, J = 4.4 Hz, 4H), 6.70 (s, 1H), 7.04 (d, J = 8.8 Hz, 2H), 7.19 (d, J = 5.6 Hz, 1H), 7.91 (d, J = 8.8 Hz, 2H), 8.33 (d, J = 6 Hz, 1H), 8.99 (br s, 1H) |

TABLE 9-continued

| Ex. No. | IUPAC name | Structure | Int. from which prepared | Analytical Data |
|---|---|---|---|---|
| A3 | 4-[[4-[4-(4-ethylpiperazin-1-yl)phenyl]-1H-pyrrolo[3,2-c]pyridin-2-yl]methyl]morpholine | 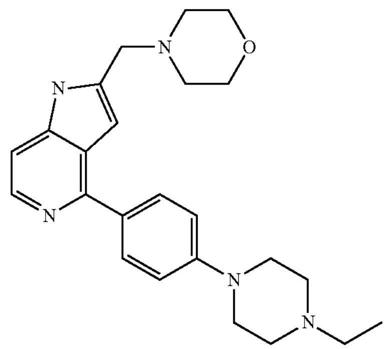 [SMILES: CCN1CCN(c2ccc(-c3nccc4[nH]c(CN5CCOCC5)cc34)cc2)CC1] | 2-I and 1-IV | LCMS: m/z 406.3 [M$^+$ + 1] $^1$H NMR (400 MHz, CDCl$_3$): δ 1.16 (t, J = 7.2 Hz, 3H), 2.48-2.54 (m, 6H), 2.66 (t, J = 4.8, Hz, 4H), 3.34 (t, J = 4.8 Hz, 4H), 3.68 (s, 2H), 3.72 (t, J = 4.4 Hz, 4H), 6.70 (s, 1H), 7.05 (d, J = 8.8 Hz, 2H), 7.19 (d, J = 6 Hz, 1H), 7.92 (d, J = 8.4 Hz, 2H), 8.35 (d, J = 5.6 Hz, 1H), 8.92 (br s, 1H) |
| A4 | 4-[[4-[4-[4-isopropylpiperazin-1-yl)phenyl]-6-methyl-1H-pyrrolo[3,2-c]pyridin-2-yl]methyl]morpholine | 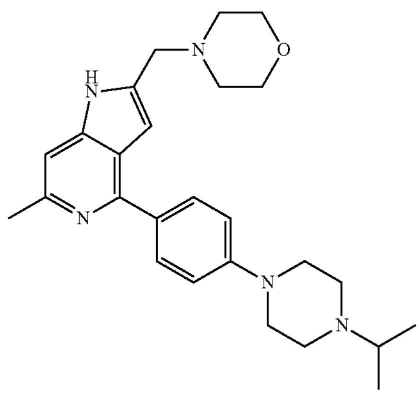 [SMILES: Cc1cc2[nH]c(CN3CCOCC3)cc2c(-c2ccc(N3CCN(C(C)C)CC3)cc2)n1] | 2-IX and 1-II | LCMS: m/z 434.3 [M$^+$ + 1] $^1$HNMR (400 MHz, CDCl$_3$): δ 1.13 (d, J = 6.8 Hz, 6H), 2.45-2.50 (m, 4H), 2.68 (s, 3H), 2.73-2.77 (m, 5H), 3.33 (t, J = 4.4 Hz, 4H), 3.64 (s, 2H), 3.71 (t, J = 4.4 Hz, 4H), 6.61 (s, 1H), 7.02 (d, J = 8.8 Hz, 2H), 7.03 (s, 1H, merged in doublet), 7.89, (d, J = 8.8 Hz, 2H), 8.74 (s, 1H) |
| A5 | 4-[[4-[4-(4-ethylpiperazin-1-yl)phenyl]-6-methyl-1H-pyrrolo[3,2-c]pyridin-2-yl]methyl]morpholine | 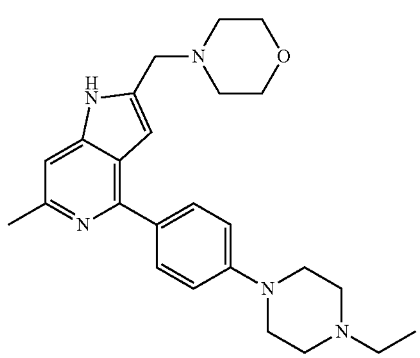 [SMILES: CCN1CCN(c2ccc(-c3nc(C)cc4[nH]c(CN5CCOCC5)cc34)cc2)CC1] | 2-IX and 1-IV | LCMS: m/z 420.3 [M$^+$ + 1] $^1$HNMR (400 MHz, DMSO-d6): δ 1.05 (t, J = 7.2 Hz, 3H), 2.35-2.44 (m, 6H), 2.48-2.51 (m, 4H, merged in solvent residual peak), 2.52 (s, 3H), 3.20-3.28 (m, 4H), 3.55-3.60 (m, 4H), 3.61 (s, 2H), 6.56 (s, 1H), 7.02-7.09 (m, 3H), 7.86 (d, J = 8.8 Hz, 2H), 11.39 (bs, 1H) |

TABLE 9-continued

| Ex. No. | IUPAC name | Structure | Int. from which prepared | Analytical Data |
|---------|------------|-----------|--------------------------|-----------------|
| A6 | tert-butyl 4-[4-[6-methyl-2-(morpholinomethyl)-1H-pyrrolo[3,2-c]pyridin-4-yl]phenyl]piperidine-1-carboxylate | 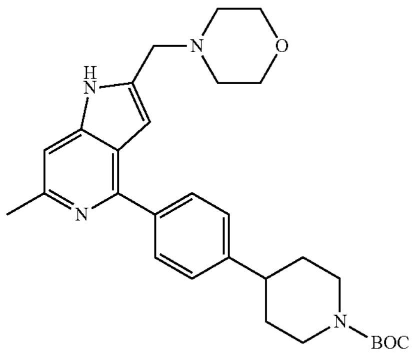 [SMILES: Cc1cc2[nH]c(CN3CCOCC3)cc2c(-c2ccc(C3CCN(C(=O)OC(C)(C)C)CC3)cc2)n1] | 2-IX and 1-IX | LCMS: m/z 491.2 [M$^+$ + 1] $^1$HNMR (400 MHz, CDCl$_3$): δ 1.49 (s, 9H), 1.82-1.89 (m, 2H), 2.45-2.52 (m, 4H), 2.68 (s, 3H), 2.70-2.89 (m, 4H), 3.65 (s, 2H), 3.72 (t, J = 4.4 Hz, 4H), 4.12-4.39 (m, 3H), 6.60 (s, 1H), 7.06 (s, 1H), 7.32 (d, J = 8.4 Hz, 2H), 7.88 (d, J = 8.4 Hz, 2H), 8.68 (bs, 1H) |
| A7 | tert-butyl 4-[4-[2-(morpholinomethyl)-1H-pyrrolo[3,2-c]pyridin-4-yl]phenyl]piperazine-1-carboxylate | 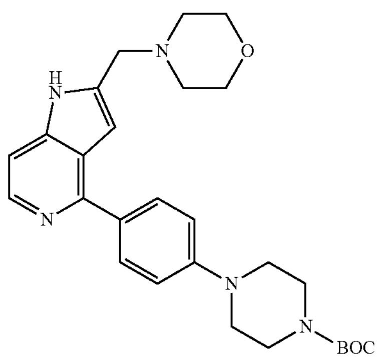 [SMILES: CC(C)(C)OC(=O)N1CCN(c2ccc(-c3nccc4[nH]c(CN5CCOCC5)cc34)cc2)CC1] | 2-I and 1-III | LCMS: m/z 478.3 [M$^+$ + 1] |
| A8 | 4-[[4-[4-(4-isopropylpiperazin-1-yl)phenyl]-1-methyl-pyrrolo[3,2-c]pyridin-2-yl]methyl]morpholine | 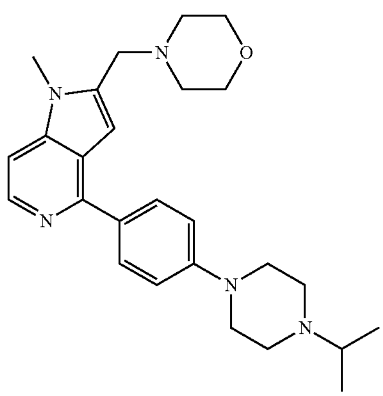 [SMILES: CC(C)N1CCN(c2ccc(-c3nccc4c3cc(CN3CCOCC3)n4C)cc2)CC1] | | LCMS: m/z 434.2 [M$^+$ + 1] $^1$H NMR (400 MHz, CDCl$_3$): 1.11 (d, J = 6.4 Hz, 6H), 2.46-2.49 (m, 4H), 2.72 (t, J = 4.8 Hz, 4H), 2.73-2.72 (m, 1H), 3.32 (t, J = 4.8 Hz, 4H), 3.65 (s, 2H), 3.68 (t, J = 4.4 Hz, 4H), 3.83 (s, 3H), 6.70 (s, 1H), 7.05 (d, J = 8.8 Hz, 2H), 7.12 (d, J = 6 Hz, 1H), 7.92 (d, J = 8.8 Hz, 2H), 8.36 (d, J = 6 Hz, 1H) |

TABLE 9-continued

| Ex. No. | IUPAC name | Structure | Int. from which prepared | Analytical Data |
|---|---|---|---|---|
| A9 | 4-[[1-methyl-4-[4-(4-methylpiperazin-1-yl)phenyl]pyrrolo[3,2-c]pyridin-2-yl]methyl]morpholine | 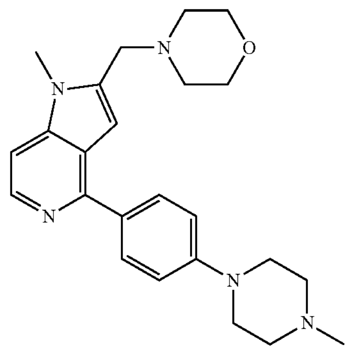 [SMILES: CN1CCN(c2ccc(-c3nccc4c3cc(CN3CCOCC3)n4C)cc2)CC1] | 2-XIX and 1-I | LCMS: m/z 406.2 [M$^+$ + 1] $^1$H NMR (400 MHz, CDCl$_3$): δ 2.37 (s, 3H), 2.45-2.50 (m, 4H), 2.60 (t, J = 4.4 Hz, 4H), 3.16-3.30 (m, 4H), 3.64 (s, 2H), 3.65-3.70 (m, 4H), 3.83 (s, 3H), 6.69 (s, 1H), 7.05 (d, J = 8.4 Hz, 2H), 7.10 (d, J = 6 Hz, 1H), 7.92 (d, J = 8.4 Hz, 2H), 8.38 (d, J = 5.6 Hz, 1H) |
| A10 | 4-methyl-1-[4-[2-(morpholinomethyl)-1H-pyrrolo[3,2-c]pyridin-4-yl]phenyl]piperidin-4-ol | 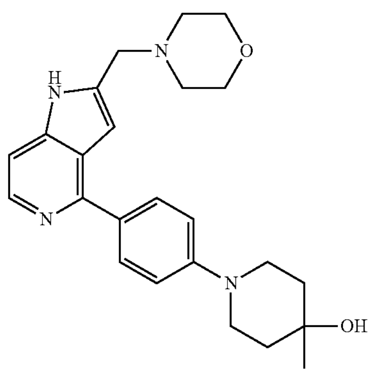 [SMILES: CC1(O)CCN(c2ccc(-c3nccc4[nH]c(CN5CCOCC5)cc34)cc2)CC1] | 2-I and 1-X | LCMS: m/z 407.1 [M$^+$ + 1] $^1$H NMR (400 MHz, (CD$_3$OD): δ 1.27 (s, 3H), 1.72-1.76 (m, 4H), 2.51 (t, J = 4.4 Hz, 4H), 3.29-3.34 (m, 2H), 3.46-3.50 (m, 2H), 3.70 (t, J = 5.8 Hz, 6H), 6.71 (s, 1H), 7.13 (d, J = 8.8 Hz, 2H), 7.32 (d, J = 6 Hz, 1H), 7.77 (d, J = 8.8 Hz, 2H), 8.11 (d, J = 6 Hz, 1H) |
| A11 | 4-[[4-[4-[1-(oxetan-3-yl)-3,6-dihydro-2H-pyridin-4-yl]phenyl]-1H-pyrrolo[3,2-c]pyridin-2-yl]methyl]morpholine | 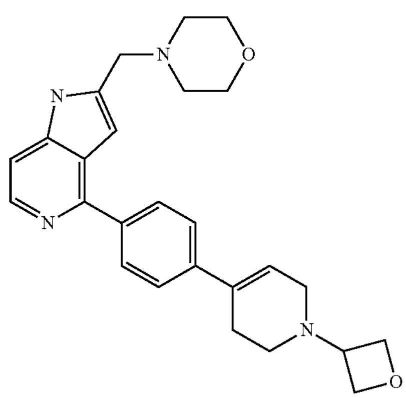 [SMILES: C1=C(c2ccc(-c3nccc4[nH]c(CN5CCOCC5)cc34)cc2)CCN(C2COC2)C1] | 2-I and 1-XI | LCMS: m/z 431.3 [M$^+$ + 1] $^1$H NMR (400 MHz, CDCl$_3$): δ 2.46-2.50 (m, 4H), 2.61-2.73 (m, 4H), 3.10 (d, J = 2.4 Hz, 2H), 3.67-3.75 (m, 7H), 4.74 (d, J = 6.8 Hz, 4H), 6.17 (m, 1H), 6.93 (s, 1H), 7.22 (d, J = 5.6 Hz, 1H), 7.53 (d, J = 8.4 Hz, 2H), 7.95 (d, J = 8.4 Hz, 2H), 8.39 (d, J = 6 Hz, 1H), 8.83 (br s, 1H) |

TABLE 9-continued

| Ex. No. | IUPAC name | Structure | Int. from which prepared | Analytical Data |
|---|---|---|---|---|
| A12 | 1-[[4-[4-(4-isopropylpiperazin-1-yl)phenyl]-1H-pyrrolo[3,2-c]pyridin-2-yl]methyl]piperidin-4-ol | 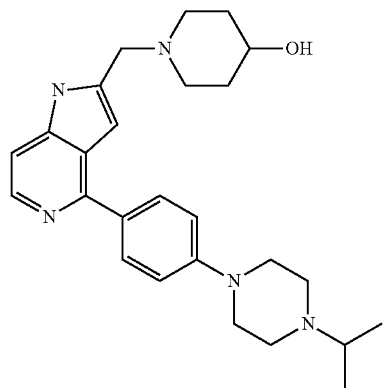 [SMILES: CC(C)N1CCN(c2ccc(-c3nccc4[nH]c(CN5CCC(O)CC5)cc34)cc2)CC1] | 2-II and 1-II | LCMS: m/z 434.3 [M+ + 1] $^1$H NMR (400 MHz, CDCl$_3$): δ 1.11 (d, J = 6.8 Hz, 6H), 1.57-1.63 (m, 2H), 1.90-1.93 (m, 2H), 2.26 (t, J = 9.6 Hz, 2H), 2.71-2.80 (m, 7H), 3.32 (t, J = 5 Hz, 4H), 3.69 (s, 2H), 3.77 (m, 1H), 6.67 (s, 1H), 7.04 (d, J = 8.8 Hz, 2H), 7.18 (d, J = 6 Hz, 1H), 7.91 (d, J = 8.8 Hz, 2H), 8.34 (d, J = 6 Hz, 1H), 9.05 (br s, 1H) |
| A13 | 7-[[4-[4-(4-isopropylpiperazin-1-yl)phenyl]-1H-pyrrolo[3,2-c]pyridin-2-yl]methyl]-7-azaspiro[3.5]nonan-2-ol | 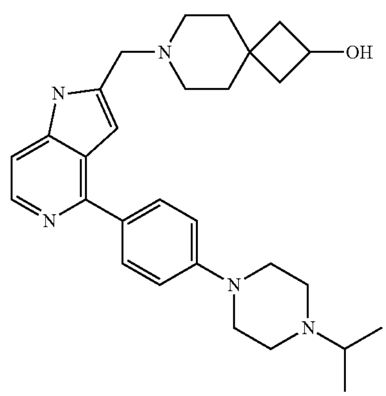 [SMILES: CC(C)N1CCN(c2ccc(-c3nccc4[nH]c(CN5CCC6(CC5)CC(O)C6)cc34)cc2)CC1] | 2-III and 1-II | LCMS: m/z 474.3 [M+ + 1] $^1$H NMR (400 MHz, (CD$_3$OD): δ 1.18 (d, J = 6.4 Hz, 6H), 1.62 (q, J = 7.7 Hz, 6H), 2.17-2.22 (m, 2H), 2.43 (s, 4H), 2.86 (t, J = 4.8 Hz, 5H), 3.40 (t, J = 5.0 Hz, 4H), 3.72 (s, 2H), 4.18 (quin, 1H), 6.77 (s, 1H), 7.16 (d, J = 8.8 Hz, 2H), 7.42 (d, J = 5.6 Hz, 1H), 7.81 (d, J = 8.8 Hz, 2H), 8.13 (d, J = 5.6 Hz, 1H) |
| A14 | tert-butyl 4-(3-[2-(morpholinomethyl)-1H-pyrrolo[3,2-c]pyridin-4-yl]pyridin-2-yl]-3,6-dihydro-2H-pyridin-1-carboxylate | 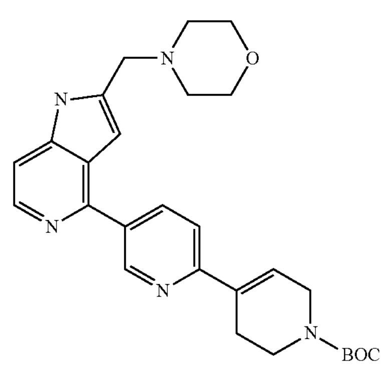 [SMILES: CC(C)(C)OC(=O)N1CC=C(c2ccc(-c3nccc4[nH]c(CN5CCOCC5)cc34)cn2)CC1] | 2-I and 1-XII | LCMS: m/z 476.2 [M+ + 1] |

TABLE 9-continued

| Ex. No. | IUPAC name | Structure | Int. from which prepared | Analytical Data |
|---|---|---|---|---|
| A15 | tert-butyl 4-[3-[2-(morpholinomethyl)-1H-pyrrolo[3,2-c]pyridin-4-yl]pyridin-2-yl]piperazine-1-carboxylate | 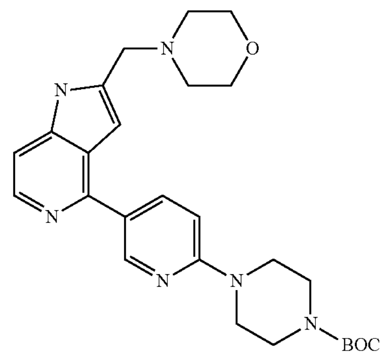 [SMILES: CC(C)(C)OC(=O)N1CCN(c2ccc(-c3nccc4[nH]c(CN5CCOCC5)cc34)cn2)CC1] | 2-I and 1-XIII | LCMS: m/z 479.2 [M$^+$ + 1] |
| A16 | 2-[(3-fluoroazetidin-1-yl)methyl]-4-[4-(4-isopropylpiperazin-1-yl)phenyl]-1H-pyrrolo[3,2-c]pyridine | 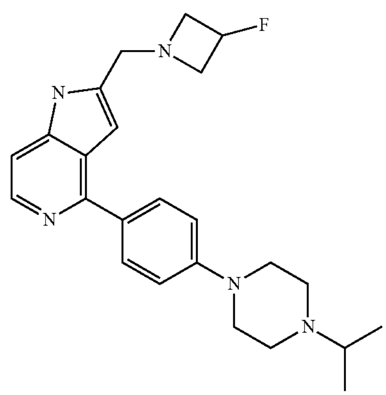 [SMILES: CC(C)N1CCN(c2ccc(-c3nccc4[nH]c(CN5CC(F)C5)cc34)cc2)CC1] | 2-IV and 1-II | LCMS: m/z 408.3 [M$^+$ + 1] $^1$H NMR (400 MHz, CDCl$_3$): δ 1.16 (dd, J = 6.8 Hz, 6H), 2.79-2.84 (m, 5H), 3.26-3.28 (m, 1H), 3.32-3.34 (m, 1H), 3.35-3.95 (m, 4H), 3.63-3.69 (m, 2H), 3.85 (s, 2H), 5.05-5.28 (m, 1H), 6.69 (s, 1H), 7.03 (d, J = 8.0 Hz, 2H), 7.21 (d, J = 5.6 Hz, 1H), 7.92 (d, J = 8.4 Hz, 2H), 8.31 (d, J = 5.6 Hz, 1H), 9.20 (br.s, 1H) |
| A17 | 4-[4-(4-isopropylpiperazin-1-yl)phenyl]-2-(1-piperidylmethyl)-1H-pyrrolo[3,2-c]pyridine | 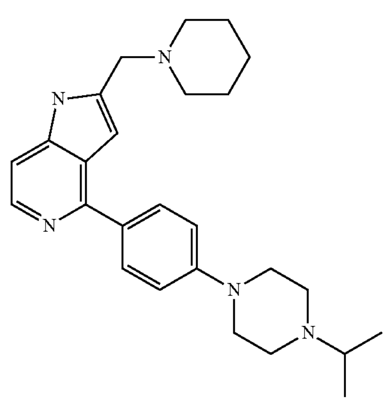 [SMILES: CC(C)N1CCN(c2ccc(-c3nccc4[nH]c(CN5CCCCC5)cc34)cc2)CC1] | 2-V and 1-II | LCMS: m/z 418.3 [M$^+$ + 1] $^1$H NMR (400 MHz, CDCl$_3$): δ 1.11 (d, J = 6.4 Hz, 6H), 1.49 (d, J = 4.4 Hz, 2H), 1.62 (quin, J = 5.6 Hz, 4H), 2.41-2.52 (m, 4H), 2.70-2.76 (m, 5H), 3.31 (t, J = 4.8 Hz, 4H), 3.67 (s, 2H), 6.67 (s, 1H), 7.04 (d, J = 8.8 Hz, 2H), 7.17 (d, J = 6 Hz, 1H), 7.92 (d, J = 8.8 Hz, 2H), 8.34 (d, J = 6 Hz, 1H), 9.20 (br s, 1H) |

TABLE 9-continued

| Ex. No. | IUPAC name | Structure | Int. from which prepared | Analytical Data |
|---|---|---|---|---|
| A18 | 2-[(3,3-difluoropyrrolidin-1-yl)methyl]-4-[4-(4-isopropylpiperazin-1-yl)phenyl]-1H-pyrrolo[3,2-c]pyridine | 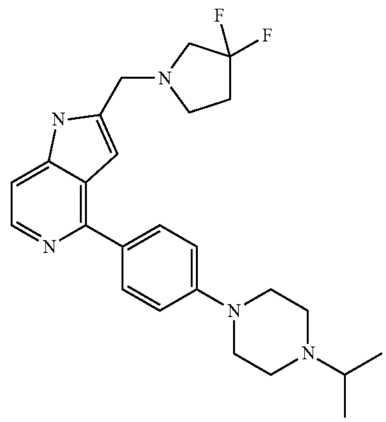 [SMILES: CC(C)N1CCN(c2ccc(-c3nccc4[nH]c(CN5CCC(F)(F)C5)cc34)cc2)CC1] | 2-VI and 1-II | LCMS: m/z 440.3 [M$^+$ + 1] $^1$H NMR (400 MHz, CDCl$_3$): δ 1.11 (d, J = 6.4 Hz, 6H), 2.31 (sep., 2H), 2.71-2.79 (m, 7H), 2.93 (t, J = 13 Hz, 2H), 3.31 (t, J = 5 Hz, 4H), 3.81 (s, 2H), 6.68 (s, 1H), 7.04 (d, J = 8.8 Hz, 2H), 7.16 (d, J = 5.2 Hz, 1H), 7.91 (d, J = 8.4 Hz, 2H), 8.35 (d, J = 6 Hz, 1H), 8.77 (br.s, 1H) |
| A19 | (4-isopropylpiperazin-1-yl)-[4-[2-(morpholinomethyl)-1H-pyrrolo[3,2-c]pyridin-4-yl]phenyl]methanone | 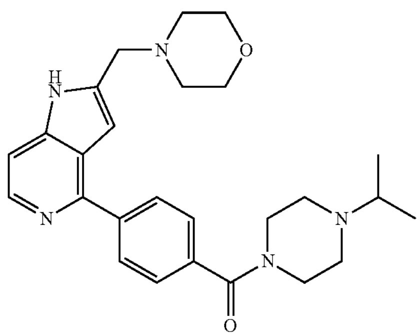 [SMILES: CC(C)N1CCN(C(=O)c2ccc(-c3nccc4[nH]c(CN5CCOCC5)cc34)cc2)CC1] | 2-I and 1-XIV | LCMS: m/z 448.20 (M$^+$ + 1) $^1$HNMR (400 MHz, CDCl$_3$): δ 1.08 (d, J = 6.4 Hz, 6H), 2.45-2.55 (m, 6H), 2.60-2.70 (m, 2H), 2.75-2.82 (m, 1H), 3.48-3.56 (m, 2H), 3.71 (s, 2H), 3.74 (t, J = 4.4 Hz, 4H), 3.80-3.90 (m, 2H), 6.65 (s, 1H), 7.28 (s, 1H), 7.55 (d, J = 7.6 Hz, 2H), 8.00 (d, J = 7.6 Hz, 2H), 8.39 (d, J = 6.0 Hz, 1H), 9.01 (bs, 1H) |
| A20 | tert-butyl 4-[4-[2-(morpholinomethyl)-1H-pyrrolo[3,2-c]pyridin-4-yl]phenylmethyl]piperazine-1-carboxylate | 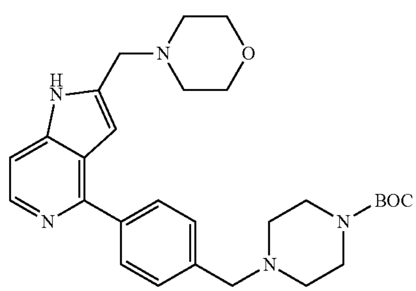 [SMILES: CC(C)(C)OC(=O)N1CCN(Cc2ccc(-c3nccc4[nH]c(CN5CCOCC5)cc34)cc2)CC1] | 2-I and 1-XVI | LCMS: m/z 492.20 [M$^+$ + 1] $^1$HNMR (400 MHz, CDCl$_3$): δ 1.46 (s, 9H), 2.41-2.45 (m, 4H), 2.49 (t, J = 4.4 Hz, 4H), 3.44 (t, J = 4.8 Hz, 4H), 3.59 (s, 2H), 3.69 (s, 2H), 3.73 (t, J = 4.4 Hz, 4H), 6.68 (s, 1H), 7.21 (d, J = 5.6 Hz, 1H), 7.45 (d, J = 7.6 Hz, 2H), 7.93 (d, J = 7.6 Hz, 2H), 8.39 (d, J = 5.2 Hz, 1H), 8.93 (bs, 1H). |

TABLE 9-continued

| Ex. No. | IUPAC name | Structure | Int. from which prepared | Analytical Data |
|---|---|---|---|---|
| A21 | tert-butyl 4-[3-[2-(morpholinomethyl)-1H-pyrrolo[3,2-c]pyridin-4-yl]phenyl]piperazine-1-carboxylate | 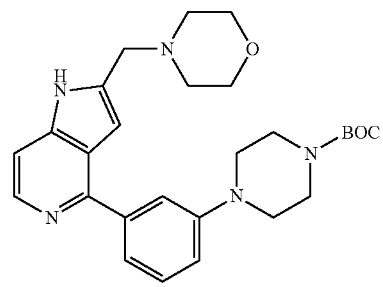 [SMILES: CC(C)(C)OC(=O)N1CCN(c2cccc(-c3nccc4[nH]c(CN5CCOCC5)cc34)c2)CC1] | 2-I and 1-VII | LCMS: m/z 478.3 [M$^+$ + 1] |
| A22 | (4-methylpiperazin-1-yl)-[4-[2-(morpholinomethyl)-1H-pyrrolo[3,2-c]pyridin-4-yl]phenyl]methanone | 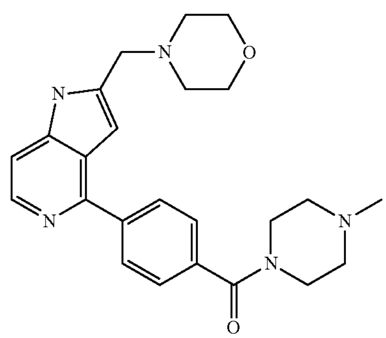 [SMILES: CN1CCN(C(=O)c2ccc(-c3nccc4[nH]c(CN5CCOCC5)cc34)cc2)CC1] | 2-I and 1-XV | LCMS: m/z 420.10 [M$^+$ + 1] $^1$HNMR (400 MHz, CDCl$_3$): δ 2.33 (s, 3H), 2.35-2.46 (m, 2H), 2.51 (t, J = 4.0 Hz, 6H), 3.47-3.52 (m, 2H), 3.70 (s, 2H), 3.73 (t, J = 4.8 Hz, 4H), 3.80-3.90 (m, 2H), 6.65 (s, 1H), 7.27 (d, J = 6.0 Hz, 1H), 7.54 (d, J = 8.4 Hz, 2H), 8.00 (d, J = 8.4 Hz, 2H), 8.39 (d, J = 5.6 Hz, 1H), 9.01 (bs, 1H) |
| A23 | tert-butyl 4-[4-[2-(morpholinomethyl)-1H-pyrrolo[3,2-c]pyridin-4-yl]phenoxy]piperidine-1-carboxylate | 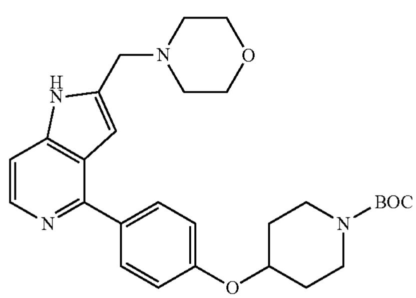 [SMILES: CC(C)(C)OC(=O)N1CCC(Oc2ccc(-c3nccc4[nH]c(CN5CCOCC5)cc34)cc2)CC1] | 2-I and 1-XVII | LCMS: m/z 493.10 [M$^+$ + 1] $^1$HNMR (400 MHz, CDCl$_3$): δ 1.48 (s, 9H), 1.80-1.85 (m, 2H), 1.90-2.00 (m, 2H), 2.50 (t, J = 4.0 Hz, 4H), 3.30-3.40 (m, 2H), 3.65-3.69 (m, 4H), 3.73 (t, J = 4.4 Hz, 4H), 4.50-4.51 (m, 1H), 6.67 (s, 1H), 7.04 (d, J = 8.8 Hz, 2H), 7.21 (d, J = 5.9 Hz, 1H), 7.92 (d, J = 8.8 Hz, 2H), 8.36 (d, J = 5.8 Hz, 1H), 8.95 (s, 1H) |

TABLE 9-continued

| Ex. No. | IUPAC name | Structure | Int. from which prepared | Analytical Data |
|---|---|---|---|---|
| A24 | 2-[(4-fluoro-1-piperidyl)methyl]-4-[4-(4-isopropylpiperazin-yl)phenyl]-1H-pyrrolo[3,2-c]pyridine | 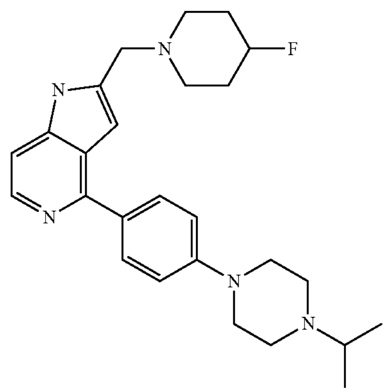 [SMILES: CC(C)N1CCN(c2ccc(-c3nccc4[nH]c(CN5CCC(F)CC5)cc34)cc2)CC1] | 2-VIII and 1-II | LCMS: m/z 436.3 [M+ + 1] $^1$H NMR (400 MHz, CDCl$_3$): δ 1.12 (d, J = 6 Hz, 6H), 1.87-1.92 (m, 4H), 2.40-2.52 (m, 2H), 2.55-2.69 (s, 2H), 2.71-2.85 (m, 5H), 3.28-3.42 (m, 4H), 3.70 (s, 2H), 4.62-4.82 (m, 1H), 6.68 (s, 1H), 7.04 (d, J = 8.4 Hz, 2H), 7.18 (d, J = 6 Hz, 1H), 7.92 (d, J = 7.6 Hz, 2H), 8.34 (d, J = 5.6 Hz, 1H), 9.01 (br s, 1H) |
| A25 | 2-[(4-fluoro-1-piperidyl) methyl]-4-[4-(4-methylpiperazin-1-yl)phenyl]-1H-pyrrolo[3,2-c]pyridine | 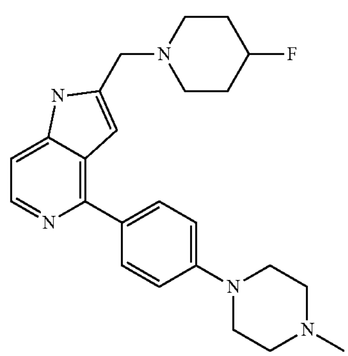 [SMILES: CN1CCN(c2ccc(-c3nccc4[nH]c(CN5CCC(F)CC5)cc34)cc2)CC1] | 2-VIII and 1-I | LCMS: m/z 408.3 [M+ + 1] $^1$H NMR (400 MHz, CDCl$_3$): δ 1.85-1.94 (m, 4H), 2.37 (s, 3H), 2.44 (t, J = 5.8 Hz, 2H), 2.61 (t, J = 4.8 Hz, 6H), 3.32 (t, J = 4.8 Hz, 4H), 3.68 (s, 2H), 4.62-4.82 (m, 1H), 6.67 (s, 1H), 7.04 (d, J = 8.8 Hz, 2H), 7.17 (d, J = 6 Hz, 1H), 7.92 (d, J = 8.8 Hz, 2H), 8.34 (d, J = 6 Hz, 1H), 9.00 (br s, 1H) |
| A26 | tert-butyl 4-[4-[2-(morpholinomethyl)-1H-pyrrolo[3,2-c]pyridin-4-yl]pyrazol-1-yl]piperidine-1-carboxylate | 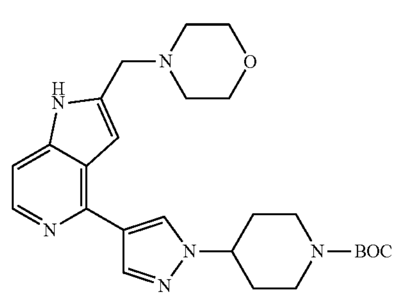 [SMILES: CC(C)(C)OC(=O)N1CCC(n2cc(-c3nccc4[nH]c(CN5CCOCC5)cc34)cn2)CC1] | 2-I and 1-XVIII | LCMS: m/z 467.3 [M+ + 1] |

TABLE 9-continued

| Ex. No. | IUPAC name | Structure | Int. from which prepared | Analytical Data |
|---|---|---|---|---|
| A27 | 2-[(4-fluoro-1-piperidyl)methyl]-4-[4-(4-isopropylpiperazin-1-yl)phenyl]-6-methyl-1H-pyrrolo[3,2-c]pyridine | 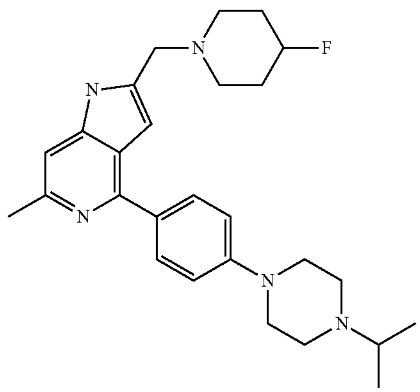 [SMILES: Cc1cc2[nH]c(CN3CCC(F)CC3)cc2c(-c2ccc(N3CCN(C(C)C)CC3)cc2)n1] | 2-X and 1-II | LCMS: m/z 450.3 [M+ + 1] <br> 1H NMR (400 MHz, CDCl3): δ 1.14 (d, J = 5.2 Hz, 6H), 1.82-2.08 (m, 5H), 2.42-2.58 (m, 3H), 2.64-2.76 (m, 9H), 3.25-3.45 (m, 3H), 3.69 (s, 2H), 4.66-4.78 (m, 1H), 6.61 (s, 1H), 7.01-7.04 (m, 3H), 7.89 (d, J = 7.6 Hz, 2H), 9.01 (br.s, 1H) |
| A28 | 4-[4-(4-isopropylpiperazin-1-yl)phenyl]-6-methyl-2-(pyrazol-1-ylmethyl)-1H-pyrrolo[3,2-c]pyridine | 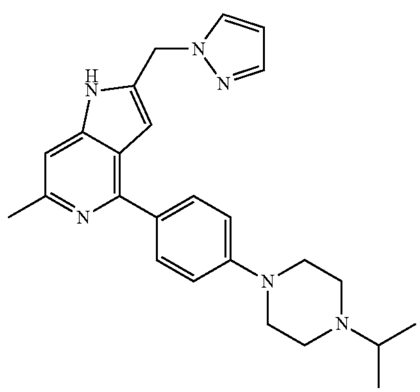 [SMILES: Cc1cc2[nH]c(Cn3cccn3)cc2c(-c2ccc(N3CCN(C(C)C)CC3)cc2)n1] | 2-XXI and 1-II | LCMS: m/z 415.3 [M+ + 1] <br> 1H NMR (400 MHz, CDCl3): δ 1.16 (d, J = 6 Hz, 6H), 2.66 (s, 3H), 2.71-2.90 (m, 5H), 3.32-3.45 (m, 4H), 5.44 (s, 2H), 6.28 (s, 1H), 6.72 (s, 1H), 6.99-7.02 (m, 3H), 7.50 (s, 1H), 7.59 (s, 1H), 7.86 (d, J = 8.8 Hz, 2H), 9.10 (br.s, 1H) |
| A29 | 7-[[4-[4-(4-isopropylpiperazin-1-yl)phenyl]-6-methyl-1H-pyrrolo[3,2-c]pyridin-2-yl]methyl]-7-azaspiro[3.5]nonan-2-ol | 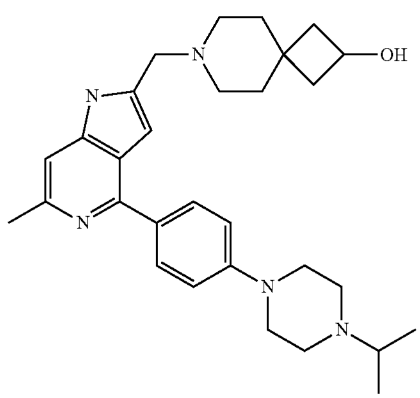 [SMILES: Cc1cc2[nH]c(CN3CCC4(CC3)CC(O)C4)cc2c(-c2ccc(N3CCN(C(C)C)CC3)cc2)n1] | 2-XI and 1-II | LCMS: m/z 488.3 [M+ + 1] <br> 1H NMR (400 MHz, CDCl3): δ 1.12 (d, J = 6.4 Hz, 6H), 1.60-1.69 (m, 6H), 2.25 (t, J = 10 Hz, 2H), 2.32-2.55 (m, 4H), 2.66 (s, 3H), 2.71-2.78 (m, 5H), 3.30 (t, J = 5 Hz, 4H), 3.67 (s, 2H), 4.29 (quin. 1H), 6.59 (s, 1H), 7.03 (d, J = 6.4 Hz, 3H), 7.88 (d, J = 8.8 Hz, 2H), 9.01 (br. s, 1H) |

TABLE 9-continued

| Ex. No. | IUPAC name | Structure | Int. from which prepared | Analytical Data |
|---|---|---|---|---|
| A30 | 4-[4-(4-isopropylpiperazin-1-yl)phenyl]-6-methyl-2-[(2-methyl-7-azaspiro[3.5]nonan-7-yl)methyl]-1H-pyrrolo[3,2-c]pyridine | 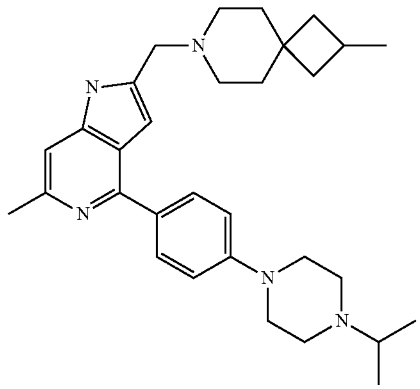 [SMILES: Cc1cc2[nH]c(CN3CCC4(CC3)CC(C)C4)cc2c(-c2ccc(N3CCN(C(C)C)CC3)cc2)n1] | 2-XII and 1-II | LCMS: m/z 486.4 [M+ + 1] $^1$H NMR (400 MHz, (CDCl$_3$)): δ 1.03 (d, J = 6.8 Hz, 3H), 1.11 (d, J = 6.4 Hz, 6H), 1.32 (t, J = 10 Hz, 2H), 1.54-1.62 (m, 2H), 1.64-1.67 (m, 2H), 1.94 (t, J = 10.2 Hz, 2H), 2.28-2.30 (m, 5H), 2.66 (s, 3H), 2.70-2.75 (m, 5H), 3.29 (t, J = 5 Hz, 4H), 3.66 (s, 2H), 6.58 (s, 1H), 7.01-7.03 (m, 3H), 7.88 (d, J = 8.4 Hz, 2H), 9.05 (br. s, 1H) |
| A31 | 4-[[4-[4-(4-methylpiperazin-1-yl)phenyl]-6-(trifluoromethyl)-1H-pyrrolo[3,2-c]pyridin-2-yl]methyl]morpholine | 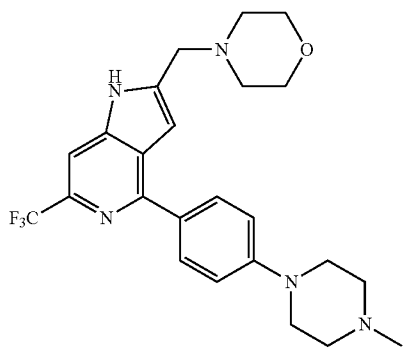 [SMILES: CN1CCN(c2ccc(-c3nc(C(F)(F)F)cc4[nH]c(CN5CCOCC5)cc34)cc2)CC1] | 2-XVI and 1-I | LCMS: m/z 460.2 (M+ + 1) $^1$HNMR (400 MHz, CDCl$_3$): δ 2.37 (s, 3H), 2.49 (t, J = 4.4 Hz, 4H), 2.61 (t, J = 4.8 Hz, 4H), 3.32 (t, J = 4.8 Hz, 4H), 3.71 (s, 2H), 3.73 (t, J = 4.8 Hz, 4H), 6.76 (s, 1H), 7.04 (d, J = 8.8 Hz, 2H), 7.57 (s,1H), 7.97 (d, J = 8.8 Hz, 2H), 9.25 (bs, 1H, —NH) |
| A32 | 4-[[4-[4-(4-isopropylpiperazin-1-yl)phenyl]-6-(trifluoromethyl)-1H-pyrrolo[3,2-c]pyridin-2-yl]methyl]morpholine | 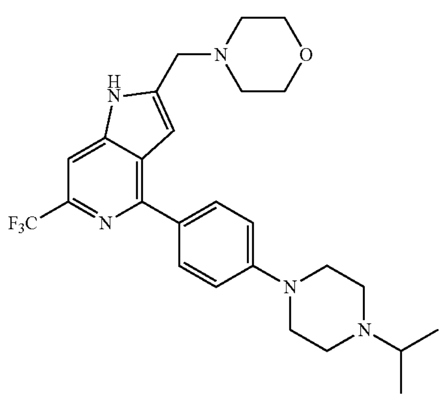 [SMILES: CC(C)N1CCN(c2ccc(-c3nc(C(F)(F)F)cc4[nH]c(CN5CCOCC5)cc34)cc2)CC1] | 2-XVI and 1-II | LCMS: m/z 488.3 (M+ + 1) $^1$HNMR (400 MHz, CDCl$_3$): δ 1.11 (d, J = 6.0 Hz, 6H), 2.49 (t, J = 4.4 Hz, 4H), 2.72 (t, J = 4.8 Hz, 4H), 2.72-2.77 (m, 1H), 3.32 (t, J = 5.2 Hz, 4H), 3.70 (s, 2H), 3.72 (t, J = 4.8 Hz, 4H), 6.76 (s, 1H), 7.04 (d, J = 8.8 Hz, 2H), 7.56 (s, 1H), 7.96 (d, J = 8.8 Hz, 2H), 9.18 (bs, 1H, —NH) |

TABLE 9-continued

| Ex. No. | IUPAC name | Structure | Int. from which prepared | Analytical Data |
|---|---|---|---|---|
| A33 | 4-[[6-cyclopropyl-4-[4-(4-isopropylpiperazin-1-yl)phenyl]-1H-pyrrolo[3,2-c]pyridin-2-yl]methyl] morpholine | 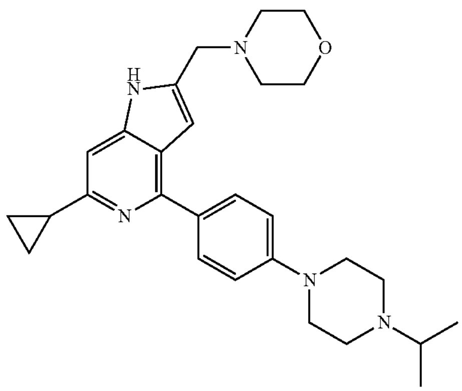 [SMILES: CC(C)N1CCN(c2ccc(-c3nc(C4CC4)cc4[nH]c(CN5CCOCC5)cc34)cc2)CC1] | 2-XVIII and 1-II | LCMS: m/z 460.4 [M$^+$ + 1]<br>$^1$HNMR (400 MHz, CDCl$_3$): δ 0.91-0.95 (m, 2H), 1.05-1.09 (m, 2H), 1.11 (d, J = 6.8 Hz, 6H), 2.11-2.15 (m, 1H), 2.45-2.49 (m, 4H), 2.68-2.75 (m, 5H), 3.29 (t, J = 5.2 Hz, 4H), 3.63 (s, 2H), 3.70 (t, J = 4.4 Hz, 4H), 6.61 (s, 1H), 6.95 (s, 1H), 7.02 (d, J = 8.8 Hz, 2H), 7.93 (d, J = 8.8 Hz, 2H), 8.57 (bs, 1H) |
| A34 | 4-[[6-cyclopropyl-4-[4-(4-methylpiperazin-1-yl)phenyl]-1H-pyrrolo[3,2-c]pyridin-2-yl]methyl] morpholine | 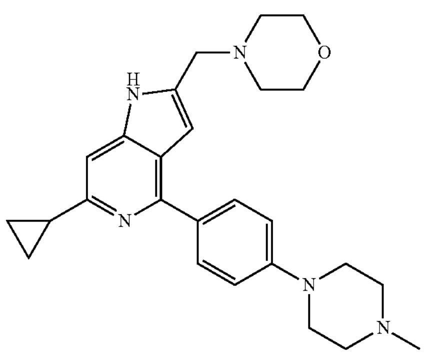 [SMILES: CN1CCN(c2ccc(-c3nc(C4CC4)cc4[nH]c(CN5CCOCC5)cc34)cc2)CC1] | 2-XVIII and 1-I | LCMS: m/z 432.3 [M$^+$ + 1]<br>$^1$HNMR (400 MHz, CDCl$_3$): δ 0.92-0.95 (m, 2H), 1.04-1.08 (m, 2H), 2.18-2.26 (m, 1H), 2.40 (s, 3H), 2.45-2.52 (m, 4H), 2.62-2.70 (m, 4H), 3.60-3.67 (m, 4H), 3.65 (s, 2H), 3.70-3.78 (m, 4H), 6.61 (s, 1H), 6.96 (s, 1H), 7.02 (d, J = 8.8 Hz, 2H), 7.93 (d, J = 8.8 Hz, 2H), 8.78 (bs, 1H) |
| A35 | 4-[[4-[4-(4-isopropylpiperazin-1-yl)phenyl]-1,6-dimethyl-pyrrolo[3,2-c]pyridin-2-yl]methyl] morpholine | 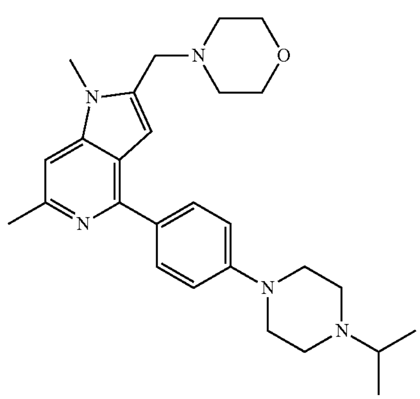 [SMILES: Cc1cc2c(cc(CN3CCOCC3)n2C)c(-c2ccc(N3CCN(C(C)C)CC3)cc2)n1] | 2-XX and 1-II | LCMS: m/z 448.3 [M$^+$ +1]<br>$^1$H NMR (400 MHz, CDCl$_3$): δ 1.13 (d, J = 6.8 Hz, 6H), 2.40-2.50 (m, 4H), 2.70-2.75 (m, 8H), 3.30-3.40 (m, 4H), 3.62 (s, 2H), 3.67 (t, J = 4.4 Hz, 4H), 3.79 (s, 3H), 6.62 (s, 1H), 6.98 (s, 1H), 7.04 (d, J = 9.3 Hz, 2H), 7.89 (d, J = 8.3 Hz, 2H) |

TABLE 9-continued

| Ex. No. | IUPAC name | Structure | Int. from which prepared | Analytical Data |
|---|---|---|---|---|
| A36 | 4-[[4-[4-(4-isopropylpiperazin-1-yl)phenyl]-6,7-dimethyl-1H-pyrrolo[3,2-c]pyridin-2-yl]methyl]morpholine | 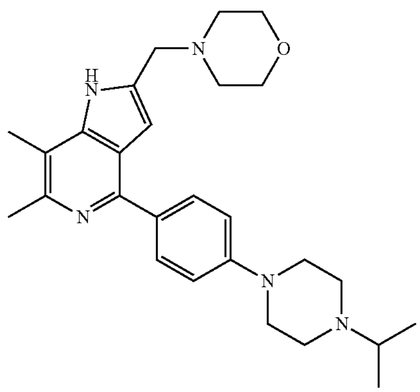 [SMILES: Cc1nc(-c2ccc(N3CCN(C(C)C)CC3)cc2)c2cc(CN3CCOCC3)[nH]c2c1C] | 2-XIII and 1-II | LCMS: m/z 448.3 [M$^+$ + 1] $^1$H NMR (400 MHz, CDCl$_3$): δ 1.12 (d, J = 6.4 Hz, 6H), 2.43 (s, 3H), 2.48 (t, J = 4.4 Hz, 4H), 2.66 (s, 3H), 2.72 (t, J = 4.8 Hz, 4H), 2.71-2.79 (m, 1H), 3.30 (t, J = 4.8 Hz, 4H), 3.65 (s, 2H), 3.72 (t, J = 4.4 Hz, 4H), 6.62 (s, 1H), 7.03 (d, J = 8.8 Hz, 2H), 7.88 (d, J = 8.8 Hz, 2H), 8.58 (bs, 1H, —NH) |
| A37 | 4-[[6,7-dimethyl-4-[4-(4-methylpiperazin-1-yl)phenyl]-1H-pyrrolo[3,2-c]pyridin-2-yl]methyl]morpholine | 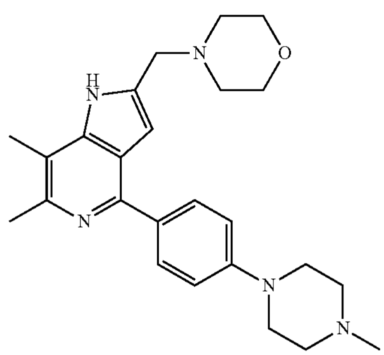 | 2-XIII and 1-I | LCMS: m/z 420.3 [M$^+$ + 1] $^1$H NMR (400 MHz, CDCl$_3$): δ 2.36 (s, 3H), 2.42 (s, 3H), 2.48 (t, J = 4.0 Hz, 4H), 2.60 (t, J = 4.8 Hz, 4H), 2.65 (s, 3H), 3.29 (t, J = 4.8 Hz, 4H), 3.65 (s, 2H), 3.72 (t, J = 4.4 Hz, 4H), 6.61 (s, 1H), 7.03 (d, J = 8.8 Hz, 2H), 7.88 (d, J = 8.8 Hz, 2H), 8.61 (bs, 1H, —NH) |
| A38 | 4-[[4-[4-(4-ethylpiperazin-1-yl)phenyl]-6,7-dimethyl-1H-pyrrolo[3,2-c]pyridin-2-yl]methyl]morpholine | 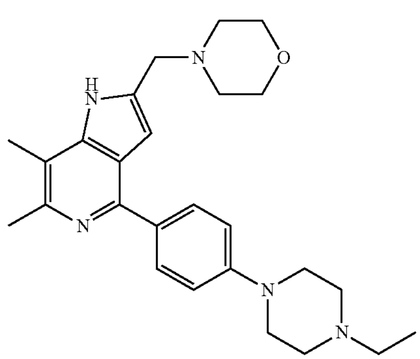 [SMILES: CCN1CCN(c2ccc(-c3nc(C)c(C)c4[nH]c(CN5CCOCC5)cc34)cc2)CC1] | 2-XIII and 1-IV | LCMS: m/z 434.3 [M$^+$ + 1] $^1$H NMR (400 MHz, CDCl$_3$): δ 1.15 (t, J = 7.2 Hz, 3H), 2.42 (s, 3H), 2.47-2.53 (m, 6H), 2.63-2.65 (m, 4H), 2.66 (s, 3H), 3.31 (t, J = 4.8 Hz, 4H), 3.66 (s, 2H), 3.72 (t, J = 5.2 Hz, 4H), 6.62 (s, 1H), 7.03 (d, J = 8.8 Hz, 2H), 7.88 (d, J = 8.8 Hz, 2H), 8.78 (bs, 1H, —NH) |

TABLE 9-continued

| Ex. No. | IUPAC name | Structure | Int. from which prepared | Analytical Data |
|---|---|---|---|---|
| A39 | 4-[4-(4-isopropylpiperazin-1-yl)phenyl]-6,7-dimethyl-2-(1-piperidylmethyl)-1H-pyrrolo[3,2-c]pyridine | 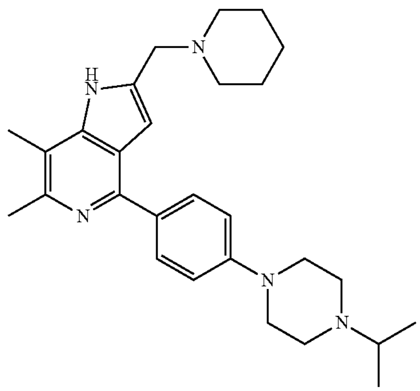 [SMILES: Cc1nc(-c2ccc(N3CCN(C(C)C)CC3)cc2)c2cc(CN3CCCCC3)[nH]c2c1C] | 2-XIV and 1-II | LCMS: m/z 446.3 [M+ + 1] <sup>1</sup>H NMR (400 MHz, CDCl<sub>3</sub>): δ 1.10 (d, J = 6.4 Hz, 6H), 1.45-1.48 (m, 2H), 1.56-1.60 (m, 4H), 2.37-2.42 (m, 4H), 2.42 (s, 3H), 2.64 (s, 3H), 2.71 (t, J = 4.8 Hz, 4H), 2.72-2.76 (m, 1H), 3.28 (t, J = 4.8 Hz, 4H), 3.60 (s, 2H), 6.57 (s, 1H), 7.02 (d, J = 8.8 Hz, 2H), 7.87 (d, J = 8.8 Hz, 2H), 8.72 (bs, 1H, —NH) |
| A40 | 4-[4-(4-isopropylpiperazin-1-yl)phenyl]-6,7-dimethyl 2-(pyrrolidin-1-ylmethyl)-1H-pyrrolo[3,2-c]pyridine | 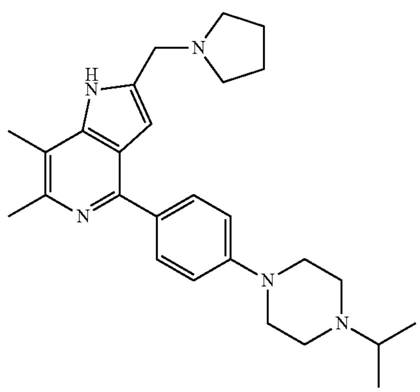 [SMILES: Cc1nc(-c2ccc(N3CCN(C(C)C)CC3)cc2)c2cc(CN3CCCC3)[nH]c2c1C] | 2-XV and 1-II | LCMS: m/z 432.3 (M+ + 1) <sup>1</sup>H NMR (400 MHz, CDCl<sub>3</sub>): δ 1.10 (d, J = 6.4 Hz, 6H), 1.81-1.89 (m, 4H), 2.41 (s, 3H), 2.53-2.59 (m, 4H), 2.64 (s, 3H), 2.71 (t, J = 4.8 Hz, 4H), 2.72-2.76 (m, 1H), 3.28 (t, J = 4.8 Hz, 4H), 3.77 (s, 2H), 6.57 (s, 1H), 7.02 (d, J = 8.8 Hz, 2H), 7.87 (d, J = 8.8 Hz, 2H), 8.69 (bs, 1H, —NH) |

Example A41

4-[[6-methyl-4-[4-(4-piperidyl)phenyl]-1H-pyrrolo[3,2-c]pyridin-2-yl]methyl]morpholine

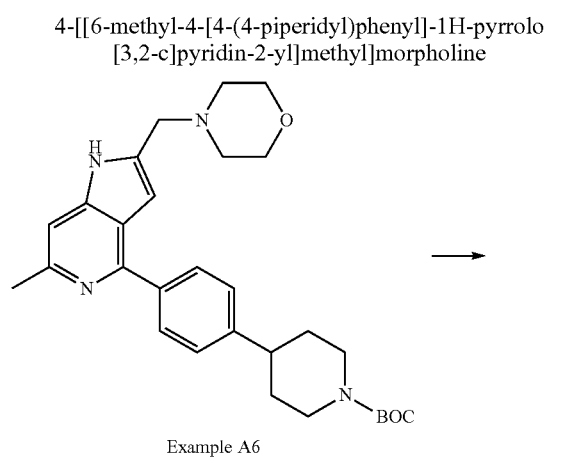

Example A6

-continued

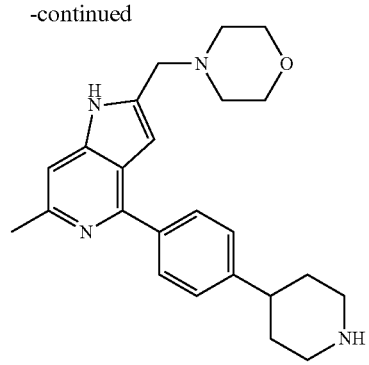

Example A41

To a solution of Example A6 (0.23 g, 0.46 mmol) in CH<sub>2</sub>Cl<sub>2</sub> (3 mL) was added 2M HCl in diethyl ether (3 mL) at room temperature, and the reaction mixture was stirred overnight. After completion of reaction (monitored by TLC), the solvent was removed in vacuum, and the residue was neutralized with aqueous saturated sodium bicarbonate solution, and the mixture was dried under vacuum. The resulting solid was washed with 5% methanol-$CH_2Cl_2$ mixture, and dried in vacuum to give the desired product Example A41 (0.17 g, 92%) as an off white solid; LCMS: m/z 391.1 [$M^+$+1].

$^1$H NMR (400 MHz, $CDCl_3$): δ 1.62-1.73 (m, 2H), 1.78-1.85 (m, 2H), 2.44-2.50 (m, 4H), 2.67 (s, 3H), 2.70-2.74 (m, 1H), 2.77-2.84 (m, 2H), 3.24-3.30 (m, 2H), 3.64 (s, 2H), 3.71 (t, J=4.40 Hz, 4H), 6.60 (s, 1H), 7.05 (s, 1H), 7.34 (d, J=8.0 Hz, 2H), 7.88 (d, J=8.0 Hz, 2H), 8.70 (bs, 1H)

The following compounds Examples A42 to A46 as shown in Table 10 were prepared in the same manner as Example A41. However, for preparation of compounds Examples A42, A43 and A44, 3M HCl in methanol was used for deprotection instead of 2M HCl in diethyl ether (as used for Examples A41). Example A46 was prepared as a tetrahydrochloride salt.

TABLE 10

| Ex. No. | IUPAC name | Structure | Ex. from which prepared | Analytical data |
|---|---|---|---|---|
| A42 | 4-[[4-(4-(piperazin-1-yl)phenyl)-1H-pyrrolo[3,2-c]pyridin-2-yl]methyl]morpholine | 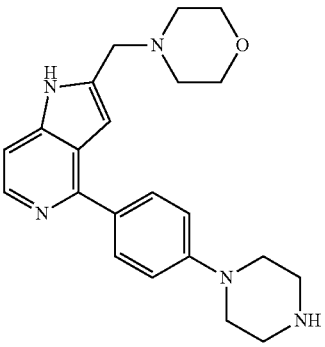 [SMILES: c1cc2[nH]c(CN3CCOCC3)cc2c(-c2ccc(N3CCNCC3)cc2)n1] | A7 | LCMS: m/z 378.3 [$M^+$ + 1]<br>$^1$H NMR (400 MHz, $CD_3OD$):<br>δ 2.51 (t, J = 4.4 Hz, 4H), 3.01 (t, J = 5.2 Hz, 4H), 3.25 (t, J = 4.8 Hz, 4H), 3.69-3.71 (m, 6H), 6.66 (s, 1H), 7.11 (d, J = 8.8 Hz, 2H), 7.27 (d, J = 5.6 Hz, 1H), 7.78 (d, J = 8.8 Hz, 2H), 8.12 (d, J = 6 Hz, 1H) |
| A43 | 4-[[4-[6-(1,2,3,6-tetrahydro-pyridin-4-yl)-3-pyridyl]-1H-pyrrolo[3,2-c]pyridin-2-yl]methyl]morpholine | 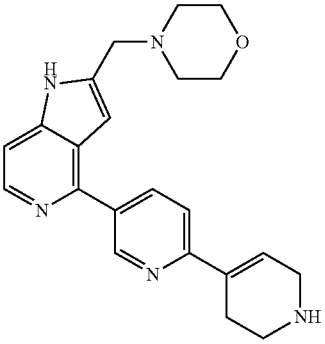 [SMILES: C1=C(c2ccc(-c3nccc4[nH]c(CN5CCOCC5)cc34)cn2)CCNC1] | A14 | LCMS: m/z 376.1 [$M^+$ + 1] |
| A44 | 4-[[4-(6-(piperazin-1-yl)-3-pyridyl)-1H-pyrrolo[3,2-c]pyridin-2-yl]methyl]morpholine | 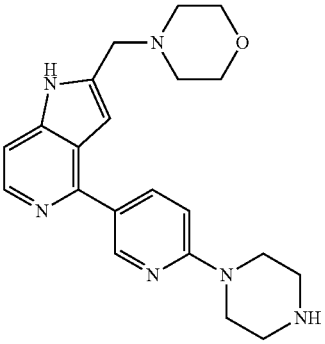 [SMILES: c1cc2[nH]c(CN3CCOCC3)cc2c(-c2ccc(N3CCNCC3)nc2)n1] | A15 | LCMS: m/z 379.1 [$M^+$ + 1] |

TABLE 10-continued

| Ex. No. | IUPAC name | Structure | Ex. from which prepared | Analytical data |
|---|---|---|---|---|
| A45 | 4-[[4-[1-(4-piperidyl)pyrazol-4-yl]-1H-pyrrolo[3,2-c]pyridin-2-yl]methyl]morpholine | 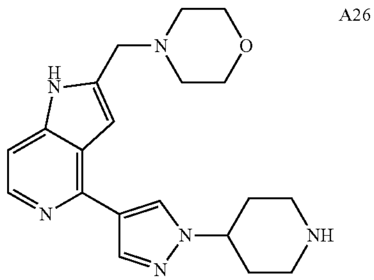 | A26 | LCMS: m/z 367.3 [M$^+$ + 1] $^1$H NMR (400 MHz, DMSO-D6): 2.17-2.32 (m, 4H), 2.40-2.43 (m, 4H), 3.09 (ddd, J = 15.6, 12.4, 3.6 Hz, 2H), 3.69-3.45 (m, 2H), 3.60 (t, J = 4.4 Hz, 4H), 3.67 (s, 2H), 4.60 (sep. 1H), 6.81 (s, 1H), 7.21 (d, 1H), 8.10 (d, J = 5.2 Hz, 1H), 8.19 (s, 1H), 8.31 (s, 1H), 8.47 (br. s, 1H), 8.74 (br. s, 1H) |
| A46 | 4-[[4-(3-(piperazin-1-yl)phenyl)-1H-pyrrolo[3,2-c]pyridin-2-yl]methyl]morpholine | 4HCl | A21 | LCMS: m/z 378.3 [M$^+$ + 1] $^1$H NMR (400 MHz, DMSO-d6): δ 3.20-3.28 (m, 6H), 3.32-3.38 (m, 2H), 3.62 (t, J = 5.4 Hz, 4H), 3.82-3.88 (m, 4H), 4.67 (s, 2H), 7.36 (dd, J = 1.9, 8.8 Hz, 1H), 7.47 (d, J = 7.4 Hz, 2H), 7.59 (apt, J = 7.4 Hz, 2H), 8.02 (d, J = 6.4 Hz, 1H), 8.43 (d, J = 6.9 Hz, 1H), 9.41 (s, 2H), 12.15 (bs, 1H), 13.60 (s, 1H), 15.4 (bs, 1H) |

Example A47 tert-butyl 4-[5-[2-(morpholinomethyl)-1H-pyrrolo[3,2-c]pyridin-4-yl]thiazol-2-yl]piperazine-1-carboxylate

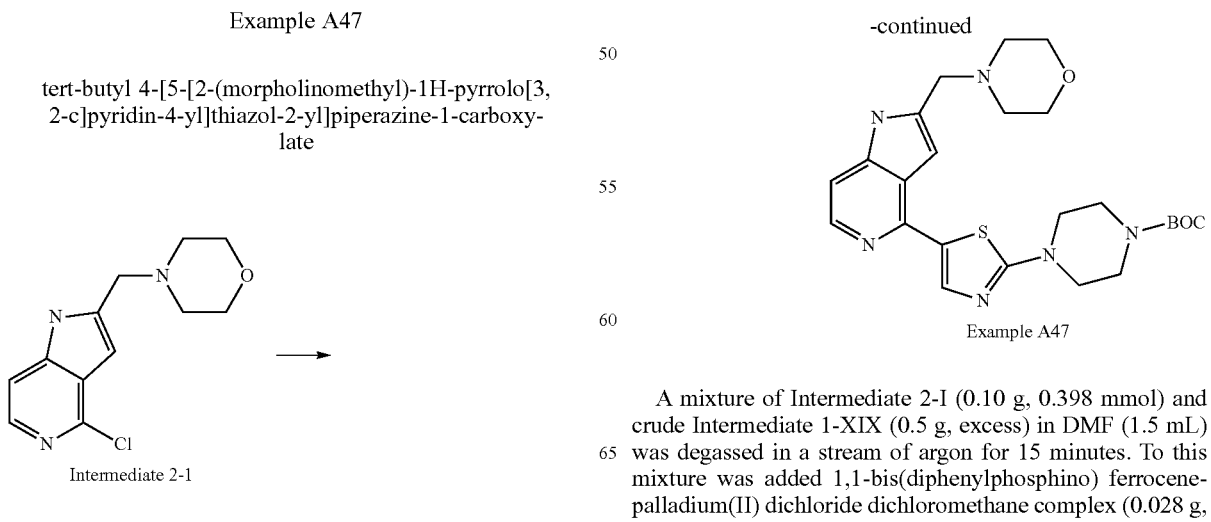

Example A47

A mixture of Intermediate 2-I (0.10 g, 0.398 mmol) and crude Intermediate 1-XIX (0.5 g, excess) in DMF (1.5 mL) was degassed in a stream of argon for 15 minutes. To this mixture was added 1,1-bis(diphenylphosphino) ferrocene-palladium(II) dichloride dichloromethane complex (0.028 g, 0.0398 mmol), and the reaction mixture was again degassed for additional 15 minutes. After stirring at 80° C. for 18 hours, the volatiles were removed by evaporation, and the obtained residue was diluted with water (20 mL), followed by extraction with ethyl acetate (20 mL×3). The combined organic layers were washed with brine (20 mL), dried over anhydrous Na$_2$SO$_4$, and concentrated under reduced pressure. The obtained residue was purified by silica gel column chromatography using 1% MeOH in dichloromethane as eluent to give the desired product Example A47 (0.042 g, 20%) as a brown solid; LCMS: m/z 485.1 [M$^+$+1].

Example A48

4-[[4-[4-(piperazin-1-ylmethyl)phenyl]-1H-pyrrolo[3,2-c]pyridin-2-yl]methyl]morpholine

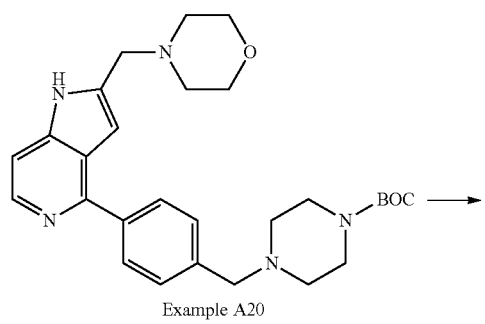

Example A20

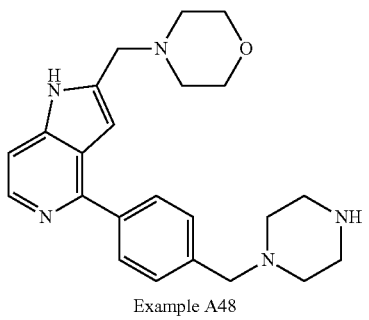

Example A48

To a stirred solution of Example A20 (0.64 g, 1.30 mmol) in dichloromethane (2 mL) was added 2 M HCl in diethyl ether (2 mL). The reaction mixture was stirred for 2 hours at room temperature. After completion of reaction (monitored by TLC), the reaction mixture was concentrated under reduced pressure to obtain a residue, which was neutralized with saturated aqueous sodium bicarbonate solution (25 mL). The resulting reaction mixture was concentrated under reduced pressure to obtain a white solid, which was dissolved in 5% MeOH in dichloromethane, and the solution was filtered through a celite pad. The obtained filtrate was concentrated under reduced pressure to give the desired product Example A48 (0.42 g, 82%) as a brown solid; LCMS: m/z 392.10 [M$^+$+1].

$^1$H NMR (400 MHz, CDCl$_3$): δ 2.43 (m, 8H), 2.90 (t, J=5.2 Hz, 4H), 3.57 (s, 2H), 3.68 (s, 2H), 3.72 (t, J=4.4 Hz, 4H), 6.67 (s, 1H), 7.21 (d, J=5.6 Hz, 1H), 7.45 (d, J=8.4 Hz, 2H), 7.92 (d, J=8.0 Hz, 2H), 8.38 (d, J=5.6 Hz, 1H), 8.93 (bs, 1H)

Example A49

4-[[4-[4-(4-piperidyloxy)phenyl]-1H-pyrrolo[3,2-c]pyridin-2-yl]methyl]morpholine

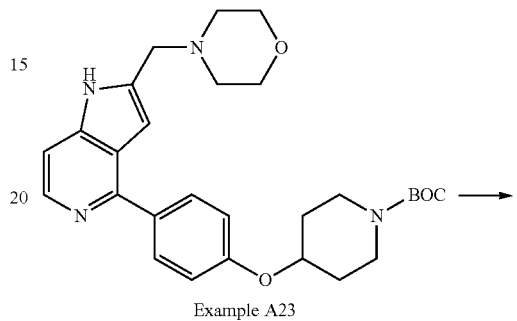

Example A23

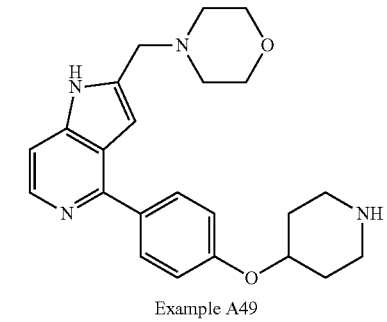

Example A49

To a stirred solution of Example A23 (0.23 g, 0.46 mmol) in dichloromethane (3 mL) was added 2 M HCl in diethyl ether (3 mL). The reaction mixture was stirred for 18 hours at room temperature. After completion of reaction (monitored by TLC), the reaction mixture was concentrated under reduced pressure to give a tetrahydrochloride salt of the desired product Example A49 (0.17 g, 92%) as a yellow solid; LCMS: m/z 393.3 [M$^+$+1].

$^1$H NMR (400 MHz, DMSO-d6): 1.85-1.98 (m, 2H), 2.12-2.23 (m, 2H), 3.05-3.30 (m, 8H), 3.80-3.95 (m, 4H), 4.63 (s, 2H), 4.85-4.95 (m, 1H), 7.36 (d, J=8.8 Hz, 2H), 7.96 (d, J=6.4 Hz, 1H), 8.00 (d, J=8.8 Hz, 2H), 8.39 (d, J=6.3 Hz, 2H), 9.04 (aromatics, 2H), 12.0 (bs, 1H), 13.4 (bs, 1H), 15.0 (bs, 1H)

Example A50

4-[[4-(2-(piperazin-1-yl)thiazol-5-yl)-1H-pyrrolo[3,2-c]pyridin-2-yl]methyl]morpholine

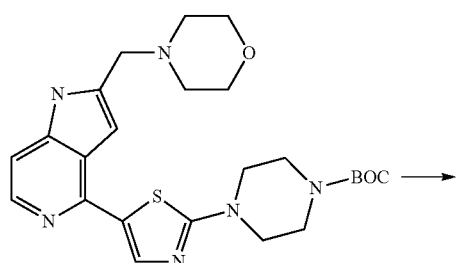

Example A47

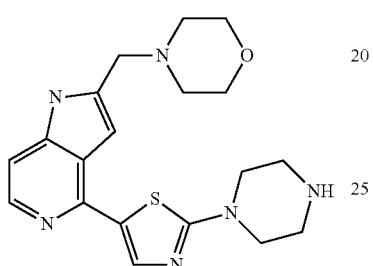

Example A50

To a solution of Example A47 (0.060 g, 0.123 mmol) in methanol (1 mL) at 0° C. was added 4M HCl in 1,4-dioxane (1 mL). After stirring at room temperature for 6 hours, the volatiles were removed by evaporation, and the obtained residue was diluted with water (2 mL), and pH was adjusted to ~8 using saturated aqueous NaHCO$_3$ solution (3 mL). The resulting solution was evaporated to dryness, and the obtained residue was diluted with 5% MeOH in dichloromethane (20 mL), and the inorganic substance was removed by filtration. The filtrate was concentrated to give the desired product Example A50 (0.048 g, 99%) as a white solid. The obtained crude product was used for next step without purification; LCMS: m/z 385.1 [M$^+$+1].

Example A51

4-[[4-[4-(1-isopropyl-4-piperidyl)phenyl]-6-methyl-1H-pyrrolo[3,2-c]pyridin-2-yl]methyl]morpholine

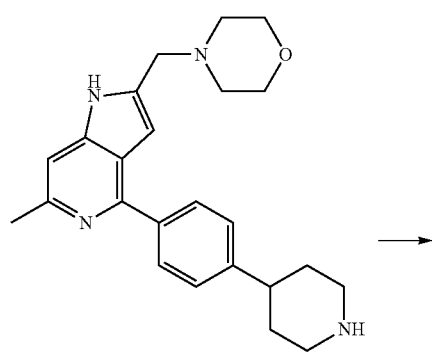

Example A41

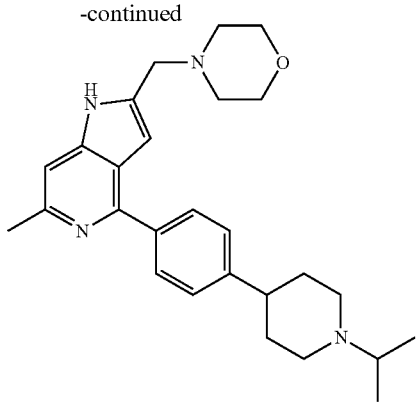

Example A51

To a solution of Example A41 (0.17 g, 0.43 mmol) and acetone (0.28 g, 0.35 mL, 4.7 mmol) in a mixture of dichloroethane and methanol (2:1, 5 mL) were added a drop of acetic acid and powdered molecular sieves. The reaction mixture was stirred for 3 hours. Sodium cyanoborohydride (0.35 g, 5.6 mmol) was added thereto, and the mixture was stirred overnight. After completion of reaction (monitored by TLC), the resulting solid was removed by filtration, and the filtrate was diluted with water and ethyl acetate. The layers were separated, and the organic layer was washed with saturated aqueous sodium bicarbonate solution and brine, dried over anhydrous Na$_2$SO$_4$, and concentrated in vacuum. The obtained residue was purified by preparative TLC to give the desired product Example A51 (0.06 g, 32%) as an off white solid; LCMS: m/z 433.4 [M$^+$+1].

$^1$HNMR (400 MHz, DMSO-d6): δ 1.02 (d, J=6.0 Hz, 6H), 1.62-1.73 (m, 2H), 1.78-1.85 (m, 2H), 2.22-2.34 (m, 2H), 2.38-2.42 (m, 4H), 2.49-2.50 (m, 1H, merged in solvent residual peak), 2.53 (s, 3H), 2.72-2.80 (m, 1H), 2.90-2.99 (m, 2H), 3.56-3.59 (m, 4H), 3.61 (s, 2H), 6.55 (s, 1H), 7.09 (s, 1H), 7.36 (d, J=8.4 Hz, 2H), 7.88 (d, J=8.0 Hz, 2H), 11.42 (s, 1H)

The following compounds Examples A52 to A58 as shown in Table 11 were prepared in the same manner as Example A51.

TABLE 11

| Ex. No. | IUPAC name | Structure | Ex. from which prepared | Analytical data |
|---|---|---|---|---|
| A52 | 4-[[4-[6-(1-isopropyl-3,6-dihydro-2H-pyridin-4-yl)-3-pyridyl]-1H-pyrrolo[3,2-c]pyridin-2-yl]methyl]morpholine | 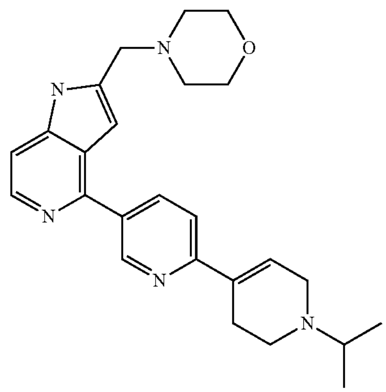 [SMILES: CC(C)N1CC=C(c2ccc(-c3nccc4[nH]c(CN5CCOCC5)cc34)cn2)CC1] | A43 | LCMS: m/z 418.3 [M$^+$ + 1]<br>$^1$H NMR (400 MHz, CD$_3$OD): δ 1.41 (d, J = 6.8 Hz, 6H), 2.49-2.5.3 (m, 4H), 3.05-3.11 (m, 2H), 3.46-3.52 (m, 3H), 3.71 (t, J = 4.4 Hz, 4H), 3.74 (s, 2H), 3.91-3.93 (m, 2H), 6.68 (s, 1H), 6.80 (br. s, 1H), 7.41 (d, J = 5.6 Hz, 1H), 7.81 (d, J = 8.4 Hz, 1H), 8.26 (d, J = 5.6 Hz, 1H), 8.31 (dd, J = 8, 2 Hz, 1H), 9.06 (d, J = 2 Hz, 1H) |
| A53 | 4-[[4-[6-(4-isopropyl-piperazin-1-yl)-3-pyridyl]-1H-pyrrolo[3,2-c]pyridin-2-yl]methyl]morpholine | 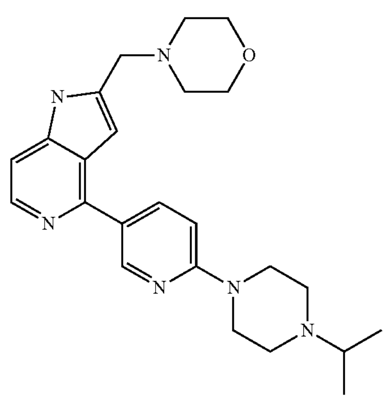 [SMILES: CC(C)N1CCN(c2ccc(-c3nccc4[nH]c(CN5CCOCC5)cc34)cn2)CC1] | A44 | LCMS: m/z 421.4 [M$^+$ + 1]<br>$^1$H NMR (400 MHz, CDCl$_3$): δ 1.13 (d, J = 6.4 Hz, 6H), 2.49 (t, J = 4.4 Hz, 4H), 2.71 (t, J = 4.4 Hz, 4H), 2.73-2.76 (m, 1H), 3.68 (s, 2H), 3.71-3.73 (m, 8H), 6.71 (s, 1H), 6.80 (d, J = 8.8 Hz, 1H), 7.21 (dd, J = 6, 1.2 Hz, 1H), 8.18 (dd, J = 8, 2.4 Hz, 1H), 8.35 (d, J = 5.6 Hz, 1H), 8.32 (d, J = 2.4 Hz, 1H), 8.85 (br s, 1H) |

TABLE 11-continued

| Ex. No. | IUPAC name | Structure | Ex. from which prepared | Analytical data |
|---|---|---|---|---|
| A54 | 4-[[4-[1-(1-isopropyl-4-piperidyl)pyrazol-4-yl]-1H-pyrrolo[3,2-c]pyridin-2-yl]methyl]morpholine | 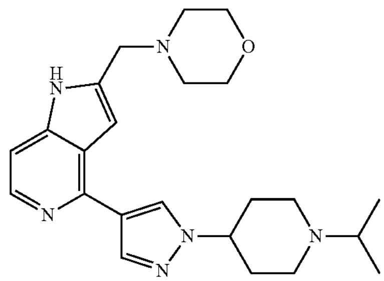 [SMILES: CC(C)N1CCC(n2cc(-c3nccc4[nH]c(CN5CCOCC5)cc34)cn2)CC1] | A45 | LCMS: m/z 409.4 [M⁺ + 1]<br>$^1$H NMR (400 MHz, CDCl$_3$): δ 1.13 (d, J = 6.8 Hz, 6H), 2.12-2.20 (m, 2H), 2.30-2.36 (m, 2H), 2.45-2.49 (m, 1H), 2.51 (t, J = 4.4 Hz, 4H), 3.10-3.13 (m, 2H), 3.49 (s, 2H), 3.71-3.74 (m, 6H), 4.24-4.28 (m, 1H), 6.67 (s, 1H), 7.17 (d, J = 6 Hz, 1H), 8.14 (s, 1H), 8.19 (s, 1H), 8.24 (d, J = 6 Hz, 1H), 9.10 (br. s, 1H) |
| A55 | 4-[[4-[4-[(4-isopropyl-piperazin-1-yl)methyl]phenyl]-1H-pyrrolo[3,2-c]pyridin-2-yl]methyl]morpholine | 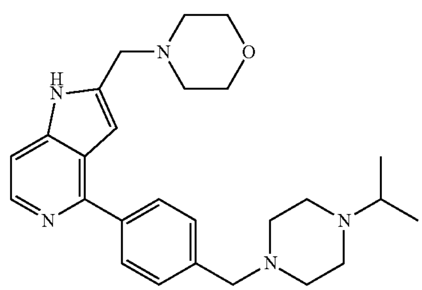 [SMILES: CC(C)N1CCN(Cc2ccc(-c3nccc4[nH]c(CN5CCOCC5)cc34)cc2)CC1] | A48 | LCMS: m/z 434.30 [M⁺ + 1]<br>$^1$HNMR (400 MHz, CDCl$_3$):<br>δ 1.11 (d, J = 6.9 Hz, 6H), 2.49 (t, J = 4.4 Hz, 4H), 2.58-2.70 (m, 8H), 2.75-2.80 (m, 1H), 3.61 (s, 2H), 3.68 (s, 2H), 3.72 (t, J = 4.4 Hz, 4H), 6.67 (s, 1H), 7.23 (d, J = 5.4 Hz, 1H), 7.45 (d, J = 7.9 Hz, 2H), 7.92 (d, J = 8.3 Hz, 2H), 8.38 (d, J = 5.9 Hz, 1H), 8.93 (bs, 1H). |
| A56 | 4-[[4-[4-[(1-isopropyl-4-piperidyl)oxy]phenyl]-1H-pyrrolo[3,2-c]pyridin-2-yl]methyl]morpholine | 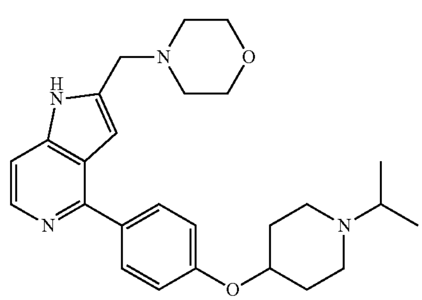 [SMILES: CC(C)N1CCC(Oc2ccc(-c3nccc4[nH]c(CN5CCOCC5)cc34)cc2)CC1] | A49 | LCMS: m/z 435.4 [M⁺ + 1]<br>$^1$H NMR (400 MHz, CDCl$_3$):<br>δ 1.05-1.20 (m, 6H), 1.85-1.95 (m, 2H), 2.10-2.20 (m, 2H), 2.45-2.55 (m, 6H), 2.80-2.92 (m, 3H), 3.68 (s, 2H), 3.73 (t, J = 4.4 Hz, 4H), 4.40-4.50 (m, 1H), 6.66 (s, 1H), 7.04 (d, J = 8.8 Hz, 2H), 7.19 (d, J = 5.7 Hz, 1H), 7.92 (d, J = 8.8 Hz, 2H), 8.36 (d, J = 5.3 Hz, 1H), 8.83 (bs, 1H) |

TABLE 11-continued

| Ex. No. | IUPAC name | Structure | Ex. from which prepared | Analytical data |
|---|---|---|---|---|
| A57 | 4-[[4-[3-(4-isopropyl-piperazin-1-yl)phenyl]-1H-pyrrolo[3,2-c]pyridin-2-yl]methyl]morpholine | 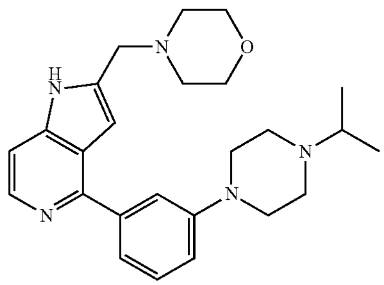 [SMILES: CC(C)N1CCN(c2cccc(-c3nccc4[nH]c(CN5CCOCC5)cc34)c2)CC1] | A46 | LCMS: m/z 420.3 [M+ + 1] <br> 1H NMR (400 MHz, CDCl3): <br> δ 1.12 (d, J = 6.3 Hz, 6H), 2.49 (t, J = 3.9 Hz, 4H), 2.74 (t, J = 4.4 Hz, 4H), 2.76-2.78 (m, 1H), 3.34 (t, J = 4.8 Hz, 4H), 3.68 (s, 2H), 3.72 (t, J = 4.4 Hz, 4H), 6.67 (s, 1H), 7.01 (dd, J = 1 Hz, 7.9 Hz, 1H), 7.23 (d, J = 5.8 Hz, 1H), 7.35-7.44 (aromatics, 2H), 7.52 (s, 1H), 8.37 (d, J = 5.8 Hz, 1 H), 8.85 (bs, 1H) |
| A58 | 4-[[4-[2-(4-isopropyl-piperazin-1-yl)thiazol-5-yl]-1H-pyrrolo[3,2-c]pyridin-2-yl]methyl]morpholine | 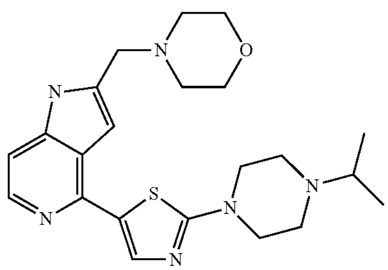 [SMILES: CC(C)N1CCN(c2ncc(-c3nccc4[nH]c(CN5CCOCC5)cc34)s2)CC1] | A50 | LCMS: m/z 427.3 [M+ + 1] <br> 1H NMR (400 MHz, CDCl3): <br> δ 1.10 (d, J = 6 Hz, 6H), 2.50-2.53 (m, 4H), 2.68-2.70 (m, 4H), 2.80-2.81 (m, 1H), 3.63-3.65 (m, 4H), 3.72-3.75 (m, 6H), 6.66 (s, 1H), 7.10 (d, J = 5.6 Hz, 1H), 7.86 (s, 1H), 8.21 (d, J = 5.6 Hz, 1H), 8.84 (br. s, 1H) |

Example A59

4-[[4-[6-(4-methylpiperazin-1-yl)-3-pyridyl]-1H-pyrrolo[3,2-c]pyridin-2-yl]methyl]morpholine

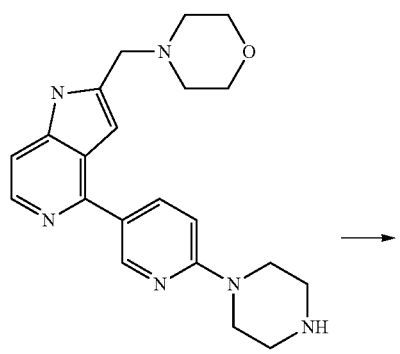

Example A44

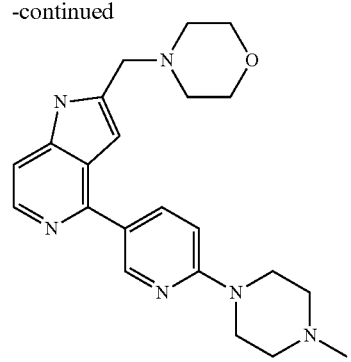

Example A59

To a solution of Example A44 (0.16 g, 0.42 mmol) in MeOH (3 mL) were added 37% aqueous HCHO (0.19 g, 6.34 mmol) and two drops of acetic acid, and the mixture was stirred at 70° C. for 2 hours. The reaction mixture was cooled to 0° C. and sodium cyanoborohydride (0.398 g, 6.34 mmol) was added thereto, and the mixture was stirred overnight. The reaction mixture was diluted with water (10 mL) and extracted with AcOEt (20 mL×3). The layers were separated, and the organic layer was washed with saturated aqueous sodium bicarbonate solution and brine, dried over anhydrous Na$_2$SO$_4$ and concentrated in vacuum. The obtained residue was purified by preparative TLC to give the desired product Example A59 (0.061 g, 37%) as a yellow solid; LCMS: m/z 393.3 [M$^+$+1].

$^1$H NMR (400 MHz, CDCl$_3$): δ 2.38 (s, 3H), 2.49 (t, J=4.4 Hz, 4H), 2.58 (t, J=5.2 Hz, 4H), 3.68 (s, 2H), 3.69-3.75 (m, 8H), 6.71 (s, 1H), 6.80 (d, J=8.8 Hz, 1H), 7.20 (dd, J=5.6, 0.8 Hz, 1H), 8.20 (dd, J=8.8, 2.4 Hz, 1H), 8.35 (d, J=5.6 Hz, 1H), 8.37 (d, J=2 Hz, 1H), 8.89 (br. s, 1H)

The following compounds Examples A60 to A63 as shown in Table 12 were prepared in the same manner as Example A59.

TABLE 12

| Ex. No. | IUPAC name | Structure | Ex. from which prepared | Analytical data |
|---|---|---|---|---|
| A60 | 4-[[4-[4-[(4-methyl-piperazin-1-yl)methyl]phenyl]-1H-pyrrolo[3,2-c]pyridin-2-yl]methyl]morpholine | 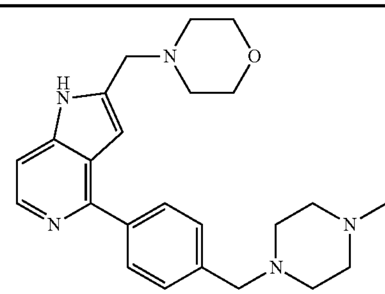 | A48 | LCMS: m/z 406.30 [M$^+$ + 1] $^1$HNMR (400 MHz, CDCl$_3$): δ 2.35 (s, 3H), 2.49 (t, J = 4.4 Hz, 4H), 2.52-2.70 (m, 8H), 3.60 (s, 2H), 3.69 (s, 2H), 3.73 (t, J = 4.9 Hz, 4H), 6.68 (s, 1H), 7.23 (d, J = 1.2 Hz, 1H), 7.46 (d, J = 8.4 Hz, 2H), 7.91 (d, J = 8.4 Hz, 2H), 8.36 (d, J = 5.3 Hz, 1H), 9.00 (bs, 1H) |
| A61 | 4-[[4-[3-(4-methyl-piperazin-1-yl)phenyl]-1H-pyrrolo[3,2-c]pyridin-2-yl]methyl]morpholine | 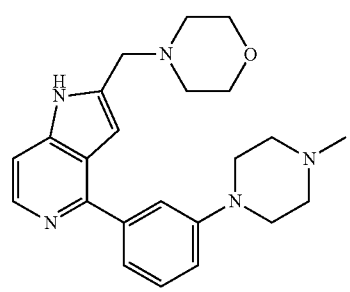 [SMILES: CN1CCN(c2cccc(-c3nccc4[nH]c(CN5CCOCC5)cc34)c2)CC1] | A46 | LCMS: m/z 392.30 [M$^+$ + 1] $^1$H NMR (400 MHz, CDCl$_3$): δ 2.37 (s, 3H), 2.49 (t, J = 4.4 Hz, 4H), 2.62 (t, J = 4.8 Hz, 4H), 3.33 (t, J = 5.3 Hz, 4H), 3.68 (s, 2H), 3.72 (t, J = 4.9 Hz, 4H), 6.66 (s, 1H), 7.01 (dd, J = 1.5, 2.4 Hz, 1H), 7.23 (d, J = 5.9 Hz, 1H), 7.35-7.44 (aromatics, 2H), 7.52 (s, 1H), 8.38 (d, J = 5.9 Hz, 1H), 8.92 (bs, 1H) |
| A62 | 4-[[4-[4-[(1-methyl-4-piperidyl)oxy]phenyl]-1H-pyrrolo[3,2-c]pyridin-2-yl]methyl]morpholine | 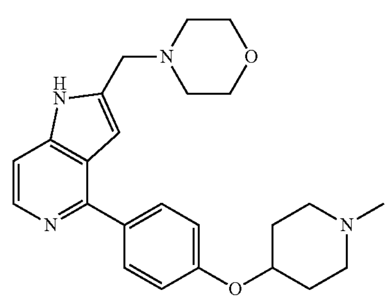 [SMILES: CN1CCC(Oc2ccc(-c3nccc4[nH]c(CN5CCOCC5)cc34)cc2)CC1] | A49 | LCMS: m/z 407.3 [M$^+$ + 1] $^1$H NMR (400 MHz, CDCl$_3$): δ 1.85-1.98 (m, 2H), 2.05-2.15 (m, 2H), 2.36 (s, 3H), 2.38-2.42 (m, 2H), 2.49 (t, J = 3.9 Hz, 4H), 2.70-2.80 (m, 2H), 3.68 (s, 2H), 3.73 (t, J = 4.4 Hz, 4H), 4.40-4.50 (m, 1H), 6.67 (s, 1H), 7.04 (d, J = 8.4 Hz, 2H), 7.19 (d, J = 5.9 |

TABLE 12-continued

| Ex. No. | IUPAC name | Structure | Ex. from which prepared | Analytical data |
|---|---|---|---|---|
| | | | | Hz, 1H), 7.92 (d, J = 8.8 Hz, 2H), 8.36 (d, J = 5.9 Hz, 1H), 8.87 (bs, 1H) |
| A63 | 4-[[4-[1-(1-methyl-4-piperidyl)pyrazol-4-yl]-1H-pyrrolo[3,2-c]pyridin-2-yl]methyl]morpholine | 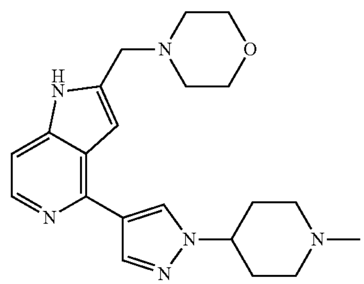 [SMILES: CN1CCC(n2cc(-c3nccc4[nH]c(CN5CCOCC5)cc34)cn2)CC1] | A45 | LCMS: m/z 381.3 [M+ + 1] $^1$H NMR (400 MHz, CDCl$_3$): δ 2.11-2.22 (m, 4H), 2.23-2.26 (m, 2H), 2.35 (s, 3H), 2.50 (t, J = 4.4 Hz, 4H), 3.00-3.03 (m, 2H), 3.70 (s, 2H), 3.73 (t, J = 4.4 Hz, 4H), 4.21 (sep. 1H), 6.66 (s, 1H), 7.15 (d, J = 6 Hz, 1H), 8.14 (s, 1H), 8.17 (s, 1H), 8.26 (d, J = 5.6 Hz, 1H), 8.40 (br. s, 1H) |

Example A64

4-[[4-[6-(1-isopropyl-4-piperidyl)-3-pyridyl]-1H-pyrrolo[3,2-c]pyridin-2-yl]methyl]morpholine

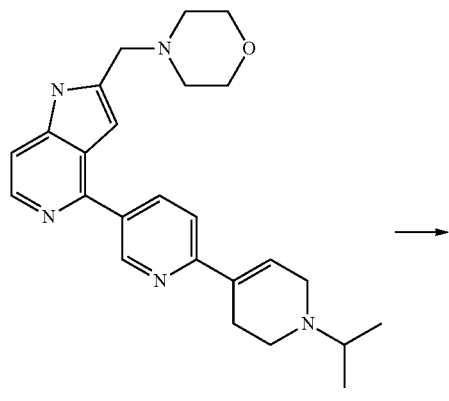

Example A52

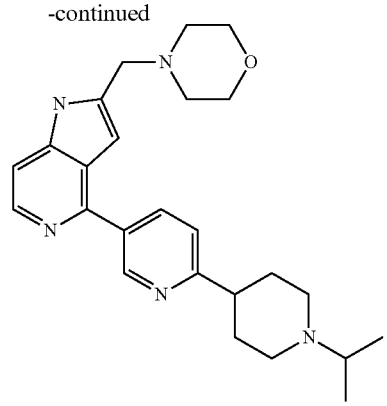

Example A64

To a solution of Example A52 (0.130 g, 0.311 mmol) in EtOAc:MeOH (9:1 ratio, 10 mL) was added 10% dry Pd/C (15 mg), and the mixture was stirred under hydrogen atmosphere at room temperature (balloon pressure). After 16 hours, the catalyst was removed by filtration, and the filtrate was evaporated to dryness. The obtained residue was purified by preparative TLC (10% MeOH in dichloromethane) to give the desired product Example A64 (0.065 g, 50%) as a yellow solid; LCMS: m/z 420.4 [M++1].

$^1$H NMR (400 MHz, CDCl$_3$): δ 1.14 (d, J=5.6 Hz, 6H), 1.96-2.10 (m, 4H), 2.40-2.45 (m, 2H), 2.49 (t, J=4.4 Hz, 4H), 2.84-2.88 (m, 2H), 3.03-3.15 (m, 2H), 3.69 (m, s, 2H), 3.72 (t, J=4.8 Hz, 4H), 6.67 (s, 1H), 7.25-7.26 (m, merged in residual solvent peak, 1H), 7.36 (d, J=8 Hz, 1H), 8.24 (dd, J=8, 2.4 Hz, 1H), 8.40 (d, J=5.6 Hz, 1H), 8.84 (br. s, 1H), 9.11 (d, J=2 Hz, 1H)

The following compound Example A65 as shown in Table 13 was prepared in the same manner as Example A64.

TABLE 13

| Ex. No. | IUPAC name | Structure | Ex. from which prepared | Analytical data |
|---|---|---|---|---|
| A65 | 4-[[4-[4-[1-(oxetan-3-yl)-4-piperidyl]phenyl]-1H-pyrrolo[3,2-c]pyridin-2-yl]methyl]morpholine | 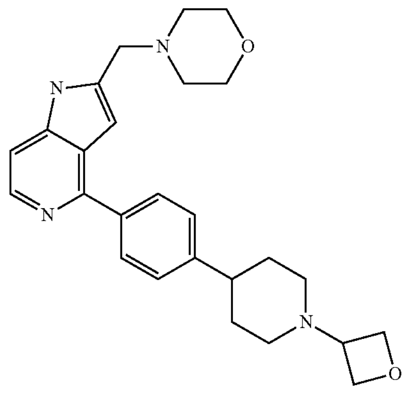 [SMILES: c1cc2[nH]c(CN3CCOCC3)cc2c(-c2ccc(C3CCN(C4COC4)CC3)cc2)n1] | A11 | LCMS: m/z 433.3 [M+ + 1] $^1$H NMR (400 MHz, CDCl$_3$): δ 1.83-2.00 (m, 6H), 2.49 (t, J = 4 Hz, 4H), 2.54-2.63 (m, 1H), 2.90 (d, J = 10.8 Hz, 2H), 3.52 (q, J = 6.8 Hz, 1H), 3.69 (s, 2H), 3.73 (t, J = 4.4 Hz, 4H), 4.66-4.71 (m, 4H), 6.70 (s, 1H), 7.22 (d, J = 5.6 Hz, 1H), 7.37 (d, J = 8.4 Hz, 2H), 7.92 (d, J = 8.4 Hz, 2H), 8.38 (d, J = 5.6 Hz, 1H), 8.92 (br s, 1H) |

Example A66 ethyl 1-[4-[2-(morpholinomethyl)-1H-pyrrolo[3,2-c]pyridin-4-yl]phenyl]piperidine-4-carboxylate

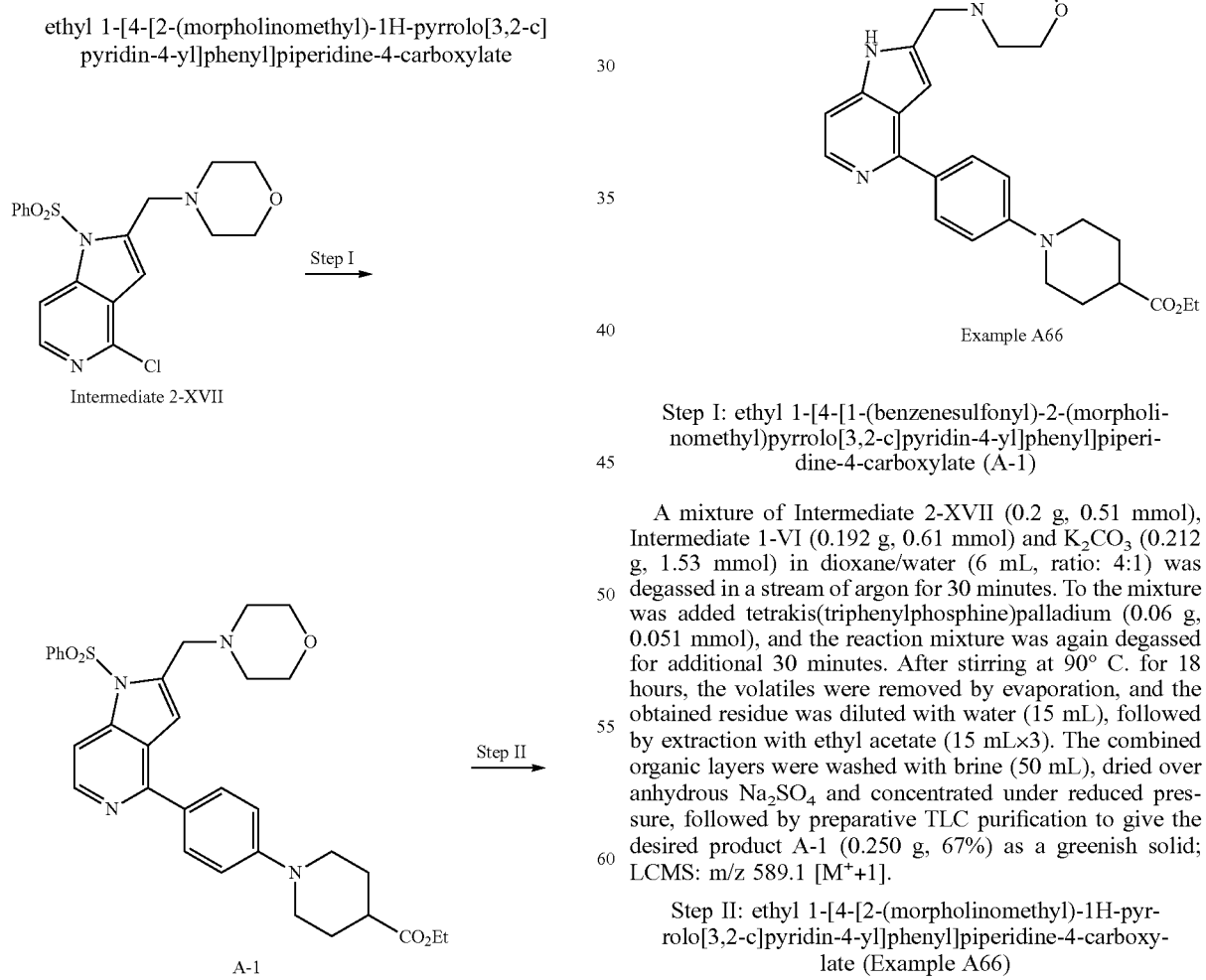

Step I: ethyl 1-[4-[1-(benzenesulfonyl)-2-(morpholinomethyl)pyrrolo[3,2-c]pyridin-4-yl]phenyl]piperidine-4-carboxylate (A-1)

A mixture of Intermediate 2-XVII (0.2 g, 0.51 mmol), Intermediate 1-VI (0.192 g, 0.61 mmol) and K$_2$CO$_3$ (0.212 g, 1.53 mmol) in dioxane/water (6 mL, ratio: 4:1) was degassed in a stream of argon for 30 minutes. To the mixture was added tetrakis(triphenylphosphine)palladium (0.06 g, 0.051 mmol), and the reaction mixture was again degassed for additional 30 minutes. After stirring at 90° C. for 18 hours, the volatiles were removed by evaporation, and the obtained residue was diluted with water (15 mL), followed by extraction with ethyl acetate (15 mL×3). The combined organic layers were washed with brine (50 mL), dried over anhydrous Na$_2$SO$_4$ and concentrated under reduced pressure, followed by preparative TLC purification to give the desired product A-1 (0.250 g, 67%) as a greenish solid; LCMS: m/z 589.1 [M$^+$+1].

Step II: ethyl 1-[4-[2-(morpholinomethyl)-1H-pyrrolo[3,2-c]pyridin-4-yl]phenyl]piperidine-4-carboxylate (Example A66)

A stirred solution of A-1 (0.24 g, 0.35 mmol) in 1,4-dioxane (8 mL) was treated with sodium tert-butoxide (0.103 g, 1.07 mmol) under argon atmosphere. After stirring at 90° C. for 8 hours, the excess solvent was removed in vacuo. The obtained residue was dissolved in ethyl acetate (25 mL), and the solution was washed successively with water (10 mL) and brine (10 mL). The organic layer was dried over anhydrous $Na_2SO_4$ and concentrated under reduced pressure. The desired crude compound Example A66 obtained as a yellow solid (0.22 g) was used in the next step without purification; LCMS: m/z 225.1 [$M^+/2+1$]

Example A67 methyl 1-[4-[2-(morpholinomethyl)-1H-pyrrolo[3,2-c]pyridin-4-yl]phenyl]piperidine-4-carboxylate and Example A68

1-[4-[2-(morpholinomethyl)-1H-pyrrolo[3,2-c]pyridin-4-yl]phenyl]piperidine-4-carboxylic acid

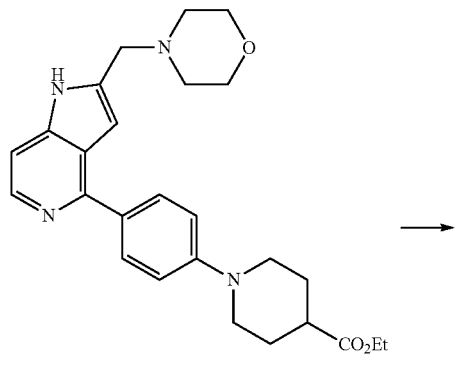

Example A66

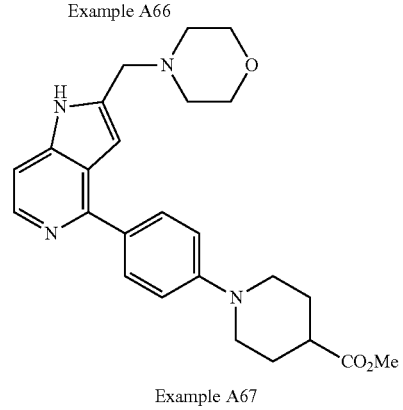

Example A67

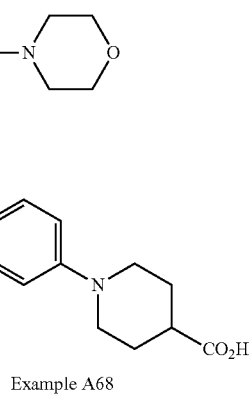

Example A68

LiOH $H_2O$ (0.206 g, 4.910 mmol) was added to a stirred solution of Example A66 (0.22 g, 0.491 mmol) in a mixture of THF:MeOH:$H_2O$ (3:2:1 ratio, 5 mL) at room temperature, and the reaction mixture was stirred for 18 hours. The volatiles were concentrated under reduced pressure, and the obtained residue was neutralized to pH 7 using aqueous 1N HCl, and the reaction mixture was concentrated to dryness. The resulting solid was suspended in 10% MeOH in DCM (100 mL), and the suspension was filtered. The filtrate was concentrated in vacuo to give the mixture of crude desired acid Example A68 as a pale brown solid (0.025 g, 12%) and transesterification product Example A67 (formed due to solvent methanol used during the hydrolysis reaction) (0.036 g, 16%) as a yellow solid.

Example A67

LCMS: m/z 435.3 [$M^++1$]
$^1$H NMR (400 MHz, $CD_3OD$): δ 1.78-1.86 (m, 2H), 1.97-2.01 (m, 2H), 2.30-2.35 (m, 1H), 2.45-2.55 (m, 4H), 2.87 (t, J=11.2 Hz, 2H), 3.67 (t, J=4.4 Hz, 4H), 3.74 (s, 2H), 3.85-3.89 (m, 2H), 3.93 (s, 3H), 6.82 (s, 1H), 7.13 (d, J=8.8 Hz, 2H), 7.48 (d, J=6.0 Hz, 1H), 7.76 (d, J=8.8 Hz, 2H), 8.17 (d, J=6.0 Hz, 1H)

Example A68

LCMS: m/z 421.3 [$M^++1$]
$^1$H NMR (400 MHz, $CD_3OD$): δ 1.78-1.81 (m, 2H), 1.99-2.01 (m, 3H), 2.45-2.52 (m, 4H), 2.97 (t, J=11 Hz, 2H), 3.71 (t, J=4.6 Hz, 4H), 3.78 (s, 2H), 3.94 (d, J=12.6 Hz, 2H), 6.95 (s, 1H), 7.18 (d, J=8.8 Hz, 2H), 7.58 (d, J=6.8 Hz, 1H), 7.80 (d, J=8.8 Hz, 2H), 8.13 (d, J=6.8 Hz, 1H)

Example A69

1-[4-[2-(morpholinomethyl)-1H-pyrrolo[3,2-c]pyridin-4-yl]phenyl]piperidin-4-ol

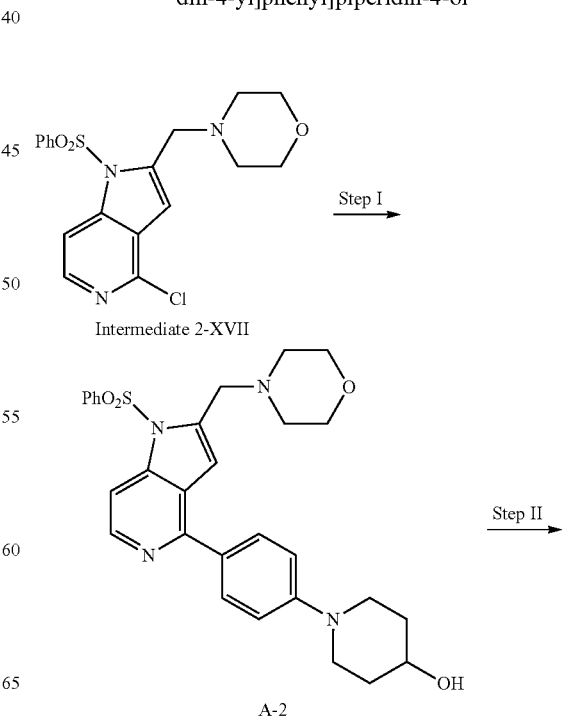

A-2

165

-continued

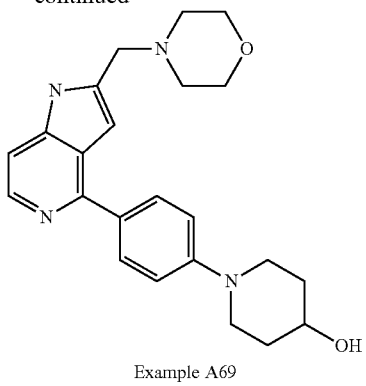

Example A69

Step I: 1-[4-[1-(benzenesulfonyl)-2-(morpholinomethyl)pyrrolo[3,2-c]pyridin-4-yl]phenyl]piperidin-4-ol (A-2)

A mixture of Intermediate 2-XVII (0.18 g, 0.46 mmol), Intermediate 1-V (0.195 g, 0.64 mmol) and $K_2CO_3$ (0.191 g, 1.38 mmol) in 4:1 mixture of dioxane/water (6 mL) was degassed in a stream of argon for 30 minutes. To the mixture was added tetrakis(triphenylphosphine)palladium(0) (0.053 g, 0.046 mmol), and the reaction mixture was again degassed for additional 30 minutes. After stirring at 90° C. for 18 hours, the volatiles were removed by evaporation, and the obtained residue was diluted with water (15 mL), followed by extraction with ethyl acetate (15 mL×3). The combined organic layers were washed with brine (50 mL), dried over anhydrous $Na_2SO_4$ and concentrated under reduced pressure, followed by preparative TLC purification to give the desired product A-2 (0.14 g, 57%) as a yellow solid; LCMS: m/z 533.1 [M$^+$+1].

Step II: 1-[4-[2-(morpholinomethyl)-1H-pyrrolo[3,2-c]pyridin-4-yl]phenyl]piperidin-4-ol (Example A69)

A stirred solution of A-2 (0.13 g, 0.24 mmol) in 1,4-dioxane (6 mL) was treated with sodium tert-butoxide (0.070 g, 0.73 mmol) under argon atmosphere. After stirring at 90° C. for 8 hours, the excess solvent was removed in vacuo. The obtained residue was dissolved in ethyl acetate (25 mL), and the solution was washed successively with water (10 mL) and brine (10 mL). The organic layer was dried over anhydrous $Na_2SO_4$ and concentrated under reduced pressure. The obtained residue was purified by HPLC to give the desired product Example A69 (0.035 g, 36%) as a dark yellow solid; LCMS: m/z 393.3 [M$^+$+1].

$^1$H NMR (400 MHz, CD$_3$OD): δ 1.60-1.68 (m, 2H), 1.93-2.00 (m, 5H), 2.48-2.60 (m, 4H), 3.06 (t, J=10 Hz, 2H), 3.70-3.85 (m, 6H), 6.82 (s, 1H), 7.16 (d, J=8.4 Hz, 2H), 7.44 (d, J=6.4 Hz, 1H), 7.79 (d, J=8.8 Hz, 2H), 8.13 (d, J=6.0 Hz, 1H)

166

Example A70

4-[[4-[4-(1-isopropyl-4-piperidyl)phenyl]-1H-pyrrolo[3,2-c]pyridin-2-yl]methyl]morpholine

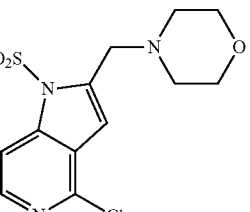

Intermediate 2-XVII

Step I →

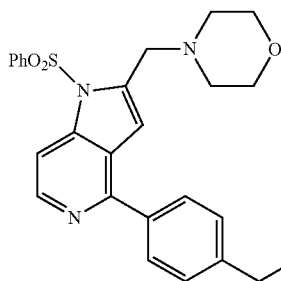

A-3

Step II →

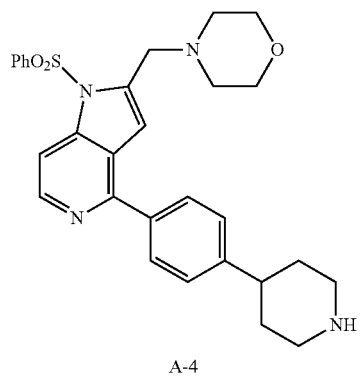

A-4

Step III →

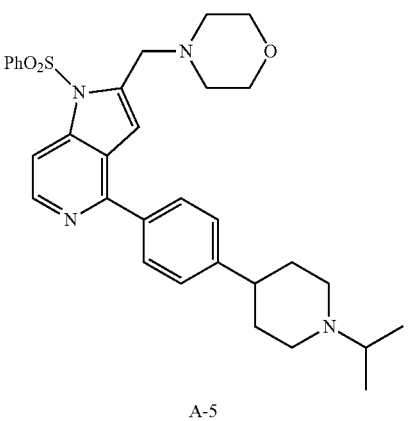

A-5

Step IV →

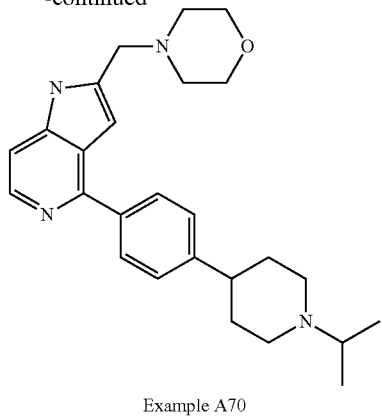

Example A70

Step I: tert-butyl 4-[4-[1-(benzenesulfonyl)-2-(morpholino methyl)pyrrolo[3,2-c]pyridin-4-yl]phenyl]piperidine-1-carboxylate (A-3)

A mixture of Intermediate 2-XVII (0.40 g, 1.02 mmol), Intermediate 1-IX (0.475 g, 1.22 mmol) and K₂CO₃ (0.424 g, 3.06 mmol) in 4:1 mixture of dioxane/water (16 mL) was degassed in a stream of argon for 30 minutes. To the mixture was added tetrakis(triphenylphosphine)palladium(0) (0.118 g, 0.102 mmol), and the reaction mixture was again degassed for additional 30 minutes. After stirring at 90° C. for 18 hours, the volatiles were removed by evaporation, and the obtained residue was diluted with water (25 mL), followed by extraction with ethyl acetate (25 mL×3). The combined organic layers were washed with brine (100 mL), dried over anhydrous Na₂SO₄ and concentrated under reduced pressure, followed by preparative TLC purification to give the desired product A-3 (0.425 g, 67%) as a white solid; LCMS: m/z 617.1 [M⁺+1].

Step II: 4-[[1-(benzenesulfonyl)-4-[4-(4-piperidyl)phenyl]pyrrolo[3,2-c]pyridin-2-yl]methyl]morpholine (A-4)

To a solution of A-3 (0.425 g, 0.688 mmol) in methanol (5 mL) at 0° C. was added 4 M HCl in diethyl ether (5 mL). After stirring at room temperature for 6 hours, the volatiles were removed by evaporation, and the obtained residue was diluted with water (2 mL), and pH was adjusted to ~8 using saturated aqueous NaHCO₃ solution (3 mL). The resulting solution was evaporated to dryness, and the obtained residue was diluted with 5% MeOH in dichloromethane (20 mL), and inorganic substance was removed by filtration. The filtrate was concentrated to give the crude desired product A-4 (0.35 g, 98%) as a white solid. The obtained crude product was used for next step without purification.

Step III: 4-[[1-(benzenesulfonyl)-4-[4-(1-isopropyl-4-piperidyl)phenyl]pyrrolo[3,2-c]pyridin-2-yl]methyl]morpholine (A-5)

To a solution of A-4 (0.20 g, 0.38 mmol) and acetone (0.247 g, 0.3 mL, 4.26 mmol) in a mixture of dichloroethane and methanol (2:1, 10 mL) were added a drop of acetic acid and powdered 4 Å molecular sieves (0.5 g). The reaction mixture was stirred for 3 hours at room temperature. Sodium cyanoborohydride (0.317 g, 5.03 mmol) was added thereto, and the mixture was stirred overnight. After completion of reaction (monitored by TLC), the resulting solid was removed by filtration, and the filtrate was diluted with water (10 mL) and ethyl acetate (25 mL). The layers were separated, and the organic layer was washed with saturated aqueous sodium bicarbonate solution (15 mL) and brine (15 mL), dried over anhydrous Na₂SO₄, and concentrated in vacuum to give the desired crude product A-5 (0.13 g, 60%) as a white solid. The obtained crude product was used in the next step without purification LCMS: m/z 559.2 [M⁺+1].

Step IV: 4-[[4-[4-(1-isopropyl-4-piperidyl)phenyl]-1H-pyrrolo[3,2-c]pyridin-2-yl]methyl]morpholine (Example A70)

A stirred solution of A-5 (0.13 g, 0.23 mmol) in 1,4-dioxane (6 mL) was treated with sodium tert-butoxide (0.067 g, 0.69 mmol) under argon atmosphere. After stirring at 90° C. for 8 hours, the excess solvent was removed in vacuo. The obtained residue was dissolved in ethyl acetate (25 mL), and the solution was washed successively with water (10 mL) and brine (10 mL), and dried over anhydrous Na₂SO₄. The organic layer was concentrated under reduced pressure. The obtained residue was purified by preparative HPLC to give the desired compound Example A70 (0.034 g, 24%) as a white solid; LCMS: m/z 419.2 [M⁺+1].
¹H NMR (400 MHz, CD₃OD): δ 1.15 (d, J=6.8 Hz, 6H), 1.84-1.97 (m, 4H), 2.43 (t, J=11 Hz, 2H), 2.51 (t, J=4.6 Hz, 4H), 2.66-2.67 (m, 1H), 2.84 (quin, J=6.6-Hz, 1H), 3.10 (d, J=12 Hz, 2H), 3.70 (t, J=5.2 Hz, 6H), 6.64 (s, 1H), 7.33 (d, J=6 Hz, 1H), 7.42 (d, J=8 Hz, 2H), 7.80 (d, J=8.4 Hz, 2H), 8.16 (d, J=5.6 Hz, 1H)

Example A71

4-[[3-chloro-4-[4-(4-isopropylpiperazin-1-yl)phenyl]-1H-pyrrolo[3,2-c]pyridin-2-yl]methyl]morpholine

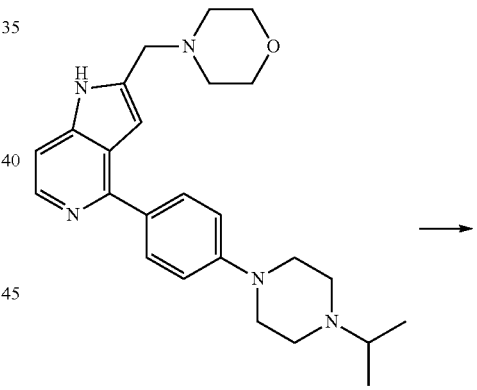

Example A1

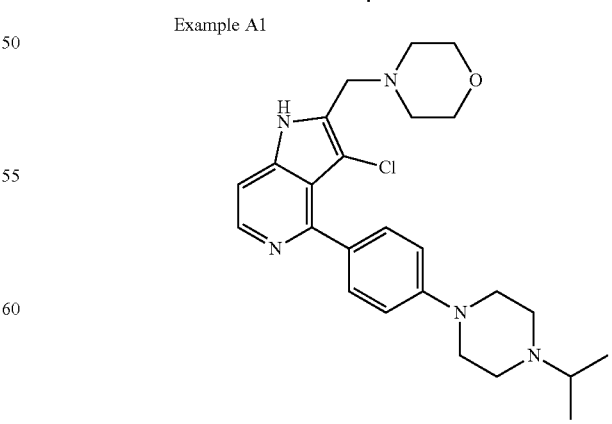

Example A71

To a solution of Example A1 (0.10 g, 0.23 mmol) in anhydrous DMF (2.3 mL) was added N-chlorosuccinamide (0.038 g, 0.29 mmol) at room temperature. The reaction mixture was stirred at room temperature for 16 hours. The excess solvent was removed in vacuo, and the obtained residue was diluted with ice water, followed by extraction with ethyl acetate (20 mL×3). The combined organic layers were washed with brine (25 mL), dried over anhydrous $Na_2SO_4$ and concentrated under reduced pressure. The obtained residue was purified by preparative TLC using 10% methanol in dichloromethane to give the desired product Example A71 (0.037 g, 35%) as a yellow solid; LCMS: m/z 454.3 [$M^+$+1].

$^1$HNMR (400 MHz, $CDCl_3$): δ 1.14 (d, J=6.8 Hz, 6H), 2.53 (t, J=4.4 Hz, 4H), 2.77 (m, 5H), 3.35 (bs, 4H), 3.73 (m, 6H), 7.01 (d, J=8.8 Hz, 2H), 7.19 (d, J=5.8 Hz, 1H), 7.61 (d, J=8.8 Hz, 2H), 8.37 (d, J=5.9 Hz, 1H), 8.89 (br s, 1H)

Example A72

1-[[4-[4-(4-isopropylpiperazin-1-yl)phenyl]-1H-pyrrolo[3,2-c]pyridin-2-yl]methyl]azetidin-3-ol

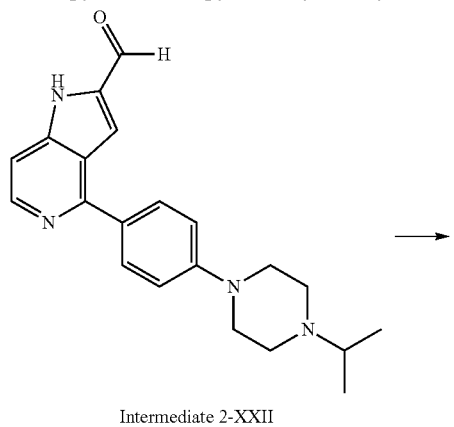

Intermediate 2-XXII

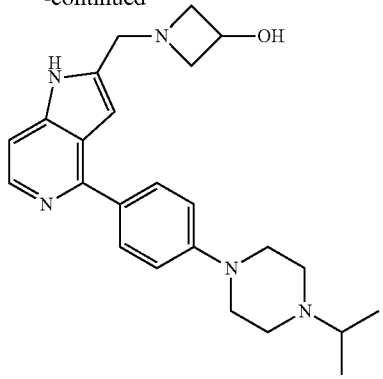

Example A72

To a solution of Intermediate 2-XXII (0.130 g, 0.373 mmol) in MeOH:DCE (2:4, 5 mL) were added azetidin-3-ol (0.136 g, 1.86 mmol), a drop of acetic acid and activated 4 Å powdered molecular sieves (0.5 g) successively. After stirring for 4 hours at room temperature, sodium cyanoborohydride (0.234 g, 3.75 mmol) was added thereto, and the mixture was stirred for 16 hours. The reaction mixture was filtered through a celite pad, and washed with EtOAc (25 mL), and the filtrate was taken into water (10 mL), and the mixture was extracted with ethyl acetate (20 mL×3). The combined organic layers were washed with brine (25 mL), dried over anhydrous $Na_2SO_4$ and concentrated under reduced pressure. The obtained residue was purified by preparative TLC using 12% MeOH in dichloromethane to give the desired product Example A72 (0.04 g, 26%) as a yellow Solid; LCMS: m/z 406.3 [$M^+$+1].

$^1$H NMR (400 MHz, $CDCl_3$): δ 1.06 (dd, J=5.8 Hz, 6H), 2.53 (t, J=9.6 Hz, 1H), 2.61-2.75 (m, 4H), 3.02-3.22 (m, 4H), 3.23-3.40 (m, 4H), 3.72-3.78 (m, 2H), 4.44 (t, J=5.8, 1H), 6.64 (s, 1H), 6.98 (d, J=8.4 Hz, 2H), 7.15 (d, J=4.8 Hz, 1H), 7.83 (d, J=8.4 Hz, 2H), 8.19 (d, J=4.8 Hz, 1H)

The following compound Example A73 as given in Table 14 was prepared in the same manner as Example A72.

TABLE 14

| Ex. No. | IUPAC name | Structure | Int. from which prepared | Analytical data |
|---|---|---|---|---|
| A73 | methyl (2R)-1-[[4-[4-(4-isopropyl-piperazin-1-yl)phenyl]-1H-pyrrolo[3,2-c]pyridin-2-yl]methyl]pyrrolidine-2-carboxylate | (structure shown) | 2-XXII | LCMS: m/z 462.3 [$M^+$ + 1] $^1$H NMR (400 MHz, $CDCl_3$): δ 1.12 (d, J = 6.8 Hz, 6H), 1.85-1.88 (m, 3H), 2.17-2.30 (m, 1H), 2.42-2.52 (m, 1H), 2.73 (t, J = 5.2 Hz, 5H), 3.06-3.12 (m, 1H), 3.32-3.37 (m, 5H), 3.66 (s, 3H), 3.77 (d, J = 14 Hz, 1H), 4.04 (d, J = 14 Hz, 1H), 6.62 (s, 1H), 7.04 (d, J = 8.8 Hz, 2H), 7.22 (d, J = 5.6 Hz, 1H), 7.91 (d, J = 8.8 Hz, 2H), 8.31 (d, J = 6 Hz, 1H), 9.60 (br s, 1H) |

Example A74

(2R)-1-[[4-[4-(4-isopropylpiperazin-1-yl)phenyl]-1H-pyrrolo[3,2-c]pyridin-2-yl]methyl]pyrrolidine-2-carboxylic acid

Example A75

4-[[4-[4-[4-(2,2,2-trifluoroethyl)piperazin-1-yl]phenyl]-1H-pyrrolo[3,2-c]pyridin-2-yl]methyl]morpholine

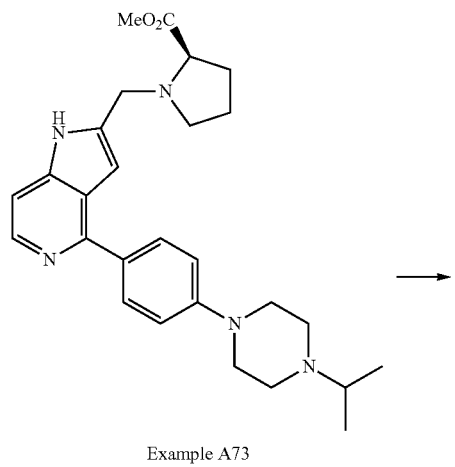

Example A73

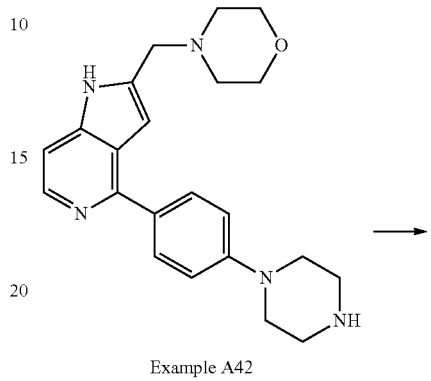

Example A42

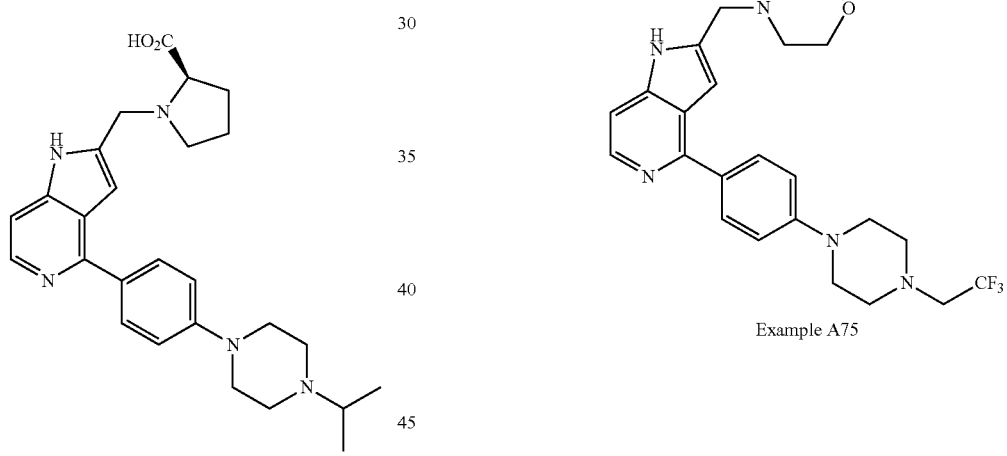

Example A74

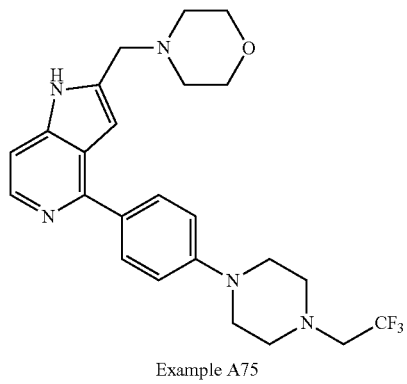

Example A75

A stirred solution of Example A73 (0.032 g, 0.072 mmol) in THF:MeOH:H₂O (3:2:1 ratio, 2.5 mL) was treated with LiOH·H₂O (0.0036 g, 0.086 mmol) at room temperature, and the mixture was stirred for 16 hours. The volatiles were concentrated under reduced pressure to give a lithium salt of the desired product Example A74 (0.025 g, 74%) as a yellow solid; LCMS: m/z 448.3 [M⁺+1].

$^1$H NMR (400 MHz, CD$_3$OD): δ 1.14 (d, J=6.4 Hz, 6H), 1.71-1.91 (m, 3H), 2.12-2.23 (m, 2H), 2.69-2.77 (m, 5H), 2.87-2.91 (m, 1H), 3.00 (t, J=8.2 Hz, 1H), 3.29-3.34 (m, 4H), 3.45 (d, J=13.6 Hz, 1H), 4.17 (d, J=13.2 Hz, 1H), 6.59 (s, 1H), 7.11 (d, J=9.2 Hz, 2H), 7.26 (d, J=6 Hz, 1H), 7.79 (d, J=8.8 Hz, 2H), 8.10 (d, J=6 Hz, 1H)

To an ice cold solution of Example A42 (0.05 g, 0.132 mmol) and N,N-diisopropylethylamine (0.025 g, 0.198 mmol) in dichloromethane (1.5 mL) was added 2,2,2-trifluoroethyl trifluoromethanesulfonate (23 μL, 0.158 mmol) at room temperature. After stirring at room temperature for 18 hours, the reaction mixture was diluted with water (10 mL) and dichloromethane (20 mL). The organic layer was separated, washed with brine (10 mL), dried over anhydrous Na$_2$SO$_4$ and concentrated under reduced pressure. The obtained residue was purified by preparative TLC using 10% MeOH in dichloromethane to give the desired product Example A75 (0.031 g, 51%) as a light yellow solid; LCMS: m/z 460.2 [M⁺+1].

$^1$H NMR (400 MHz, CDCl$_3$): δ 2.49 (t, J=4.4 Hz, 4H), 2.86 (t, J=5.2 Hz, 4H), 3.06 (q, J=9.6 Hz, 2H), 3.32 (t, J=4.8 Hz, 4H), 3.69 (s, 2H), 3.72 (t, J=4.8 Hz, 4H), 6.71 (s, 1H), 7.03 (d, J=8.4 Hz, 2H), 7.21 (d, J=6 Hz, 1H), 7.92 (d, J=8.4 Hz, 2H), 8.34 (d, J=5.6 Hz, 1H), 9.10 (br. s, 1H)

Example A76

4-[[4-[4-[4-(oxazol-4-ylmethyl)piperazin-1-yl]phenyl]-1H-pyrrolo[3,2-c]pyridin-2-yl]methyl]morpholine

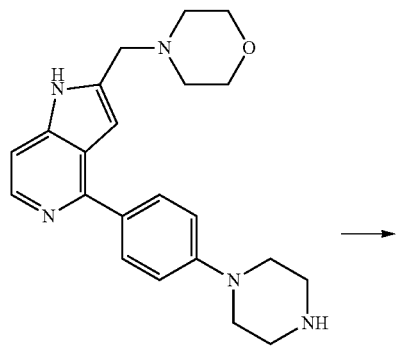

Example A42

↓

Example A76

A mixture of Example A42 (0.100 g, 0.264 mmol), oxazol-4-ylmethyl methanesulfonate hydrochloride salt (0.093 g, 0.66 mmol) and $K_2CO_3$ (0.128 g, 0.092 mmol) in DMF (3 mL) was heated at 60° C. for 18 hours. The excess solvent was removed under reduced pressure, and the obtained residue was diluted with ice water (10 mL) and EtOAc (20 mL). The organic layer was washed with brine (15 mL), dried over anhydrous $Na_2SO_4$ and concentrated under reduced pressure. The obtained residue was purified using preparative TLC (solvent system: 10% MeOH in dichloromethane) to give the desired product Example A76 (0.023 g, 19%) as a yellow solid; LCMS: m/z 459.3 [M$^+$+1].

$^1$H NMR (400 MHz, CDCl$_3$): δ 2.45-2.58 (m, 4H), 2.68-2.75 (m, 4H), 3.28-3.40 (m, 4H), 3.59 (s, 2H), 3.69-3.72 (m, 6H), 6.72 (s, 1H), 7.03 (d, J=8.4 Hz, 2H), 7.23 (s, 1H), 7.62 (s, 0.1H), 7.88 (s, 1H), 7.92 (d, J=8.4 Hz, 2H), 8.33 (d, J=6 Hz, 1H), 9.30 (br. s, 1H)

Example A77

4-[[4-[4-(4-isopropylpiperazin-1-yl)cyclohexen-1-yl]-1H-pyrrolo[3,2-c]pyridin-2-yl]methyl]morpholine Intermediate 2-I

→

Example A77

A stirred solution of Intermediate 2-I (0.10 g, 0.39 mmol), Intermediate 1-XXVIII (0.26 g, 0.79 mmol) and $K_2CO_3$ (0.16 g, 1.19 mmol) in a mixture of dioxane/water (4:1, 5 mL) was degassed in a stream of argon for 15 minutes. To this mixture was added Pd(PPh$_3$)$_4$ (0.046 g, 0.039 mmol), and the reaction mixture was again degassed for additional 15 minutes. After stirring at 100° C. for 18 hours, the volatiles were removed by evaporation, and the obtained residue was diluted with water (20 mL), followed by extraction with ethyl acetate (25 mL×3). The combined organic layers were washed with brine (25 mL), dried over anhydrous $Na_2SO_4$ and concentrated under reduced pressure. The obtained residue was purified by preparative TLC to give the desired product Example A77 (0.085 g, 50%) as a yellow solid; LCMS: m/z 212.7 [M$^+$/2+1].

$^1$H NMR (400 MHz, CDCl$_3$): δ 1.10 (d, J=6.4 Hz, 6H), 2.17-2.23 (m, 1H), 2.28-2.40 (m, 1H), 2.48 (t, J=4.4 Hz, 5H), 2.60-2.88 (m, 12H), 2.91-2.99 (m, 1H), 3.66 (s, 2H), 3.72 (t, J=4.4 Hz, 4H), 6.40 (t, J=2.0 Hz, 1H), 6.56 (s, 1H), 7.11 (d, J=5.6 Hz, 1H), 8.24 (d, J=6.0 Hz, 1H), 8.46 (bs, 1H)

Example A78

4-[[4-[4-(4-isopropylpiperazin-1-yl)cyclohexyl]-1H-pyrrolo[3,2-c]pyridin-2-yl]methyl]morpholine

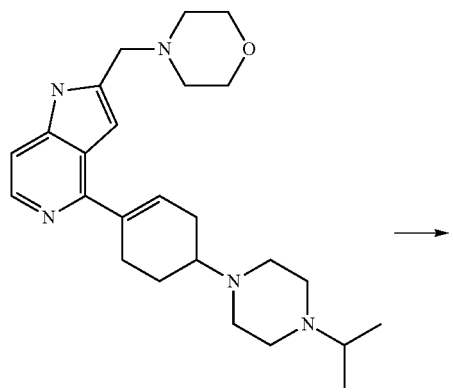

Example A77

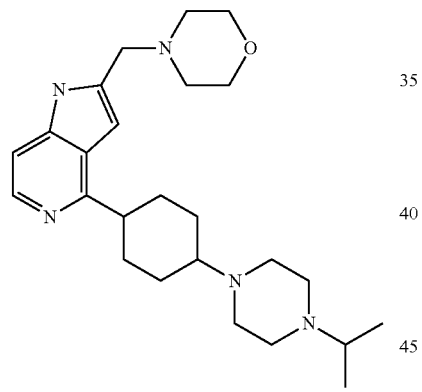

Example A78

Examples A79 and A80

Cis and trans-4-[[4-[4-(4-isopropylpiperazin-1-yl)cyclohexyl]-1H-pyrrolo[3,2-c]pyridin-2-yl]methyl]morpholine

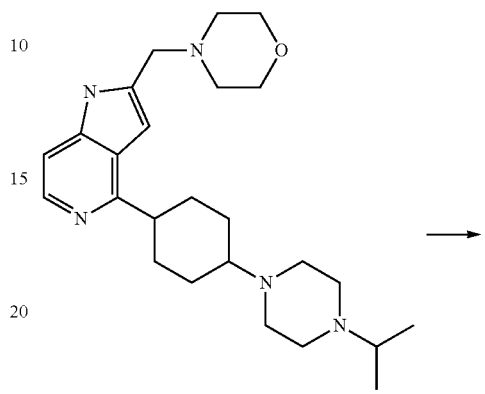

Example A78

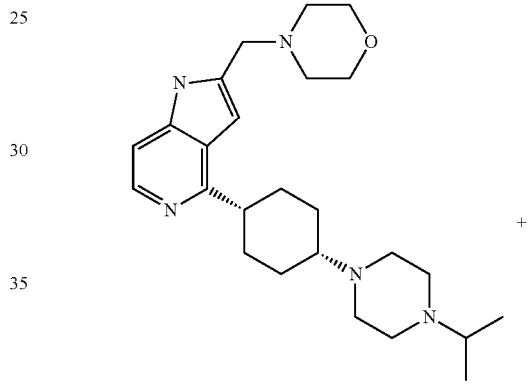

Example A79

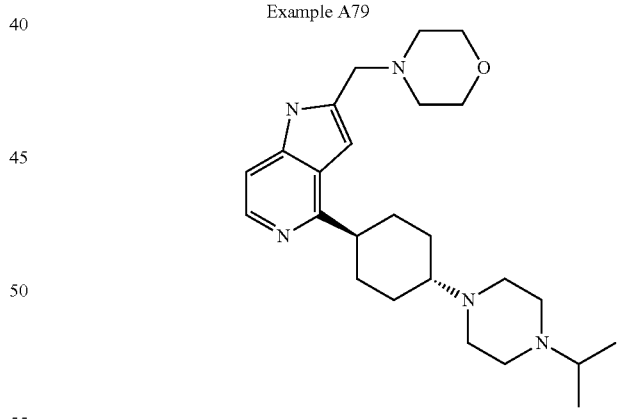

Example A80

To a stirred solution of Example A77 (0.085 g, 0.2 mmol) in EtOAc (3 mL) was added Pd/C (0.017 g, 20% W/W). The flask was evacuated and filled with hydrogen gas (this procedure was repeated twice). The reaction mixture was then stirred for 18 hours under hydrogen atmosphere. After completion of reaction, the reaction mixture was filtered through a celite pad. The obtained filtrate was concentrated under reduced pressure to give the desired product Example A78 (0.06 g, 70%) as a yellow oil. LCMS: m/z 213.7 [M$^+$/2+1].

Example A78 (0.06 g, 0.14 mmol) was dissolved in a mixture of methanol:dichloromethane (9:1, 0.7 mL). 41 µL of this solution was loaded onto a 150×21.2 mm 5µ phenomenex Gem column and eluted with a mobile phase comprising of acetonitrile:water (6:4; modified with 0.05% Triethylamine) at a flow rate of 16 mL/min. Example A79 was collected between 2.5 minutes and 3.2 minutes, while Example A80 was collected between 3.6 minutes and 4.5 minutes. 17 such injections were carried out and the pooled fractions were concentrated under reduced pressure to give the desired products Example A79 (0.015 g, 0.035 mmol) and Example A80 (0.022, 0.051 mmol) as white solids. Examples A79 and A80 were subjected to hydrochloride salt formation by following procedure:

To a solution of Example A79 (0.015 g, 0.035 mmol) in dichloromethane (3 mL) was added 4M HCl in dioxane (1 mL) drop wise over 10 minutes. The obtained white precipitate was stirred at ambient temperature for 1 hour, the volatiles were removed by evaporation, and the obtained solid was dried under vacuum to give a 4HCl salt of Example A79 (0.015 g, 0.035 mmol) as a white solid; LCMS: m/z 426.2 [M$^+$+1].

$^1$H NMR (400 MHz, DMSO): δ 1.31 (d, J=6.8 Hz, 6H), 1.72-1.77 (m, 2H), 2.05-2.18 (m, 4H), 2.28-2.39 (m, 2H), 3.10-3.19 (m, 2H), 3.61-3.86 (m, 15H, merged in residual solvent peak), 4.09-4.20 (m, 2H), 4.52-4.71 (m, 2H), 7.45 (s, 1H), 7.90 (s, 1H), 8.30 (s, 1H), 11.95 (bs, 1H), 12.25 (bs, 1H), 13.20 (bs, 1H), 15.05 (bs, 1H)

A tetrahydrochloride salt of Example A80 (0.022, 0.051 mmol) was obtained in a similar manner as Example A79; LCMS: m/z 426.2 [M$^+$+1].

$^1$H NMR (400 MHz, DMSO): δ 1.33 (d, J=6.4 Hz, 6H), 1.85-1.99 (m, 4H), 2.30-2.46 (m, 2H), 3.10-3.29 (m, 3H), 3.66-4.05 (m, 16H, merged in residual solvent peak), 3.90-4.05 (m, 2H), 4.52-4.66 (m, 2H), 7.53 (s, 1H), 7.91 (s, 1H), 8.34 (s, 1H), 10.50 (bs, 1H), 12.00 (bs, 1H), 13.22 (bs, 1H), 14.80 (bs, 1H)

Example A81

4-[[4-[4-[4-(oxetan-3-yl)piperazin-1-yl]phenyl]-1H-pyrrolo[3,2-c]pyridin-2-yl]methyl]morpholine

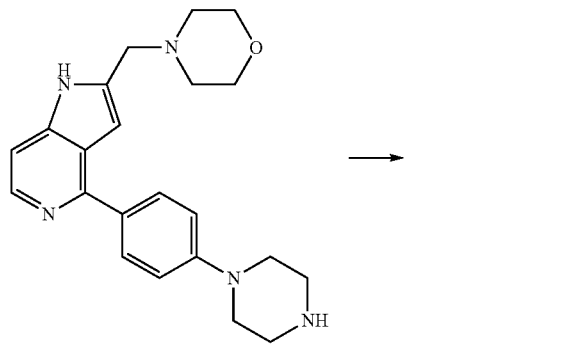

Example A42

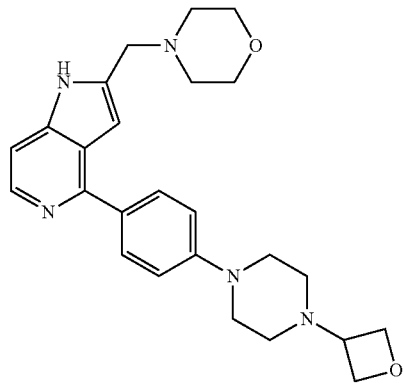

Example A81

To a solution of Example A42 (0.22 g, 0.583 mmol) and oxetan-3-one (0.21 g, 2.91 mmol) in MeOH (5 mL) were added ZnCl$_2$ (0.4 g, 2.91 mmol) and activated 4 Å powdered molecular sieves (0.4 g) at room temperature. After stirring for 2 hours at room temperature, sodium cyanoborohydride (0.183 g, 2.91 mmol) was added thereto at 0° C., and the reaction mixture was stirred for 4 hours at room temperature. The reaction mixture was filtered through a celite pad, and washed with EtOAc (25 mL), and the filtrate was taken into water (20 mL) and saturated aqueous NaHCO$_3$ solution (10 mL), and the mixture was extracted with ethyl acetate (20 mL×3). The combined organic layers were washed with brine (20 mL), dried over anhydrous Na$_2$SO$_4$ and concentrated under reduced pressure. The obtained residue was purified by preparative TLC using 10% MeOH in dichloromethane to give the desired product Example A81 (0.180 g, 71%) as an off white solid; LCMS: m/z 434.3 [M$^+$+1].

$^1$H NMR (400 MHz, CDCl$_3$): δ 2.51 (t, J=4.8 Hz, 8H), 3.37 (t, J=5.2 Hz, 4H), 3.56 (quin. 1H), 3.71-3.75 (m, 6H), 4.65-4.73 (m, 4H), 6.78 (s, 1H), 7.05 (d, J=8.8 Hz, 2H), 7.35 (d, J=6.4 Hz, 1H), 7.93 (d, J=8.8 Hz, 2H), 8.26 (d, J=6.4 Hz, 1H), 9.81 (br. s, 1H)

Example A82

[4-[4-(4-isopropylpiperazin-1-yl)phenyl]-1H-pyrrolo[3,2-c]pyridin-2-yl]-morpholino-methanone

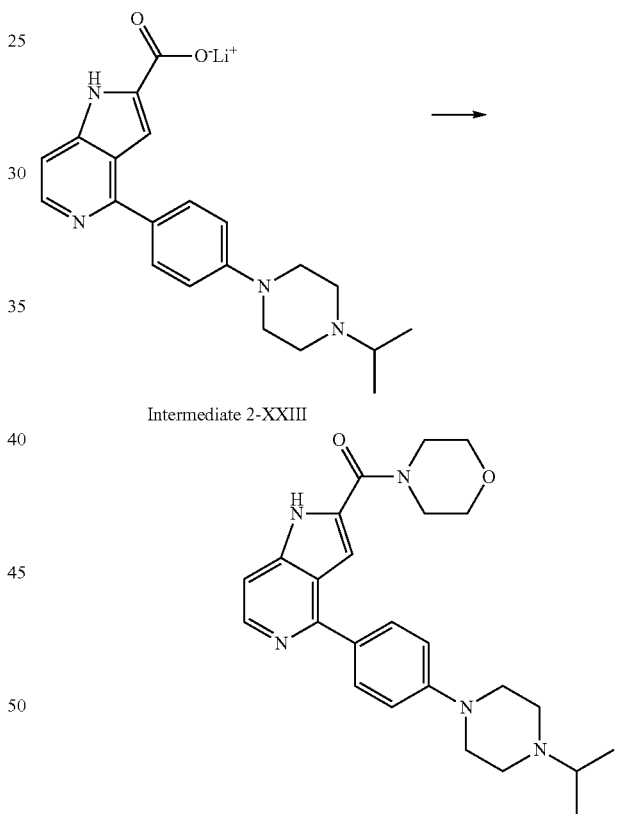

To a solution of Intermediate 2-XXIII (0.140 g, 0.385 mmol), N,N-diisopropylethylamine (0.163 mL, 0.964 mmol) and morpholine (0.083 mL, 0.964 mmol) in DMF (2 mL) were added EDC HCl (0.110 g, 0.587 mmol) followed by HOBt (0.026 g, 0.192 mmol) at room temperature. After 18 hours, the reaction mixture was diluted with EtOAc (15 mL) and water (15 mL). The organic layer was separated, and the aqueous layer was extracted with ethyl acetate (15 mL×3). The combined organic layers were washed with brine (15 mL), dried over anhydrous Na$_2$SO$_4$ and concentrated under reduced pressure. The obtained residue was purified by preparative HPLC using 10% MeOH in dichloromethane to give the desired product Example A82 (0.016 g, 9%) as a yellow solid; LCMS: m/z 434.3 [M$^+$+1].

$^1$H NMR (400 MHz, CD$_3$OD): δ 1.15 (d, J=6.4 Hz, 6H), 2.73-2.78 (m, 5H), 3.30-3.35 (m, 4H), 3.74 (d, J=4.4 Hz, 4H), 3.80-3.90 (m, 4H), 7.06 (s, 1H), 7.13 (d, J=9.2 Hz, 2H), 7.37 (d, J=8 Hz, 1H), 7.80 (d, J=8.4 Hz, 2H), 8.24 (d, J=6 Hz, 1H)

Example A83

4-[4-[2-(morpholinomethyl)-1H-pyrrolo[3,2-c]pyridin-4-yl]phenyl]morpholine

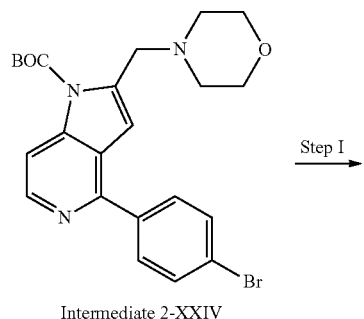

Intermediate 2-XXIV

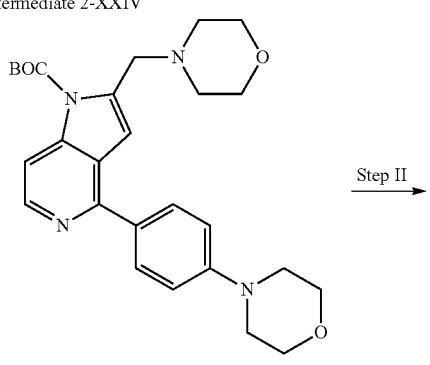

A-6

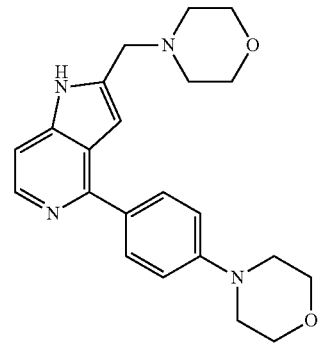

Example A83

Step I: tert-butyl 2-(morpholinomethyl)-4-(4-morpholinophenyl)pyrrolo[3,2-c]pyridine-1-carboxylate (A-6)

A solution of Intermediate 2-XXIV (0.17 g, 0.36 mmol), morpholine (0.078 g, 0.90 mmol), 2,2'-bis(diphenylphosphino)-1,1'-binaphthyl (0.013 g, 0.021 mmol) and Cs$_2$CO$_3$ (0.176 g, 0.54 mmol) in anhydrous 1,4-dioxane (2.5 mL) was degassed under a stream of argon for 15 minutes. Tris(dibenzylideneacetone)dipalladium(0) (0.07 g, 0.007 mmol) was added thereto, and degassing was continued for another 15 minutes. The reaction mixture was heated to 100° C. for 24 hours. The reaction mixture was cooled to room temperature and diluted with water (10 mL) and EtOAc (15 mL). The organic layer was separated, and the aqueous layer was back extracted with EtOAc (15 mL×2). The combined organic layers were washed with brine (15 mL) and dried over anhydrous Na$_2$SO$_4$. The obtained residue after evaporation of solvent was purified by preparative TLC (solvent system: 5% MeOH in dichloromethane) to give the desired product A-6 (0.080 g, 46%) as a white solid. LCMS: m/z 479.2 [M$^+$+1].

Step II: 4-[4-[2-(morpholinomethyl)-1H-pyrrolo[3,2-c]pyridin-4-yl]phenyl]morpholine (Example A83)

A solution of A-6 (0.08 g, 0.167 mmol) in diethyl ether (2 mL) was treated with 2 M HCl in diethyl ether (1 mL) at 0° C. After 2 hours, the reaction mixture was evaporated and pH was adjusted to ~7 using saturated aqueous NaHCO$_3$ solution. The resulting mixture was evaporated to dryness (product is water soluble). The obtained residue was taken into 20% MeOH in dichloromethane (25 mL), and the mixture was filtered. The filtrate was evaporated to give the desired product Example A83 (0.02 g, 32%) as a yellow solid; LCMS: m/z 379.3 [M$^+$+1].

$^1$HNMR (400 MHz, CDCl$_3$): δ 2.50 (t, J=4.4 Hz, 4H), 3.26 (t, J=4.8 Hz, 4H), 3.69 (s, 2H), 3.72 (t, J=4.4 Hz, 4H), 3.89 (t, J=4.8 Hz, 4H), 6.71 (s, 1H), 7.04 (d, J=9.2 Hz, 2H), 7.22 (d, J=5.6 Hz, 1H), 7.95 (d, J=8.8 Hz, 2H), 8.35 (d, J=6.0 Hz, 1H), 9.19 (bs, 1H)

Example B1

4-[2-[4-[4-(4-isopropylpiperazin-1-yl)phenyl]-1H-pyrrolo[3,2-c]pyridin-2-yl]ethyl]morpholine

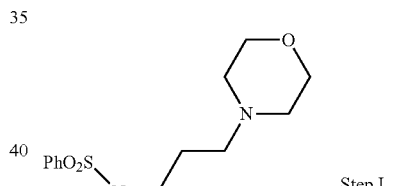

Intermediate 3-I

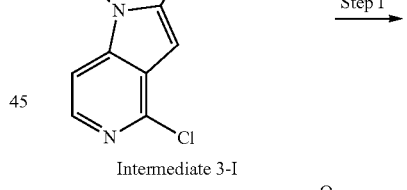

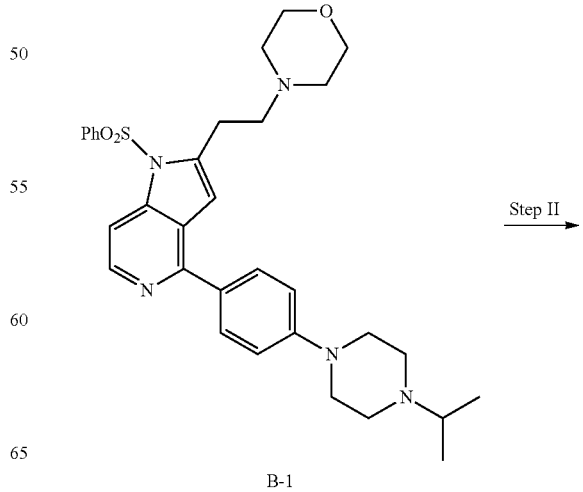

B-1

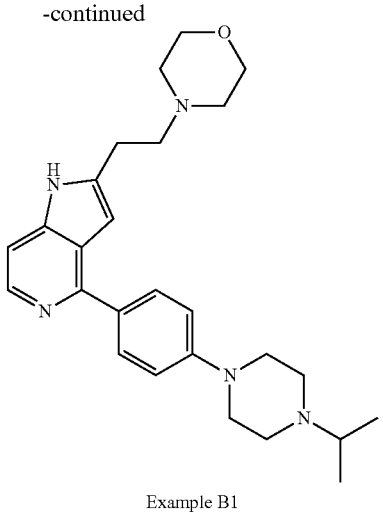

Example B1

Step I: 4-[2-[1-(benzenesulfonyl)-4-[4-(4-isopropylpiperazin-1-yl)phenyl]pyrrolo[3,2-c]pyridin-2-yl]ethyl]morpholine (B-1)

A mixture of Intermediate 3-I (0.166 g, 0.40 mmol), 1-isopropyl-4-[4-(4,4,5,5-tetramethyl-1,3,2-dioxaborolan-2-yl)phenyl]piperazine (Intermediate 1-II) (0.175 g, 0.53 mmol) and $K_2CO_3$ (0.17 g, 1.22 mmol) in dioxane/water (4:1, 5 mL) was degassed in a stream of argon for 15 minutes. To this mixture was added 1,1-bis(diphenylphosphino)ferrocene-palladium(II) dichloride dichloromethane complex (0.005 g, 0.0061 mmol), and the reaction mixture was again degassed for additional 15 minutes. After stirring at 100° C. for 18 hours, the volatiles were removed by evaporation, and the obtained crude reaction mixture was diluted with water (20 mL), followed by extraction with ethyl acetate (25 mL×3). The combined organic layers were washed with brine (25 mL), dried over anhydrous $Na_2SO_4$, concentrated in vacuo, followed by preparative TLC purification to give the desired product B-1 (0.152 g, 66%) as a brown solid; LCMS: m/z 574.2 [M$^+$+1].

Step II: 4-[2-[4-[4-(4-isopropylpiperazin-1-yl)phenyl]-1H-pyrrolo[3,2-c]pyridin-2-yl]ethyl]morpholine (Example B1)

A stirred solution of B-1 (0.15 g, 0.26 mmol) in 1,4-dioxane (5 mL) was treated with sodium tert-butoxide (0.075 g, 0.784 mmol)) under argon atmosphere. After stirring at 90° C. for 8 hours, the excess solvent was removed in vacuo. The obtained residue was dissolved in ethyl acetate (25 mL), and the solution was washed successively with water (10 mL) and brine (10 mL), dried over anhydrous $Na_2SO_4$ and concentrated in vacuo. The obtained residue (0.14 g) was purified by preparative TLC to give the desired compound Example B1 (0.076 g, 67%) as a pale yellow solid; LCMS: m/z 434.4 [M$^+$+1].

$^1$HNMR (400 MHz, CDCl$_3$): 1.13 (d, J=6.4 Hz, 6H), 2.60-2.62 (m, 4H), 2.73-2.79 (m, 7H), 2.99 (t, J=5.6 Hz, 2H), 3.34 (t, J=4.8 Hz, 4H), 3.83 (t, J=4.8 Hz, 4H), 6.57 (s, 1H), 7.04 (d, J=8.8 Hz, 2H), 7.20 (d, J=6 Hz, 1H), 7.92 (d, J=8.8 Hz, 2H), 8.31 (d, J=5.2 Hz, 1H), 10.39 (br s, 1H).

The following compounds Examples B2-B5 as shown in Table 15 were prepared from the corresponding intermediates in the same manner as Example B1.

TABLE 15

| Ex. No. | IUPAC name | Structure | Int. from which prepared | Analytical data |
|---|---|---|---|---|
| B2 | 4-[2-[4-[4-(4-methyl-piperazin-1-yl)phenyl]-1H-pyrrolo[3,2-c]pyridin-2-yl]ethyl]morpholine | 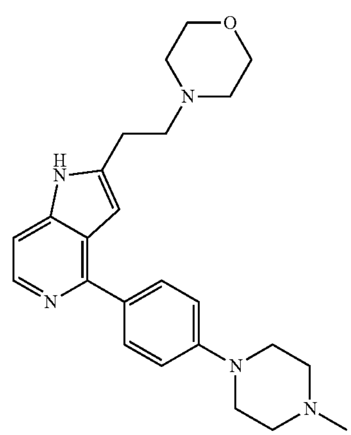 [SMILES: CN1CCN(c2ccc(-c3nccc4[nH]c(CCN5CCOCC5)cc34)cc2)CC1] | 3-I and 1-I | LCMS: m/z 406.3 [M$^+$ + 1] $^1$H NMR (400 MHz, CDCl$_3$): δ 2.37 (s, 3H), 2.60-2.63 (m, 8H), 2.75 (t, J = 6 Hz, 2H), 2.98 (t, J = 6 Hz, 2H), 3.31 (t, J = 4.4 Hz, 4H), 3.84 (t, J = 4 Hz, 4H), 6.54 (s, 1H), 7.05 (d, J = 8.8 Hz, 2H), 7.16 (d, J = 6 Hz, 1H), 7.92 (d, J = 8.8 Hz, 2H), 8.32 (d, J = 5.6 Hz, 1H), 10.9 (s, 1H) |

TABLE 15-continued

| Ex. No. | IUPAC name | Structure | Int. from which prepared | Analytical data |
|---|---|---|---|---|
| B3 | 4-[2-[4-[4-(4-isopropyl-piperazin-1-yl)phenyl]-6-methyl-1H-pyrrolo[3,2-c]pyridin-2-yl]ethyl]morpholine | 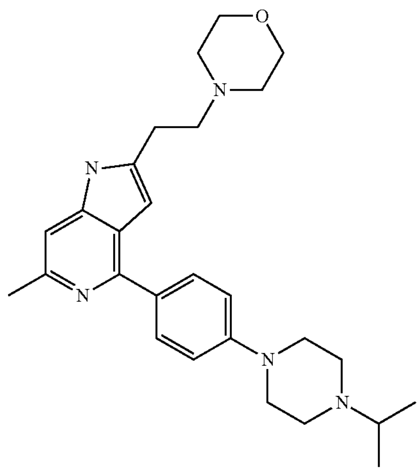 [SMILES: Cc1cc2[nH]c(CCN3CCOCC3)cc2c(-c2ccc(N3CCN(C(C)C)CC3)cc2)n1] | 3-II and 1-II | LCMS: m/z 448.3 [M$^+$ + 1] $^1$H NMR (400 MHz, CDCl$_3$): δ 1.11 (d, J = 6.3 Hz, 6H), 2.58-2.62 (m, 4H), 2.66 (s, 3H), 2.70-2.75 (m, 7H), 2.93 (t, J = 5.9 Hz, 2H), 3.29 (t, J = 4.9 Hz, 4H), 3.82 (t, J = 4.9 Hz, 4H), 6.46 (s, 1H), 7.07 (s, 1H), 7.30 (d, J = 8.8 Hz, 2H), 7.89 (d, J = 8.8 Hz, 2H), 9.82 (bs, 1H) |
| B4 | 4-[2-[6-methyl-4-[4-(4-methyl-piperazin-1-yl)phenyl]-1H-pyrrolo[3,2-c]pyridin-2-yl]ethyl]morpholine | 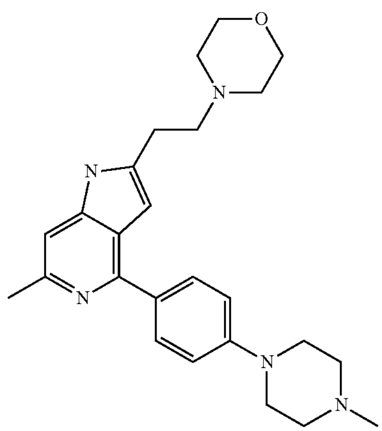 | 3-II and 1-I | LCMS: m/z 420.3 [M$^+$ + 1] $^1$HNMR (400 MHz, CDCl$_3$): δ 2.38 (s, 3H), 2.57-2.65 (m, 8H), 2.74-2.80 (m, 5H), 2.96 (t, J = 5.6 Hz, 2H), 3.30 (t, J = 4.8 Hz, 4H), 3.82 (t, J = 4.4 Hz, 4H), 6.49 (s, 1H), 7.02 (d, J = 8.8 Hz, 2H), 7.07 (s, 1H), 7.91 (d, J = 8.8 Hz, 2H), 10.40 (bs, 1H) |
| B5 | 4-[4-(4-isopropyl-piperazin-1-yl)phenyl]-6-methyl-2-[2-(1-piperidyl)ethyl]-1H-pyrrolo[3,2-c]pyridine | 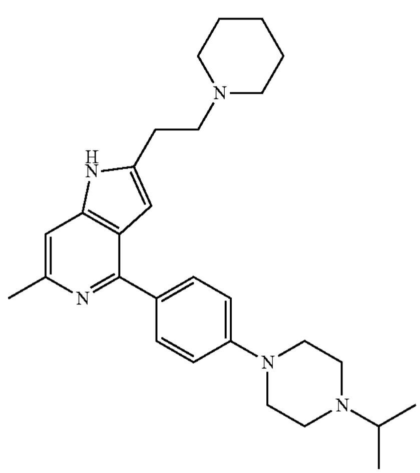 [SMILES: Cc1cc2[nH]c(CCN3CCCCC3)cc2c(-c2ccc(N3CCN(C(C)C)CC3)cc2)n1] | 3-III and 1-II | LCMS: m/z 446.3 [M$^+$ + 1] $^1$HNMR (400 MHz, CDCl$_3$): δ 1.11 (d, J = 6.4 Hz, 6H), 1.70-1.80 (m, 4H), 2.20-2.45 (m, 3H), 2.50-2.63 (m, 5H), 2.65-2.78 (m, 8H), 2.95 (t, J = 6.0 Hz, 2H), 3.29 (t, J = 4.4 Hz, 4H), 6.44 (s, 1H) 7.00-7.04 (m, 3H), 7.89 (d, J = 8.4 Hz, 2H), 10.40 (bs, 1H) |

Example B6

4-[2-[4-[4-(4-isopropylpiperazin-1-yl)phenyl]-6,7-dimethyl-1H-pyrrolo[3,2-c]pyridin-2-yl]ethyl]morpholine

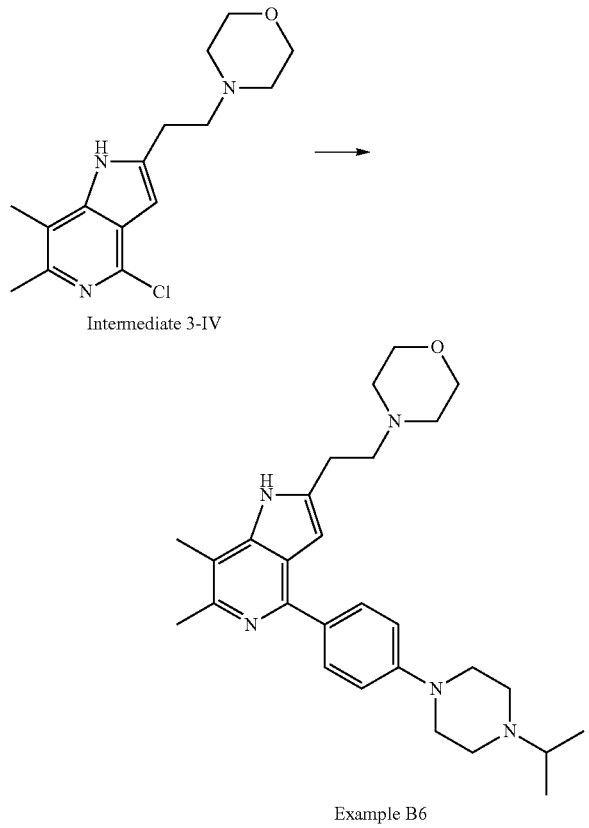

A mixture of Intermediate 3-IV (0.200 g, 0.68 mmol), Intermediate 1-II (0.337 g, 1.02 mmol) and $K_2CO_3$ (0.282 g, 2.04 mmol) in 4:1 mixture of dioxane/water (5 mL) was degassed in a stream of argon for 30 minutes. To the mixture was added $PdCl_2$(dppf) DCM (0.008 g, 0.010 mmol), and the reaction mixture was again degassed for additional 30 minutes. After stirring at 90° C. for 18 hours, the reaction mixture was diluted with water (10 mL), followed by extraction with ethyl acetate (20 mL×3). The combined organic layers were dried over anhydrous $Na_2SO_4$ and concentrated under reduced pressure. The obtained residue was purified by silica gel column chromatography using 5-10% MeOH in dichloromethane to give the desired product Example B6 (0.16 g, 51%) as a light yellow solid; LCMS: m/z 462.4 [M$^+$+1].

$^1$HNMR (400 MHz, CDCl$_3$): δ1.11 (d, J=6.4 Hz, 6H), 2.40 (s, 3H), 2.61-2.64 (m, 4H), 2.65 (s, 3H), 2.70-2.73 (m, 5H), 2.77 (t, J=6.0 Hz, 2H), 2.96 (t, J=6.0 Hz, 2H), 3.28 (t, J=4.8 Hz, 4H), 3.84 (t, J=4.4 Hz, 4H), 6.45 (s, 1H), 7.02 (d, J=8.8 Hz, 2H), 7.88 (d, J=8.8 Hz, 2H), 10.32 (bs, 1H, —NH)

The following compounds Examples B7-B10 as shown in Table 16 were prepared from their corresponding intermediates in the same manner as Example B6.

TABLE 16

| Ex. No. | IUPAC name | Structure | Int. from which prepared | Analytical Data |
|---|---|---|---|---|
| B7 | 4-[2-[6,7-dimethyl-4-[4-(4-methylpiperazin-1-yl)phenyl]-1H-pyrrolo[3,2-c]pyridin-2-yl]ethyl]morpholine | 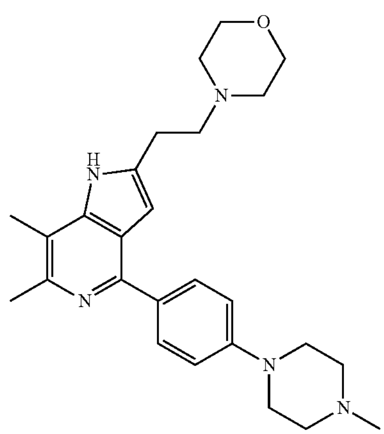 | 3-IV and 1-I | LCMS: m/z 434.4 [M$^+$ + 1] $^1$HNMR (400 MHz, CDCl$_3$): δ 2.36 (s, 3H), 2.40 (s, 3H), 2.5-2.63 (m, 8H), 2.66 (s, 3H), 2.77 (t, J = 6.0 Hz, 2H), 2.96 (t, J = 6.0 Hz, 2H), 3.28 (t, J = 4.8 Hz, 4H), 3.84 (t, J = 4.4 Hz, 4H), 6.46 (s, 1H), 7.02 (d, J = 8.8 Hz, 2H), 7.89 (d, J = 8.4 Hz, 2H), 10.30 (bs, 1H) |

TABLE 16-continued

| Ex. No. | IUPAC name | Structure | Int. from which prepared | Analytical Data |
|---|---|---|---|---|
| B8 | 4-[2-[4-[4-(4-ethylpiperazin-1-yl)phenyl]-6,7-dimethyl-1H-pyrrolo[3,2-c]pyridin-2-yl]ethyl]morpholine | 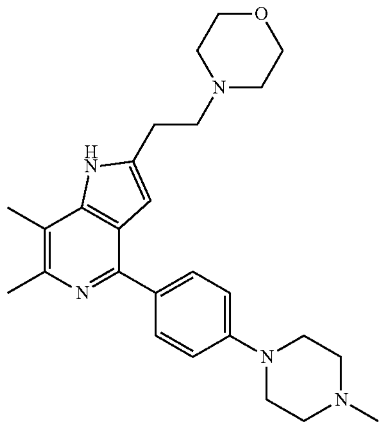 | 3-IV and 1-IV | LCMS: m/z 448.4 (M+ + 1) $^1$HNMR (400 MHz, CDCl$_3$): δ 1.14 (t, J = 7.2 Hz, 3H), 2.39 (s, 3H), 2.46-2.52 (m, 2H), 2.61-2.64 (m, 8H), 2.65 (s, 3H), 2.77 (t, J = 6.0 Hz, 2H), 2.96 (t, J = 6.0 Hz, 2H), 3.30 (t, J = 4.8 Hz, 4H), 3.84 (t, J = 4.4 Hz, 4H), 6.46 (s, 1H), 7.02 (d, J = 8.8 Hz, 2H), 7.88 (d, J = 8.8 Hz, 2H), 10.39 (bs, 1H, —NH) |
| B9 | 4-[4-(4-isopropylpiperazin-1-yl)phenyl]-6,7-dimethyl-2-[2-(1-piperidyl)ethyl]-1H-pyrrolo[3,2-c]pyridine | 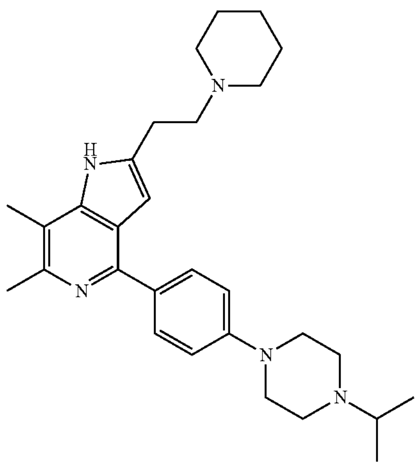 [SMILES: Cc1nc(-c2ccc(N3CCN(C(C)C)CC3)cc2)c2cc(CCN3CCCCC3)[nH]c2c1C] | 3-V and 1-II | LCMS: m/z 460.4 [M+ + 1] $^1$HNMR (400 MHz, CDCl$_3$): δ 1.10 (d, J = 6.4 Hz, 6H), 1.55-1.57 (m, 2H), 1.69-1.73 (m, 4H), 2.40 (s, 3H), 2.52-2.62 (m, 4H), 2.64 (s, 3H), 2.68-2.76 (m, 7H), 2.93 (t, J = 6.0 Hz, 2H), 3.27 (t, J = 4.8 Hz, 4H), 6.42 (s, 1H), 7.02 (d, J = 8.8 Hz, 2H), 7.88 (d, J = 8.8 Hz, 2H), 10.81 (bs, 1H, —NH). |
| B10 | 4-[4-(4-isopropylpiperazin-1-yl)phenyl]-6,7-dimethyl-2-(2-pyrrolidin-1-ylethyl)-1H-pyrrolo[3,2-c]pyridine | 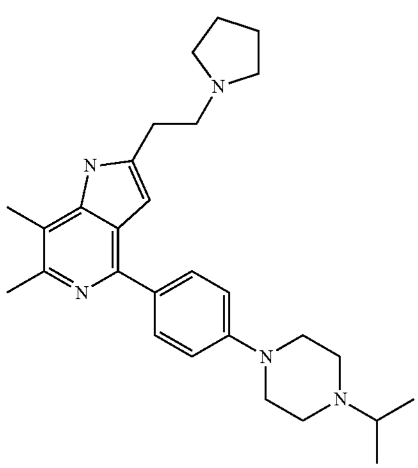 [SMILES: Cc1nc(-c2ccc(N3CCN(C(C)C)CC3)cc2)c2cc(CCN3CCCC3)[nH]c2c1C] | 3-VI and 1-II | LCMS: m/z 446.3 [M+ + 1] $^1$HNMR (400 MHz, CDCl$_3$): δ 1.10 (d, J = 6.4 Hz, 6H), 1.89-1.91 (m, 4H), 2.36 (s, 3H), 2.64 (s, 3H), 2.68-2.76 (m, 9H), 2.88 (t, J = 6.4 Hz, 2H), 2.97 (t, J = 6.4 Hz, 2H), 3.28 (t, J = 4.4 Hz, 4H), 6.44 (s, 1H), 7.02 (d, J = 8.8 Hz, 2H), 7.88 (d, J = 8.8 Hz, 2H), 10.42 (bs, 1H, —NH) |

Example B11

4-[2-[4-[4-(4-isopropylpiperazin-1-yl)phenyl]-1,6-dimethyl-pyrrolo[3,2-c]pyridin-2-yl]ethyl]morpholine

Example B12 tert-butyl 4-[4-[1,6-dimethyl-2-(2-morpholinoethyl)pyrrolo[3,2-c]pyridin-4-yl]-2-fluoro-phenyl]piperazine-1-carboxylate

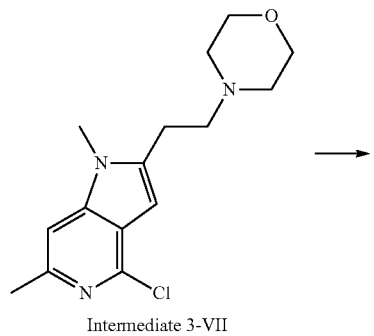

Intermediate 3-VII

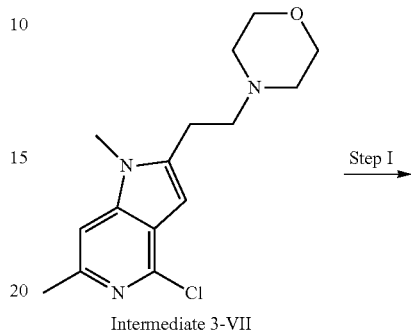

Intermediate 3-VII

Step I

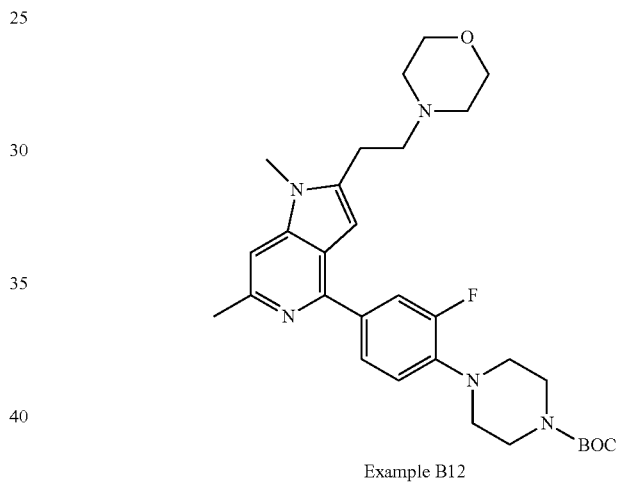

Example B11

Example B12

A mixture of Intermediate 3-VII (11.2 g, 38.12 mmol), Intermediate 1-II (15.09 g, 45.74 mmol) and $K_2CO_3$ (15.7 g, 114.36 mmol) in 4:1 mixture of dioxane/water (100 mL) was degassed in a stream of argon for 30 minutes. To the mixture was added tetrakis(triphenylphosphine)palladium(0) (4.4 g, 3.82 mmol), and the reaction mixture was again degassed for additional 30 minutes. After stirring at 95° C. for 18 hours, the volatiles were removed by evaporation, and the obtained residue was diluted with water (150 mL), followed by extraction with ethyl acetate (250 mL×3). The combined organic layers were washed with brine (100 mL), dried over anhydrous $Na_2SO_4$ and concentrated under reduced pressure. The obtained residue was purified by silica gel column chromatography using 3% MeOH in dichloromethane to give the desired product Example B11 (14.4 g, 70%) as a light brown solid; LCMS: m/z 462.3 [M$^+$+1].

$^1$HNMR (400 MHz, CDCl$_3$): δ 1.14 (d, J=6.4 Hz, 6H), 2.55 (t, J=4.4 Hz, 4H), 2.71-2.85 (m, 10H), 2.95 (t, J=7.2 Hz, 2H), 3.33-3.40 (m, 4H), 3.68 (s, 3H), 3.75 (t, J=4.4 Hz, 4H), 6.52 (s, 1H) 6.95 (s, 1H), 7.05 (d, J=8.8 Hz, 2H), 7.90 (d, J=8.8 Hz, 2H)

A mixture of Intermediate 3-VII (0.2 g, 0.682 mmol), Intermediate 1-XX (0.387 g, 0.954 mmol) and $K_2CO_3$ (0.282 g, 2.046 mmol) in 4:1 mixture of dioxane/water (5 mL) was degassed in a stream of argon for 30 minutes. To this mixture was added tetrakis(triphenylphosphine)palladium (0.079 g, 0.0682 mmol), and the reaction mixture was again degassed for additional 15 minutes. After stirring at 95° C. for 16 hours, the volatiles were removed by evaporation, and the obtained residue was diluted with water (15 mL), followed by extraction with ethyl acetate (25 mL×3). The combined organic layers were washed with brine (25 mL), dried over anhydrous $Na_2SO_4$ and concentrated under reduced pressure. The obtained residue was purified by Combiflash using 4% MeOH in dichloromethane to give the desired product Example B12 (0.201 g, 55%) as a light brown solid; LCMS: m/z 169.2 (M$^+$/2-BOC+1).

$^1$HNMR (400 MHz, DMSO): δ 1.43 (s, 9H), 2.44-2.54 (m, 4H), 2.55 (s, 3H), 2.65 (t, J=7.6 Hz, 2H), 2.94 (t, J=7.6 Hz, 2H), 3.03 (t, J=4.8 Hz, 4H), 3.50-3.51 (m, 4H), 3.59 (t, J=4.4 Hz, 4H), 3.69 (s, 3H), 6.56 (s, 1H), 7.16 (app. t, J=8.8 Hz, 1H), 7.24 (s, 1H), 7.72 (dd, J=2 Hz, J=14 Hz, 1H), 7.77 (dd, J=1.6 Hz, J=10.4 Hz, 1H)

Example B13

4-[2-[4-(3-fluoro-4-(piperazin-1-yl)-phenyl)-1,6-dimethyl-pyrrolo[3,2-c]pyridin-2-yl]ethyl]morpholine

Example B14

4-[2-[4-[3-fluoro-4-(4-isopropylpiperazin-1-yl)phenyl]-1,6-dimethyl-pyrrolo[3,2-c]pyridin-2-yl]ethyl]morpholine

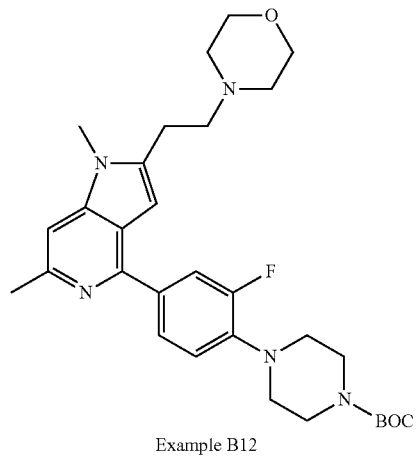

Example B12

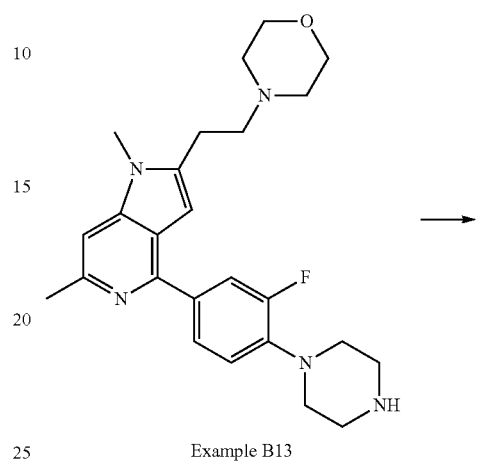

Example B13

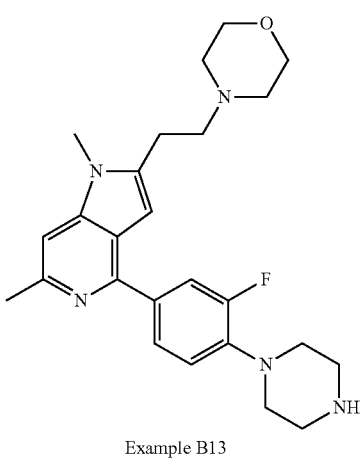

Example B13

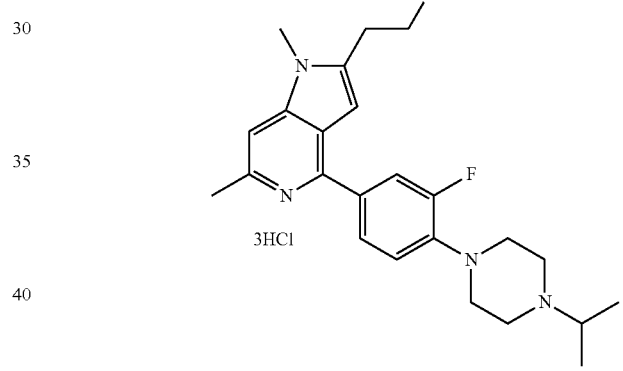

Example B14

To a solution of Example B12 (0.200 g, 0.372 mmol) in 1,4-dioxane (2 mL) at 0° C. was added 4M HCl in 1,4-dioxane (4 mL). After stirring at room temperature for 16 hours, the volatiles were removed by evaporation, and the obtained residue was diluted with water (2 mL) and pH was adjusted to ~8 using saturated aqueous NaHCO$_3$ solution (10 mL). The resulting solution was evaporated to dryness, and the obtained residue was diluted with 5% MeOH in dichloromethane (20 mL) and inorganic substance was removed by filtration. The filtrate was concentrated to give the desired product Example B13 (0.158 g, 97%) as a white solid. The obtained crude product was used for next step without purification; LCMS: m/z 219.6 (M$^+$/2+1).

To a solution of Example B13 (0.158 g, 0.363 mmol) in a mixture of MeOH:DCE (1:1, 4 mL) were added acetone (0.251 g, 4.33 mmol), a drop of acetic acid and activated 4 Å powdered molecular sieves (0.4 g) successively. After stirring for 4 hours at room temperature, sodium cyanoborohydride (0.034 g, 0.542 mmol) was added thereto, and the mixture was stirred for 16 hours. The reaction mixture was filtered through a celite pad, and washed with EtOAc (25 mL), and the filtrate was taken into water (20 mL), and the mixture was extracted with ethyl acetate (20 mL×3). The combined organic layers were washed with brine (25 mL), dried over anhydrous Na$_2$SO$_4$ and concentrated under reduced pressure. The obtained residue was purified by preparative TLC using 10% MeOH in dichloromethane to give the desired product Example B14 (0.14 g, 80%) as a pale yellow liquid. To the solution of Example B14 (0.07 g, 0.146 mmol) in dioxane (0.5 mL) was added 4M HCl in dioxane (1 mL) at 0° C. After stirring for 2 hours at room temperature, the volatiles were removed by evaporation, and the obtained solid was dried under vacuum to give a 3HCl salt of Example B14 (0.055 g, 63%) as a yellow solid; LCMS: m/z 480.2 [M$^+$+1].

¹HNMR (400 MHz, DMSO): δ 1.35 (d, J=6.4 Hz, 6H), 2.79 (s, 3H), 3.12-3.26 (m, 4H), 3.42-3.46 (m, 4H), 3.49-3.56 (m, signal merged in DMSO, 7H), 3.70 (d, J=12 Hz, 2H), 3.85 (t, J=12 Hz, 2H), 3.91 (s, 3H), 4.00 (d, J=12 Hz, 2H), 6.90 (s, 1H), 7.40 (app. t, J=8.8 Hz, 1H), 7.74 (d, J=8.4 Hz, 1H), 7.83 (dd, J=1.6 Hz, J=13.2 Hz, 1H), 7.96 (s, 1H), 11.20 (s, 1H), 12.00 (s, 1H), 14.30 (s, 1H)

The following compounds Examples B15-B23 as shown in Table 17 were prepared from their corresponding intermediates in the same manner as in the preparation of Example B14 from Intermediate 3-VII.

TABLE 17

| Ex. No. | IUPAC name | Structure | Int. from which prepared | Analytical Data |
|---|---|---|---|---|
| B15 | 4-[2-[4-[4-(4-isopropylpiperazin-1-yl)-2-methylphenyl]-1,6-dimethylpyrrolo[3,2-c]pyridin-2-yl]ethyl]morpholine | 3HCl | 3-VII and 1-XXIV | LCMS: m/z 476.20 [M⁺ + 1] ¹HNMR (400 MHz, DMSO): δ 1.37 (d, J = 4 Hz, 6H), 2.18 (s, 3H), 2.76 (s, 3H), 3.11 (m, 4H), 3.35-3.38 (m, 4H), 3.49-3.56 (m, 7H), 3.81-3.88 (m, 2H), 3.90 (s, 3H) 3.98-4.02 (m, 4H), 6.49 (s, 1H), 7.08 (d, J = 8.8 Hz, 1H), 7.13 (s, 1H), 7.39 (d, J = 8.8 Hz, 1H), 7.96 (s, 1H), 11.23 (bs, 1H), 11.97 (bs, 1H), 14.23 (bs, 1H) |
| B16 | 4-[2-[4-[4-(4-isopropylpiperazin-1-yl)-3-methylphenyl]-1,6-dimethylpyrrolo[3,2-c]pyridin-2-yl]ethyl]morpholine | 3HCl | 3-VII and 1-XXI | LCMS: m/z 476.20 [M⁺ + 1] ¹HNMR (400 MHz, DMSO): δ 1.37 (d, J = 4 Hz, 6H), 2.42 (s, 3H), 2.78 (s, 3H), 3.10-3.14 (m, 3H), 3.23-3.24 (m, 2H), 3.32-3.38 (m, 4H), 3.45-3.47 (m, 2H), 3.50-3.56 (m, 6H), 3.82-3.88 (m, 2H)), 3.91 (s, 3H), 3.99-4.02 (m, 2H), 6.87 (s, 1H), 7.33 (d, J = 8 Hz, 1H), 7.75 (d, J = 8 Hz, 2H), 7.94 (s, 1H), 11.12 (bs, 1H), 11.98 (bs, 1H), 14.23 (bs, 1H) |

| Ex. No. | IUPAC name | Structure | Int. from which prepared | Analytical Data |
|---|---|---|---|---|
| B17 | 4-[2-[4-[4-(4-isopropylpiperazin-1-yl)-2-(trifluoromethyl)phenyl]-1,6-dimethyl-pyrrolo[3,2-c]pyridin-2-yl]ethyl]morpholine | (structure, 3HCl) | 3-VII and 1-XXV | LCMS: m/z 530.2 [M$^+$ + 1] $^1$HNMR (400 MHz, DMSO): δ 1.35 (d, J = 4 Hz, 6H), 2.75 (s, 3H), 3.03-3.22 (m, 5H), 3.38-3.56 (m, 12H), 3.83-3.86 (m, 2H), 3.91 (s, 3H), 3.96-3.98 (m, 2H), 6.41 (s, 1H), 7.49 (d, J = 8 Hz, 1H), 7.54 (s, 1H), 7.59 (d, J = 8.8 Hz, 1H), 8.04 (s, 1H), 11.44 (br.s, 1H), 11.86 (br.s, 1H), 14.85 (br.s, 1H) |
| B18 | 4-[2-[4-[4-(4-isopropylpiperazin-1-yl)-3-(trifluoromethyl)phenyl]-1,6-dimethyl-pyrrolo[3,2-c]pyridin-2-yl]ethyl]morpholine | (structure, 3HCl) | 3-VII and 1-XXII | LCMS: m/z 530.2 [M$^+$ + 1] $^1$HNMR (400 MHz, DMSO): δ 1.37 (d, J = 4 Hz, 6H), 2.81 (s, 3H), 3.09-3.16 (m, 4H), 3.23-3.26 (m, 3H), 3.54-3.611 (m, 9H), 3.68-3.70 (m, 2H), 3.86-3.93 (m, 4H), 3.99-4.02 (m, 2H), 6.86 (s, 1H), 7.79 (d, J = 8 Hz, 1H), 8.01 (s, 1H), 8.24 (d, J = 8 Hz, 2H), 11.21 br.s, 1H), 11.90 (br.s, 1H), 14.60 (br.s, 1H) |

TABLE 17-continued

| Ex. No. | IUPAC name | Structure | Int. from which prepared | Analytical Data |
|---|---|---|---|---|
| B19 | 4-[2-[4-[2-fluoro-4-(4-isopropylpiperazin-1-yl)phenyl]-1,6-dimethyl-pyrrolo[3,2-c]pyridin-2-yl]ethyl]morpholine | 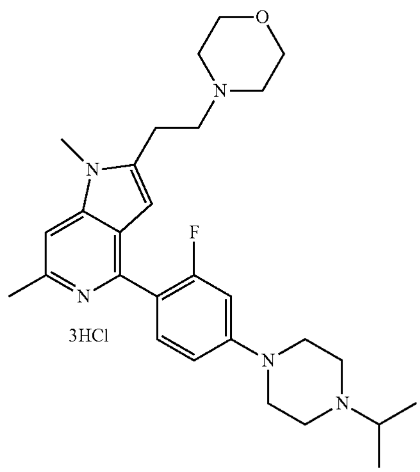 [SMILES: Cc1cc2c(cc(CCN3CCOCC3)n2C)c(-c2ccc(N3CCN(C(C)C)CC3)cc2F)n1] | 3-VII and 1-XXVII | LCMS: m/z 480.2 [M$^+$ + 1] $^1$HNMR (400 MHz, DMSO): δ 1.34 (d, J = 8.0 Hz, 6H), 2.75 (s, 3H), 3.12-3.20 (m, 4H), 3.45-3.54 (m, 11H), 3.81-3.90 (m, 2H), 3.88 (s, 3H), 4.00 (d, J = 12.0 Hz, 2H), 4.09 (d, J = 12.0 Hz, 2H), 4.09 (d, J = 12.0 Hz, 2H), 6.64 (s, 1H), 7.10 (d, J = 8.8 Hz, 1H), 7.15-7.19 (d, J = 14.8 Hz, 1H), 7.65 (app. t, J = 8.8 Hz, 1H), 7.95 (s, 1H), 11.10 (br.s, 1H), 12.71 (br. s, 1H), 14.45 (br. s, 1H) |
| B20 | 4-[2-[4-[4-(4-isopropylpiperazin-1-yl)-2-methoxy-phenyl]-1,6-dimethyl-pyrrolo[3,2-c]pyridin-2-yl]ethyl]morpholine | 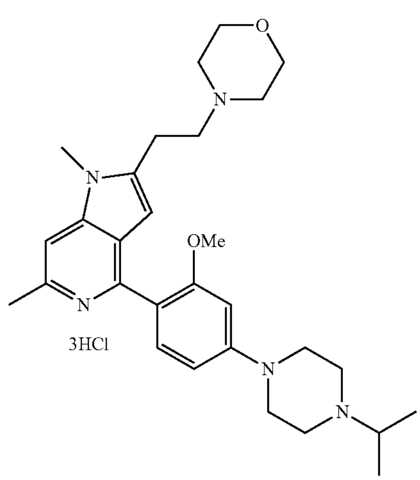 [SMILES: COc1cc(N2CCN(C(C)C)CC2)ccc1-c1nc(C)cc2c1cc(CCN1CCOCC1)n2C] | 3-VII and 1-XXVI | LCMS: m/z 492.2 [M$^+$ + 1] $^1$HNMR (400 MHz, DMSO): δ 1.34 (d, J = 8.0 Hz, 6H), 2.73 (s, 3H), 3.12-3.21 (m, 4H), 3.45-3.50 (m, 11H), 3.86-3.95 (m, 8H), 3.99 (d, J = 12.0 Hz, 2H), 4.10 (d, J = 12.0 Hz, 2H), 6.58 (s, 1H), 6.82-6.88 (m, 2H), 7.46 (d, J = 12 Hz, 1H), 7.88 (s, 1H), 11.42 (br. s, 1H), 11.95 (br.s, 1H), 14.1 (br.s, 1H) |

TABLE 17-continued

| Ex. No. | IUPAC name | Structure | Int. from which prepared | Analytical Data |
|---|---|---|---|---|
| B21 | 4-[2-[4-[3-(4-isopropylpiperazin-1-yl)phenyl]-1,6-dimethylpyrrolo[3,2-c]pyridin-2-yl]ethyl]morpholine | (3HCl) | 3-VII and 1-VII | LCMS: m/z 462.2 [M$^+$ + 1] $^1$HNMR (400 MHz, DMSO): δ 1.34 (d, J = 7.2 Hz, 6H), 2.81 (s, 3H), 3.09-3.19 (m, 5H), 3.34-3.69 (m, 10H), 3.82-3.88 (t, J = 2.4 Hz, 2H), 3.92 (s, 3H), 3.97-4.08 (m, 4H), 6.84 (s, 1H), 7.33-7.38 (m, 2H), 7.45-7.46 (m, 1H), 7.56-7.60 (app. t, J = 8.4 Hz, 1H), 7.98 (s, 1H), 11.02 (br.s, 1H), 11.81 (br.s, 1H), 14.45 (br.s, 1H) |
| B22 | 4-[2-[4-[4-(4-isopropylpiperazin-1-yl)-3-methoxyphenyl]-1,6-dimethylpyrrolo[3,2-c]pyridin-2-yl]ethyl]morpholine | 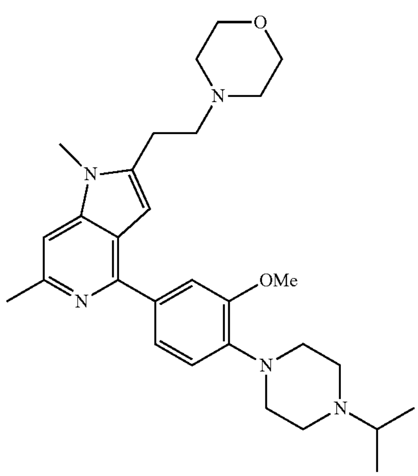 [SMILES: COc1cc(-c2nc(C)cc3c2cc(CCN2CCOCC2)n3C)ccc1N1CCN(C(C)C)CC1] | 3-VII and 1-XXIII | LCMS: m/z 492.2 [M$^+$ + 1] $^1$HNMR (400 MHz, CDCl$_3$): δ 1.13 (d, J = 6.4 Hz, 6H), 2.54-2.56 (m, 4H), 2.71 (s, 3H), 2.72-2.75 (m, 2H), 2.76-2.80 (m, 5H), 2.96 (t, J = 7.2 Hz, 2H), 3.19-3.21 (m, 4H), 3.68 (s, 3H), 3.75 (t, J = 4.4 Hz, 4H), 3.97 (s, 3H), 6.52 (s, 1H), 6.98 (s, 1H), 7.05 (d, J = 8.8 Hz, 1H), 7.47-7.51 (m, 2H) |

TABLE 17-continued

| Ex. No. | IUPAC name | Structure | Int. from which prepared | Analytical Data |
|---|---|---|---|---|
| B23 | 4-[2-[4-[4-[(3S)-4-isopropyl-3-methyl-piperazin-1-yl]phenyl]-1,6-dimethyl-pyrrolo[3,2-c]pyridin-2-yl]ethyl]morpholine | 3HCl | 3-VII and 1-XXIX | LCMS: m/z 476.2 [M$^+$ + 1] $^1$HNMR (400 MHz, DMSO): δ 1.18 (d, J = 7 Hz, 3H), 1.35-1.48 (m, 1H), 1.43 (d, 7 Hz, 6H), 2.78 (s, 3H), 3.00-3.20 (m, 3H), 3.25-3.35 (m, 2H), 3.45-3.60 (m, 6H), 3.65-3.75 (m, 1H), 3.80-3.95 (m, 6H), 3.95-4.05 (m, 2H), 4.09 (t, J = 11.8 Hz, 2H), 6.87 (s, 1H), 7.31 (d, J = 8.6 Hz, 2H), 7.85 (d, J = 8.6 Hz, 2H), 7.88 (s, 1H), 11.30 (s, 1H), 11.90 (s, 1H), 14.10 (s, 1H) |

Example B24

4-[2-[4-[4-(4-isopropylpiperazin-1-yl)cyclohexen-1-yl]-1,6-dimethyl-pyrrolo[3,2-c]pyridin-2-yl]ethyl]morpholine

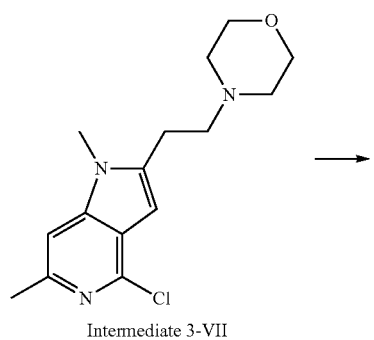

Intermediate 3-VII

→

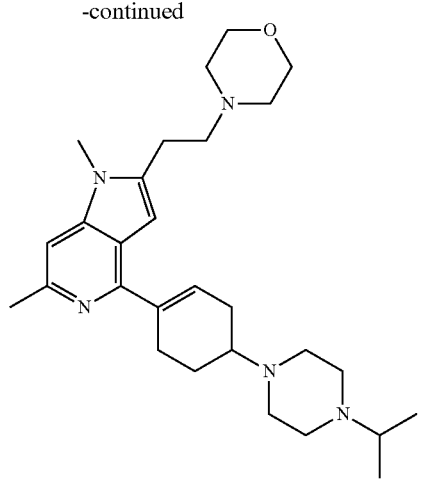

Example B24

A stirred solution of Intermediate 3-VII (0.15 g, 0.51 mmol), Intermediate 1-XXVIII (0.34 g, 1.02 mmol) and K$_2$CO$_3$ (0.21 g, 1.53 mmol) in a mixture of dioxane/water (4:1, 5 mL) was degassed in a stream of argon for 15 minutes. To this mixture was added Pd(PPh$_3$)$_4$ (0.06 g, 0.05 mmol), and the reaction mixture was again degassed for additional 15 minutes. After stirring at 100° C. for 18 hours, the volatiles were removed by evaporation, and the obtained residue was diluted with water (20 mL), followed by extraction with ethyl acetate (25 mL×3). The combined organic layers were washed with brine (25 mL), dried over anhydrous Na$_2$SO$_4$ and concentrated under reduced pressure. The obtained residue was purified by preparative TLC to give the desired product Example B24 (0.12 g, 50%) as a yellow solid; LCMS: m/z 233.7 [M$^+$/2+1].

$^1$H NMR (400 MHz, CDCl$_3$): δ 1.09 (d, J=6.4 Hz, 6H), 2.12-2.21 (m, 1H), 2.26-2.38 (m, 1H), 2.45-2.49 (m, 2H), 2.56 (t, J=4.4 Hz, 4H), 2.62 (s, 3H), 2.62-2.68 (m, 4H), 2.70-2.74 (m, 9H), 2.93 (t, J=7.2 Hz, 3H), 3.63 (s, 3H), 3.75 (t, J=4.8 Hz, 4H), 6.32 (t, J=2.8 Hz, 1H), 6.37 (s, 1H), 6.88 (s, 1H).

Example B25

4-[2-[4-[4-(4-isopropylpiperazin-1-yl)cyclohexyl]-1,6-dimethyl-pyrrolo[3,2-c]pyridin-2-yl]ethyl]morpholine

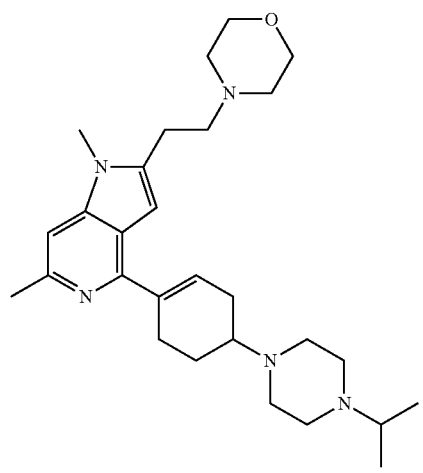

Example B24

Example B25

To a stirred solution of Example B24 (0.12 g, 0.25 mmol) in EtOAc (3 mL) was added Pd/C (0.024 g, 20% W/W). The flask was evacuated and filled with hydrogen gas (this procedure was repeated twice). The reaction mixture was then stirred for 18 hours under hydrogen atmosphere. After completion of reaction, the reaction mixture was filtered through a celite pad. The obtained filtrate was concentrated under reduced pressure to give the desired product Example B25 (0.08 g, 66%) as a yellow oil; LCMS: m/z 234.7 [M$^+$/2+1].

Example B26 and Example B27

Cis and trans-4-[2-[4-[4-(4-isopropylpiperazin-1-yl)cyclohexyl]-1,6-dimethyl-pyrrolo[3,2-c]pyridin-2-yl]ethyl]morpholine

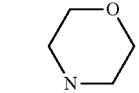

Example B25

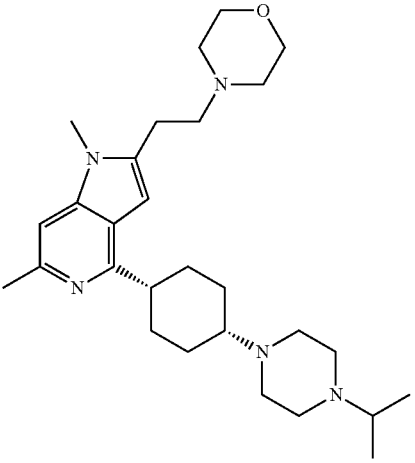

Example B26

+

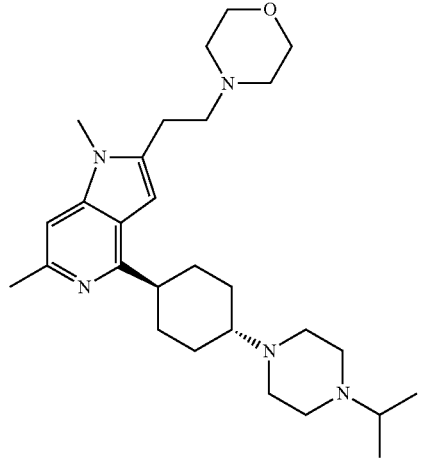

Example B27

Example B25 (0.08 g, 0.17 mmol) was dissolved in a mixture of methanol:dichloromethane (9:1, 2 mL). 83 μL of this solution was loaded onto a 150×21.2 mm 5μ phenomenex Gem column and eluted with a mobile phase comprising of acetonitrile:water (6:4; modified with 0.05% Triethylamine) at a flow rate of 16 mL/min. Example B26 was collected between 3.0 minute and 4.0 minute time points, while Example B27 was collected between 4.3 minute and 5.6 minute time points. 24 such injections were carried out and the pooled fractions were concentrated under reduced pressure to give the desired products Example B26 (0.03 g, 0.064 mmol) and Example B27 (0.05, 0.10 mmol). Examples B26 and B27 were subjected to hydrochloride salt formation by following procedure:

To a solution of Example B26 (0.03 g, 0.064 mmol) in dichloromethane (3 mL) was added 4M HCl in dioxane (1 mL) drop wise over 10 minutes. The resulting white precipitate was stirred at ambient temperature for 1 hour. The volatiles were removed by evaporation, and the solid obtained was dried under vacuum to give a 4HCl salt of Example B26 (0.030 g, 0.064 mmol) as a white solid; LCMS: m/z 468.3 [M$^+$+1].

$^1$H NMR (400 MHz, DMSO-d6): δ 1.31 (d, J=6.4 Hz, 6H), 1.68-1.82 (m, 2H), 2.01-2.09 (m, 2H), 2.15-2.28 (m, 2H), 2.30-2.39 (m, 2H), 2.74 (s, 3H), 3.13-3.22 (m, 2H), 3.40-3.49 (m, 3H), 3.52-3.62 (m, 8H), 3.70-3.73 (m, 5H, merged in residual solvent peak), 3.85 (s, 3H), 3.87-3.90 (m, 3H), 4.00-4.05 (m, 2H), 7.11 (s, 1H), 7.84 (s, 1H), 11.90 (bs, 1H), 12.02 (bs, 1H), 12.38 (bs, 1H), 14.42 (bs, 1H)

A tetrahydrochloride salt of Example B27 (0.050, 0.10 mmol) was prepared in a similar manner as Example B26; LCMS: m/z 468.3 [M$^+$+1].

$^1$HNMR (400 MHz, DMSO-d6): δ 1.34 (d, J=6.4 Hz, 6H), 1.78-1.90 (m, 4H), 2.41-2.49 (m, 3H), 2.79 (s, 3H), 3.12-3.25 (m, 2H), 3.40-3.45 (m, 2H), 3.52-3.62 (m, 12H, merged in solvent residual peak), 3.86 (s, 3H), 3.89-3.99 (m, 4H), 4.01-4.05 (m, 2H), 4.12-4.18 (m, 2H), 7.20 (s, 1H), 7.85 (s, 1H), 10.42 (bs, 1H), 11.88 (bs, 1H), 12.00 (bs, 1H), 14.20 (bs, 1H)

Example B28 tert-butyl 4-[4-[1,6-dimethyl-2-(2-morpholinoethyl)pyrrolo[3,2-c]pyridin-4-yl]phenyl]-3,6-dihydro-2H-pyridine-1-carboxylate

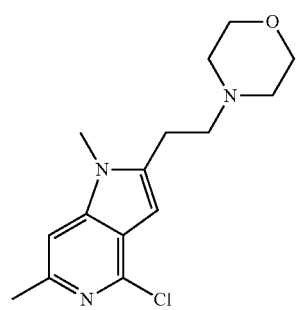

Intermediate 3-VII

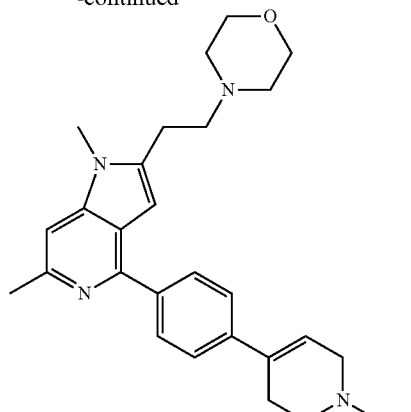

Example B28

A mixture of Intermediate 3-VII (0.15 g, 0.511 mmol), Intermediate 1-VIII (0.236 g, 0.614 mmol) and K$_2$CO$_3$ (0.211 g, 1.53 mmol) in 4:1 mixture of dioxane/water (4 mL) was degassed in a stream of argon for 30 minutes. To this mixture was added tetrakis(triphenylphosphine)palladium (0) (0.059 g, 0.0511 mmol) and the reaction mixture was again degassed for additional 15 minutes. After stirring at 95° C. for 16 hours, the volatiles were removed by evaporation, and the obtained residue was diluted with water (15 mL), followed by extraction with ethyl acetate (25 mL×3). The combined organic layers were washed with brine (25 mL), dried over anhydrous Na$_2$SO$_4$ and concentrated under reduced pressure. The obtained residue was purified by Combiflash using 4% MeOH in dichloromethane as eluent to give the desired product Example B28 (0.19 g, 72%) as a brown solid.

Example B29

4-[2-[1,6-dimethyl-4-[4-(1,2,3,6-tetrahydropyridin-4-yl)phenyl]pyrrolo[3,2-c]pyridin-2-yl]ethyl]morpholine

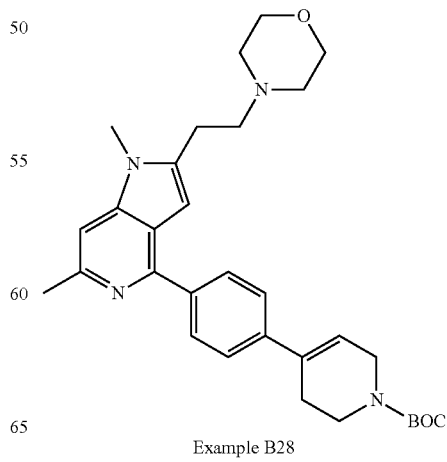

Example B28

Example B29

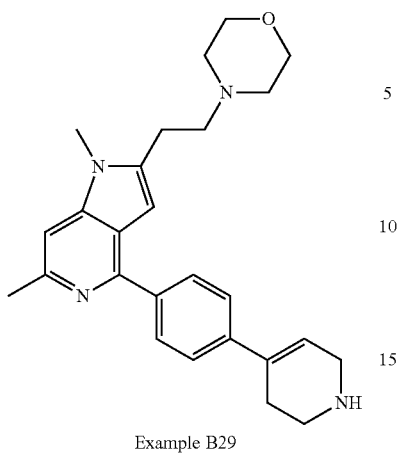

Example B30

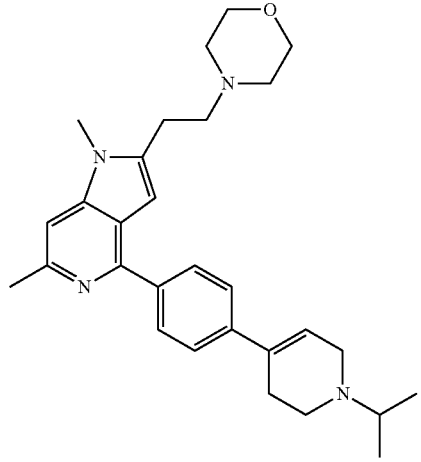

To a solution of Example B28 (0.19 g, 0.368 mmol) in 1,4-dioxane (2 mL) at 0° C. was added 4M HCl in 1,4-dioxane (3 mL). After stirring at room temperature for 16 hours, the volatiles were removed by evaporation, and the obtained residue was diluted with water (2 mL) and pH was adjusted to ~8 using saturated aqueous NaHCO$_3$ solution (10 mL). The resulting solution was evaporated to dryness, and the obtained residue was diluted with 5% MeOH in dichloromethane (20 mL) and inorganic substance was removed by filtration. The filtrate was concentrated to give the desired product Example B29 (0.13 g, 85%) as an off white solid. The obtained crude product was used for next step without purification; LCMS: m/z 417.3 (M$^+$+1).

Example B30

4-[2-[4-[4-(1-isopropyl-3,6-dihydro-2H-pyridin-4-yl)phenyl]-1,6-dimethyl-pyrrolo[3,2-c]pyridin-2-yl]ethyl]morpholine To a solution of Example B29 (0.13 g, 0.310 mmol) in a mixture of MeOH:DCE (1:1, 4 mL) were added acetone (0.904 g, 1.50 mmol), a drop of acetic acid and activated 4 Å powdered molecular sieves (0.25 g) successively. After stirring for 4 hours at room temperature, sodium cyanoborohydride (0.096 g, 1.50 mmol) was added thereto, and the mixture was stirred for 16 hours. The reaction mixture was filtered through a celite pad, and washed with EtOAc (20 mL), and the filtrate was taken into water (20 mL), and the mixture was extracted with ethyl acetate (20 mL×3). The combined organic layers were washed with brine (20 mL), dried over anhydrous Na$_2$SO$_4$ and concentrated under reduced pressure. The obtained residue was purified by preparative TLC using 3% MeOH in dichloromethane as eluent to give the desired product Example B30 (0.07 g, 48%) as a white solid; LCMS: m/z 230.2 [M$^+$/2+1].

Example B31

4-[2-[4-[4-(1-isopropyl-4-piperidyl)phenyl]-1,6-dimethyl-pyrrolo[3,2-c]pyridin-2-yl]ethyl]morpholine

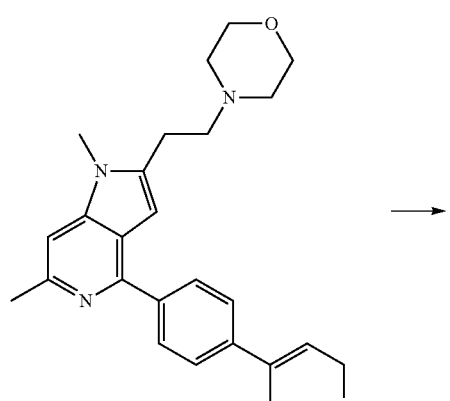

Example B29

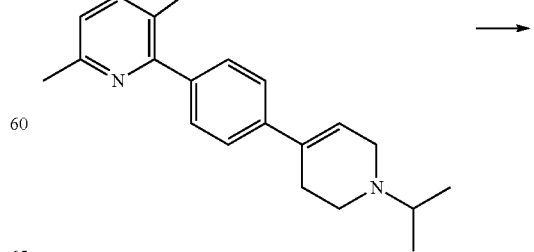

Example B30

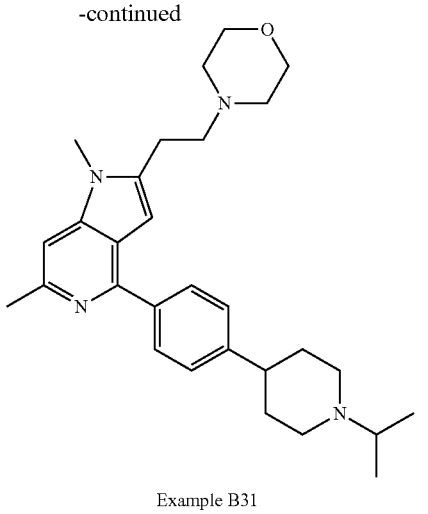

Example B31

To a stirred solution of Example B30 (0.07 g, 0.15 mmol) in EtOAc (3 mL) was added Pd/C (0.02 g, 20% W/W). The flask was evacuated and filled with hydrogen gas (this procedure was repeated twice). The reaction mixture was then stirred for 18 hours under hydrogen atmosphere. After completion of reaction, the reaction mixture was filtered through a celite pad. The obtained residue after the evaporation of filtrate was purified using preparative TLC (mobile phase 10% MeOH:DCM) to give the desired product Example B31 (0.04 g) as a white solid.

To a solution of Example B31 (0.04 g, 0.146 mmol) in dioxane (0.5 mL) was added 4M HCl in dioxane (3 mL) at 0° C. After stirring for 2 hours at room temperature, the volatiles were removed by evaporation, and the obtained solid was dried under vacuum to give a 3HCl salt of Example B31 (0.05 g, 57%) as an off white solid; LCMS: m/z 461.2 [M+1].

$^{1}$HNMR (400 MHz, DMSO): δ 1.33 (d, J=6.4 Hz, 6H), 2.03 (d, J=12.4 Hz, 2H), 2.30-2.41 (m, 3H), 2.79 (s, 3H), 3.01-3.20 (m, 5H), 3.30-3.56 (m, 8H), 3.82 (t, J=12.4 Hz, 2H), 3.91 (s, 3H), 4.01 (d, J=11.2 Hz, 2H), 6.87 (s, 1H), 7.59 (d, J=8.4 Hz, 2H), 7.90 (d, J=8 Hz, 2H), 7.97 (s, 1H), 10.81 (br. s, 1H), 11.71 (br. s, 1H), 14.41 (bs, 1H)

Example C1

4-[3-[4-[4-(4-isopropylpiperazin-1-yl)phenyl]-1H-pyrrolo[3,2-c]pyridin-2-yl]propyl]morpholine

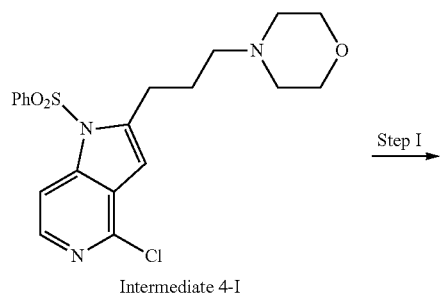

Intermediate 4-I

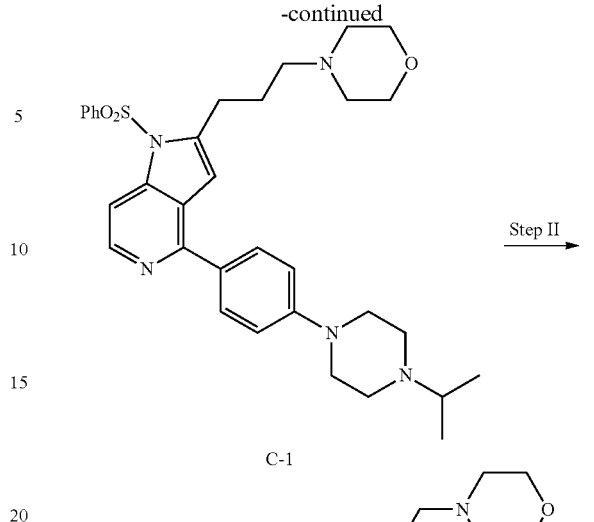

C-1

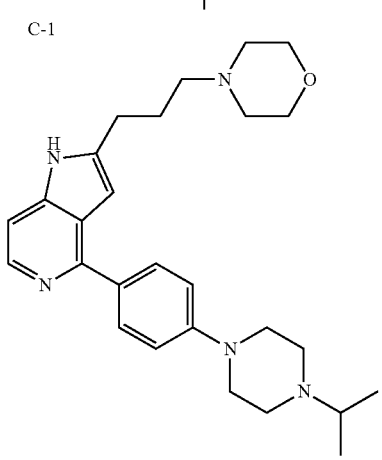

Example C1

Step I: 4-[3-[1-(benzenesulfonyl)-4-[4-(4-isopropylpiperazin-1-yl)phenyl]pyrrolo[3,2-c]pyridin-2-yl]propyl]morpholine (C-1)

A mixture of Intermediate 4-I (0.120 g, 0.285 mmol), Intermediate 1-II (0.122 g, 0.371 mmol) and K$_2$CO$_3$ (0.118 g, 0.857 mmol) in a mixture of dioxane/water (4:1, 5 mL) was degassed in a stream of argon for 15 minutes. To this mixture was added tetrakis(triphenylphosphine)palladium (0) (0.033 g, 0.0285 mmol), and the reaction mixture was again degassed for additional 15 minutes. After stirring at 90° C. for 18 hours, the volatiles were removed by evaporation, and the obtained residue was diluted with water (20 mL), followed by extraction with ethyl acetate (25 mL×3). The combined organic layers were washed with brine (25 mL), dried over anhydrous Na$_2$SO$_4$ and concentrated under reduced pressure. The obtained residue was purified by preparative TLC (8% MeOH in dichloromethane) to give the desired product C-1 (0.135 g, 80%) as a brown solid; LCMS: m/z 420.0 [M$^+$+1].

Step II: 4-[3-[4-[4-(4-isopropylpiperazin-1-yl)phenyl]-1H-pyrrolo[3,2-c]pyridin-2-yl]propyl]morpholine (Example C1)

A stirred solution of C-1 (0.135 g, 0.230 mmol) in 1,4-dioxane (2.5 mL) was treated with sodium tert-butoxide (0.132 g, 1.38 mmol) under argon atmosphere. After stirring at 70° C. for 18 hours, the excess solvent was removed in vacuo. The obtained residue was dissolved in ethyl acetate (25 mL). The organic layer was washed successively with water (10 mL) and brine (10 mL) and dried over anhydrous Na₂SO₄ and concentrated under reduced pressure. The obtained residue was purified by preparative TLC to give the desired compound Example C1 (0.076 g, 73%) as a pale brown solid; LCMS: m/z 448.3 [M⁺+1].

¹H NMR (400 MHz, CDCl₃): δ 1.13 (d, J=6.8 Hz, 6H), 1.92 (quin. 2H), 2.49-2.53 (m, 6H), 2.72 (t, J=4.8 Hz, 4H), 2.73-2.77 (m, 1H), 2.92 (t, J=6 Hz, 2H), 3.32 (t, J=5.6 Hz, 4H), 3.82 (t, J=4.4 Hz, 4H), 6.54 (s, 1H), 7.04 (d, J=8.8 Hz, 2H), 7.16 (d, J=5.6 Hz, 1H), 7.93 (d, J=8.8 Hz, 2H), 8.31 (d, J=6 Hz, 1H), 10.70 (br. s, 1H)

The following compounds Examples C2-C5 as shown in Table 18 were prepared from their corresponding intermediates in the same manner as Example C1.

TABLE 18

| Ex. No. | IUPAC name | Structure | Int. from which prepared | Analytical Data |
|---|---|---|---|---|
| C2 | 4-[3-[4-[4-(4-methylpiperazin-1-yl)phenyl]-1H-pyrrolo[3,2-c]pyridin-2-yl]propyl]morpholine | 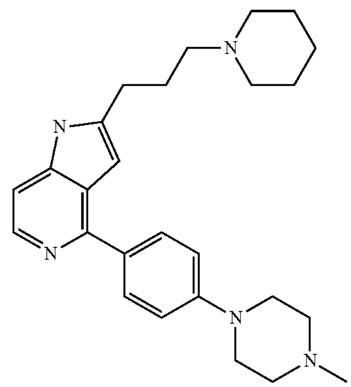 [SMILES: CN1CCN(c2ccc(-c3nccc4[nH]c(CCCN5CCCCC5)cc34)cc2)CC1] | 4-I and 1-I | LCMS: m/z 420.4 [M⁺ + 1] ¹H NMR (400 MHz, CDCl₃): δ 1.92 (quin. 2H), 2.37 (s, 3H), 2.50-2.54 (m, 6H), 2.60 (t, J = 5.2 Hz, 4H), 2.93 (t, J = 6.4 Hz, 2H), 3.32 (t, J = 5.2 Hz, 4H), 3.82 (t, J = 4.4 Hz, 4H), 6.54 (s, 1H), 7.04 (d, J = 8.8 Hz, 2H), 7.16 (d, J = 5.6 Hz, 1H), 7.93 (d, J = 8.8 Hz, 2H), 8.31 (d, J = 5.6 Hz, 1H), 10.72 (br. s, 1H) |
| C3 | 4-[3-[4-[4-(4-isopropylpiperazin-1-yl)phenyl]-6-methyl-1H-pyrrolo[3,2-c]pyridin-2-yl]propyl]morpholine | 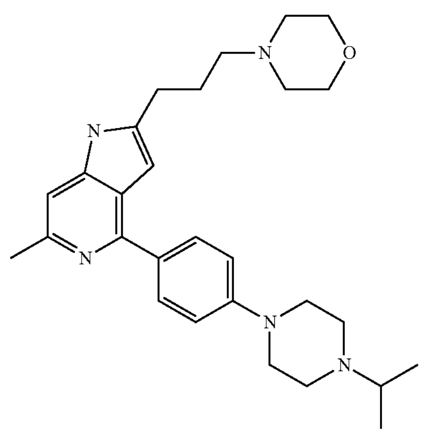 [SMILES: Cc1cc2[nH]c(CCCN3CCOCC3)cc2c(-c2ccc(N3CCN(C(C)C)CC3)cc2)n1] | 4-II and 1-II | LCMS: m/z 462.3 [M⁺ + 1] ¹H NMR (400 MHz, CDCl₃): δ 1.10 (d, J = 6 Hz, 6H), 1.89 (quin., 2H), 2.48-2.53 (m, 6H), 2.68 (s, 3H), 2.69-2.73, (m, 5H), 2.88 (t, J = 4.8 Hz, 2H), 3.29-3.31 (m, 4H), 3.81-3.83 (m, 4H), 6.54 (s, 1H), 6.99 (s, 1H), 7.02 (d, J = 8 Hz, 2H), 7.89 (d, J = 8 Hz, 2H), 10.40 (br. s, 1H) |

TABLE 18-continued

| Ex. No. | IUPAC name | Structure | Int. from which prepared | Analytical Data |
|---|---|---|---|---|
| C4 | 4-[3-[6-methyl-4-[4-(4-methylpiperazin-1-yl)phenyl]-1H-pyrrolo[3,2-c]pyridin-2-yl]propyl]morpholine | 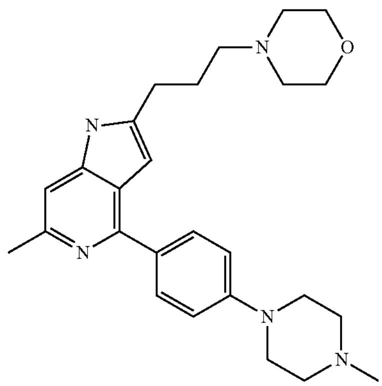 | 4-II and 1-I | LCMS: m/z 434.3 [M$^+$ + 1] $^1$H NMR (400 MHz, CDCl$_3$): δ 1.89 (quin., 2H), 2.37 (s, 3H), 2.47-2.53 (m, 6H), 2.62 (t, J = 4.8 Hz, 4H), 2.66 (s, 3H), 2.88 (t, J = 6.8 Hz, 2H), 3.30 (t, J = 4.8 Hz, 4H), 3.82 (t, J = 4.8 Hz, 4H), 6.44 (s, 1H), 6.98 (s, 1H), 7.03 (d, J = 8.8 Hz, 2H), 7.89 (d, J = 8.8 Hz, 2H), 10.25 (br. s, 1H) |
| C5 | 4-[4-(4-isopropylpiperazin-1-yl)phenyl]-6-methyl-2-[3-(1-piperidyl)propyl]-1H-pyrrolo[3,2-c]pyridine | 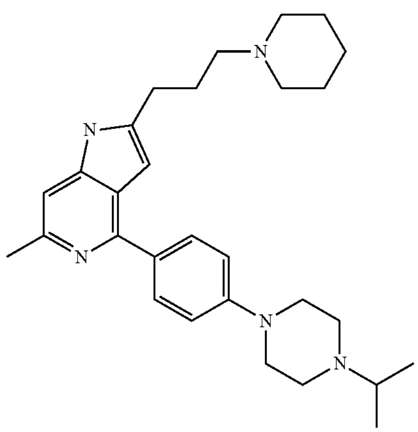 [SMILES: Cc1cc2[nH]c(CCCN3CCCCC3)cc2c(-c2ccc(N3CCN(C(C)C)CC3)cc2)n1] | 4-III and 1-II | LCMS: m/z 460.3 [M$^+$ + 1] $^1$HNMR (400 MHz, CDCl$_3$): δ 1.11 (d, J = 6.4 Hz, 6H), 1.50-1.82 (m, 10H), 1.95-1.99 (m, 2H), 2.56 (t, J = 12 Hz, 2H), 2.71-2.76 (m, 8H), 2.92-2.95 (t, J = 6 Hz, 2H), 3.29-3.31 (t, J = 10 Hz, 4H), 6.44 (s, 1H), 7.00-7.08 (m, 3H), 7.90 (d, J = 8.8 Hz, 2H) |

Example C6

4-[3-[4-[4-(4-isopropylpiperazin-1-yl)phenyl]-1,6-dimethyl-pyrrolo[3,2-c]pyridin-2-yl]propyl]morpholine

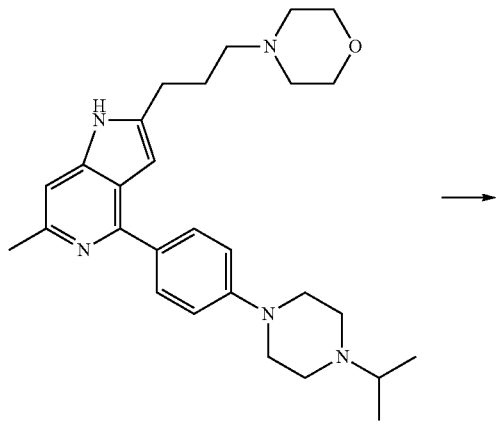

Example C3

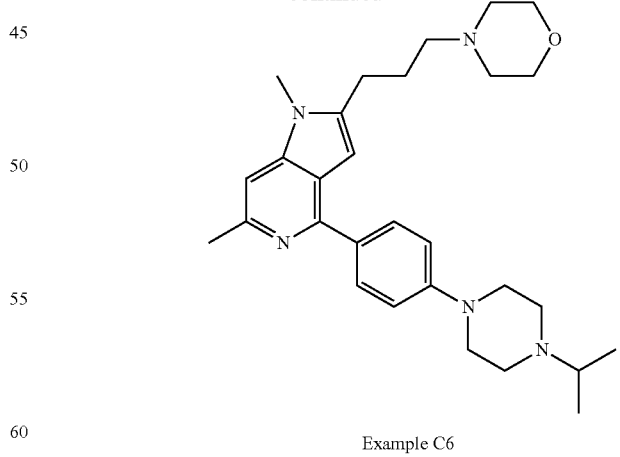

Example C6

NaOtBu (0.537 g, 5.60 mmol) was added to a solution of Example C3 (0.52 g, 1.12 mmol) in 1,4-dioxane (5 mL) at room temperature. After stirring for 15 minutes, methyl benzenesulfonate (0.193 g, 1.12 mmol) was added thereto, and stirring was continued for 3 hours. The reaction mixture was diluted with EtOAc (30 mL) and water (10 mL). The organic layer was separated, dried over Na₂SO₄ and concentrated under reduced pressure. The obtained residue was purified using preparative HPLC to give the desired product Example C6 (0.178 g) as a pale yellow liquid. The obtained liquid product was taken into dioxane (0.5 mL), and 4M HCl in dioxane (1.5 mL) was added thereto at 0° C. After 3 hours at room temperature, the volatiles were removed by evaporation, and the obtained solid was dried under vacuum to give a 3HCl salt of Example C6 (0.198 g, 30%) as a dark yellow solid; LCMS: m/z 476.6 [M$^+$+1]. $^1$H NMR (400 MHz, DMSO-D6): 1.32 (d, J=6.8 Hz, 6H), 2.19 (quin., 2H), 2.75 (s, 3H), 2.94 (t, J=7.6 Hz, 2H), 3.01-3.04 (m, 2H), 3.12-3.15 (m, 5H), 3.35-3.41 (m, 4H), 3.50-3.54 (m, 4H), 3.81-3.86 (m, 2H), 3.84 (s, 3H), 4.05-4.41 (m, 2H), 6.84 (s, 1H), 7.27 (d, J=8.8 Hz, 2H), 7.83-7.86 (m, 3H), 11.10 (br. s, 1H), 11.50 (br. s, 1H), 14.05 (br. s, 1H).

The following compounds as shown in Table 19 can also be prepared according to Schemes 1-13 or in the same manner as in the above mentioned Examples.

TABLE 19

| Structure | Name |
|---|---|
| 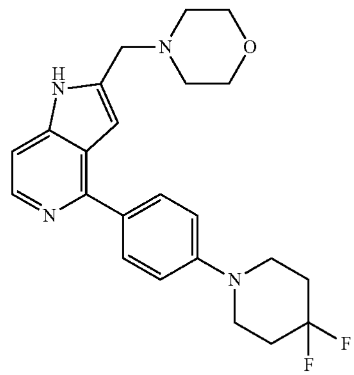 [SMILES: FC1(F)CCN(c2ccc(-c3nccc4[nH]c(CN5CCOCC5)cc34)cc2)CC1] | 4-[(4-[4-(4,4-difluoro-1-piperidyl)phenyl]-1H-pyrrolo[3,2-c]pyridin-2-yl]methyl]morpholine |
| 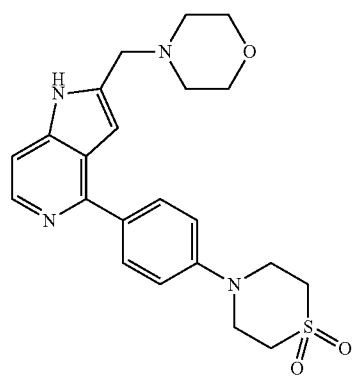 [SMILES: O=S1(=O)CCN(c2ccc(-c3nccc4[nH]c(CN5CCOCC5)cc34)cc2)CC1] | 4-[4-[2-(morpholinomethyl)-1H-pyrrolo[3,2-c]pyridin-4-yl]phenyl]-thiomorpholine 1,1-dioxide |
| 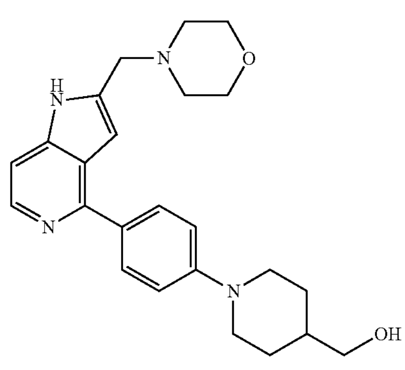 [SMILES: OCC1CCN(c2ccc(-c3nccc4[nH]c(CN5CCOCC5)cc34)cc2)CC1] | [1-[4-[2-(morpholinomethyl)-1H-pyrrolo[3,2-c]pyridin-4-yl]phenyl]-4-piperidyl]methanol |

TABLE 19-continued
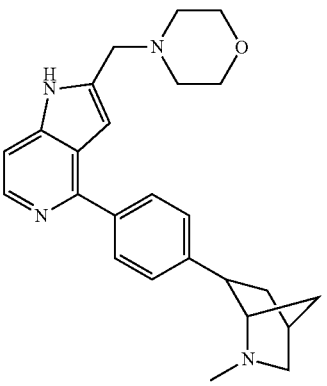 [SMILES: CN1CC2CC(c3ccc(-c4nccc5[nH]c(CN6CCOCC6)cc45)cc3)C1C2]
4-[[4-[4-(3-methyl-3-azabicyclo[2.2.1]heptan-5-yl)phenyl]-1H-pyrrolo[3,2-c]pyridin-2-yl]methyl]morpholine
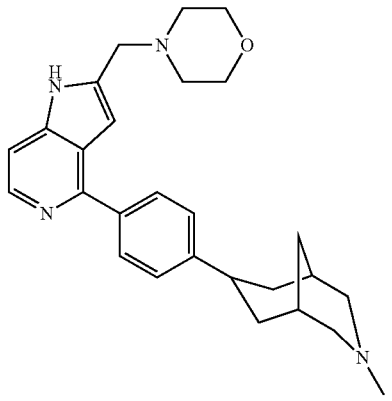 [SMILES: CN1CC2CC(CC(c3ccc(-c4nccc5[nH]c(CN6CCOCC6)cc45)cc3)C2)C1]
4-[[4-[4-(3-methyl-3-azabicyclo[3.3.1]nonan-7-yl)phenyl]-1H-pyrrolo[3,2-c]pyridin-2-yl]methyl]morpholine
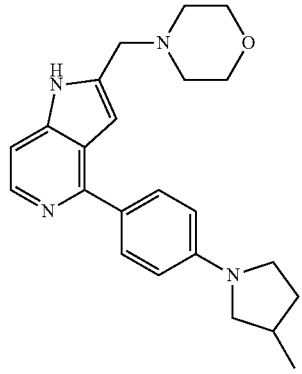 [SMILES: CC1CCN(c2ccc(-c3nccc4[nH]c(CN5CCOCC5)cc34)cc2)C1]
4-[[4-[4-(3-methylpyrrolidin-1-yl)phenyl]-1H-pyrrolo[3,2-c]pyridin-2-yl]methyl]morpholine
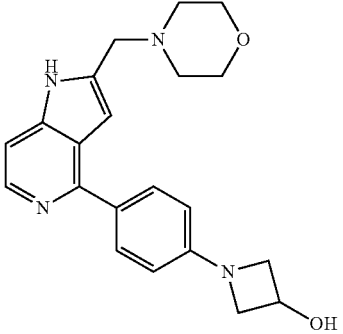 [SMILES: OC1CN(c2ccc(-c3nccc4[nH]c(CN5CCOCC5)cc34)cc2)C1]
1-[4-[2-(morpholinomethyl)-1H-pyrrolo[3,2-c]pyridin-4-yl]phenyl]azetidin-3-ol TABLE 19-continued

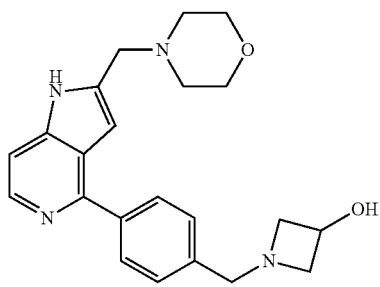 [SMILES: OC1CN(Cc2ccc(-c3nccc4[nH]c(CN5CCOCC5)cc34)cc2)C1] 1-[[4-[2-(morpholinomethyl)-1H-pyrrolo[3,2-c]pyridin-4-yl]phenyl]methyl]azetidin-3-ol

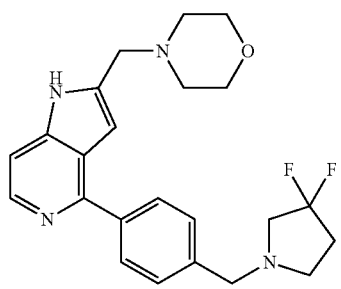 [SMILES: FC1(F)CCN(Cc2ccc(-c3nccc4[nH]c(CN5CCOCC5)cc34)cc2)C1] 4-[[4-[4-[(3,3-difluoropyrrolidin-1-yl)methyl]phenyl]-1H-pyrrolo[3,2-c]pyridin-2-yl]methyl]morpholine

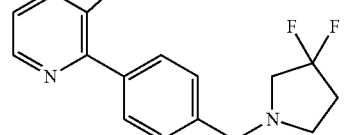 4-[4-(4-methylpiperazin-1-yl)phenyl]-2-(pyrrolidin-1-ylmethyl)-1H-pyrrolo[3,2-c]pyridine

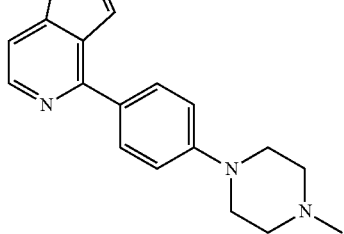 1-[[4-[4-(4-methylpiperazin-1-yl)phenyl]-1H-pyrrolo[3,2-c]pyridin-2-yl]methyl]pyrrolidin-3-ol

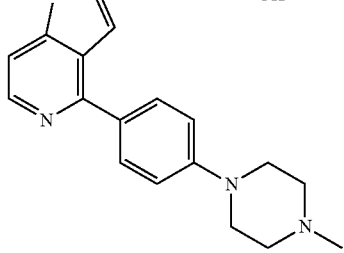 1-[[4-[4-(4-methylpiperazin-1-yl)phenyl]-1H-pyrrolo[3,2-c]pyridin-2-yl]methyl]azetidin-3-ol TABLE 19-continued
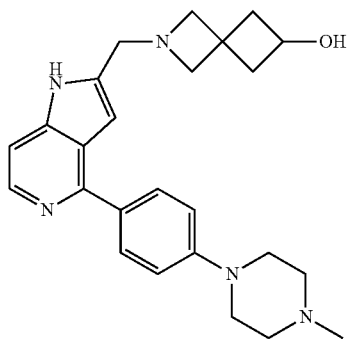 [SMILES: CN1CCN(c2ccc(-c3nccc4[nH]c(CN5CC6(CC(O)C6)C5)cc34)cc2)CC1]
6-[[4-[4-(4-methylpiperazin-1-yl)phenyl]-1H-pyrrolo[3,2-c]pyridin-2-yl]methyl]-6-azaspiro[3.3]heptan-2-ol
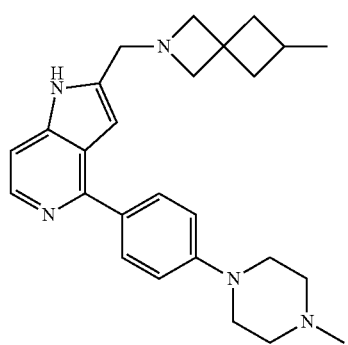 [SMILES: CC1CC2(C1)CN(Cc1cc3c(-c4ccc(N5CCN(C)CC5)cc4)nccc3[nH]1)C2]
2-[(2-methyl-6-azaspiro[3.3]heptan-6-yl)methyl]-4-[4-(4-methylpiperazin-1-yl)phenyl]-1H-pyrrolo[3,2-c]pyridine
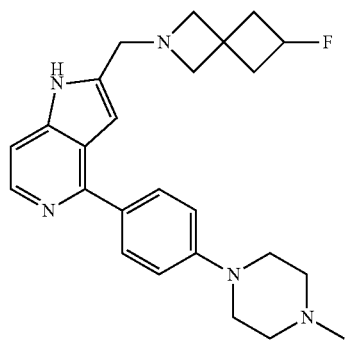 [SMILES: CN1CCN(c2ccc(-c3nccc4[nH]c(CN5CC6(CC(F)C6)C5)cc34)cc2)CC1]
2-[(2-fluoro-6-azaspiro[3.3]heptan-6-yl)methyl]-4-[4-(4-methylpiperazin-1-yl)phenyl]-1H-pyrrolo[3,2-c]pyridine
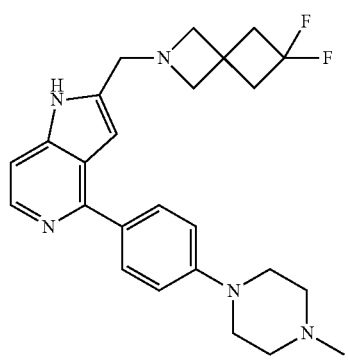 [SMILES: CN1CCN(c2ccc(-c3nccc4[nH]c(CN5CC6(C5)CC(F)(F)C6)cc34)cc2)CC1]
2-[(2,2-difluoro-6-azaspiro[3.3]heptan-6-yl)methyl]-4-[4-(4-methylpiperazin-1-yl)phenyl]-1H-pyrrolo[3,2-c]pyridine TABLE 19-continued
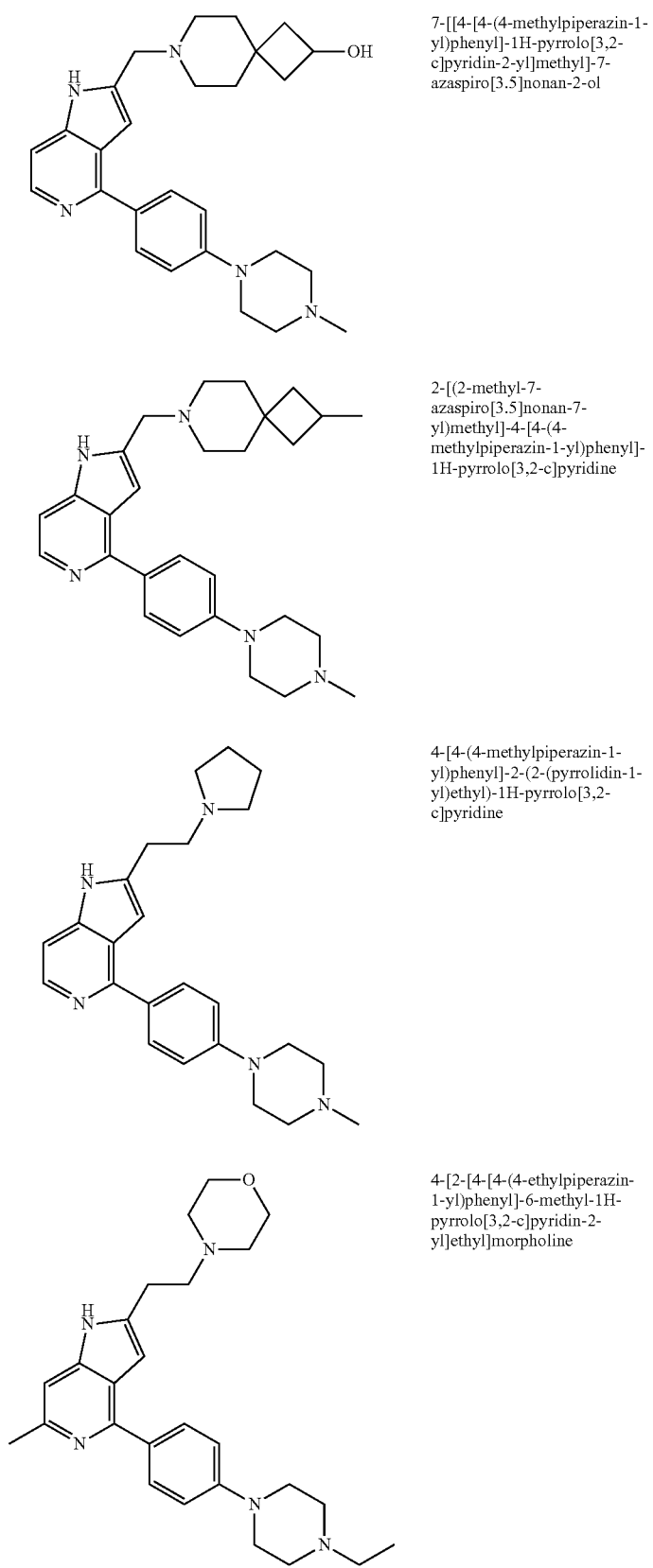
7-[[4-[4-(4-methylpiperazin-1-yl)phenyl]-1H-pyrrolo[3,2-c]pyridin-2-yl]methyl]-7-azaspiro[3.5]nonan-2-ol
2-[(2-methyl-7-azaspiro[3.5]nonan-7-yl)methyl]-4-[4-(4-methylpiperazin-1-yl)phenyl]-1H-pyrrolo[3,2-c]pyridine
4-[4-(4-methylpiperazin-1-yl)phenyl]-2-(2-(pyrrolidin-1-yl)ethyl)-1H-pyrrolo[3,2-c]pyridine
4-[2-[4-[4-(4-ethylpiperazin-1-yl)phenyl]-6-methyl-1H-pyrrolo[3,2-c]pyridin-2-yl]ethyl]morpholine TABLE 19-continued
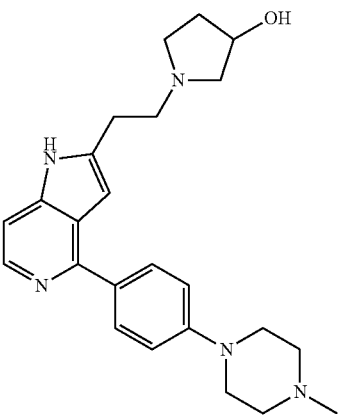 [SMILES: CN1CCN(c2ccc(-c3nccc4[nH]c(CCN5CCC(O)C5)cc34)cc2)CC1]
1-[2-[4-[4-(4-methylpiperazin-1-yl)phenyl]-1H-pyrrolo[3,2-c]pyridin-2-yl]ethyl]pyrrolidin-3-ol
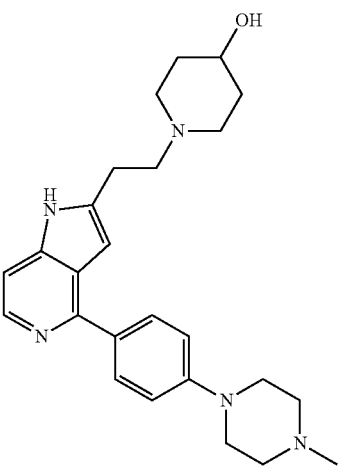 [SMILES: CN1CCN(c2ccc(-c3nccc4[nH]c(CCN5CCC(O)CC5)cc34)cc2)CC1]
1-[2-[4-[4-(4-methylpiperazin-1-yl)phenyl]-1H-pyrrolo[3,2-c]pyridin-2-yl]ethyl]piperidin-4-ol
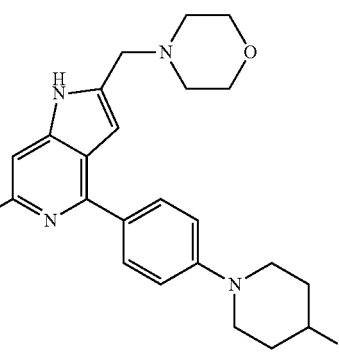
1-[4-[6-methyl-2-(morpholinomethyl)-1H-pyrrolo[3,2-c]pyridin-4-yl]phenyl]piperidin-4-ol
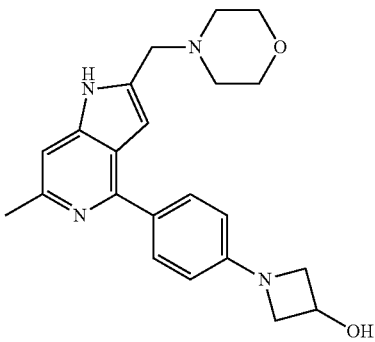 [SMILES: Cc1cc2[nH]c(CN3CCOCC3)cc2c(-c2ccc(N3CC(O)C3)cc2)n1]
1-[4-[6-methyl-2-(morpholinomethyl)-1H-pyrrolo[3,2-c]pyridin-4-yl]phenyl]azetidin-3-ol TABLE 19-continued
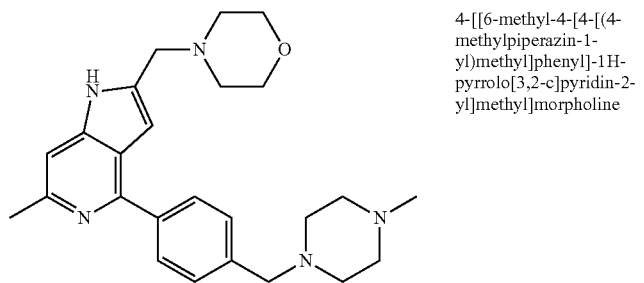
4-[[6-methyl-4-[4-[(4-methylpiperazin-1-yl)methyl]phenyl]-1H-pyrrolo[3,2-c]pyridin-2-yl]methyl]morpholine
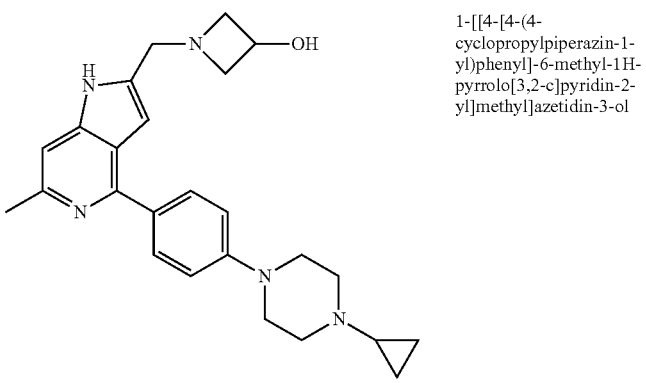
1-[[4-[4-(4-cyclopropylpiperazin-1-yl)phenyl]-6-methyl-1H-pyrrolo[3,2-c]pyridin-2-yl]methyl]azetidin-3-ol
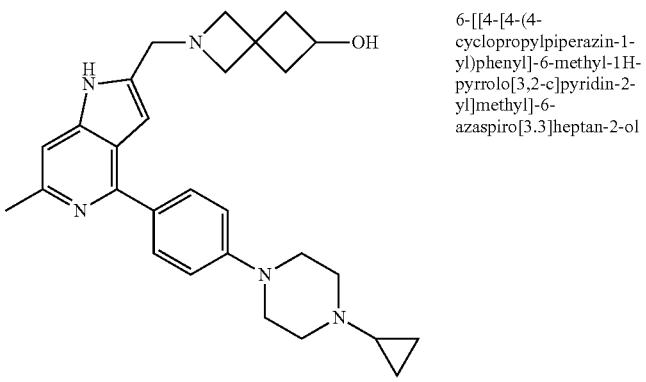
6-[[4-[4-(4-cyclopropylpiperazin-1-yl)phenyl]-6-methyl-1H-pyrrolo[3,2-c]pyridin-2-yl]methyl]-6-azaspiro[3.3]heptan-2-ol
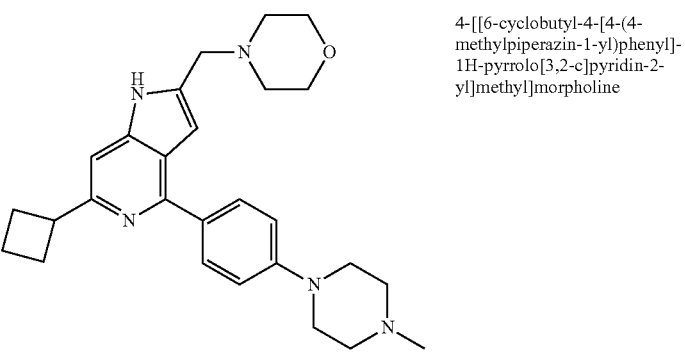
4-[[6-cyclobutyl-4-[4-(4-methylpiperazin-1-yl)phenyl]-1H-pyrrolo[3,2-c]pyridin-2-yl]methyl]morpholine TABLE 19-continued
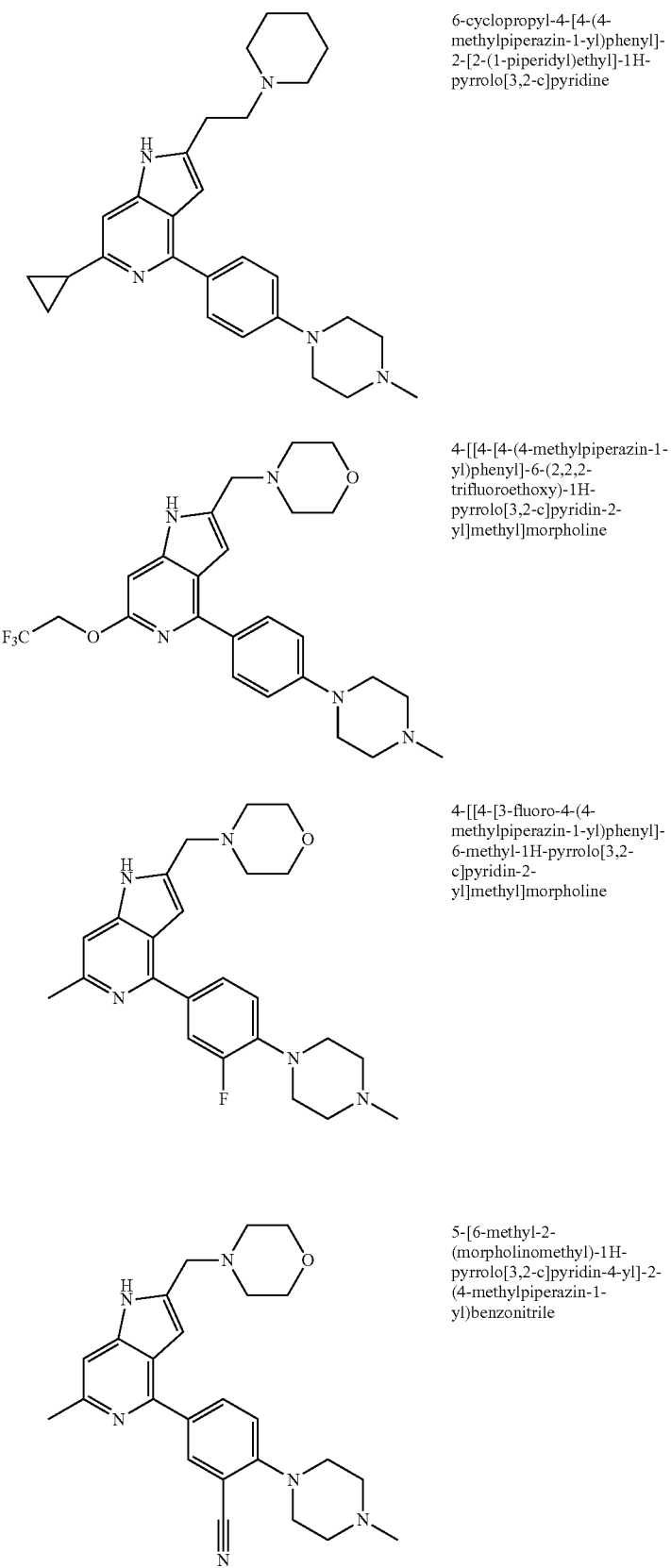
6-cyclopropyl-4-[4-(4-methylpiperazin-1-yl)phenyl]-2-[2-(1-piperidyl)ethyl]-1H-pyrrolo[3,2-c]pyridine
4-[[4-[4-(4-methylpiperazin-1-yl)phenyl]-6-(2,2,2-trifluoroethoxy)-1H-pyrrolo[3,2-c]pyridin-2-yl]methyl]morpholine
4-[[4-[3-fluoro-4-(4-methylpiperazin-1-yl)phenyl]-6-methyl-1H-pyrrolo[3,2-c]pyridin-2-yl]methyl]morpholine
5-[6-methyl-2-(morpholinomethyl)-1H-pyrrolo[3,2-c]pyridin-4-yl]-2-(4-methylpiperazin-1-yl)benzonitrile TABLE 19-continued
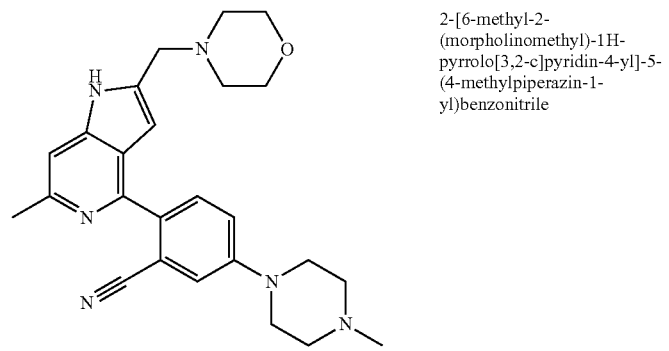
2-[6-methyl-2-
(morpholinomethyl)-1H-
pyrrolo[3,2-c]pyridin-4-yl]-5-
(4-methylpiperazin-1-
yl)benzonitrile
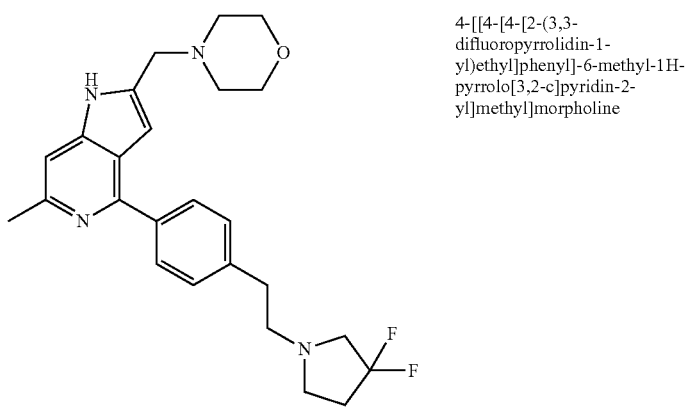
4-[[4-[4-[2-(3,3-
difluoropyrrolidin-1-
yl)ethyl]phenyl]-6-methyl-1H-
pyrrolo[3,2-c]pyridin-2-
yl]methyl]morpholine
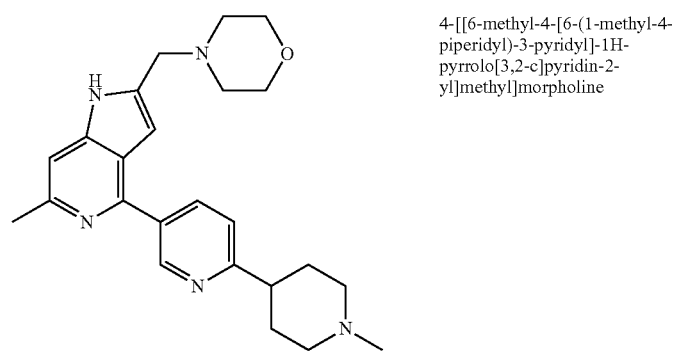
4-[[6-methyl-4-[6-(1-methyl-4-
piperidyl)-3-pyridyl]-1H-
pyrrolo[3,2-c]pyridin-2-
yl]methyl]morpholine
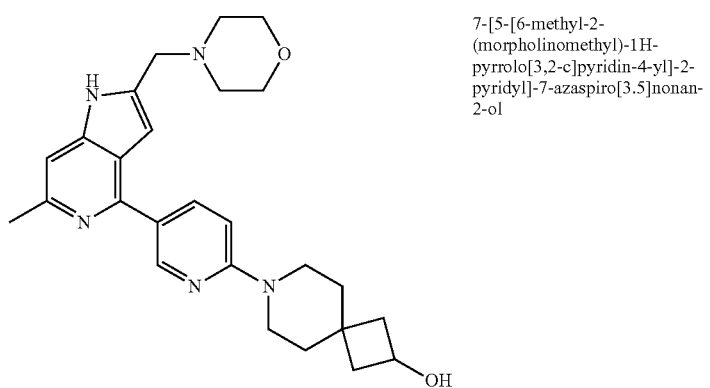
7-[5-[6-methyl-2-
(morpholinomethyl)-1H-
pyrrolo[3,2-c]pyridin-4-yl]-2-
pyridyl]-7-azaspiro[3.5]nonan-
2-ol TABLE 19-continued

| Structure | Name |
|---|---|
| (structure) | 4-[[6-methyl-4-[1-(1-methyl-4-piperidyl)indol-3-yl]-1H-pyrrolo[3,2-c]pyridin-2-yl]methyl]morpholine |
| (structure) | 4-[[6-methyl-4-[1-(oxetan-3-yl)indol-3-yl]-1H-pyrrolo[3,2-c]pyridin-2-yl]methyl]morpholine |
| (structure) | 4-[[6-methyl-4-[1-(oxetan-3-yl)pyrazol-4-yl]-1H-pyrrolo[3,2-c]pyridin-2-yl]methyl]morpholine |
| (structure) | 7-[5-[6-methyl-2-(2-morpholinoethyl)-1H-pyrrolo[3,2-c]pyridin-4-yl]-2-pyridyl]-7-azaspiro[3.5]nonan-2-ol |

TABLE 19-continued
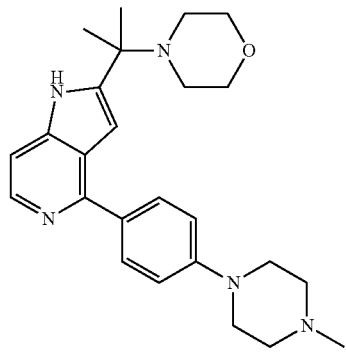 [SMILES: CN1CCN(c2ccc(-c3nccc4[nH]c(C(C)(C)N5CCOCC5)cc34)cc2)CC1]
4-[1-methyl-1-[4-[4-(4-methylpiperazin-1-yl)phenyl]-1H-pyrrolo[3,2-c]pyridin-2-yl]ethyl]morpholine
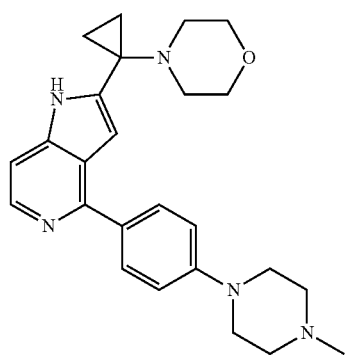 [SMILES: CN1CCN(c2ccc(-c3nccc4[nH]c(C5(N6CCOCC6)CC5)cc34)cc2)CC1]
4-[1-[4-[4-(4-methylpiperazin-1-yl)phenyl]-1H-pyrrolo[3,2-c]pyridin-2-yl]cyclopropyl]morpholine
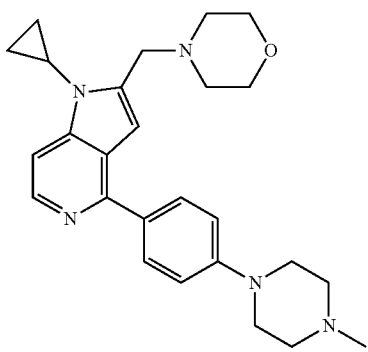 [SMILES: CN1CCN(c2ccc(-c3nccc4c3cc(CN3CCOCC3)n4C3CC3)cc2)CC1]
4-[[1-cyclopropyl-4-[4-(4-methylpiperazin-1-yl)phenyl]pyrrolo[3,2-c]pyridin-2-yl]methyl]morpholine
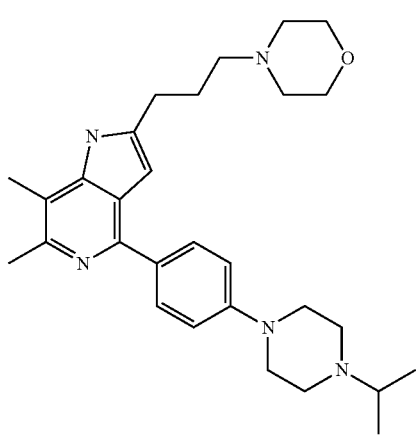 [SMILES: Cc1nc(-c2ccc(N3CCN(C(C)C)CC3)cc2)c2cc(CCCN3CCOCC3)[nH]c2c1C]
4-[3-[4-[4-(4-isopropylpiperazin-1-yl)phenyl]-6,7-dimethyl-1H-pyrrolo[3,2-c]pyridin-2-yl]propyl]morpholine TABLE 19-continued
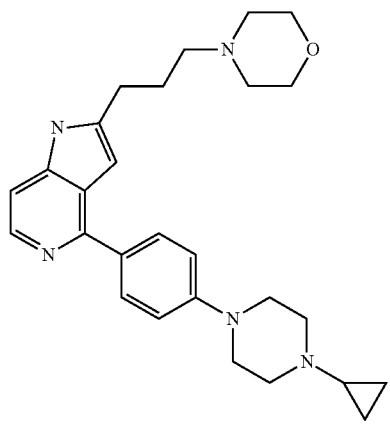 [SMILES: c1cc2[nH]c(CCCN3CCOCC3)cc2c(-c2ccc(N3CCN(C4CC4)CC3)cc2)n1]
4-[3-[4-[4-(4-cyclopropylpiperazin-1-yl)phenyl]-1H-pyrrolo[3,2-c]pyridin-2-yl]propyl]morpholine
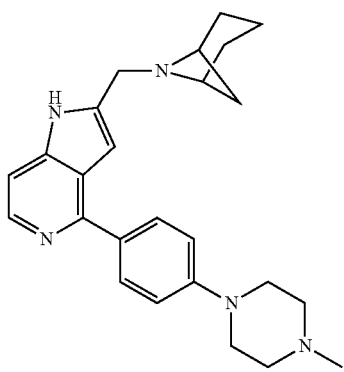 [SMILES: CN1CCN(c2ccc(-c3nccc4[nH]c(CN5C6CCCC5C6)cc34)cc2)CC1]
2-(6-azabicyclo[3.1.1]heptan-6-ylmethyl)-4-[4-(4-methylpiperazin-1-yl)phenyl]-1H-pyrrolo[3,2-c]pyridine
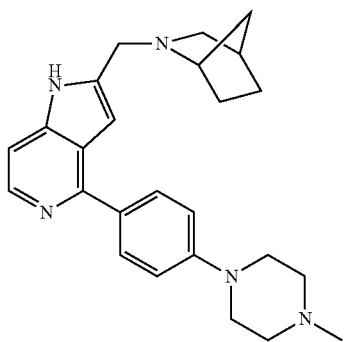 [SMILES: CN1CCN(c2ccc(-c3nccc4[nH]c(CN5CC6CCC5C6)cc34)cc2)CC1]
2-(3-azabicyclo[2.2.1]heptan-3-ylmethyl)-4-[4-(4-methylpiperazin-1-yl)phenyl]-1H-pyrrolo[3,2-c]pyridine
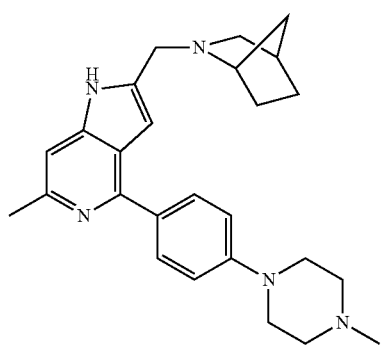
2-(3-azabicyclo[2.2.1]heptan-3-ylmethyl)-6-methyl-4-[4-(4-methylpiperazin-1-yl)phenyl]-1H-pyrrolo[3,2-c]pyridine TABLE 19-continued
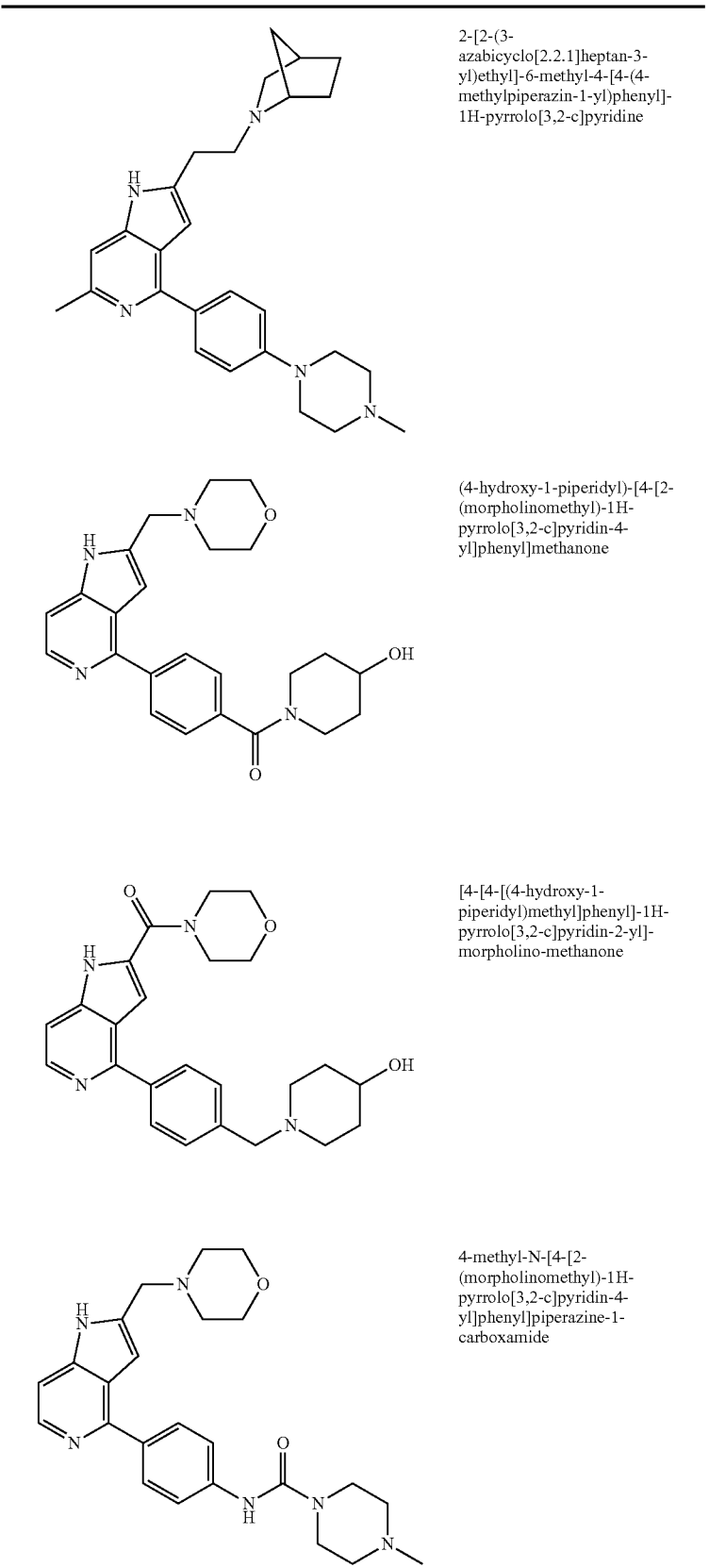
2-[2-(3-azabicyclo[2.2.1]heptan-3-yl)ethyl]-6-methyl-4-[4-(4-methylpiperazin-1-yl)phenyl]-1H-pyrrolo[3,2-c]pyridine
(4-hydroxy-1-piperidyl)-[4-[2-(morpholinomethyl)-1H-pyrrolo[3,2-c]pyridin-4-yl]phenyl]methanone
[4-[4-[(4-hydroxy-1-piperidyl)methyl]phenyl]-1H-pyrrolo[3,2-c]pyridin-2-yl]-morpholino-methanone
4-methyl-N-[4-[2-(morpholinomethyl)-1H-pyrrolo[3,2-c]pyridin-4-yl]phenyl]piperazine-1-carboxamide TABLE 19-continued

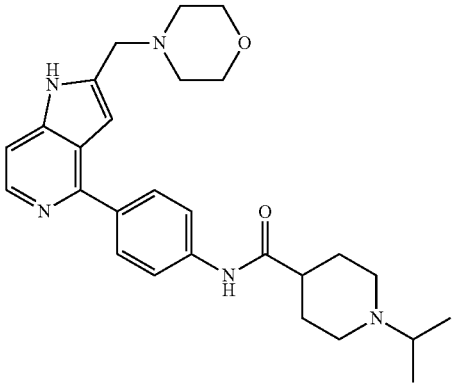 [SMILES: CC(C)N1CCC(C(=O)Nc2ccc(-c3nccc4[nH]c(CN5CCOCC5)cc34)cc2)CC1] 1-isopropyl-N-[4-[2-(morpholinomethyl)-1H-pyrrolo[3,2-c]pyridin-4-yl]phenyl]piperidine-4-carboxamide

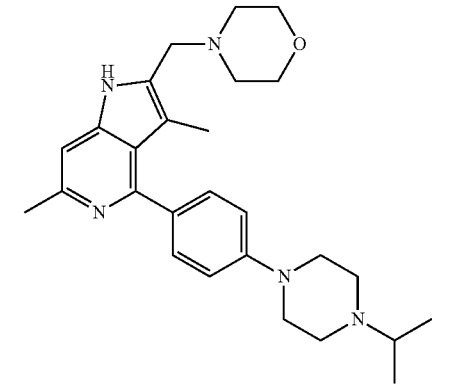 [SMILES: Cc1cc2[nH]c(CN3CCOCC3)c(C)c2c(-c2ccc(N3CCN(C(C)C)CC3)cc2)n1] 4-[[4-[4-(4-isopropylpiperazin-1-yl)phenyl]-3,6-dimethyl-1H-pyrrolo[3,2-c]pyridin-2-yl]methyl]morpholine

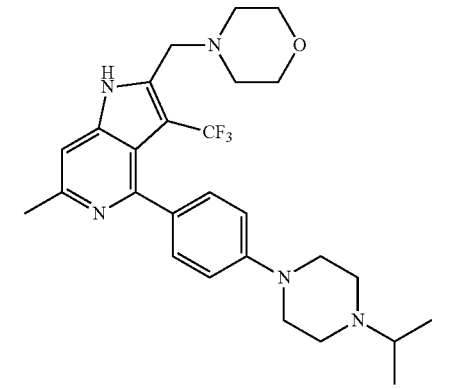 [SMILES: Cc1cc2[nH]c(CN3CCOCC3)c(C(F)(F)F)c2c(-c2ccc(N3CCN(C(C)C)CC3)cc2)n1] 4-[[4-[4-(4-isopropylpiperazin-1-yl)phenyl]-6-methyl-3-(trifluoromethyl)-1H-pyrrolo[3,2-c]pyridin-2-yl]methyl]morpholine

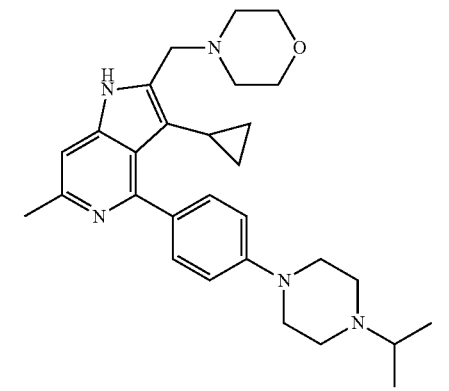 [SMILES: Cc1cc2[nH]c(CN3CCOCC3)c(C3CC3)c2c(-c2ccc(N3CCN(C(C)C)CC3)cc2)n1] 4-[[3-cyclopropyl-4-[4-(4-isopropylpiperazin-1-yl)phenyl]-6-methyl-1H-pyrrolo[3,2-c]pyridin-2-yl]methyl]morpholine Experimental Example 1 hTLR9 Antagonism (SEAP Inhibition Assay) in HEK293 Cell Lines

The SEAP reporter gene in HEK-Blue™-hTLR9 cells is placed under the control of the IFN-b minimal promoter fused to five NF-kB and AP-1 binding sites. The stimulation with a TLR9 ligand (ODN-2006) activates NF-kB and AP-1 which induces the production of SEAP. Levels of SEAP are determined with QUANTI-Blue™ detection medium that turns purple/blue in the presence of alkaline phosphatase. Decrease in the levels of SEAP production as indicated by reduction in absorbance at 650 nm is directly co-related with the TLR9 inhibitory activity of the antagonist (NCE).

HEK-Blue™-hTLR9 cells were maintained in DMEM with 10% FBS, 1% Penicillin/Streptomycin/Amphotericin (complete growth medium) and 0.2% Normocin. For the assay, cells were dissociated by washing in 1×PBS and re-suspended in complete DMEM. Cells were seeded at a density of 20000 cells per well; (40 µl per well) in a 384 well assay plate.

5 µl of 10× antagonist (NCE) was added to the cells in triplicates for each concentration. The plate was incubated for half an hour at 37° C. with 5% $CO_2$. 5 µl of agonist (ODN-2006) was added and the plate was incubated overnight for 18 hours at 37° C. with 5% $CO_2$. 5 µl of supernatant was transferred to a 384 well reading plate and to this 45 µl of Quanti-Blue™ detection reagent was added. The plate was then incubated for an hour at 37° C. SEAP activity in the supernatant was indicated by change in the pink color of Quanti-Blue™ detection reagent to purple/blue and the absorbance was read at 650 nm in the end point mode.

Experimental Example 2 mTLR9 and mTLR7 Antagonism (Cytokine Release Assay) in Mouse Splenocytes

Materials:
Splenocytes isolated from male C57/BL6 mice
TLR7 ligand R0006 (IDT, 5'-rU*rU*rG*rU*rU*rG*rU*rU*rG*rU*rG*rU*rU*rG*rU*rU*rG*rU*rU*rG*rU*rU*rG*rU*rU*rG*rU*rU*rG*rU*rU*rG*rU*rU*rG*rU*rU*rG*rU*rU*rG*rU-3' (SEQ ID NO:1)), Liposomal transfection reagent—DOTAP (Roche, Cat. No. 11202375001), TLR9 ligand CpG ODN2006 (Sequence: T*C*G*T*C*G*T*T*T*T*G*T*C*G*T*T*T*T*G*T*C*G*T*T; *=phosphorothioate (SEQ ID NO:2))
DMSO (Sigma, D2650), RPMI Powder (Sigma, R6504), Fetal Bovine Serum (Gibco, 10270), Dulbecco's Phosphate Buffered Saline (Sigma, D1408), 96 well plate (Flat bottom, Costar 3599), ELISA kit for IL-6 (EBioscience, 88-7064-77 and TNFa (EBioscience, 88-7346-88), MACS Buffer (AutoMACS Rinsing Solution (Miltenyl Biotec, 130-091-222)+ 0.05% BSA), RBC lysis buffer (0.85% NH4Cl), 40 µm cell strainer (BD Falcon, 352340)
Method:
A. Isolation of Mouse Splenocytes Mouse spleen was isolated from C57BL6 mouse and stored in 1× chilled PBS buffer until further processed. Spleen was transferred to a sterile petriplate and chopped in to 5-6 pieces in presence of MACS buffer (100 µl) with the help of fresh surgical blade and crushed with flat plunger of a sterile syringe. A uniform suspension was prepared by passing cells through a 40 µm cell strainer. Cells were centrifuged at 450×g for 5 minutes at 4° C., supernatant was discarded and pellet dislodged gently, resuspended in 2 ml of pre-warmed (37° C.) RBC lysis buffer at room temperature with continuous gentle mixing with 1 ml pipette. Lysis buffer was neutralized with 12 ml of chilled MACS buffer and cells were passed through 40 µm cell strainer. Cell suspension was collected in 15 ml MACS buffer and centrifuged at 450×g for 5 minutes at 4° C. Pellet was resuspended in 15 ml MACS buffer and centrifuged at 400×g for 5 minutes. Cells were resuspended in 10 ml of RPMI complete medium and viability was estimated by Trypan blue method.
Expected yield: 60-70 million cells from single mouse spleen.
mTLR9 Antagonism (IL-6 and TNF-α Release Assay):

500 µM stock of CpG ODN-2006 was prepared in sterile, endotoxin-free water. Dilutions of 10× concentrations of NCEs were prepared in incomplete RPMI media, maintaining a final DMSO concentration of 0.3%. NCEs were added in a concentration range of 30 µM to 1 nM in respective wells of assay plate, assay medium containing 0.3% DMSO were added to control wells. 0.2 million splenocytes were added to all the wells and incubated at 37° C. in 5% $CO_2$ incubator for 30 minutes. 1 µg/ml of respective agonist was added to all the wells except those were assigned as negative controls and mixed thoroughly. Incomplete RPMI was added to negative control wells and incubated overnight at 37° C./5% $CO_2$. The plate was centrifuged at 450×g for 5 minutes at room temperature and the supernatant was collected. ELISA was performed as per manufacturer's protocol. S/B Ratio, % Activity and % Inhibition was calculated using MS Excel. $IC_{50}$ and inhibition curve was generated using Graph Pad Prism.
mTLR7 Antagonism (IL-6 and TNF-α Release Assay):

1 mg/ml stock of R0006 was prepared in sterile, endotoxin-free water. R0006 stock was diluted 10 fold with DOTAP and incubated for 30 minutes to form liposome complex (100 µg/ml of R0006). This complex was further diluted 10 fold with incomplete RPMI media (10 µg/ml of R0006) to achieve the final agonist concentration of 1 µg/ml. DOTAP alone was diluted 10 fold in incomplete RPMI media. NCEs were added in a concentration range of 30 µM to 1 nM in respective wells of assay plate, assay medium containing 0.3% DMSO were added to control wells. 0.2 million splenocytes were added to all the wells and incubated at 37° C. in 5% $CO_2$ incubator for 30 minutes. 1 µg/ml of respective agonist was added to all the wells except those were assigned as negative controls and mixed thoroughly. DOTAP was added to negative control wells and incubated overnight at 37° C./5% $CO_2$. The plate was centrifuged at 450×g for 5 minutes at room temperature and the supernatant was collected. ELISA was performed as per manufacturer's protocol. S/B Ratio, % Activity and % Inhibition was calculated using MS Excel. $IC_{50}$ and inhibition curve was generated using Graph Pad Prism.

hTLR9% inhibition and mTLR7 and mTLR9, IL-6 and TNF-α release % inhibition at 1 µM concentration are given in Table 20 below

TABLE 20

| Example No. | hTLR9 inhibitory activity (% at 1 µM) | mTLR7 inhibitory activity (% at 1 µM) (IL-6, TNF-α) | mTLR9 inhibitory activity (% at 1 µM) (IL-6, TNF-α) |
|---|---|---|---|
| A1 | 100 | 97, 100 | 100, 94 |
| A2 | 100 | 90, 100 | 100, 94 |
| A3 | 100 | 100, 100 | 100, 85 |

TABLE 20-continued

| Example No. | hTLR9 inhibitory activity (% at 1 µM) | mTLR7 inhibitory activity (% at 1 µM) (IL-6, TNF-α) | mTLR9 inhibitory activity (% at 1 µM) (IL-6, TNF-α) |
|---|---|---|---|
| A4 | 100 | 100, 100 | 100, 100 |
| A5 | 100 | 100, 100 | 100, 91 |
| A8 | 100 | 100, 100 | ND, 100 |
| A9 | 100 | ND, 100 | ND, 94 |
| A10 | 29 | ND | ND |
| A11 | 77.5 | ND | ND |
| A12 | 100 | 80, 45 | 95, 52 |
| A13 | 100 | 98, 91 | 100, 91 |
| A16 | 100 | 100, 99 | 100, 100 |
| A17 | 100 | 100, 100 | 100, 100 |
| A18 | 100 | ND | ND |
| A19 | 90 | ND | ND |
| A22 | 62 | ND | ND |
| A24 | 95.1 | ND, 100 | ND, 100 |
| A25 | 95.2 | 100, 100 | 100, 100 |
| A27 | 96.4 | ND | ND |
| A28 | 91 | 88, 100 | 100, 100 |
| A29 | 100 | 97, 82 | 96, 64 |
| A30 | 96.7 | 100, 100 | 100, 100 |
| A31 | 66 | ND | ND |
| A32 | 49 | ND | ND |
| A33 | 90.4 | ND, 83 | ND, 85 |
| A34 | 82 | ND, 100 | ND, 93 |
| A35 | 96.3 | 100, 100 | 100, 90 |
| A36 | 96.7 | 100, 99 | ND, 100 |
| A37 | 100 | ND, 100 | ND, 100 |
| A38 | 98.5 | 100, 100 | 100, 100 |
| A39 | 74.3 | ND, 100 | ND, 100 |
| A40 | 80 | ND, 100 | ND, 100 |
| A42 | 96 | 34, 9 | 84, 41 |
| A45 | 76.1 | ND | ND |
| A46 | 83.5 | ND | ND |
| A49 | 91 | 2, 3 | 65, 15 |
| A51 | 100 | 100, 96 | 100, 90 |
| A52 | 84.5 | 71, 10 | 100, 29 |
| A53 | 77 | 100, 83 | 100, 80 |
| A54 | 95.4 | ND, 0 | ND, 0 |
| A55 | 96.5 | 100, 33 | 96, 59 |
| A56 | 99.5 | ND, 64 | ND, 71 |
| A57 | 96.9 | 80, 79 | 100, 34 |
| A58 | 98 | ND | ND |
| A59 | 94.7 | ND | ND |
| A60 | 86 | ND, 29 | 0, 38 |
| A61 | 89.5 | 78, 74 | 100, 45 |
| A62 | 98.2 | ND, 75 | ND, 79 |
| A63 | 93.4 | ND, 0 | ND, 0 |
| A64 | 73 | 13, 4 | 25, 0 |
| A65 | 70.5 | ND | ND |
| A67 | 27.5 | ND | ND |
| A68 | 21 | ND | ND |
| A69 | 73.5 | ND | ND |
| A70 | 100 | 100, 36 | 95, 52 |
| A71 | 86.1 | ND | ND |
| A72 | 100 | 0, 14 | 72, 0 |
| A73 | 72 | ND | ND |
| A74 | 89.4 | ND, 32 | ND, 95 |
| A75 | 34.9 | ND | ND |
| A76 | 81.2 | ND | ND |
| A79 | 100 | ND | ND |
| A80 | 95.8 | 18, 16 | ND |
| A81 | 64 | 25, 24 | 37, 20 |
| A82 | 98 | 86, 24 | 100, 52 |
| A83 | 29.5 | ND | ND |
| B1 | 100 | 100, 100 | 100, 100 |
| B2 | 100 | 100, 100 | 100, 95 |
| B3 | 100 | ND, 100 | 100, 100 |
| B4 | 100 | ND, 100 | ND, 100 |
| B5 | 78 | ND, 100 | ND, 100 |
| B6 | 79.7 | 100, 100 | 100, 100 |
| B7 | 81.6 | ND, 100 | ND, 100 |
| B8 | 93.7 | ND, 88 | ND, 93 |
| B9 | 95.2 | ND | ND |
| B10 | 93.1 | 100, 100 | 100, 100 |
| B11 | 80 | 100, 100 | 100, 100 |
| B14 | 88.7 | 100, 100 | ND |
| B15 | 93.3 | 88, 83 | ND |
| B16 | 91 | 100, 100 | ND |
| B17 | 91.5 | 93, 90 | ND |
| B18 | 99.3 | 100, 100 | ND |
| B19 | 100 | 100, 100 | 100, 100 |
| B20 | 100 | 70, 57 | ND |
| B21 | 100 | 100, 100 | 100, 100 |
| B22 | 99.7 | 100, 100 | 100, 92 |
| B23 | 99.2 | 100, 100 | ND |
| B26 | 89.9 | 62, 47 | ND |
| B27 | 95.8 | 88, 77 | 100, 72 |
| B31 | 99.4 | 100, 100 | 100, 92 |
| C1 | 99.2 | ND, 100 | ND, 100 |
| C2 | 100 | ND, 100 | ND, 100 |
| C3 | 94.8 | 100, 100 | 100, 100 |
| C4 | 98.7 | ND | ND |
| C5 | 94.7 | 100, 97 | 94, 100 |
| C6 | 99.1 | 100, 100 | 100, 100 |

ND: Not Determined

Experimental Example 3

Mouse Lupus Disease Model

Examples B6 and B11 were tested in well studied mouse model of lupus, lupus-prone MRL lpr/lpr mice that develop disease similar to human SLE [J Exp Med., 1978, 148 (5), 1198-1215]. These mice develop spontaneous systemic autoimmunity with both molecular (IFN signature) and clinical (autoantibody production and glomerulonephritis) features similar to human SLE. Anti-dsDNA antibodies are correlated with human SLE and the reduction in anti-dsDNA antibodies is believed to be of potential clinical benefit. Positive TLR7 and/or TLR9 target validation results have been reported for this disease model.

Mouse Lupus Disease Model Strain:

Female MRL/lpr mice were purchased from Jackson Laboratories (USA) which manifest spontaneous lupus disease. Female MRL/lpr mice were treated for 9 weeks by oral route once a day with TLR-7/9 antagonists [Examples B6 and B11] at 3, 10 and 30 mg/kg doses. Prednisolone (2 mg/kg, P.O., QD) was used as a positive control during the studies. At the end of treatment period, animals were sacrificed and blood samples were collected to estimate anti-dsDNA IgG titers using anti-dsDNA IgG ELISA kit, Alpha Diagnostics, USA.

Key findings for Example B6 in the SLE disease model are as follows.

Mice treated with Example B6 showed trend towards dose dependent reduction in mean anti-dsDNA IgG titers after 6 weeks of treatment at 3, 10 and 30 mg/kg doses (QD) [FIG. 1A].

Significant reduction in anti-dsDNA IgG was observed with 10 mg/kg once daily oral dose after 9 weeks of treatment [FIG. 1B].

Key findings for Example B11 in the SLE disease model are as follows.

Mice treated with Example B11 showed dose dependent reduction in mean anti-dsDNA IgG titers after 6 weeks of treatment at 3, 10 and 30 mg/kg doses (QD), significant at 30 mg/kg dose [QD] [FIG. 2A].

Formulation Example 1

| | | |
|---|---|---|
| (1) Compound of Example A1 | 10.0 g | |
| (2) Lactose | 70.0 g | |
| (3) Cornstarch | 50.0 g | |
| (4) Soluble starch | 7.0 g | |
| (5) Magnesium stearate | 3.0 g | |

After 10.0 g of the compound of Example A1 and 3.0 g of magnesium stearate are granulated in 70 ml aqueous solution of soluble starch (7.0 g as soluble starch) and then dried, and the resulting mixture is mixed with 70.0 g of lactose and 50.0 g of cornstarch (lactose, cornstarch, soluble starch and magnesium stearate are all products in compliance with Japanese Pharmacopoeia 14$^{th}$ Edition). The mixture is compressed to obtain a tablet.

INDUSTRIAL APPLICABILITY

According to the present invention, the compound having a TLR7, TLR9, TLR7/8, TLR7/9 or TLR7/8/9-inhibitory action, which is useful as an agent for the prophylaxis or treatment of autoimmune diseases, inflammatory diseases and the like, in particular, systemic lupus erythematosus, Sjogren's syndrome, rheumatoid arthritis, psoriasis, inflammatory bowel disease and the like, can be provided.

This application is based on patent application No. 3656/DELNP/2013 filed on Dec. 13, 2013 in India, the to contents of which are encompassed in full herein.

The invention claimed is:

1. A compound represented by the formula (I):

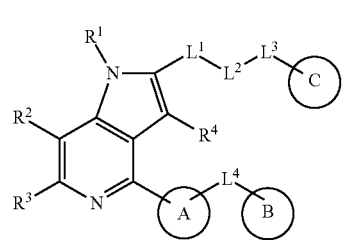

wherein $R^1$ is a hydrogen atom, an optionally substituted hydrocarbon group, an optionally substituted heterocyclic group, an optionally substituted hydroxy group, an optionally substituted amino group, an optionally substituted sulfanyl group, or an acyl group, $R^2$, $R^3$ and $R^4$ are independently a hydrogen atom or a substituent selected from the group consisting of a halogen atom, a cyano group, a nitro group, an optionally substituted hydrocarbon group, an optionally substituted heterocyclic group, an optionally substituted hydroxy group, an optionally substituted amino group, an optionally substituted sulfanyl group, and an acyl group, Ring A is an optionally substituted ring, Ring B is an optionally substituted heterocycle, Ring C is an optionally substituted 3- to 10-membered nitrogen-containing heterocycle, $L^1$ is a bond or a divalent hydrocarbon group,

SEQUENCE LISTING

```
<160> NUMBER OF SEQ ID NOS: 2

<210> SEQ ID NO 1
<211> LENGTH: 20
<212> TYPE: RNA
<213> ORGANISM: Artificial Sequence
<220> FEATURE:
<223> OTHER INFORMATION: TLR7 ligand R0006
<220> FEATURE:
<221> NAME/KEY: misc_feature
<222> LOCATION: (1)..(20)
<223> OTHER INFORMATION: Each base is phosphorothioate

<400> SEQUENCE: 1
uuguuguugu uguuguuguu                                                  20

<210> SEQ ID NO 2
<211> LENGTH: 24
<212> TYPE: DNA
<213> ORGANISM: Artificial Sequence
<220> FEATURE:
<223> OTHER INFORMATION: TLR9 ligand CpG ODN2006
<220> FEATURE:
<221> NAME/KEY: misc_feature
<222> LOCATION: (1)..(24)
<223> OTHER INFORMATION: Each base is phosphorothioate

<400> SEQUENCE: 2
tcgtcgtttt gtcgttttgt cgtt                                             24
```

L² is a bond, —O—, —C(O)—, —NH—C(O)—, —C(O)—NH—, —S—, —SO—, —SO₂—, —SO₂—O—, —O—SO₂— or —CH(CN)—, L³ is a bond or a divalent hydrocarbon group, with the proviso that at least one of L¹, L² and L³ is not a bond, and L⁴ is a bond or a spacer having 1 to 6 atoms, or a salt thereof.

2. The compound or salt of claim 1, wherein

R¹ is a hydrogen atom, a $C_{1-10}$ alkyl group or a $C_{3-10}$ cycloalkyl group, R² is a hydrogen atom or a $C_{1-10}$ alkyl group, R³ is a hydrogen atom, an optionally substituted hydrocarbon group or an optionally substituted hydroxy group, R⁴ is a hydrogen atom, a halogen atom or an optionally substituted hydrocarbon group, Ring A is an optionally substituted $C_{3-10}$ cycloalkane, an optionally substituted $C_{3-10}$ cycloalkene, an optionally substituted $C_{6-14}$ aromatic hydrocarbon or an optionally substituted aromatic heterocycle optionally fused with benzene, Ring B is an optionally substituted 3- to 10-membered non-aromatic heterocycle, Ring C is an optionally substituted 5- or 6-membered nitrogen-containing aromatic heterocycle or an optionally substituted 3- to 10-membered nitrogen-containing non-aromatic heterocycle, L¹ and L³ are independently (1) a bond, (2) a $C_{1-10}$ alkylene group, or (3) a $C_{3-8}$ cycloalkylene group, L² is a bond or —C(O)—, and L⁴ is a bond, a straight chain $C_{1-6}$ alkylene group, —X¹—O—X²—, —X¹—C(O)—X²— or —X¹—NH—C(O)—X²—, wherein X¹ and X² are independently a bond or a straight chain $C_{1-5}$ alkylene group, and the total atom number is 6 or less.

3. The compound or salt of claim 1, which is 4-[2-[4-[4-(4-isopropylpiperazin-1-yl)phenyl]-6,7-dimethyl-1H-pyrrolo[3,2-c]pyridin-2-yl]ethyl]morpholine or a salt thereof.

4. The compound or salt of claim 1, which is 4-[2-[4-[4-(4-isopropylpiperazin-1-yl)phenyl]-1,6-dimethyl-pyrrolo[3,2-c]pyridin-2-yl]ethyl]morpholine or a salt thereof.

5. The compound or salt of claim 1, which is 4-[[4-[4-(4-isopropylpiperazin-1-yl)phenyl]-1H-pyrrolo[3,2-c]pyridin-2-yl]methyl]morpholine or a salt thereof.

6. The compound or salt of claim 1, which is 4-[4-(4-isopropylpiperazin-1-yl)phenyl]-2-(1-piperidylmethyl)-1H-pyrrolo[3,2-c]pyridine or a salt thereof.

7. A pharmaceutical composition comprising the compound or salt of claim 1.

8. The pharmaceutical composition of claim 7, which is a TLR7, TLR9, TLR7/8, TLR7/9 or TLR7/8/9 inhibitor.

9. The pharmaceutical composition of claim 7, which is an agent for the treatment of an autoimmune disease and/or an inflammatory disease, wherein the autoimmune disease and/or inflammatory disease is selected from the group consisting of systemic lupus erythematosus, Sjogren's syndrome, rheumatoid arthritis, psoriasis and inflammatory bowel disease.

10. A method of inhibiting TLR7, TLR9, TLR7/8, TLR7/9 or TLR7/8/9 in a mammal, which comprises administering an effective amount of the compound or salt of claim 1 to the mammal.

11. A method for the treatment of an autoimmune disease and/or an inflammatory disease in a mammal, wherein the autoimmune disease and/or inflammatory disease is selected from the group consisting of systemic lupus erythematosus, Sjogren's syndrome, rheumatoid arthritis, psoriasis and inflammatory bowel disease, which comprises administering an effective amount of the compound or salt of claim 1 to the mammal.

\* \* \* \* \*